(12) United States Patent
Selden et al.

(10) Patent No.: US 9,314,795 B2
(45) Date of Patent: *Apr. 19, 2016

(54) UNITARY BIOCHIP PROVIDING SAMPLE-IN TO RESULTS-OUT PROCESSING AND METHODS OF MANUFACTURE

(71) Applicant: NetBio, Inc., Waltham, MA (US)

(72) Inventors: Richard F. Selden, Lincoln, MA (US); Eugene Tan, Lexington, MA (US)

(73) Assignee: NetBio Inc., Waltham, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/276,993

(22) Filed: May 13, 2014

(65) Prior Publication Data

US 2014/0371108 A1     Dec. 18, 2014

Related U.S. Application Data

(63) Continuation of application No. 13/228,263, filed on Sep. 8, 2011, now Pat. No. 8,720,036, which is a continuation-in-part of application No. 13/044,485, filed on Mar. 9, 2011, application No. 14/276,993, which is a continuation-in-part of application No. 13/044,485, filed on Mar. 9, 2011, and a continuation of application No. 13/826,592, filed on Mar. 14, 2013, and a continuation of application No. 13/829,263, filed on Mar. 14, 2013.

(60) Provisional application No. 61/339,743, filed on Mar. 9, 2010.

(51) Int. Cl.
*B01L 3/00* (2006.01)
*B29B 11/08* (2006.01)
(Continued)

(52) U.S. Cl.
CPC . *B01L 7/52* (2013.01); *B01L 3/502* (2013.01); *B01L 3/502707* (2013.01); *B01L 3/502715* (2013.01); *B01L 3/502753* (2013.01); *B29B 11/08* (2013.01); *C12Q 1/6806* (2013.01); *G01N 27/26* (2013.01); *G01N 27/44704* (2013.01); *G01N 27/44791* (2013.01); *B01D 69/02* (2013.01); *B01L 2200/10* (2013.01); *B01L 2200/12* (2013.01); *B01L 2200/142* (2013.01); *B01L 2200/16* (2013.01); *B01L 2300/0681* (2013.01); *B01L 2300/087* (2013.01); *B01L 2300/0874* (2013.01); *B01L 2300/123* (2013.01); *B01L 2300/1822* (2013.01);
(Continued)

(58) Field of Classification Search
None
See application file for complete search history.

(56) References Cited

U.S. PATENT DOCUMENTS 6,375,817 B1    4/2002  Taylor et al.
6,403,037 B1    6/2002  Chang et al.
(Continued)

FOREIGN PATENT DOCUMENTS

JP    2008-151770    7/2008
WO    2006/032044    3/2006
(Continued)

OTHER PUBLICATIONS

American National Standards Institute ANSI/SLAS Jan. 2004, Footprint Dimensions for Microplates. Oct. 21, 2011.
(Continued)

*Primary Examiner* — Lyle Alexander
*Assistant Examiner* — Jennifer Wecker
(74) *Attorney, Agent, or Firm* — Proskauer Rose LLP

(57) ABSTRACT

A biochip for the integration of all steps in a complex process from the insertion of a sample to the generation of a result, performed without operator intervention includes microfluidic and macrofluidic features that are acted on by instrument subsystems in a series of scripted processing steps. Methods for fabricating these complex biochips of high feature density by injection molding are also provided.

8 Claims, 90 Drawing Sheets

(51) Int. Cl.
*B01L 7/00* (2006.01)
*G01N 27/447* (2006.01)
*G01N 27/26* (2006.01)
*C12Q 1/68* (2006.01)
*G01N 1/10* (2006.01)
*B01D 69/02* (2006.01)

(52) U.S. Cl.
CPC . *B01L 2400/0421* (2013.01); *B01L 2400/0481* (2013.01); *B01L 2400/0487* (2013.01); *B01L 2400/0655* (2013.01); *B01L 2400/0677* (2013.01); *B01L 2400/0688* (2013.01); *Y10T 29/4998* (2015.01)

(56) References Cited

U.S. PATENT DOCUMENTS

| | | | |
|---|---|---|---|
| 7,279,134 | B2 | 10/2007 | Chan et al. |
| 7,435,381 | B2 * | 10/2008 | Pugia ............... B01L 3/502707 422/421 |
| 7,473,397 | B2 | 1/2009 | Griffin et al. |
| 7,998,708 | B2 | 8/2011 | Handique et al. |
| 8,018,593 | B2 | 9/2011 | Tan et al. |
| 8,245,378 | B2 | 8/2012 | Dean et al. |
| 2004/0053422 | A1 * | 3/2004 | Chan ................... B01D 61/022 436/180 |
| 2004/0063198 | A1 | 4/2004 | Tilles et al. |
| 2005/0196779 | A1 | 9/2005 | Ho et al. |
| 2006/0260941 | A1 | 11/2006 | Tan |
| 2007/0166200 | A1 | 7/2007 | Zhou et al. |
| 2007/0259348 | A1 | 11/2007 | Phadke et al. |
| 2007/0292941 | A1 | 12/2007 | Handique et al. |
| 2008/0199872 | A1 | 8/2008 | Barnard et al. |
| 2009/0000690 | A1 | 1/2009 | Oldham et al. |
| 2009/0059222 | A1 | 3/2009 | Tan et al. |
| 2009/0072436 | A1 | 3/2009 | Dean |
| 2009/0181412 | A1 | 7/2009 | Cho et al. |
| 2009/0286327 | A1 | 11/2009 | Cho et al. |
| 2010/0112717 | A1 | 5/2010 | Augstein et al. |
| 2010/0285578 | A1 | 11/2010 | Selden et al. |
| 2010/0304986 | A1 * | 12/2010 | Chen ................. B01L 3/502715 506/9 |
| 2012/0115212 | A1 | 5/2012 | Weigl et al. |

FOREIGN PATENT DOCUMENTS

| | | |
|---|---|---|
| WO | 2006/032044 A2 | 3/2006 |
| WO | 2008/087405 | 7/2008 |
| WO | 2008/124104 | 10/2008 |
| WO | 2009/049268 | 4/2009 |
| WO | 2009/108260 | 9/2009 |

OTHER PUBLICATIONS

Burns, M.A., et al., "An Integrated Nanoliter DNA Analysis Device," SCIENCE, vol. 282, Oct. 16, 1998, pp. 484-487.
International Search Report for PCT Application No. PCT/US2011/027787, 7 pages, Nov. 2011.
Kim, J., et al. "A Disposable, Self-Contained PCR Chip", Lab Chip. Feb. 21, 2009; 9(4): 606-612.
Lutz, S., et al. "Microfluidic lab-on-a-foil for nucleic acid analysis based on isothermal recombinase polymerase amplification (RPA)", Lab Chip, 2010, 10, 887-893.
Stevens, D. Y., et al"Enabling a microfluidic immunoassay for the developing world by integration of on-card dry reagent storage", Lab Chip, 2008, 8, 2038-2045.
Tsao, C.W., et al., "Bonding of Thermoplastic Polymer Microfluidics" Microfluid Nanofluid, 2009, pp. 1-16.
Von Lode, P., et a"Fully Automated, Homogeneous Nucleic Acid Detection Technology Based on Dry-Reagent Assay Chemistry and Time-Resolved Fluorometry", 2007 Clinical Chemistry 53, No. 11, 2014-2017.

* cited by examiner

Figure 20 Fluidics

403

(Pneumatic Plate: 277.62mm x 117.70mm x 2.50mm)

Figure 77

| Scripted Step | Hold Time (s) | DL6 Pressure (psig) | DL7 Pressure (psig) | V10 State | V11 State |
|---|---|---|---|---|---|
| 1 |  | 0 | 0 | Closed | Closed |
| 2 | 40 | 0 | 0 | Opened | Closed |
| 3 |  | 1 | 0 | Opened | Closed |
| 4 |  | 0 | 0 | Opened | Closed |
| 5 |  | 0 | 0 | Closed | Closed |
| 6 |  | 0 | 0 | Opened | Closed |
| 7 |  | 0 | 0 | Opened | Opened |
| 8 | 25 | 0 | 2 | Opened | Opened |
| 9 |  | 0 | 0 | Closed | Opened |
| 10 |  | 0 | 0 | Closed | Closed |

Figure 80

| Run # | Without bandpass filter | | | With bandpass filter | | |
|---|---|---|---|---|---|---|
| | 1 | 2 | Average | 1 | 2 | Average |
| Allele signal strength | 1426 | 1615 | 1520 | 1323 | 1149 | 1236 |
| Peak-Peak Noise | 68 | 66 | 67 | 40 | 37 | 39 |
| Signal-Noise | 21 | 25 | 23 | 33 | 31 | 32 |

UNITARY BIOCHIP PROVIDING SAMPLE-IN TO RESULTS-OUT PROCESSING AND METHODS OF MANUFACTURE

PRIORITY CLAIM

This application is a continuation of U.S. patent application Ser. No. 13/228,263 (which is now U.S. Pat. No. 8,720, 036), filed on Sep. 8, 2011, which is a continuation in part of U.S. patent application Ser. No. 13/044,485 entitled "Unitary Biochip Providing Sample-in to Results-out Processing and Methods of Manufacture" filed on Mar. 9, 2011. U.S. patent application Ser. No. 13/044,485 claims priority from U.S. Provisional Application Ser. No. 61/339,743 filed Mar. 9, 2010. This application is also a continuation of U.S. patent application Ser. No. 13/829,263 entitled "Unitary Biochip Providing Sample-in to Results-out Processing and Methods of Manufacture" filed on Mar. 14, 2013. This application is also a continuation of U.S. patent application Ser. No. 13/826,592 entitled "Unitary Biochip Providing Sample-in to Results-out Processing and Methods of Manufacture" filed on Mar. 14, 2013. The disclosures of U.S. patent application Ser. No. 13/228,263, U.S. patent application Ser. No. 13/044, 485, U.S. patent application Ser. No. 13/829,263, U.S. patent application Ser. No. 13/826,592 and U.S. Provisional Application Ser. No. 61/339,743 are hereby incorporated by reference in their entirety.

STATEMENT AS TO FEDERALLY SPONSORED RESEARCH

This invention was made with Government support under a Contract awarded by MIT Lincoln Laboratory pursuant to RFP 800002471. The government may have certain rights in this invention.

BACKGROUND OF THE INVENTION

The field of microfluidics can be broadly defined as related to the manipulation of small fluidic volumes, typically those that are less than one milliliter. The concept that using microfluidic volumes in clinical assays would represent a significant improvement over conventional methods dates back to the late 1960's and early 1970's. While those working in the field appreciated that small volume analyses would lead to portable instruments that required less laboratory space, improved precision and accuracy, increased throughput, reduced cost, and compatibility with true automation, the systems developed at that time were simple and did not realize the desired advantages of microfluidics. One early system was based on the analysis of 1-10 l of sample and 70-110 l of reagents that were transferred and mixed in a small centrifugal rotor (Anderson, N. (1969). Computer interfaced fast analyzers. Science 166: 317-24; and Burtis, C et al. (1972). Development of a miniature fast analyzer. Clinical Chemistry 18: 753-61). That rotor is likely the first reported microfluidic biochip.

In 1990, the theoretical foundation of the field of microfluidics was further characterized by Manz, who coined the term "miniaturized total chemical analysis system" or "μ-TAS", to define what he considered should be the next generation of microfluidic devices. Manz proposed that such devices should be capable of performing all required sample handling steps. Manz stated objectives helped establish the major goal in the modern era of microfluidics: to deliver a total, that is to say, fully integrated, analysis systems capable of performing a complex series of process steps from the insertion of a sample to the generation of a result without operator intervention. It is the promise of integrating a complex series of sample manipulations and process steps that has led to the widespread adoption of the phrase "laboratory on a chip."

Work on centrifugal systems continued after the first early efforts and resulted in a commercial centrifugal system for sandwich immunoassays that used a microfluidic compact disc drive. The system was not fully integrated, however; and more accurately should be termed a workstation in which reagents were transferred to and from the compact disc robotically. Furthermore, the immunoassays were quite simple, based on passing a sample through a capture column. Although the system used microfluidic volumes to reduce reagent costs, it delivered neither on the promise of microfluidics to provide a fully-integrated system nor on the promise of microfluidics to integrate a complex series of sample manipulations and process steps.

Similarly, other workers fabricated a spinning biochip in poly(methyl methacrylate) [PMMA] by soft embossing to fractionate plasma from whole blood. There have been applications of spinning microfluidic biochips, for measurement of various analytes of interest in a blood sample. However, the devices have been developed for simple analytic tests, for example establishing the amounts of analytes of interest in a blood sample. The samples are not subjected to a complex series of sample manipulations and process steps, and even after almost two decades of development, can still have significant reliability problems correlating with established conventional assays.

In general, CD-based biochips have major drawbacks and limitations. First, they do not enable sufficient process complexity. These biochips are limited to relatively simple processes such as certain cell separations (serving as replacements for conventional centrifugation instrumentation) and for high throughput immunoassays (serving as replacements for the mixing and incubation of conventional assays). Second, the use of centrifugal force as the driver of fluidic transport is limiting. For example, the requirement to rotate the biochip places profound limitations on the approach to sample handling—either the sample must be introduced indirectly (requiring either manual intervention or additional instrumentation) or directly (e.g. a blood collection tube or swab would need to be subjected to centrifugation as well). Furthermore, process flow in spinning biochips proceeds unidirectionally, and the radius of the biochip limits the area available for sample process steps to take place (one of the factors that limits process complexity).

Concomitantly, alternatives to CD-based biochips have been studied. A number of groups have worked on microfluidic biochips based on microtiter plates using SBS (Society for Biomolecular Screening, Microplate Standards Development Committee, ANSI/SBS1, Danbury, Conn., 2004) standards. The SBS developed a series of published standards for microtiter plates that include footprint (127.76 by 85.48 mm, 10,920.9 mm$^2$), height, and bottom outside flange dimensions and well positions. These standards have been incorporated by commercial manufacturers and academic groups, regardless of the fabrication process utilized. Microfluidic microtiter plates have been developed for a number of processes, including DNA purification and protein crystallization. These biochips require sample pre-processing prior to introduction, perform only two steps of the DNA purification process, and do not perform any analysis of the DNA product of the process.

Similarly, other groups have used rectangular microfluidic plates based on SBS standards for tasks such as the mixing of nanoliter volume reagents, medium exchange during live cell microscopy, and dispensing cells and reagents. Still other workers have adapted rectangular biochips to be used in robotic systems for the high-throughput dispensing of reagents into wells. Another group developed a rectangular biochip for protein detection by biological signal amplification in a well-in-a-well device.

In the progression of biochip development, a number of "integrated fluidic circuit" products based on the use of microfluidic features in an SBS format have been commercialized. For example, a biochip performs single nucleotide polymorphism (SNP) genotyping using an array that can interrogate 48 samples for each of 48 SNPs. The process is conducted by first preparing purified DNA and reaction mixes outside the microfluidic plate, placing the plate on a controller, priming the plate, loading and mixing reagents over 45 minutes on the plate, placing the plate on a thermal cycler for PCR, and transferring the plate to a fluorescence detection instrument. These biochips require sample pre-processing prior to introduction, require several manual steps during on-chip sample processing, do not incorporate reagents, and do not perform any analysis of the DNA product of the process.

A similar commercial approach measures platelet adhesion using a well plate microfluidic technology that integrates micron scale flow cell devices into SBS-standard well plates. The process requires a number of pre-processing steps, including manually introducing a protein of interest to coat the microfluidic channels, perfusing the channels, washing, manually preparing the cell sample of interest, adding the cell sample to the microfluidic channels, and placing the plate onto a workstation for further processing and analysis. A similar approach has been applied to studying wound healing by exposing epithelial cells to a variety of compounds. These biochips require extensive sample pre-processing prior to introduction.

Much of the microfluidic biochip prior art is based on the use of materials such as silicon or glass to fabricate biochips. However, silicon and glass biochips are prohibitively expensive to fabricate for high volume commercial applications (costing up to thousands of dollars for a single biochip) and are therefore impractical to be single-use disposables. Moreover, the need to reuse these biochips leads to problems with run-to-run contamination (an issue for human identity and clinical diagnostics), problems with instrumentation complexity if the biochips are prepared for reuse in the instrument, and problems with logistics if the biochips are prepared for reuse outside the instrument.

In order to realize the unfulfilled potential of microfluidics, microfluidic biochips and systems that are capable of performing a complex series of processing steps for one or more samples in parallel in the setting of a fully-integrated, sample-in to results out system in which there is no requirement for operator manipulation is needed. However, the biochips developed to date perform only a subset of the steps required for analysis, cannot perform complex series of processing steps, and are not capable of producing analytical results on a single device. Furthermore, these biochips and systems use materials and methods ill-suited to mass production.

SUMMARY OF THE TECHNOLOGY

In general, in one aspect, the technology described herein relates to biochips having integration of all steps in a complex process from the insertion of a sample to generation of a result, performed without operator intervention. In an embodiment, a biochip in accordance with the present technology includes microfluidic and macrofluidic features that are acted upon by instrument subsystems in a series of processing steps.

In another aspect, the technology relates to methods for fabrication of complex biochips to include a high feature density. In one embodiment, the method includes injection molding of plastic materials to form the biochip.

In another aspect, the technology relates to a biochip, which upon insertion into an electrophoresis instrument having pneumatic, thermal, high voltage, and optical subsystems, and a process controller, generates a nucleic acid sequencing or sizing profile from at least one sample. The biochip includes: a macrofluidic processing subassembly in connection with a fluidic subassembly and a pneumatic subassembly. The macrofluidic processing subassembly includes at least one chamber adapted to receive a sample. The fluidic subassembly includes a fluidic plate, and at least one fluid transport channel and an amplification chamber adapted to connecting to the thermal subsystem. The pneumatic subassembly is adapted to connecting to the pneumatic subsystem of the instrument, and to the subassemblies of the biochip. The pneumatic subassembly includes a pneumatic plate and one or a plurality of drive lines to pneumatically drive fluids on instructions from said process controller. The biochip also includes a separation and detection subassembly adapted for connecting to the high voltage and optical subsystems and process controller on the instrument. The separation and detection subassembly including a separation channel and a detection region positioned to send signals from each of the channels to the optical subsystem on the instrument. The biochip is plastic, stationary, and unitary and a footprint of the fluidic and/or pneumatic plates is about 86 mm by 128 mm or greater (e.g., is about 100×150 mm or greater, about 115×275 mm or greater, about 115×275 mm or greater, about 140×275 or greater, 165×295 or greater.)

In another aspect, the technology relates to a biochip, which upon insertion into an electrophoresis instrument having pneumatic, thermal, high voltage, and optical subsystems, and a process controller, generates a nucleic acid sequencing or sizing profile from at least one sample. The biochip includes: a macrofluidic processing subassembly in connection with a fluidic subassembly and a pneumatic subassembly. The macrofluidic processing subassembly includes at least one chamber adapted to receive a sample. The fluidic subassembly includes a fluidic plate, and at least one fluid transport channel and an amplification chamber adapted to connecting to the thermal subsystem. The pneumatic subassembly is adapted to connecting to the pneumatic subsystem of the instrument, and to the subassemblies of the biochip. The pneumatic subassembly includes a pneumatic plate and one or a plurality of drive lines to pneumatically drive fluids on instructions from said process controller. The biochip also includes a separation and detection subassembly adapted for connecting to the high voltage and optical subsystems and process controller on the instrument. The separation and detection subassembly including a separation channel and a detection region positioned to send signals from each of the channels to the optical subsystem on the instrument. The biochip is plastic, stationary, and unitary and a footprint of the fluidic and/or pneumatic plates is less than 10,920.0 mm$^2$ and does not conform to SBS standards In another aspect, the technology relates to a biochip, which upon insertion into an electrophoresis instrument having pneumatic, thermal, high voltage, and optical subsystems, and a process controller, generates a nucleic acid sequencing or sizing profile from at least one sample. The biochip includes a macrofluidic processing subassembly in connection with a fluidic subassembly and a pneumatic subassembly. The macrofluidic processing subassembly includes at least one macrofluidic feature located therein or thereon and a chamber capable of receiving a sample. The fluidic subassembly includes a fluidic plate, and at least one feature located therein or thereon. The fluidic subassembly further comprising at least one fluid transport channel and an amplification chamber adapted to connecting to the thermal subsystem. The pneumatic subassembly is adapted to connecting to the pneumatic subsystem of the instrument and to the subassemblies of the biochip. The pneumatic subassembly includes a pneumatic plate and at least one feature located therein or thereon. The pneumatic subassembly further includes one or a plurality of drive lines to pneumatically drive fluids on instructions from said process controller. The biochip also includes a separation and detection subassembly adapted for connecting to the high voltage and optical subsystems and process controller on the instrument. The separation and detection subassembly includes at least one feature located therein or thereon. The separation and detection subassembly further includes a separation channel and a detection region positioned to send signals from each of the channels to the optical subsystem on the instrument. The biochip is plastic, stationary, and unitary, and a physical state of the one or more features of the fluidic, pneumatic, and/or separation and detection subassemblies are adapted to change in scripted processes of 25 or more steps (e.g., 50 or more, 100 or more, 200 or more.) In some embodiments, the scripted process steps result in two or more resultant processing steps to occur within the biochip.

In another aspect, the technology relates to a unitary, stationary biochip, which upon insertion into an electrophoresis instrument having pneumatic, thermal, high voltage and optical subsystems, and a process controller, generates a nucleic acid sequencing or sizing profile from at least one sample. The biochip includes a macrofluidic processing subassembly in connection with a fluidic subassembly and a pneumatic subassembly. The macrofluidic processing subassembly includes at least one chamber adapted to receive a sample. The fluidic subassembly includes a fluidic plate having a top and bottom patterned thermoplastic sheet bonded thereon, to form at least one fluid transport channel on each sides of the plate and an amplification chamber adapted to connecting to the thermal subsystem. The pneumatic subassembly which is adapted to connecting to the pneumatic subsystem of the instrument, and to the subassemblies of said biochip. The pneumatic subassembly includes a pneumatic plate having a top patterned thermoplastic sheet bonded thereon, and one or a plurality of drive lines to pneumatically drive fluids on instructions from the process controller. The biochip also includes a valve subassembly, positioned between and connected to the fluidic and pneumatic subassemblies and a separation and detection subassembly adapted for connecting to the high voltage and optical subsystems and process controller on the instrument. The separation and detection subassembly including at least one separation channel, and further comprising a detection region positioned to send signals from each of the at least one separation channels to the optical subsystem on said instrument.

Some of the embodiments of this aspect of the technology include one or more of the following features. One or more of the macrofluidic, pneumatic, fluidic, and separation and detection subsystems is formed from plastic. In some embodiments, the valve subassembly includes at least one elastomeric valve. In some embodiments, the valve subassembly includes at least one non-elastomeric valve. In embodiments, the separation and detection subassembly is oriented such that electrophoresis of the sample within the separation and detection subassembly is conducted in the opposite direction from a general flow of sample through the fluidic plate. In embodiments, the biochip includes all reagents needed to process the at least one sample within the biochip.

In another aspect, the technology relates to a system for processing a biological sample. The system includes a biochip and a process controller. The biochip upon insertion into an electrophoresis instrument having pneumatic, thermal, high voltage and optical subsystems, and the process controller, generates a nucleic acid sequencing or sizing profile from at least one sample. The biochip includes a macrofluidic processing subassembly in connection with a fluidic subassembly and a pneumatic subassembly. The macrofluidic processing subassembly includes at least one chamber adapted to receive a sample. The fluidic subassembly includes a fluidic plate having a top and bottom patterned thermoplastic sheet bonded thereon, to form at least one fluid transport channel on each sides of the plate and an amplification chamber adapted to connecting to the thermal subsystem. The pneumatic subassembly which is adapted to connecting to the pneumatic subsystem of said instrument, and to the subassemblies of said biochip, includes a pneumatic plate having a top patterned thermoplastic sheet bonded thereon, and one or a plurality of drive lines to pneumatically drive fluids on instructions from the process controller. The biochip also includes a valve subassembly positioned between and connected to said fluidic and pneumatic subassemblies and a separation and detection subassembly adapted for connecting to the high voltage and optical subsystems and process controller on the instrument. The separation and detection subassembly includes at least one separation channel, and a detection region positioned to send signals from each of the at least one separation channels to the optical subsystem on the instrument. The process controller of the instrument includes instructions to perform 25 or more automated scripted process steps.

In another aspect, the technology features a method of manufacturing a biochip. The method includes injection molding a fluidic plate to include a fluidic top surface, a fluidic bottom surface and at least one through hole extending from the fluidic top surface to the fluidic bottom surface to connect the fluidic top surface to the bottom surface. Each of the fluidic top and bottom surfaces include a plurality of microfluidic features. The method further includes injection molding a pneumatic plate to include a pneumatic top surface, a pneumatic bottom surface and at least one through hole extending from the pneumatic top surface to the pneumatic bottom surface to connect the pneumatic top surface to the bottom surface. Each of the pneumatic top and bottom surfaces comprise a plurality of microfluidic features. The method also includes aligning the pneumatic and fluidic plates to form the biochip, wherein a footprint of the fluidic and/or pneumatic plates is 86 mm by 128 mm or greater, and at least one of the plurality of microfluidic features of the fluidic plate and/or the pneumatic plate includes a draft angle of less than 2 degrees.

In another aspect, the technology features a method of performing sample-in to results out automated electrophoresis on at least one unprocessed sample in a unitary biochip having a macrofluidic processing subassembly in fluid communication with a fluidic subassembly and a pneumatic subassembly. The method includes: (a) inserting the at least one unprocessed sample into a chamber in the macrofluidic processing subassembly; (b) inserting the biochip into an instrument having a pneumatic subsystem, a thermal subsystem, a high voltage subsystem, an optical system, and a process controller that can accept a predefined process script and implement the process script automatically by reading the process script and controlling the pneumatic subsystem, a thermal subsystem, a high voltage subsystem, and optical system; (c) activating the process controller to carry out the process script, the process script including instructions to: (i) initialize the biochip by applying pressure from the pneumatic subsystem to valve lines of the pneumatic subsystem or in fluid communication with the pneumatic subassembly; (ii) purify DNA from the unprocessed sample by applying pressure from the pneumatic subsystem to the macrofluidic processing subassembly to release reagents stored therein, applying a pressure from the pneumatic subsystem to the released reagents to form a cell lysate from the unprocessed sample, applying a pressure from the pneumatic subsystem to pull the lysate through a purification filter in the fluidics subassembly into a holding chamber to bind DNA in the lysate to the filter, applying a pressure from the pneumatic subsystem to release a wash solution stored in the macrofluidic processing subassembly to flow through the purification filter to remove contaminants from the bound DNA; applying a pressure to flow air through the purification filter to dry the bound DNA, applying a pressure from the pneumatic subsystem to release an elution solution stored in the macrofluidics processing subassembly to release the bound DNA from the purification filter, generating an eluate containing purified DNA; (iii) transport the eluate to a reconstitution chamber containing a lyophilized PCR reaction mix by applying pressure from the pneumatic subsystem to the pneumatic subassembly; (iv) transport the reconstituted PCR reaction mix to a thermal cycling chamber in the fluidics subassembly; (v) apply heat to the thermal cycling chamber by initiating a thermal cycle protocol to generate labeled amplicons from the PCR mixture; (vi) transport the labeled amplicons and a formamide reagent stored in the macrofluidic processing subassembly to a joining chamber in the fluidics subassembly by applying pressure from the pneumatics subsystem to the pneumatic subassembly; the labeled amplicons and formamide reagent forming a formamide-PCR product mixture; (vii) transport the formamide-PCR product mixture by applying a pressure from the pneumatic system to the pneumatic subassembly to flow the mixture to an ILS cake chamber for mixing with an ILS cake to generate a separation and detection sample; (viii) transport the separation and detection sample into a cathode chamber within the fluidics subassembly by applying a pressure from the pneumatic subsystem to the pneumatic subassembly; (ix) prepare cathode and anode of the fluidics subassembly for separation of the separation and detection by applying a voltage from the high voltage subsystem to bias the cathode and anode; (x) transport gel from a gel reagent reservoir in the fluidics subassembly to a cathode chamber and waste chamber of the fluidics subassembly by application of pressure from the pneumatics subsystem to the pneumatic subassembly; (xi) inject and separate the separation and detection sample in the separation channel by applying a voltage through the high voltage subsystem to a cathode and anode; and (xii) effect fluorescence of separated components of the separation and detection sample by activating a laser in the optical subsystem. The method also includes automatically detecting a fluorescent signal of the separated components to provide separation and detection sample results from at least one unprocessed samples.

In another aspect, the technology relates to a system for providing at least two types of sample-in to results-out processing for at least one biological sample. The system includes a stationary biochip and an instrument including pneumatic, thermal, high voltage and optical subsystems for interfacing with the biochip, and a process controller. The stationary biochip includes a macrofluidic processing subassembly in connection with a fluidic subassembly and a pneumatic subassembly. The macrofluidic processing subassembly including at least one chamber adapted to receive a sample. The fluidic subassembly includes a fluidic plate, and at least one fluid transport channel and an amplification chamber adapted to connecting to the thermal subsystem. The pneumatic subassembly which is adapted to connecting to the pneumatic subsystem of said instrument, and to the subassemblies of said biochip, includes a pneumatic plate and one or a plurality of drive lines to pneumatically drive fluids on instructions from the process controller. The biochip also includes a separation and detection subassembly adapted for connecting to the high voltage and optical subsystems and process controller on the instrument. The separation and detection subassembly including a separation channel, and a detection region positioned to send signals from each of the channels to the optical subsystem on the instrument. The biochip further includes at least two distinct pathways for sample processing. Each of the at least two distinct pathways is dedicated to different analytical processes. The process controller of the instrument includes a set of instructions to process the at least one biological sample in the different analytical processes. In some embodiments, the different analytical processes are STR analysis and single nucleotide polymorphism analysis. In some embodiments, the different analytical processes are multiplexed amplification and DNA sequencing. In some embodiments, the different analytical processes are STR analysis and mitochondrial DNA sequencing. In some embodiments, the different analytical processes are reverse transcription PCR and conventional PCR. In some embodiments, the different analytical processes are DNA sequencing and single nucleotide polymorphism analysis.

In another aspect, the technology relates to a reagent storage container for a biochip including a macrofluidic block and cover. The macrofluidic block includes a reagent storage chamber having a top end and a bottom end; a first foil seal bonded to the bottom end; and a second foil seal bonded to the top end. A reagent is stored in the foil-sealed chamber and is released by the application of pneumatic pressure through the cover such that the top and bottom foils burst, releasing the contents of the reagent storage chamber.

Embodiments of the above aspect can include one or more of the following features. In some embodiments, the reagent storage container is connected to a fluidic subassembly. In some embodiments, the reagent storage container further includes a spacer plate placed between the container and the fluidic subassembly such that the spacer plate is sized to accommodate expansion of the first foil prior to bursting.

There are numerous advantages of the present technology including, but not limited to, minimal to no operator intervention and reduced fabrication costs.

DESCRIPTION OF THE DRAWINGS

The advantages of the technology described above, together with further advantages, may be better understood by referring to the following description taken in conjunction with the accompanying drawings. The drawings are not necessarily to scale, emphasis instead generally being placed upon illustrating the principles of the technology.

FIG. 77 is a table representing a relationship of scripted processing steps and resulting processing steps for a portion of an automated process for use on a biochip.

FIG. 80 is a table summarizing results of fluorescence data collected with and without a notch filter.

DETAILED DESCRIPTION OF THE INVENTION

Figure 1:
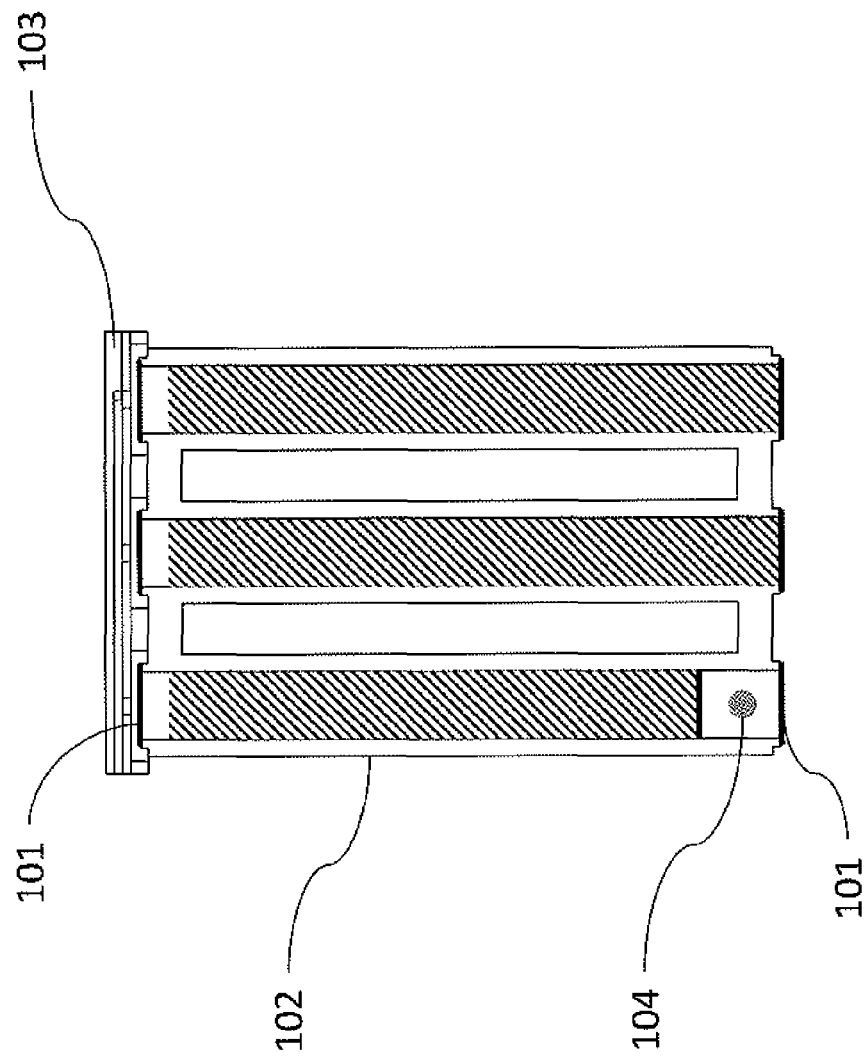
FIG. 1 is a side view schematic of an embodiment of a single tube reagent storage and release device.

The biochips described herein achieve the fundamental goal of the field of microfluidics: the integration of all steps in a complex process, from the insertion of a sample to the generation of a result, performed in a single instrument without operator intervention. In one aspect, we present herein novel biochips that are fully integrated and capable of performing complex sample in to results out analyses including cell lysis, DNA purification, multiplexed amplification, and electrophoretic separation and detection to generate short tandem repeat (STR) profiles from forensic samples; cell lysis, DNA purification, multiplexed amplification, Sanger sequencing, ultrafiltration, and electrophoretic separation and detection to generate DNA sequence from clinical samples; nucleic acid purification, reverse transcription, multiplexed amplification, Sanger sequencing, ultrafiltration, and electrophoretic separation and detection to generate DNA sequence from biothreat samples, and nucleic acid purification, library construction, and single molecule sequencing to generate genomic DNA sequences from human, bacterial, and viral clinical and research samples.

Sample manipulations that can be performed in the biochips of the invention include combinations of nucleic acid extraction; cell lysis; cell separation; differential cell lysis; differential filtration; total nucleic acid purification; DNA purification; RNA purification; mRNA purification; protein purification; pre-nucleic acid amplification cleanup; nucleic acid amplification (e.g. both singleplex and multiplex end-point PCR, Real-time PCR, reverse transcription PCR, asymmetric PCR, nested PCR, LATE PCR, touchdown PCR, digital PCR, rolling circle amplification, strand displacement amplification, and multiple displacement amplification); Y-STR amplification; mini-STR amplification; single nucleotide polymorphism analysis; VNTR analysis; RFLP analysis; post-nucleic acid amplification cleanup; pre-nucleic acid sequencing cleanup; nucleic acid sequencing (e.g. Sanger sequencing, pyrosequencing, and single molecule sequencing); post-nucleic acid sequencing cleanup; reverse transcription; pre-reverse transcription cleanup; post-reverse transcription cleanup; nucleic acid ligation; SNP analysis; nucleic acid hybridization; electrophoretic separation and detection; immunoassays; binding assays; protein assays; enzymatic assays; mass spectroscopy; and nucleic acid and protein quantification.

When characterizing the structure and functions of a biochip, at least two classes of complexity can be considered. Sample number complexity refers to the number of independent samples that are processed on the biochip. Process complexity refers to the number of sequential manipulations to which each sample (and sample byproducts) is subjected on the biochip. The biochips of the invention have high levels of both sample number and process complexities.

In another aspect, the novel biochips of the invention integrate a large number of processing steps in order to achieve a fully integrated, sample-in to results-out system. We define two categories of biochip processing steps to express the complexity of these biochips. Scripted processing steps are the actions performed as a result of automated, computer-controlled scripts that cause a direct action on a feature within or on the biochip and involve various subsystems of the instrument that interface with the biochip. The actions cause a change to the physical state of a feature in the biochip (e.g. a valve membrane is moved to close a valve) or to a sample or air within the biochip (e.g. a fluorescent dye in a sample is excited, air is passed through a pneumatic drive). In addition, the action can cause a change to the physical state of a feature in the biochip and a sample within the biochip simultaneously (e.g. when the thermal chambers are heated, the sample within them are also heated).

The instrument subsystems perform the scripted actions and include the pneumatic subsystem, which applies pressure to burst foils, increase and reduce pressure on valves, and push liquids, gasses, and solids; the high voltage subsystem, which applies an electrical current to electrophorese macromolecules; the optical subsystem, which applies light to excite and detect a sample in electrophoresis, quantitation, amplification, immunoassays, and chemical assays; and the thermal subsystem, which applies heat for cell lysis, nucleic acid denaturation, electrophoretic uniformity, thermal cycling, and cycle sequencing. That is, every scripted processing step is a specific instruction of an automated script.

The scripted process steps define direct actions that take place on features within or on the biochip via an interface with a subsystem of the instrument. The biochip features can be microfluidic, macrofluidic, or a combination of both, and the script acts upon these features at defined locations in a defined sequence. For example, the actuation of a given valve on the biochip is considered a single scripted process step, even if several changes to the instrument are required as prerequisites to effect that single step (e.g. activating a pump and drive line to allow the valve to be closed).

In quantifying the number of scripted process steps, directly repetitive steps such as those in PCR amplification (e.g. many directly repeating cycles of denaturation, annealing, and extension, each characterized by a change in temperature) are considered as the number of steps in a single cycle. That is to say, a PCR amplification reaction that consists of Hotstart 93° C. for 20 seconds (1 step) followed by 31 cycles of [93° C. for 4 seconds, 56° C. for 15 seconds, and 70° C. for 7 seconds] (3 steps) followed by a final extension of 70° C. for 90 seconds (1 step) represents a total of 5 scripted processing steps. One feature can be acted upon during one or more scripted process steps. In this case, each independent act counts as one step; for example, if a given valve is actuated seven times during a process, this would count as 7 steps. Several features can be acted upon in parallel during the process of an individual sample. For example, if three valves are actuated while a chamber of the biochip is heated, this would count as four scripted processing steps (in other words, four new actions performed on features on or within the biochip). Finally, once raw data is generated from the process, any data processing (e.g. color correction) or data analysis (e.g. allele or base calling) are not scripted processing steps. The biochips of the current invention perform 25, 50, 75, 100, 125, 150, 175, 200, 250, 300, 400, 500, 750, 1000, and greater than 1000 scripted processing steps.

Resultant processing steps are the effects of scripted processing steps and include the movement of the liquid sample throughout the biochip through channels, chambers, and filter and membrane features; the drying of filters and membranes, the thermal cycling of reaction mixes; the resuspension of lyophilized reagents, the joining of various liquids, the mixing of liquids, the homogenization of liquids, the electrophoretic transport of sample macromolecules through various matrices, and the excitation of those macromolecules. It follows that the number of scripted processing steps will generally be greater than (and never be less than) the resultant processing steps. For example, it may be necessary to close several valves and change several driveline pneumatic pressures (multiple scripted processing steps) to cause the movement of a fluid plug from a given channel to an adjacent chamber (a single resultant processing step). Example 6 and FIG. 77 describe the relationship between scripted and resultant processing steps for a portion of an automated scripted. The biochips of the current invention perform 2, 5, 10, 15, 20, 25, 30, 35, 40, 45, 50, 60, 70, 80, 90, 100, 125, 150, 175, 200, 250, and greater than 250 resultant process steps.

Total processing steps is the sum of the scripted and resultant processing steps. The greater the number of total processing steps, the greater the process complexity. The biochips of the current invention perform 25, 50, 75, 100, 125, 150, 175, 200, 250, 300, 400, 500, 750, 1000, 1500, 2000, and greater than 2000 total processing steps. Scripted, resultant, and total processing steps refer to the processing of a single sample. If multiple samples are processed in parallel on a given biochip, the total number of processing steps is, by convention, the same as if only one sample is processed. Similarly, if multiple samples are processed identically in series (e.g. if a first sample passes through the biochip and then a second sample follows behind it, undergoing the same process), the total number of processing steps is the same as if only single sample is processed. The importance of these distinctions is that the complexity biochips of the invention is based on the intricate series of manipulations of a single sample as opposed to biochips that perform relatively small numbers of process steps but repeat them on small or large numbers of samples.

The biochips of the invention allow integration of two or more of the functions noted above. Accordingly, a limitless number of combinations can be designed into the biochip, allowing a complex set of manipulations to be completed on the biochip. Process complexity will involve a number of manipulations based on the microfluidic elements noted above. For example, the biochips of the invention accepting a sample, potentiate mixing of lysis reagents, lyse the sample by chaotic bubbling, filter the lysate, meter the lysate, bind the lysate to a silica membrane, washing the membrane, elute nucleic acids from the membrane, homogenize the eluate to yield a purified DNA solution, meter the DNA solution, reconstitute a lyophilized PCR reaction mix to yield a PCR reaction, mix and homogenize the reaction mix, meter the reaction mix, conduct rapid multiplexed amplification, meter a portion of the completed PCR reaction, reconstitute a sizing standard with the metered PCR reaction to yield a solution for electrophoresis, mix and homogenize the solution, combine the solution with reagents for electrophoresis, inject the material into an electrophoretic channel, conduct electrophoretic separation, detect the separated DNA fragments based on fluorescence, generate an electropherogram based on the raw fluorescence data, color correct the raw data, identify the PCR peaks in the processed data, and analyze the called peaks (e.g. to generate an STR profile for human forensic identification, to generate a multiplexed profile for diagnosing an infectious disease, or to generate a multiplexed profile to identify a biothreat agent). One skilled in the art will appreciate that the biochips of the invention can be designed to perform a multitude of different types of analysis with essentially limitless process complexity.

Overview of Biochip Design

The biochips of the invention are unitary and represent a single, solitary structure. These unitary biochips are comprised of many component parts, but all the parts, whether microfluidic or macrofluidic, are directly and permanently attached, without the use of tubing to carry liquid, solids, or gasses from one portion of the biochip to another. An advantage of unitary biochips is that it can be placed into the corresponding instrument as a unit, requiring no technical skill on the part of the operator. Furthermore, the absence of connecting tubes enhances robustness by minimizing leakage.

Preferably, the major components of the unitary biochips of the invention are plastics. Glass, quartz, and silicon wafers are absent or minimized in the inventive biochips as they are quite costly to fabricate. It is preferable that all components (with the exception of inserted elements such as reagents, filters, membranes, metal foils, electrode pins, and electrode strips and assembly materials such as gaskets, pressure sensitive adhesives (PSA) and tapes) are made of plastic. It is also preferred that each sample pathway in the biochip is single use; this prevents run-to-run contamination, simplifies design, and enhances ease of use. Accordingly, in one aspect, this invention provides single use, disposable plastic biochips.

We define two broad classes of microfluidic biochips based on the drive mechanisms used to transfer solutions within them. Centrifugal microfluidic biochips have circular footprints and rotate to provide centrifugal force to drive fluids from location to location within the biochip. Stationary (or non-centrifugal) microfluidic biochips have a wide range of footprints (including rectangular or substantially-rectangular footprints) and are characterized by drives that are not provided by rotation of the biochip.

Biochips of this invention are stationary, meaning that they do not require rotation to generate centrifugal force to drive fluids throughout the biochip (although the biochips can be subjected to movement in general and translational movement in particular). Instead, the biochips of the inventions have drive mechanisms that include pneumatic, mechanical, magnetic, and fluidic. A variety of methods can be used for liquid transport and controlled liquid flow. One method is positive-displacement pumping, in that a plunger in contact with either the liquid or an interposing gas drives the liquid a precise distance based on the volume displaced by the plunger during the motion. An example of such a method is a syringe pump. Another method is the use of integrated elastomeric membranes that are pneumatically, magnetically, or otherwise actuated. A preferred method for driving fluids and controlling flow rates is to use a pneumatic drive to apply vacuum or pressure directly on the liquids themselves, by altering the pressure at the leading, trailing, or both menisci of the liquids. Appropriate pressures (typically in the range of 0.05-300 psig and usually in the range of 0.5-30 psig) are applied to achieve desired flow characteristics. Flow can also be controlled by selecting appropriate sizing of the fluidic channels, as the flow rate is proportional to the pressure differential across the fluid and the hydraulic diameter to the fourth power and inversely proportional to the length of the channel or the liquid plug and the viscosity. Furthermore, flow can be controlled and parallel samples aligned by incorporating vent membranes along the flow channel.

The biochips of the invention function with a single instrument to carry out a complex chemical analysis. The inventive biochips described herein improve processing efficiency and data quality by eliminating sample transfer from instrument to instrument, improving ease of use by minimizing or eliminating operator requirements (a single machine may, using an appropriate script and user interface), eliminate any need for operator actions, improving the ability to ruggedize the system (all ruggedization subsystems can be incorporating into a single instrument), and reducing the cost of the instrumentation required as well as the laboratory infrastructure required to process samples. In fact, in one embodiment, having the biochip function in a single instrument can obviate the need for a laboratory environment.

The instrument provides all the subsystems required for the completion of sample processing. These subsystems include high and low voltage power subsystems, thermal cycling subsystems, pneumatic subsystems, magnetic subsystems, mechanical subsystems, ultrasonic subsystems, optical subsystems, ruggedization subsystems, process control subsystems, and computer subsystems. The instrument to biochip interface may involve one or more of these subsystems, depending on the microfluidic drive and the series of processes to be performed within the biochip. In the case of the examples herein, the interface of the biochips and the instrument are pneumatic, electrical, optical, and mechanical. The size of the instrument is determined by subsystem dimensions, biochip dimensions, and throughput. The instruments may weigh approximately 10 pounds, 25 pounds, 50 pounds, 100 pounds, 150 pounds, 200 pounds, or greater than 200 pounds. Similarly, the volume of the instrument may be 0.5 cubic feet, or 1, 2, 4, 6, 10, 15, 20 or greater than 20 cubic feet.

Furthermore, the biochip and instrumentation of the invention are designed to be operable outside of conventional laboratory environments. Depending upon the application, they can be ruggedized to withstand transport and extremes of temperature, humidity, and airborne particulates. Use of the invention by non-technical operators in offices, out of doors, in the battlefield, in airports, at borders and ports, and at the point-of-care will allow much broader application of genetic technology in society. The use of unprocessed samples further supports the broad application of the teachings of the invention.

The inventive microfluidic systems, instruments and biochips set forth herein can be single- or multi-use. The advantages of single-use disposable biochips include:

Minimization of cross contamination. In a multi-use device, the sample or a component of the sample may be present in the device following washing; the remnant may contaminate a subsequent analysis. Single-use disposable devices are inherently free of remnant sample. This is achieved, in part, by the novel sample processing channels and methods of manufacturing them, in which there is no sample-to-sample channel communication.

Minimization of technical requirements. A multi-use device requires equipment to clean a spent device and prepare it for subsequent reuse. The single-use disposables of this invention are not burdened by these requirements.

Minimization of operator requirements. In addition to the skill required to carefully clean and prepare a spent device for subsequent use, reagents must be reloaded into a multiuse device either by insertion into the device or the instrument. By incorporating all reagents into a single-use disposable microfluidic device, the operator need not manipulate or be exposed to reagents at all. The operator need only insert the sample into the device and press a start button. It follows that the inventive biochips described herein can be operated by unskilled or minimally trained operators and may be performed outside the typical laboratory environment. Analysis of samples at the point-of-care, the battlefield, military checkpoints, embassies, sites critical to national security, and developing regions of the world is possible with these inventive biochips. Autonomous collection and analysis of samples as applied to applications including biothreat detection also benefit from a minimization of operator requirements. Work describing an approach that essentially eliminates sample handling requirements, further simplifying and broadening the possibilities for analytic methodologies is described in U.S. patent application Ser. No. 12/699,564, filed Feb. 3, 2010, entitled "Nucleic Acid Purification," which is hereby incorporated by reference in its entirety.

Increase in System Throughput. The minimization of technical and operator requirements allows an increase of the number of samples analyzed per unit time. The dense packing of features allows for processing multiple samples in parallel, and the use of large biochips allows further increase in throughput. Furthermore, the reversal of the direction of process flow (e.g. electrophoresis vis a vis purification and amplification) allows for a smaller, more compact biochip and instrument.

Minimization of Cost. Minimization of labor requirements and elimination of overhead reduce costs.

The inventive biochips described herein may have dimensions greater than that of the SBS standard microtiter plate. The dimensions of the biochip footprint are 86 by 128 or greater, 100×150 mm or greater, 115×275, mm or greater, 140×275 or greater, and 165×295 or greater. Also the inventive biochips encompass footprints of less than 10,920.0 mm$^2$ that do not conform to SBS standards. The teachings of the invention allow the design and fabrication of biochips with an unprecedented degree of sample number complexity and process complexity. There is no limit to the possible dimensions of the biochip footprint. The footprint can be made in accordance to the needs of a particular user and requirements of a given application.

As the sample number and process complexities of the biochips of the invention increase, the feature density of the biochips increases. In this context, microfluidic features are defined as any area of the layer in question that is either cut into by CNC-machining or molded around by injection molding. Feature density is the ratio of the number of microfluidic features to the surface area of the layer in question. For example, the biochips of Example 5 and 6 have the following densities: the top and bottom of the fluidics layer have approximately 20.2% and 6.6% respectively of their surface areas occupied by microfluidic features. The top and bottom of the pneumatics layer have 7.5% and 8.8% of their surface areas occupied by microfluidic features. The 16-sample version of the same biochip occupies essentially the same footprint yet has even higher densities: 19% and 13.7% for fluidics and 18.3% and 25% for pneumatics. Local densities on the layers can be 60% or higher (certain regions of the biochips of Examples 4, 5, and 6 have local densities of over 64% in regions of approximately 3 cm$^2$. The pneumatics and fluidic biochips of the invention have 5, 10, 15, 20, 25, 30, 40, 50, 60, 70, 80, and greater than 80% of their surface areas occupied by microfluidic features. Macrofluidic features also contribute to density.

Features of the Biochips of the Invention

The biochips of the invention comprise thermoplastic layers that contain microfluidic features such as one or more fluid transport channels (which may be independent, connected, or networked), through holes, alignment features, liquid and lyophilized reagent storage chambers, reagent release chambers, pumps, metering chambers, lyophilized cake reconstitution chambers, ultrasonic chambers, joining and mixing chambers, mixing elements, membrane regions, filtration regions, venting elements, heating elements, magnetic elements, reaction chambers, waste chambers, membrane regions, thermal transfer regions, anodes, cathodes, and detection regions, drives, valve lines, valve structures, assembly features, instrument interface regions, optical windows, thermal windows, and detection regions. The biochips may also contain macrofluidic features, that is, features that are larger versions of the same types as the microfluidic features listed above. For example, the biochip may contain a microfluidic reagent storage chamber that fold 30 microliters of liquid and a macrofluidic reagent storage chamber that holds five milliliters of liquid. The incorporation of both microfluidic and macrofluidic features on the biochips of the invention allow a given biochip to meet both macrofluidic and microfluidic processing requirements. This is an advantage when samples requiring relatively large volumes (such as a forensic swab or a clinical blood sample) are to be processed at a microfluidic scale.

The biochips may also incorporate thin films including patterned thin films, spacer layers, adhesive layers, elastic and non-elastic layers, and detection regions. The biochips may also incorporate layers with features based on particular drive mechanisms (e.g. actuation lines for pneumatic, mechanical, magnetic, and fluidic drives). Note that the microfluidic biochips may also contain macrofluidic regions, particularly for processing forensic, clinical diagnostic, and biothreat samples.

The biochips of the invention allow nucleic acids and other biological components from unprocessed biological samples to be purified, manipulated, and analyzed. Unprocessed biological samples are those that are collected by an individual and then inserted into the sample receiving chamber of the biochip with no intermediate processing steps (although the sample collection device may be labeled and/or stored prior to processing). The operator need only collect or otherwise obtain the sample, insert the sample into the apparatus, insert the apparatus into the instrument (not necessary if the apparatus was previously placed in the instrument), and press a start button. No processing, manipulation, or modification of the sample is required prior to insertion in the apparatus—the operator does not have to cut a swab, open a blood tube, collect a tissues or biologic fluid, transfer a sample to another holder, or expose the sample to a reagent or a condition (e.g. heat, cold, vibration). Accordingly, the operator need not have extensive training in the biological sciences or laboratory techniques. Optionally, the biochips of the invention can accept processed biological samples (e.g. a cell lysate for subsequent purification), but such applications may require an operator with technical training.

In practice, biological samples are collected using a myriad of collection devices, all of which can be used with the biochips of the invention. The collection devices will generally be commercially available but can also be specifically designed and manufactured for a given application. For clinical samples, a variety of commercial swab types are available including nasal, nasopharyngeal, buccal, oral fluid, stool, tonsil, vaginal, cervical, and wound swabs. The dimensions and materials of the sample collection devices vary, and the devices may contain specialized handles, caps, scores to facilitate and direct breakage, and collection matrices. Blood samples are collected in a wide variety of commercially available tubes of varying volumes, some of which contain additives (including anticoagulants such as heparin, citrate, and EDTA), a vacuum to facilitate sample entry, a stopper to facilitate needle insertion, and coverings to protect the operator from exposure to the sample. Tissue and bodily fluids (e.g. sputum, purulent material, aspirates) are also collected in tubes, generally distinct from blood tubes. These clinical sample collection devices are generally sent to sophisticated hospital or commercial clinical laboratories for testing (although certain testing such as the evaluation of throat/tonsillar swabs for rapid streptococcal tests can be performed at the point of care). Environmental samples may be present as filters or filter cartridges (e.g. from air breathers, aerosols or water filtration devices), swabs, powders, or fluids.

A common collection technique for forensic evidence is performed using a swab. Swabs are commercially available from Bode (Lorton, Va.), Puritan (Guilford, Me.), Fitzco (Spring Park, Minn.), Boca (Coral Springs, Fla.), Copan (Murrieta, Calif.) and Starplex (Etobicoke, ON, Canada). Swabbing can also be performed using gauze-like materials, disposable brushes, or commercially available biological sampling kits. Forensic samples may contain blood, semen, epithelial cells, urine, saliva, stool, various tissues, and bone. Biological evidence from an individual that is present in person is often collected using buccal swabs. A widely used commercial buccal swab is the SecurSwab (The Bode Technology Group, Lorton, Va.). Buccal samples are collected by instructing the subject or operator to place the swab into the mouth on the inner cheek surface and to move the swab up and down one or more times.

Another major advantage of the biochips of the invention is the ability to perform complex processes on multiple samples in parallel. It is important to note that the biochip's flexibility allows multiple samples to be processed using the identical set of manipulations or each sample (or subset of samples) to be processed using a tailored set of manipulations. In addition, several independent analyses can be performed on a given sample. For example, a forensic sample could be analyzed by isolating DNA and then performing STR analysis, SNP analysis, and mitochondrial sequencing on the purified material. Similarly, a clinical sample could be analyzed by purifying nucleic acids and proteins and performing PCR, reverse-transcription PCR, DNA sequencing, and immunoassays, allowing (for example) a given sample to be interrogated for a large number of pathogens and cellular processes simultaneously on a single biochip. We describe herein numerous solutions to different desired functionalities as well as solutions to different integration issues. These are provided for illustration and not by way of limitation, as one skilled in the art will be able to adapt these components and integration techniques to a variety of biochips and instruments for a variety of uses.

A series of software and firmware is required for biochip operation and data analysis. The instrument hardware is controlled by software and firmware that dictate component function and perform instrument self-testing. An automated script controls all interactions of the instrument with the biochip, including the application of all scripted process steps. Analytical software performs both the processing of raw data (e.g. color correction of an electropherogram) and analysis if the results of the assay (e.g. fragment sizing, STR allele calling, DNA sequence analysis). The instrument may contain a graphical user interface that allows the user to initiate the process and inform the user of process status. Finally, the system may store relevant analytical comparators (e.g. STR profiles from individuals of interest or DNA sequence of pathogens), or the system may port out results for external database matching and further analyses.

Biochip Fabrication

The invention provides methods for fabricating biochips that are fully integrated, require no pre-process sample preparation, are not limited by the SBS size range and can be significantly larger, are not limited to microtiter formats, incorporate sample number complexity and process complexity.

The biochips can be fabricated from thermoplastic polymers including polyethylene, polypropylene, polycarbonate, polystyrene, polymethyl methacrylate (PMMA), polyethylene terephthalate (PET), cyclic olefin polymer (COP), and cyclic olefin copolymer (COC), and other polymers which are suitable to mass-production in accordance with the novel methods claimed herein. The biochips can be fabricated by CNC-machining of large plates (including those larger than SBS standard plates), and the blank plates for CNC-machining may be injected molded themselves. The biochips can also be made by injection molding of large plates (including those larger than SBS standard plates). Optionally, the biochips can be coated (either prior to, at an intermediate step during, or following assembly) to enhance performance. A wide range of coatings and treatments can be applied. For example, exposing channels with 0.5% bovine serum albumin reduces binding of proteins present in the sample to channel walls. Hydrophobic products such as PFC 502A (Cytonix, Beltsville, Md.) can be applied to channels, chambers, and valves to minimize bubble formation. Similarly, the elastomeric or non-elastomeric membranes of pneumatic and mechanical valve structures can be coated or otherwise treated to provide optimal sealing properties.

Yet another aspect of this invention is biochips and methods for making them that solve the problems of fabricating large biochips to perform intricate series of processing steps in parallel to allow multiple samples to be processed on the same biochip. Whether the biochip is fabricated by CNC-machining or injection molding, this complexity is achieved by packing the fine features densely together, in certain regions of the biochip, leaving space between them to allow bonding while maximizing aspect ratios. The injection molded biochips are designed and fabricated such that they are flat, suffer minimal warpage, have defined shrinkage characteristics during fabrication and bonding, and have appropriate alignment tolerances to support the features that allow process step complexity.

The biochips of the invention include several subassemblies including fluidic subassemblies, pneumatic subassemblies, valve subassemblies, macrofluidic processing subassemblies, and separation and detection subassemblies. Not all subassemblies are required for a given biochip. For example, if macrofluidic sample volumes and on-chip reagents are not required, the macrofluidic subassembly is not necessary. Nevertheless, the biochips of the invention will generally have at least one CNC-machined, embossed, extruded, or injection-molded layer. A single layer would contain both fluidic features and the control features required to transfer fluids from one region of the biochip to another. In many cases, a separate fluidic layer and control layer are preferred, allowing for increased process complexity. The layer or layers may have features on either one or both sides; the advantages of dual-sided features is increased process complexity, feature density, and sample number, decreased fabrication cost, and ease of assembly. When multiple layers are utilized, they may be bonded together using a number of techniques known in the art such as thermal bonding, solvent bonding, adhesive bonding, and ultrasonic welding (reviewed in Tsao. C.-W. (2009). Bonding of thermoplastic polymer microfluidics. Microfluidics and Nanofluidics 6: 1-16). In considering the number of layers in a microfluidic biochip, it is advisable to utilize the fewest number of layers that allows both the desired complexity to be achieved. Minimizing layer number reduces the complexity of fabrication and assembly and ultimately, the cost of manufacturing the biochip.

Another aspect of the fabrication of the biochips of the invention concerns the layers located on the top and bottom of the various subassemblies. The purpose of these intermediate layers, termed "thin films", includes bonding the CNC-machined or injection molded layers to each other, externally sealing the CNC-machined or injection molded layers, providing thermal coupling between the instrument and chambers within the layers, providing appropriate optical characteristics to allow efficient excitation and detection by components within the instrument, providing conduits between layers, supporting membranes, filters, and other elements, and providing material for valving in tandem with the injection molded layers. Non-elastomeric thin film materials include polyethylene, polypropylene, polycarbonate, polystyrene, cyclic olefin polymer, cyclic olefin copolymer, acrylic, polyethylene terephthalate, aluminum, and cellulose triacetate. Elastomeric thin film materials include a wide range of rubbers (including silicone) and thermoplastic elastomers as described in Plastics: Materials and Processing Third Edition (ibid). These films can range in thickness from 1 micron to 500 microns.

As the CNC-machined or injection molded layers and thin films are bound together to form the biochip, fluid communication between and across layers is provided by through-holes. Through-holes are features that pass from top to bottom of a given layer to allow a liquid to move from one layer to another. Through-holes can take essentially any shape and are frequently cylindrical. The biochips of the invention provide large numbers of through holes to enable sample number complexity and process complexity. For example, the injection molded 6-sample biochips of Example 6 and their 16-sample counterparts contain the following through-holes:

|  | 6-Sample | 16-Sample |
| --- | --- | --- |
| Top Pneumatic Film | 117 | 346 |
| Pneumatic Plate | 334 | 848 |
| Rigid Patterned Film | 131 | 346 |
| Fluidics Plate | 299 | 1019 |
| Bottom Fluidic Film | 14 | 94 |
| Embossed S&D Film | 34 | 94 |
| S&D Cover Film | 0 | 0 |

Note that "S&D" refers to "separation and injection." Taken together, these parts of the 6-sample biochip (exclusive of the macrofluidic processing subassembly) contain 929 through-holes and the 16-sample assembly contains 2747 though-holes. The biochips of the invention contain 50, 100, 200, 300, 400, 500, 600, 700, 800, 900, 1000, 1500, 2000, 2500, or more than 2000 through-holes. When total microfluidic features (including through-holes) are considered, the biochips of the invention have 1000, 2000, 3000, 4000, 5000, 7500, 10,000 or more features.

With a large number of features per layer, the layers of the biochips of the invention must be aligned properly to all layers as well as to the various sites of instrument interfacing. A factor in alignment concerns the shrinkage of parts during bonding, and particularly during thermal bonding; the alignment problem is exacerbated by differential shrinkage of parts. The biochips of the invention are designed and assembled to account for differential shrinkage. For ease of assembly, the part with the greatest number of features is utilized as the shrinkage standard. That is to say, it is designed such that, following bonding, its size is that required for interfacing with the instrument. The sizes of all other parts are scaled such that, following bonding, they align with the standard plate.

Alignment at the sites of instrument interfacing is achieved by sizing and placing interface features appropriately. For example, the pneumatic interfaces of the invention consist of several dozen ports. Instead of being spread throughout the pneumatic layer of the biochip, they are concentrated centrally. Although the pneumatic layer as a whole shrinks, the much smaller pneumatic interface region shrinks much less. In addition, the biochips have alignment features for assembly, which include alignment holes incorporated within the fluidic and pneumatic layers. To align the fluidic to the pneumatic layer, a dowel pin is inserted into the corresponding alignment holes of the pneumatic layer and fluidic layers. Alignment features to ensure appropriate placement within the instrument include guides within the instrument which register to the pneumatic layer (and not the fluidic layer), where the pneumatic port features are located. Although parts shrinkage can be estimated, it is prudent to measure shrinkage following the actual assembly process. For example, the pneumatic plate and fluidic plate of Example 5 shrunk by (−0.063%, 0.116% in the X and Y directions, respectively) and (0.151% and 0.401%) respectively, and the pneumatic plate was increased in size by (0.214%, 0.285%)% to compensate for this differential shrinkage.

Both layer-to-layer alignment and biochip to instrument alignment are managed by minimizing the number of parts to be aligned. For example, the CNC-machined or injection molded pneumatic and fluidic plates of the biochips of the invention generally have features present on both sides. This halves the number of parts required for assembly.

In tandem with alignment features, the features of a given layer that must communicate with those of another layer are designed with tolerances. In particular, valve features (as described in Example 2 require pneumatic features to align with fluidic chambers and valve seats. In addition, through holes in the pneumatic layer connect the output of chambers within the macrofluidic processing subassembly to corresponding input holes within the fluidic layer. In general when two through holes need to be aligned, one of the through holes is made 0.5 mm in diameter larger to ensure that alignment of the two through holes is achieved.

The biochips of the invention represent closed systems in that the samples are inserted and sealed into the biochip and no liquids escape from the biochip (i.e., the process reagents that are contained within the biochip at the initiation of sample processing are contained within the biochip at the conclusion of sample processing (and are removed from the instrument when the biochip is removed). Air from the pneumatic drivelines enters the biochip and air exits the biochip through vent membranes. The closed system biochips of the invention do not expose the operator to sample or chemicals, and important safety feature, and simplify the instrument in that neither unused or spent reagents need be stored within the instrument.

Injection molding of microfluidic features presents many challenges because of the large number of fine features which must be present in a complex fully integrated biochip. These microfluidic features are sometimes present on a given part along with macrofluidic features, further increasing the challenges of injection molding. We present herein specific solutions to design considerations for specific types of biochips, but, one skilled in the art will be able to apply these specific solutions to a fabricate a number of types of biochips for specific functionalities.

Among the design considerations in these examples are: geometrical aspects such as shrinkage and shape stability in precision injection molding, flatness of biochips, warping of biochips, minimum feature sizes, feature density, and appropriate aspect ratios. The design features of the injection molded parts of the biochips of the invention will be described in the context of the injection molding process. Injection molding is a process for fabricating plastic parts in which a mold is clamped under pressure to accommodate the molten plastic injection and cooling process. Plastic granules (pelletized resins) are fed into the injection molding machine, followed by the appropriate colorants. The resins fall into an injection barrel, where they are heated to a melting point and injected into the mold through either a reciprocating screw or ramming device. The molten plastics are contained within the mold, and hydraulic or mechanical pressure is applied to make sure all of the cavities within the mold are filled. The plastics are allowed to cool within the mold, the mold is opened, and the plastic part is ejected with ejecting pins. The entire process is cyclical, with cycle times ranging from between ten and 100 seconds, depending on the required cooling time.

The mold consists of two primary components, the injection mold and the ejector mold. Plastic resin enters the mold through a sprue in the injection mold; the sprue bushing is sealed tightly against the nozzle of the injection barrel to allow molten plastic to flow from the barrel into the mold cavity. The sprue bushing directs the molten plastic to the cavity images through channels (or runners) that are machined into the faces of the plates. The molten plastic flows enters one or more gates and into the cavity geometry to form the desired part. The mold is usually designed so that the completed part reliably remains on the ejector side of the mold when it opens. The part then falls freely when ejected. Molds can be manufactured with a combination of machining methods including CNC milling and Electrical Discharge Machining.

The overall approach to the design of the inventive biochips for injection molding include:

Reduction in the number of layers. The number of injection molded layers was reduced to one fluidic layer and one pneumatic layer by fabricating features on both sides of the layers. This was accomplished in part by routing the fluidic and pneumatic lines in a manner such that channels that cross over each other were routed onto separate sides of the layers. On some occasions, up-down transitions were required. These were minimized as vertical transitions lead to large pressure drops and reduction in the channel conductance. Features to allow ultrasonic welding of vent and filter membranes have been designed. The incorporation of welded features allowed an injection molded layer to be eliminated.

Increase in feature density. Increasing the packing density of channels and features reduces the number and size of the injection molded layers, reducing shrinkage and improving alignability. In the pneumatic manifold region FIG. 44, 61 of the pneumatic layer of the biochips of Example 5, for example, the pitch of channels is 1.0 mm, and 10 channels are located within a 1 $cm^2$ region. This density was accomplished by developing a thermal bonding procedure that sealed the channels despite the narrow (0.5 mm) walls between channels. Thermal bonding of features with fine pitch and narrow walls is accomplished by using bonding fixtures with uniform surfaces and low surface roughness to ensure flatness. Furthermore, two bonding platens were used and set to have be parallel with tolerance of 0.0005" to ensure consistent bonding of fine features across a given injection molded assembly or subassembly. Finally, temperature uniformity across the platens to within 0.25° C. also ensures consistent bonding across the assembly or subassembly.

Minimization of draft angles. Vertical sides of all features have been angled slightly with draft to ease release of the part from the mold. Draft angles in injection molding typically range from range from 2-7°. The injection molded plates of the invention used even smaller draft angles of 0.5%; the smaller the draft angle, the more densely packed the injection molded features. To accommodate for these small draft angles, ejector pins were placed much closer to the microfluidic features than typical in a molding process.

Through holes. The number of knit/weld lines was reduced by appropriate placement of gates in the injection mold. In addition, large open features on the molded parts were minimized as it is difficult to hold feature dimensions and resin flow around large features.

Wall thickness. A 1.0 mm wall thickness at feature floors and 0.5 mm wall thickness between features was maintained throughout the design.

Flatness and Warpage. Appropriate layer thicknesses and transitions between features to minimize thickness have been adopted. The flatness of the resulting plate is characterized and adjustments to the injection molding process to minimize part internal stresses is performed. Areas of the molded plate that are warped are adjusted by modifying placement of ejector pins. In addition, fine machining of the uneven areas improves flatness.

Feature aspect ratio. High aspect ratio features have been minimized and aspect ratios have been kept below 2. Higher aspect ratio features tend to prevent the molded parts from ejecting effectively from the mold tool.

Ejection features. Ejector pin locations have been minimized and placed only on the ejector half of the mold.

The ejector pins generate local deformation in the surface of the part which in turn can lead to regions that bond poorly or not at all. The travel of each ejector pin within the mold was adjusted to minimize the travel required for repeatable part ejection.

Injection molding shrinkage. The shrinkage on injection molding for the resin was thoroughly characterized to accommodate shrinkage. Furthermore, shrinkage was further fine tuned by adjusting the molding temperature and hold times. Shrinkage of the pneumatic and fluidic parts are adjusted such that all features within the injection molded plates are aligned within defined tolerances.

Block molding. The approaches described above are applicable to the molding of both flat plates (e.g. the fluidic plate, pneumatic plate, and macrofluidic processing cover plate). To mold higher volume blocks such as the macrofluidic processing block, these approaches are modified in that the aspect ratios are typically greater than 2. For block molding, draft angles of less than 1° C. are incorporated into the design and allow effective pin removal from the molded part while maximizing volume of the large chambers.

The fully integrated biochips of this invention realize the potential of microfluidics, by providing biochips that can carry out complex series of process steps from the insertion of a sample to the generation of a result, performed in a single instrument without operator intervention. Moreover, these inventive biochips may be disposable and manufactured cost-effectively.

EXAMPLES

Example 1

Reagent Storage and Release

Biochips of the invention require reagents to perform various processes, and these reagents must be compatible with the biochip materials and operating and environmental conditions to which they are exposed.

The reagents of the invention can be introduced into the biochip in several ways. First, reagents can be added to the biochip manually, generally shortly before use. The advantage of manual addition is that the biochip need not hold the reagents for extended periods, minimizing the need for long-term stability on the biochip. The disadvantages of manual loading are that the operator must have technical training and expertise, the reagents can be placed incorrectly preventing proper processing, and reagent placement can be a source of contamination. A second method of placement is by storing the reagents in containers within or near the instrument; tubing or other conduits would then transfer the reagents to the biochip at the desired process time. An advantage of this approach is that placing reagent containers once may allow multiple analytic runs of the system. Disadvantages are the need for substantial transfer conduits within the instrument, compromised flow through the conduits as, for example, as residual reagents dry on the conduit, the need to open the instrument, allowing for the potential of damage or contamination, a relative increase in the size of the instrument to allow reagent storage for multiple analytic runs, and the need for an operator with technical training and expertise.

A preferred approach is to store the reagents within the biochip, with the pre-loaded reagents being an integral part of the biochip and essentially inaccessible to the operator. The advantage of this approach is that the operator need never come in contact with the reagents or require technical training or expertise, and, if the biochip is a closed system, the potential for contamination is minimized. Furthermore, the instrument accepts the biochip but does not have to be opened to place separate reagent tubes or cartridges. When combined with a drive system that ensures that the on-chip reagents do not come in contact with the instrument, the biochip is a closed system, further enhancing ease of use while minimizing the possibility of contamination.

In order to store reagents on-chip, they must be compatible with all biochip materials with which they come in contact and must be accessible to the process when required. We term one approach to these requirements "Reagent Storage and Release (RSR)," indicating that the reagents are stored and sequestered within the biochip and released on demand as required during processing.

Approaches to RSR include blister packages, tube-in-tube structures (in which reagent-containing tubes are inserted into biochip reagent reservoirs), and single tube structures (in which reagents are filled directly into the biochip reagent reservoirs). Actuation methods include pressure-based methods (which may optionally involve the use of scored foils), pin-based methods (in which mechanically or pneumatically actuated pins puncture foil seals), and mechanical methods (in which an instrument component exerts pressure on the stored reagent).

Blister packages. In this approach, aluminum foil sealed blisters or stick packages are used to store reagents. Mechanical force is applied to the packages to release the contents into the reagent reservoir.

Tube-in-tube structures. In this approach, reagent tubes are fabricated in a thermoplastic, and a foil seal is applied to the bottom of the tube prior to reagent filling and a second foil seal applied to the top of the tube following filling. The sealed reagent tube is then inserted into the appropriate reagent chamber of the biochip. A wide selection of laminated aluminum sealing foils is available for heat sealing. These foils feature a polymeric heat sealing surface laminated to a thin aluminum film. Coatings used on aluminum foil for protection are selected for resistance to the reagents themselves, heat, and scuffing. The protective coating may also serve as a heat-seal surface.

Single tube structures. In this approach, chambers within the biochip itself are the storage vehicles. In this approach, the advantage is that the biochip is relatively smaller (as the tube-in-tube requires an additional wall) and is easier to fabricate. FIG. 1 illustrates the single tube RSR approach. Foil seals (101) are bonded (thermally, by ultrasonic welding, or by adhesives) to the top and bottom of each reagent storage chamber (102). The bottom foil is bonded first, liquid reagents are filled (indicated by shading of 102), and the top foil is then bonded, sealing the reagent storage chamber. A top cover (103) contains pneumatic drive lines that provide pressure required to burst the foils. Lyophilized reagents (104) can also be stored between foils.

Figure 2:
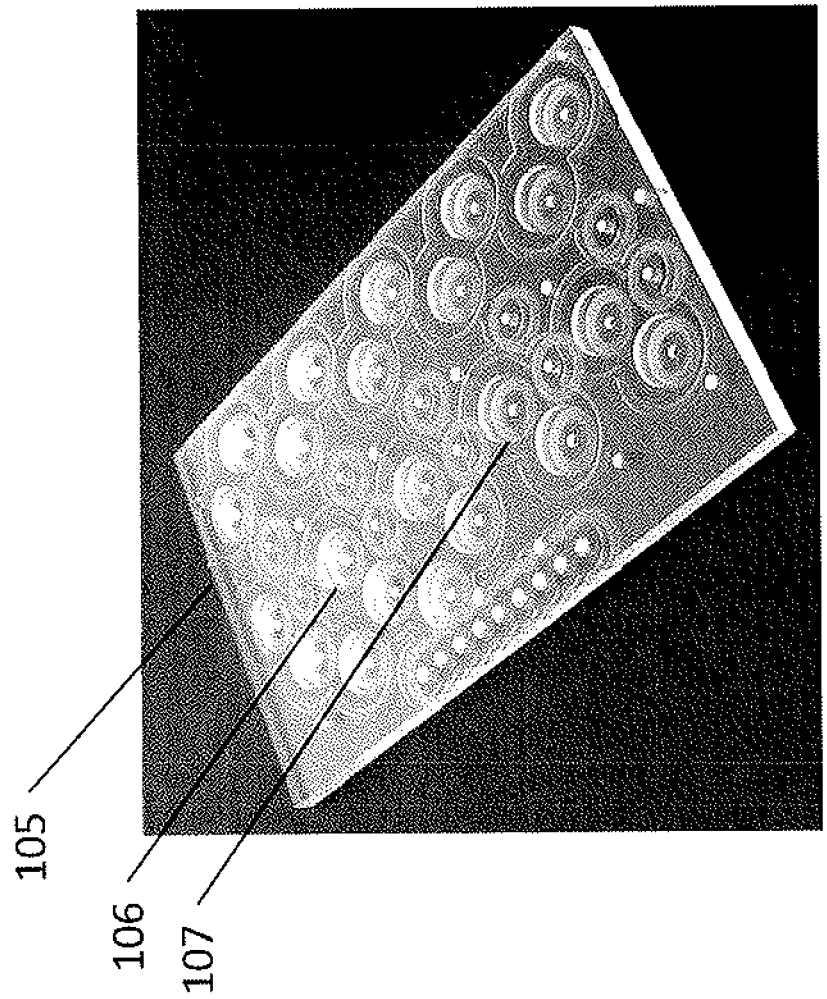
FIG. 2 is a photograph of an embodiment of a spacer plate included in a 5-sample biochipset embodiment utilizing reagent storage release bursting.
Figure 3:
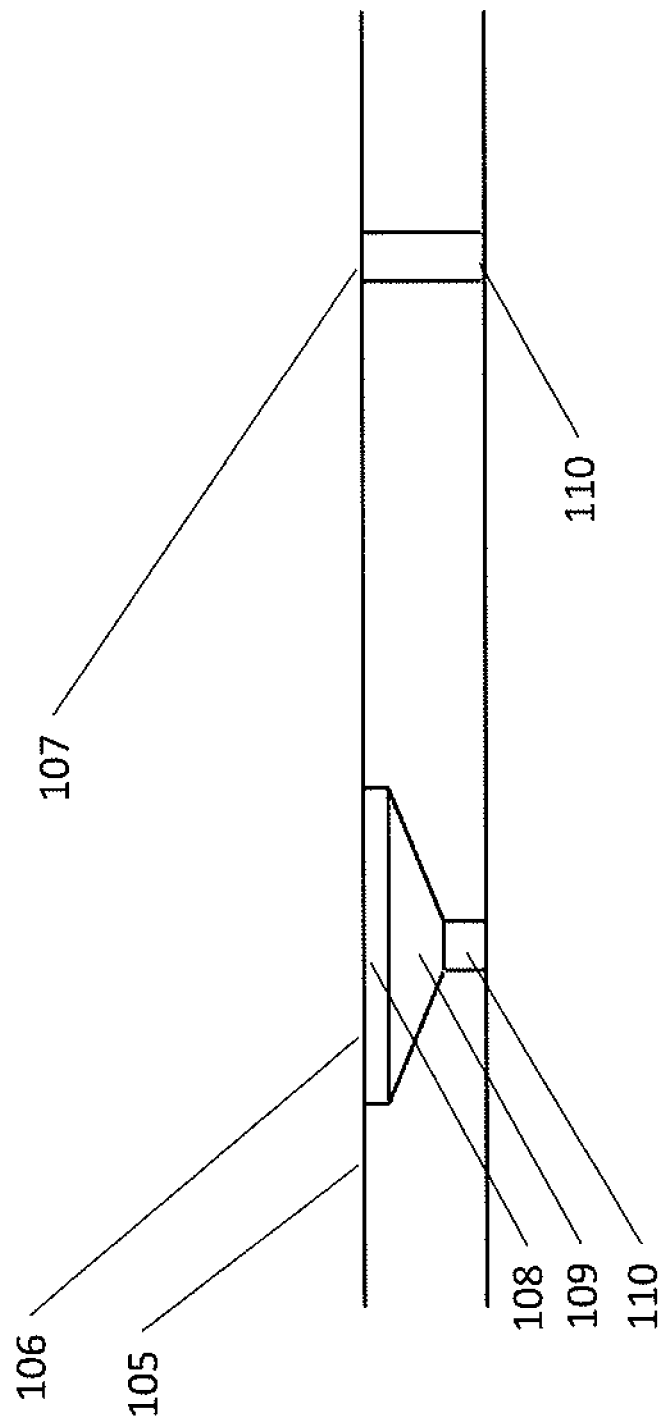
FIG. 3 is a cross-section view schematic of a portion of a spacer plate.

The pressure required to burst the top and bottom foils causes reagents to flow rapidly out of the reagent chamber. In order to reduce reagent flow, flow-control orifices are fabricated at the bottoms of the chambers. The diameter of the orifices are sized to allow the desired flow at the applied foil bursting pressures. Valves and vent membranes can also be utilized to control fluidic flow and queue liquids as described in Example 2. In addition, when the RSR chambers are subjected to pneumatic drive pressure, the foil must have enough space to expand prior to bursting. To accommodate this space requirement (approximately 1 mm for a foil of 25 micron thickness and diameter of 8 mm), an RSR spacer plate was designed to provide an expansion space for bursting. The RSR spacer plate also provides the interface to couple the larger diameter (8 mm in this instance) outlets of the reagent chamber and the smaller diameter (0.5 to 1 mm) inlet holes of the biochip, and transitions the reagent flow between the two interfaces with tapers. The inlet holes may be through holes in the pneumatic subassembly leading to features in the fluidic subassembly, or may couple directly to the fluidic subassembly or the separation and detection subassembly. FIG. 2 is a photograph of the spacer plate 105 used for a 5-sample biochip showing RSR transitions 106 to couple liquid reagents chambers which require RSR bursting. Conventional transition 107 couples process chambers utilized for mixing and holding (but not reagent storage as they do not require expansions space) to the inlet holes of the biochip. FIG. 3 is a cross-sectional view of an RSR transition 106 which is composed of a RSR chamber interface 108, a conical taper section 109, and a biochip interface 110. Also shown is a conventional transition 107 which is a through hole transition between the process chambers and another biochip subassembly. The spacer plate is attached to the reagent chambers and to the by pressure sensitive adhesive and mechanical fasteners. Other forms of attachment include the use of gaskets with and without adhesives, screws, heat staking, and rivets.

Pneumatic bursting of foils is the preferred method, as it requires only pneumatics for actuation. The foil seals are burst by pneumatic pressure that is delivered to the tops of the tubes via pneumatic drive lines within the biochip. In this configuration, the pressure applied to the reagent chamber is imposed on the top foil, causing it to rupture. On rupture, the pressure is applied directly to the reagents within the tube. This in turn causes the bottom foil to rupture and release the solution for processing. Several factors must be considered in the selection of foils for pneumatic bursting. To be compatible for pneumatic bursting, the bursting pressure must be appropriate for the structure of the biochip and tolerated by the biochip. For the biochips of the present invention, assembled by thermal bonding, solvent bonding, and adhesive bonding, the desired bursting pressure is approximately 20-500 psig. Thin foil films of 10-500 microns are appropriate for this purpose, preferably 10-30 microns.

Figure 4:
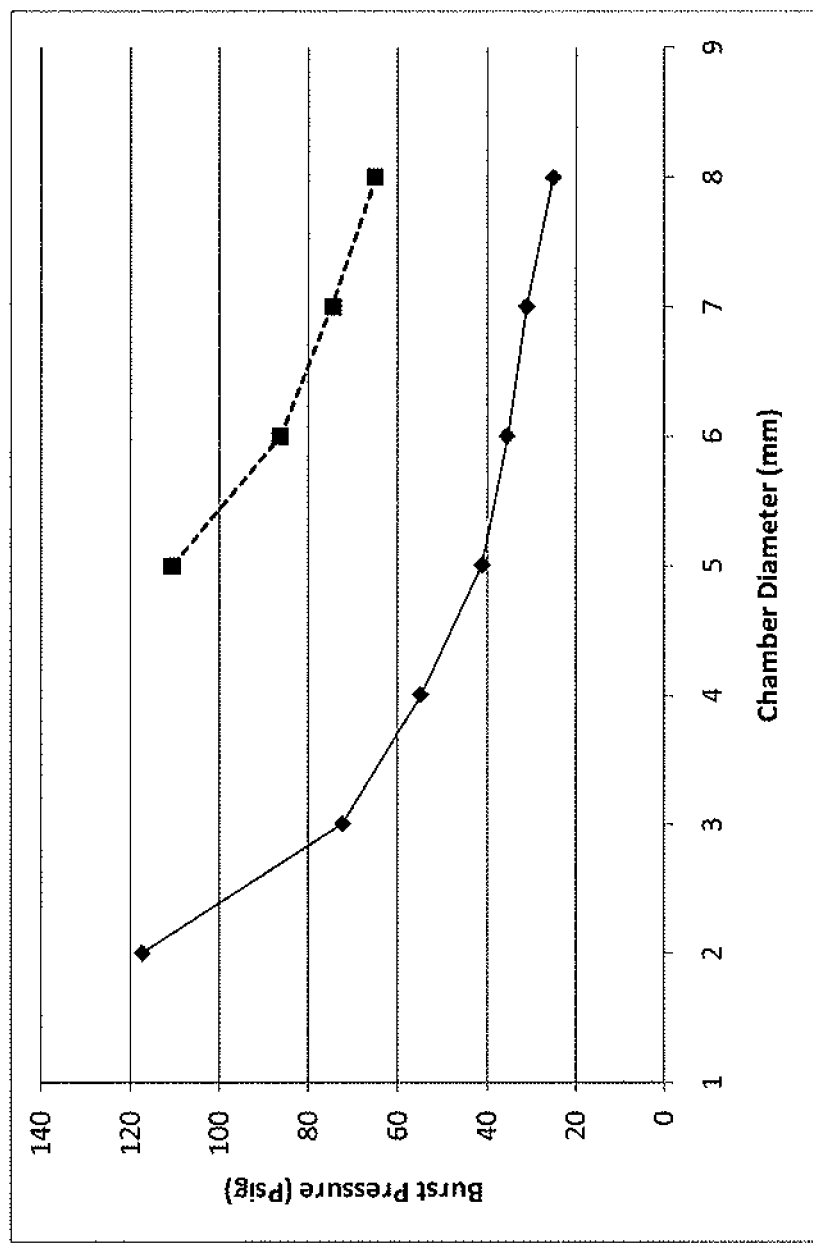
FIG. 4 is a graph of burst pressure versus chamber diameter for aluminum foils of various thicknesses.

FIG. 4 shows pneumatic bursting pressures required for 12 (solid line) and 18 (dashed line) micron aluminum foils bonded to chamber diameters of 2-8 mm. Pressure required for bursting increases with increasing foil thickness and decreases with increasing chamber/foil diameter. Each point shows the average pressure required for bursting (For 2 mm diameter, n=2, for 3 mm diameter, n=6, for 4 mm diameter, n=10, for 5 mm diameter, n=9, for 6 mm diameter, n=10, for 7 mm diameter, n=4, and for 8 mm diameter, n=4). Bursting pressure can also be affected by the type of foil material.

Figure 5:
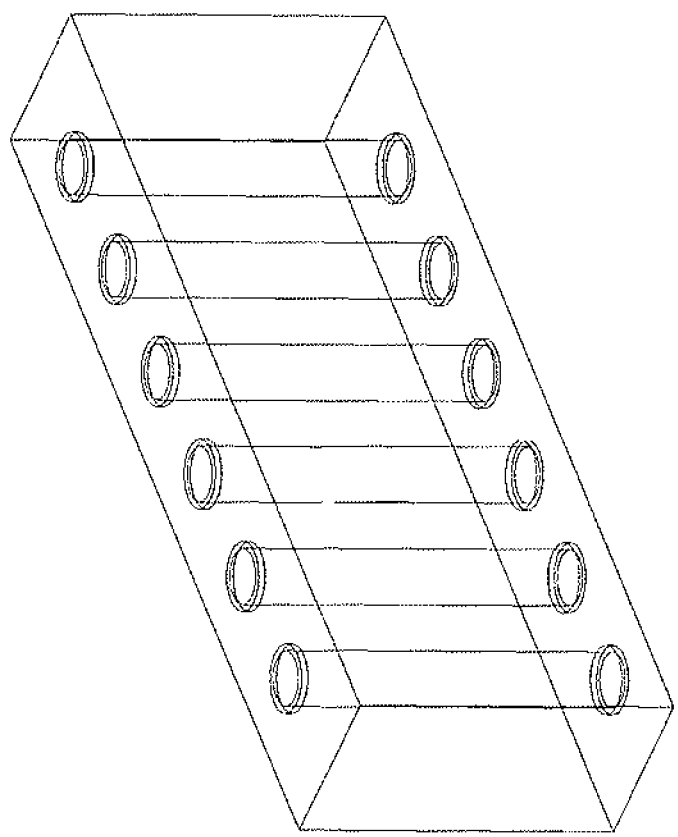
FIG. 5 is a perspective view schematic of a reagent storage release unit including six chambers of reagent storage.

Optionally, scoring of the thin foils allows a reduction in bursting pressure; scores of various sizes and shapes on the foil can be utilized as well. For example, laser or mechanical die scoring of lines, crosses, and circles to varying depths can be used to further modulate burst pressure. FIG. 5 shows an RSR unit with six chambers (each with 8 mm diameter and 50 mm height). A 25 micron aluminum foil was subjected to laser scoring (crossed 4.5 mm centrally placed lines of depth of approximately 10 microns) and thermally bonded to the unit using a heat staker. The bottom foil was placed initially, the liquid reagents with food coloring were filled into each chamber, and the top foil was bonded (FIG. 6).

Figure 6:
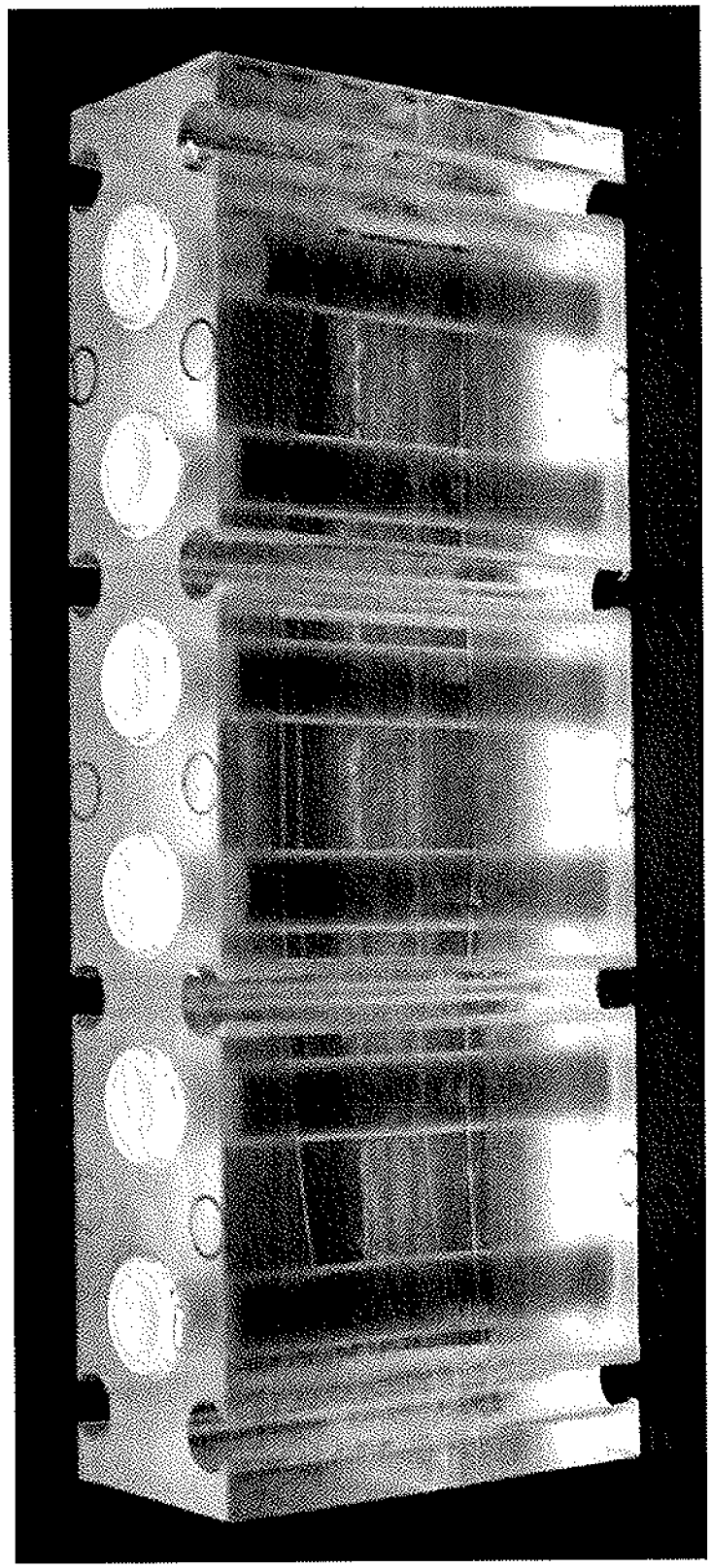
FIG. 6 is top perspective view of the reagent storage release unit of FIG. 5 showing a top foil bonded to a top end of each chamber.
Figure 7:
FIG. 7 is a top view illustration of two foils of a reagent storage release unit after bursting.

Two-sided bursting of reagent chambers was performed by filling and sealing 2 ml of reagents into the chambers of FIG. 6. The foils used for sealing the chambers were scored (crossed 4.5 mm centrally placed lines of depth of approximately 10 microns) to achieve a nominal burst pressure of 32 psig. Each chamber was attached to an RSR spacer plate which was in turn attached to a microfluidic channel. The output of the microfluidic channel was sealed with a vent membrane to allow air from the bursting to vent but not to block the fluid that is released from the chambers. A cover was fastened to the top of the chamber. The cover couples each of the 6 chambers to a pneumatic drive line. The pneumatic system was configured to apply pressure to only one chamber at a time. The pneumatic drive pressure was increased gradually until liquid was observed to flow into the microfluidic channel, and this pressure was recorded. All of the 24 foils used in the testing (4 RSR units) burst with a pressure of 32 psig±3 psig. FIG. 7 shows foils after bursting. Foil materials, scoring depth and configuration, and burst pressures are chosen in tandem to avoid having pieces of the foil become separated during bursting, potentially blocking exit channels for the reagents. The scored foil presented here does not generate separated pieces of foil.

In a second experiment, the reagent chambers were filled and sealed with scored foils as above. The chambers were attached to an RSR spacer plate which was attached to a microfluidic channel. The output of each of the microfluidic channel was sealed with a vent membrane. A cover was fastened to the top of the chamber and 45 psig of pressure was applied to all the reagent chambers simultaneously for 1 second. All of the foils ruptured and reagent was observed to flow into the microfluidic channels and stop at the vent membrane. The liquid within the channel was composed of a single plug without bubbles.

Together these experiments demonstrate the RSR including reagent sealing within the chambers, pneumatic bursting of sealing foils, control of bursting pressure with chamber diameter and scoring, reagent transition into a microfluidic channel, and queuing of the reagent with a vent membrane.

A related approach to RSR utilizes mechanical rather than pneumatic pressure to burst the foils. In this method, sharp pins are fabricated in plastic at the top and bottom of each foil-sealed reagent tube (metal pins can be inserted to serve the same purpose). Both foils are pierced by pins, releasing the reagents at the required process time.

Example 2

Flow Control in Biochips

The biochips of the invention comprise thermoplastic layers that contain fine features, and control of fluid flow is required to execute the set of processing steps required to generate the analytic results. Fluidic functions that require the use of flow control elements include:

Directing fluid flows from one feature to another via channels in the biochip. The scripted use of drive lines, valves, and vent membranes directs liquid and air flow through specific channels and features in the biochip. For example, the purification filter (FIG. 39, 12) is connected by fluidic channels to reagent and process chambers. The sequence of fluid flows and valves that control flow into and out of the purification filter is described by the DNA binding step, Wash, Dry, Elution steps of Example 5. In these steps, several vent membranes, valves (FIGS. 39, 46, 47, 43, 42, and 44) and pneumatic drive lines are used to direct fluid flows through this chamber.

Figure 40:
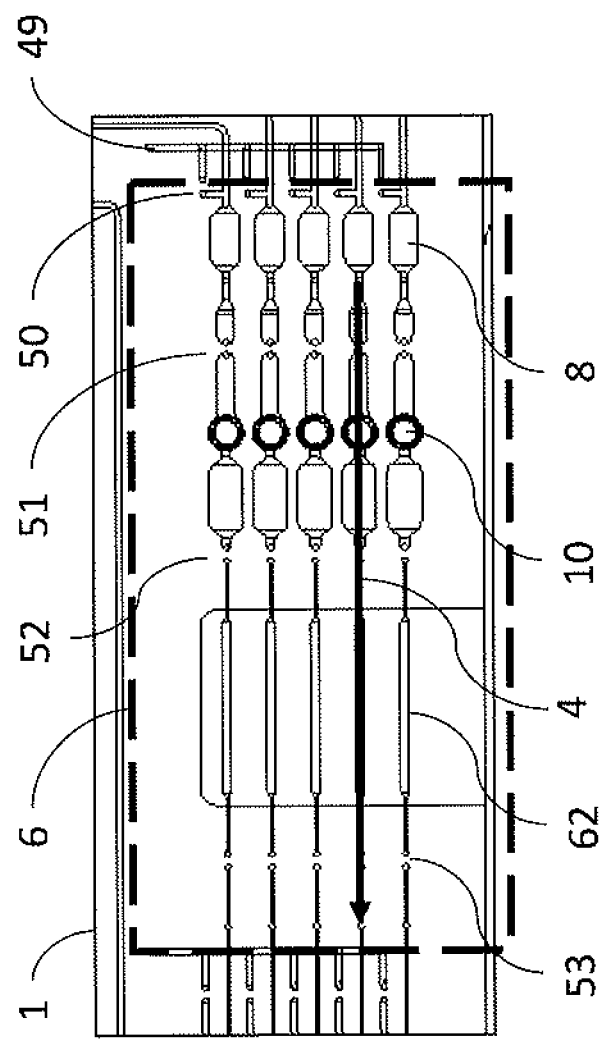
FIG. 40 is a top expanded view schematic of the fluidic plate of FIG. 38 showing a portion of the path through an amplification region.
Figure 52:
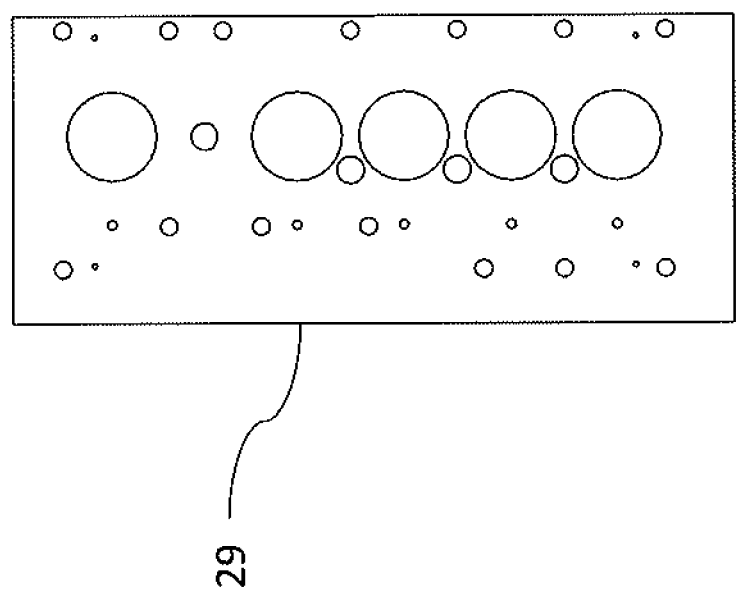
FIG. 52 is a top view schematic of another embodiment of a third layer of a cover to the macrofluidic block.
Figure 53:
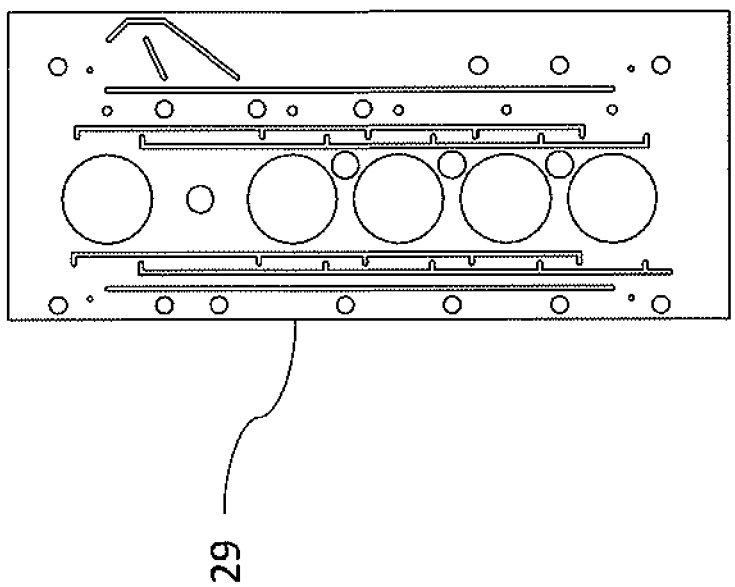
FIG. 53 is a bottom view schematic of an embodiment of a third layer to the cover of FIG. 52.

Sealing of chambers. Certain reactions such as thermal cycling and cycle sequencing require elevated temperatures. A high integrity seal is important in such settings because the pressure of the fluid within the chamber increases as the reaction is heated. A poor seal will result in fluid leaks out of the chamber and will allow gases within the reaction to outgas and generate bubbles. Sealing the chambers minimizes these problems and improves reaction efficiency. For example, the thermal cycling chambers of Examples 5 and 6 are sealed during the thermal cycling process by valves V13 and V14 (FIGS. 40, 52 and 53).

Reciprocal mixing. Reciprocal mixing is an approach to mixing based on forcing two liquids against an air ballast and releasing pressure to allow reverse flow. Repeated application and reduction of applied pressure accomplishes mixing by moving solutions to be mixed "back and forth." This approach is illustrated in the biochip of Example 6, which uses an air chamber (FIG. 70, 610) as a spring which is initially compressed by the fluid by pressure when the fluid is pushed against it, and then to push the fluid back when pressure is released. The air chamber is sealed during reciprocal mixing by valve V13 (FIG. 69, 52) where a linearly increasing pressure of 0 to 15 psig and then 15 to 0 psig is applied. After the mixing, V13 is opened to allow the mixed solutions to flow through into the PCR chambers.

Queuing vent membranes—Variations in flow velocity of multiple samples being processed in parallel in a given biochip can result from factors including differences in sample viscosity (e.g. DNA content) and variations in channel dimension (and hence conductance). The use of queuing functions accommodates variations in the fluid flows for multiple samples through parallel channels within the biochip. In this approach, the maximum possible time required for a given step is used as the step time. Samples that arrive at the vent membrane early will halt and wait while the other samples with slower flow velocities arrive at the queuing point. This approach provides tolerance to process multiple samples simultaneously by ensuring that they are synchronized. Queuing of fluids is practiced in Example 5 and 6 "Transfer into thermal cycling chamber" by using a vent membrane (FIG. 40 and FIG. 69, 100) and a valve (V29) (FIG. 40 and FIG. 69, 99) to halt the PCR solution for multiple samples at a common position. An alternative but more complicated approach to synchronizing multiple samples is to control each sample separately and to incorporate detection features (e.g. optical, thermal, chemical, mechanical) that allow the script to receive feedback when a given sample arrives at a given point on the biochip.

Figure 70:
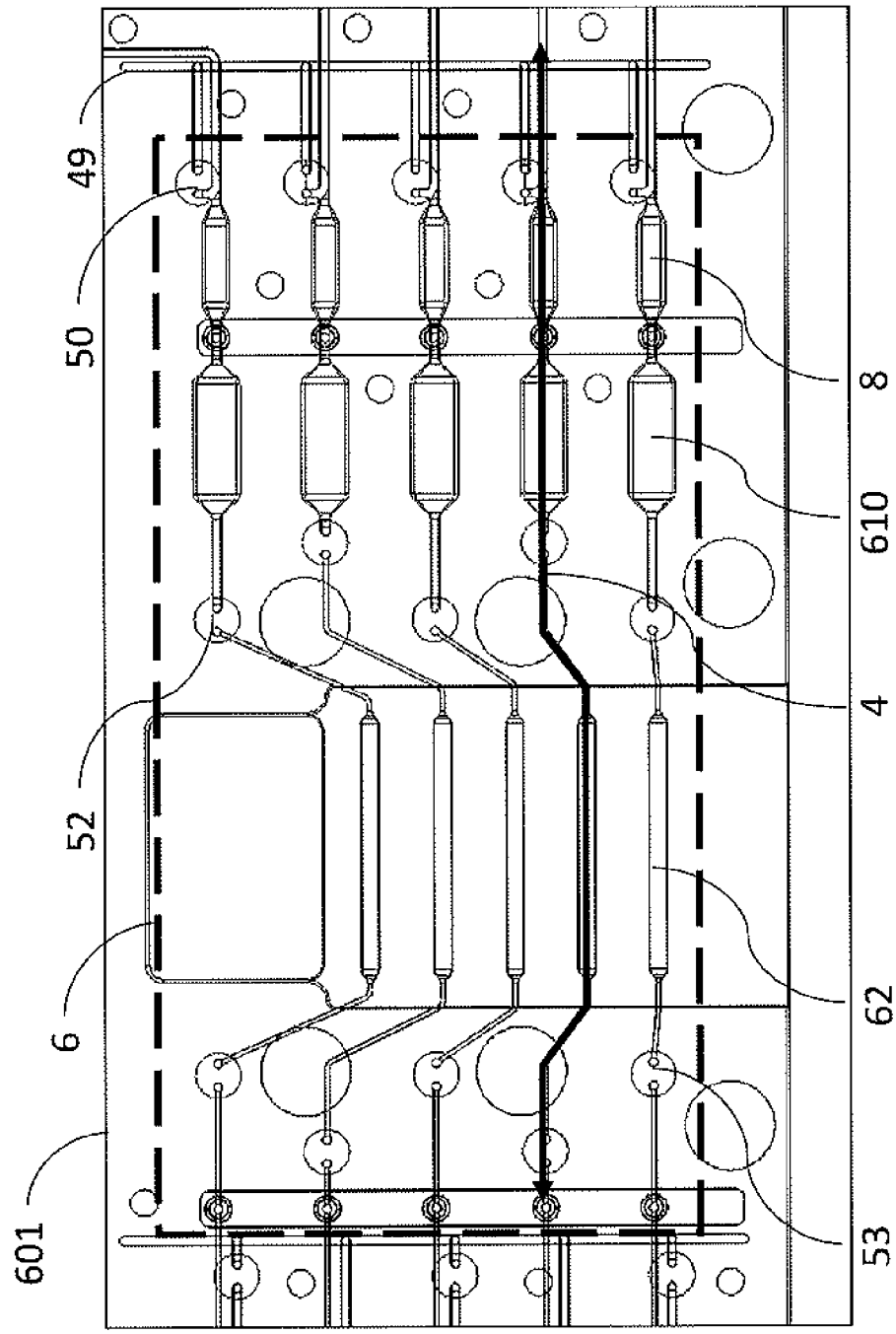
FIG. 70 is a top expanded view schematic of the fluidic plate of FIG. 68 showing a portion of the path through a PCR section.

Metering chambers—Solutions are metered in multiple instances through the process flow. An example of metering in Examples 5 and example 6 is the "Eluate metering" step employs a metering chamber (FIGS. 40 and 70, 8), valve V12 (FIGS. 40 and 70, 51) and vent membrane VM (FIGS. 40 and 70, 100).

Joining of solutions with air plugs in between. During sample processing, there are instances in which two discrete fluid plugs from different inputs and separated by air need to be combined. An example of this is the "joining of the PCR product and formamide" step. In this step, a joining chamber (FIGS. 41 and 71, 78), Vent membrane, and valves (FIG. 41, Elements 100, 56, 81) are used. The joining function uses the above elements to receive each of the fluid plugs into the chamber, remove air between the fluids, and allow the joined fluid plug to advance. In this step, valves are used to halt liquid and air flow. The vent membrane is used to vent air between the fluid plugs.

Figure 41:
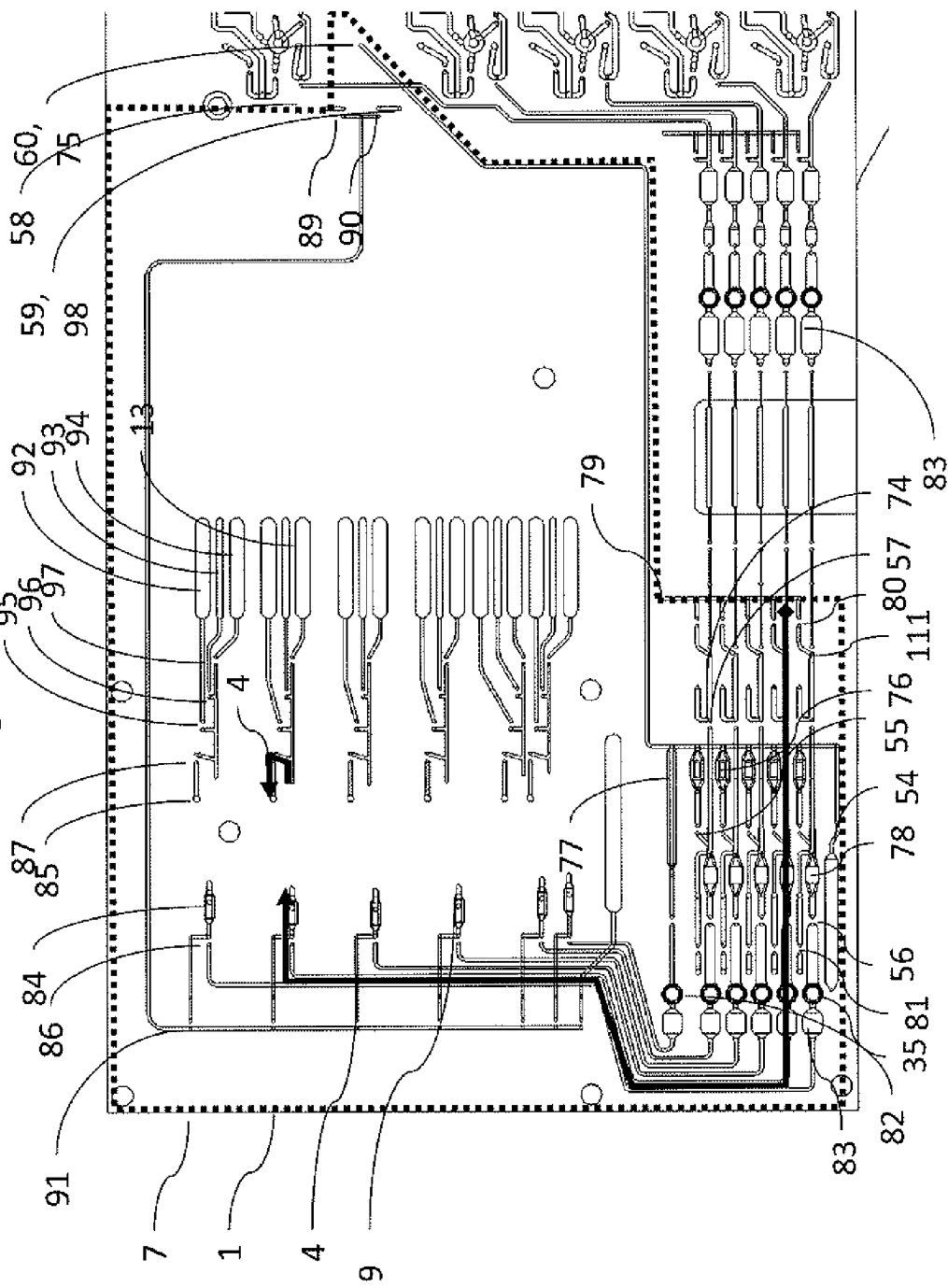
FIG. 41 is a top expanded view schematic of the fluidic plate of FIG. 38 showing a portion of the path through a separation and detection region.
Figure 54:
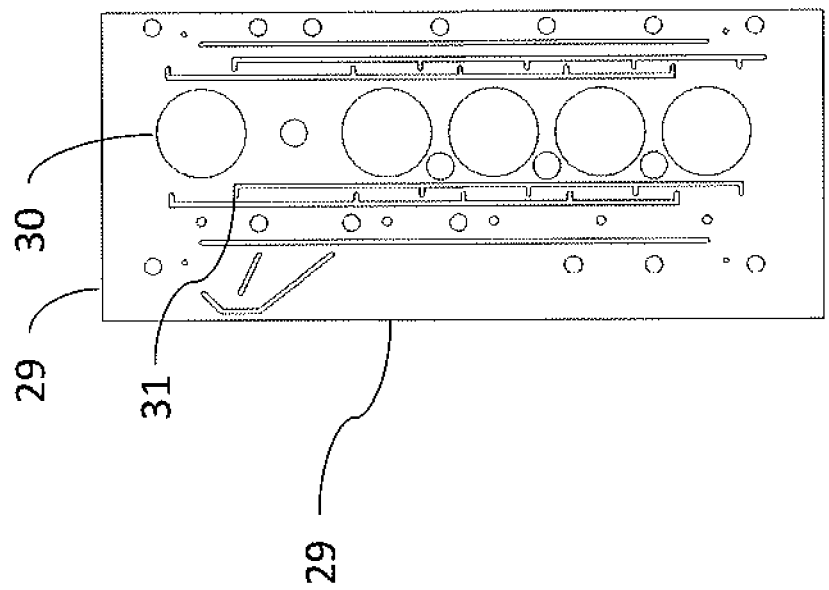
FIG. 54 is a transparent top view schematic of a third layer to the cover.
Figure 71:
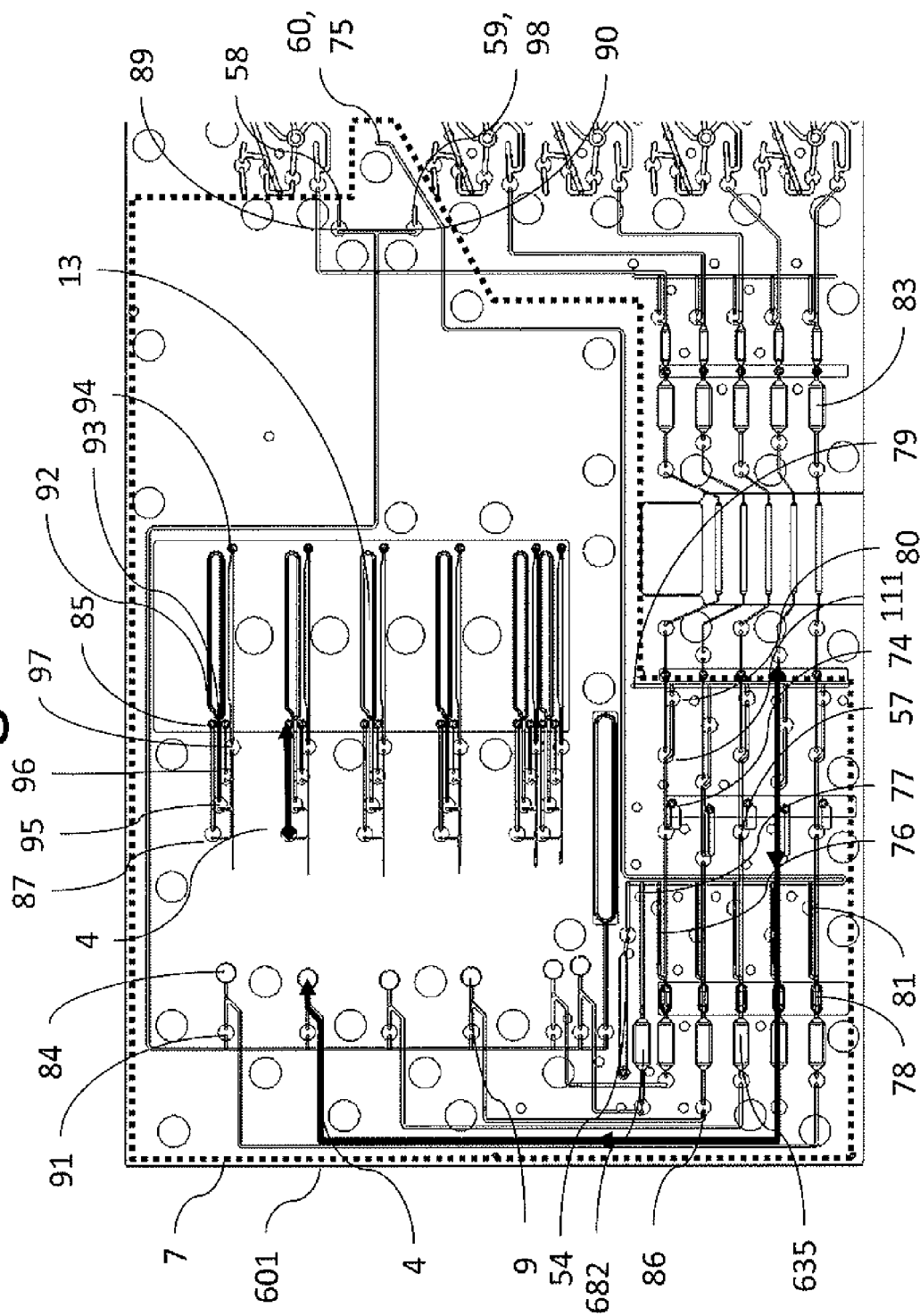
FIG. 71 is a top expanded view schematic of the fluidic plate of FIG. 68 showing a portion of the path through a separation and detection region.

Filling of waste chambers. Waste chambers within the biochip are designed to accept excess solutions, particularly during metering steps. An example of waste handling is the "meter formamide" step. In this step, a waste chamber (FIGS. 41 and 71, 77) consists of a chamber that has a vent membrane to seal the entire top surface and Valve V15 (FIGS. 41 and 71, 54). The valve and waste design accommodates excess fluids that may be variable in volume and may contain air bubbles (and therefore samples that are discontinuous fluid plugs). The use of a fully vented waste chamber allows air that is present within fluid plugs to be ejected, and the use of valves allows the waste to be directed into the chambers and sealed.

Passive sample splitting. The use of a passive differential conductance feature to spit the flows of two fluids that are separated by air into two paths may be advantageous. In this design, a single flow path splits in two flow paths that end with vented chambers. The flow conductance of a first channel is significantly reduced relative to that of a second channel by incorporating a passive flow restriction along its fluidic pathway. The flow restriction generates resistance, and liquids that flow to the split will flow in the higher conductance channel until the vented chamber is filled or the vent membrane is completely wetted. When either occurs, the restriction of this flow channel is high and additional liquid flows into the second channel (despite the flow restriction element). This design is used to passively control flow of fluid between two paths based on conductance. It is particularly useful when two liquids in a channel are separated by an air plug; the first liquid flows toward the first path and the second liquid is diverted to a second path.

Venting of macrofluidic chambers. The "chaotic bubbling" steps of Example 5 and 6 result in significant agitation of a large volume of solution. The lysis solution on chaotic bubbling must be contained within the chamber to prevent the reagent from leaving the biochip and ending up in the instrument, while large volumes of air must be exhausted to allow adequate air flows to facilitate bubbling. This is accomplished by using a vent membrane in the cover that acts as a barrier to the fluid flow but allows air from chaotic bubbling to be exhausted. A similar design is utilized to vent any chamber subjected to chaotic bubbling or substantial air flow for any reason.

Isolation of drive lines—Vent membranes are also incorporated into the cover and other portions of the biochip to isolate the drive lines of the instrument from fluids within the biochip.

Valving Structures

The above functions rely on two flow control structures: valves and vent membranes. The biochip uses valves for flow control to halt or allow flow of fluids within channels. Valves can be passive or active, and passive valves include in-line polymerized gel, passive plug, and hydrophobic valves. Active valve structures include mechanical (thermopneumatic and shape memory alloy), non-mechanical (hydrogel, sol-gel, paraffin, and ice), and external (modular built-in, pneumatic, and non-pneumatic) valves. The pneumatic and mechanical valve structures can also make use of either elastomeric or non-elastomeric membranes. In either case, the membranes can be treated to provide optimal sealing properties.

Many types of valve structures can be utilized in the biochips of the invention, and several types may be incorporated in an individual biochip. The selection of a valve structure is based primarily on ease of fabrication and assembly in concert with the approach to instrumentation. For example, mechanical valves controlled by rods that actuate biochip features would be appropriate in an instrument with sophisticated mechanical alignment and control mechanisms. Similarly, valves based on localized melting of wax require an instrument with controlled special heating mechanisms. In Examples 5 and 6, the instrument is capable of sophisticated pneumatic control, and the incorporate valves types (described below) are based on pneumatic actuation. Other pneumatic and non-pneumatic (e.g. mechanical, liquid, wax, electrical) actuation mechanisms and corresponding valves can be utilized in the inventive biochips.

Figure 8:
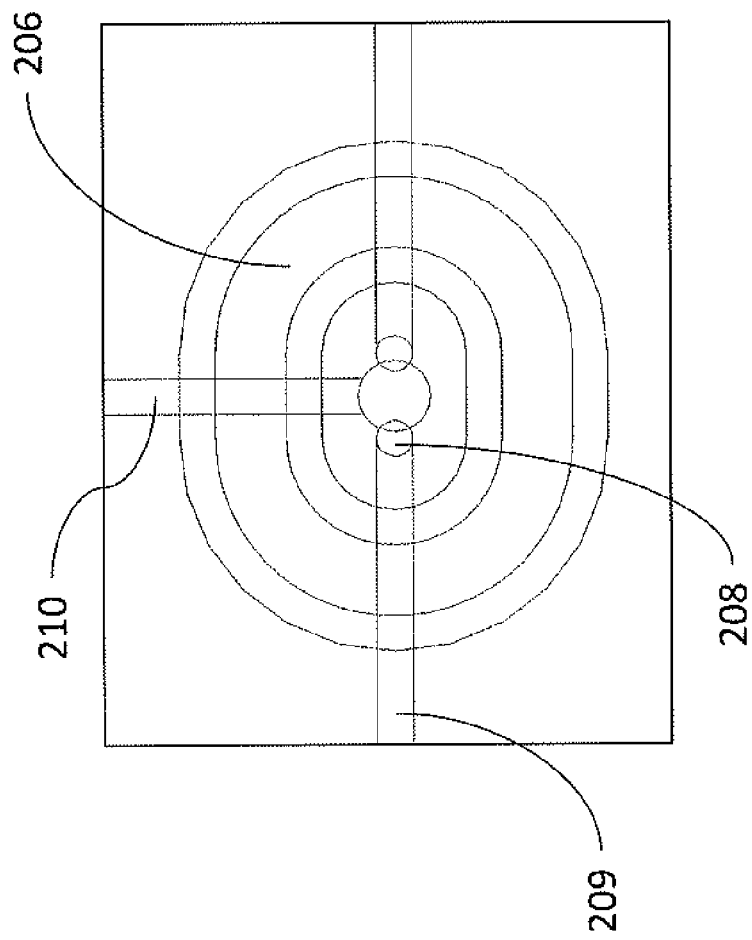
FIG. 8 is a top view schematic of an embodiment of a pneumatically actuated elastomeric valve structure.
Figure 9:
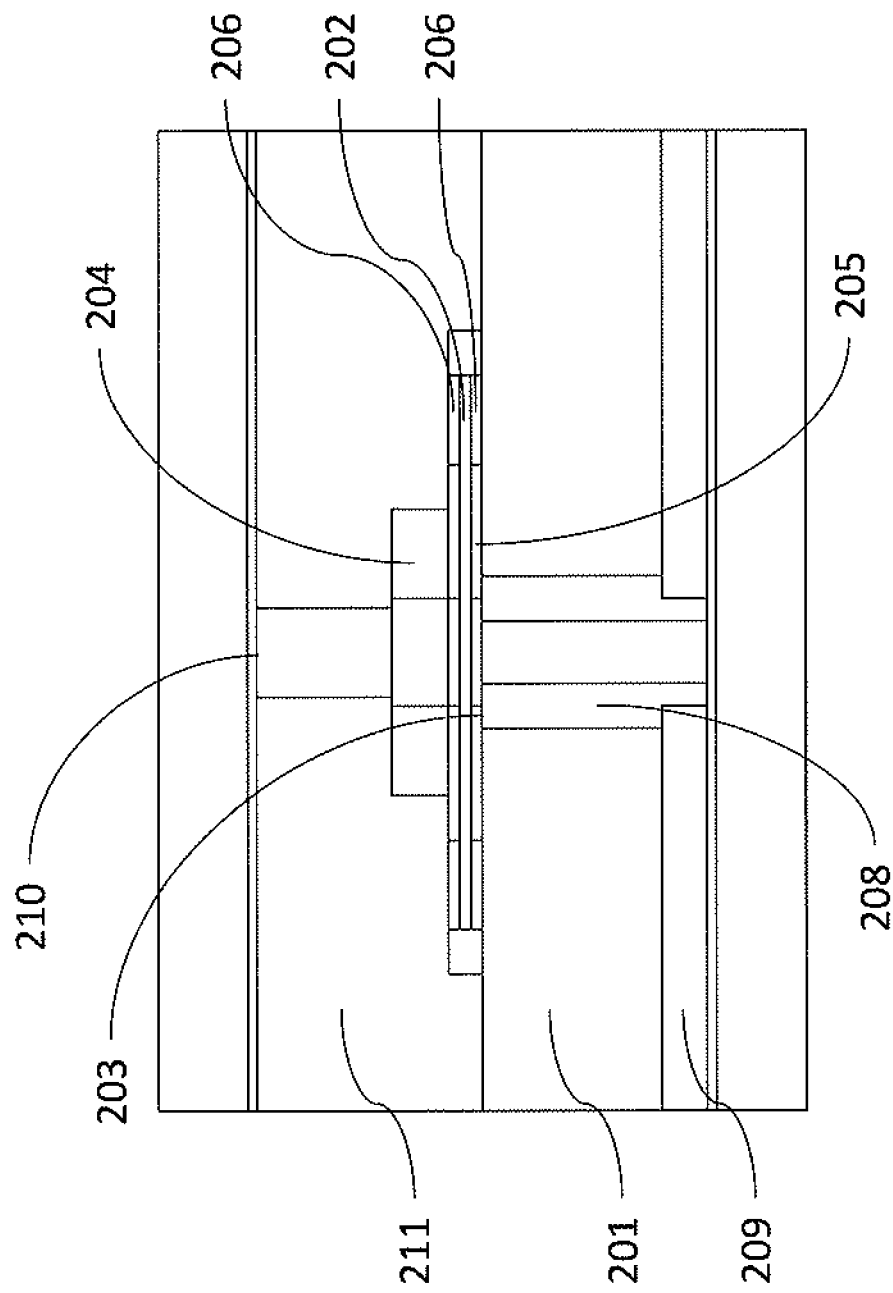
FIG. 9 is a cross-sectional view schematic of the pneumatically actuated valve structure of FIG. 8.

The top view of a pneumatically actuated elastomeric valve structure is shown in FIG. 8. The top view of shows pressure sensitive adhesive (PSA) tape and an elastomeric membrane for the normally open valve. A cross-sectional view of the pneumatically actuated valve for control of fluids and air is shown in FIG. 9. Components of the valve structure include a valve membrane 202, valve seats 203, pneumatic chamber 204, fluidic chamber 205, double sided PSA tape 206, fluidic through holes 208, fluidic channel 209, and pneumatic channel 210. This valve is fabricated by assembling 3 components:

Fluidic subassembly. This subassembly contains a channel for fluid 209 (liquid or air) flow. The channel is interrupted by a set of through holes 208 that pass through to the surface. At the surface these through holes form the valve seats 203 for the valve assembly. It is fabricated by CNC machining the channels and through holes in a thermoplastic sheet (FIG. 33) and covering both sides with thin plastic films. In this case the thin film plastic is a thermoplastic film that is bonded. The films have themselves been patterned by CNC machining, and have features including through holes that are aligned to the corresponding features on the CNC machined layer to provide access to the fluidic sandwich layer. Similarly, the same features within the fluidic and pneumatic layers can also be fabricated by injection molding.

Figure 44:
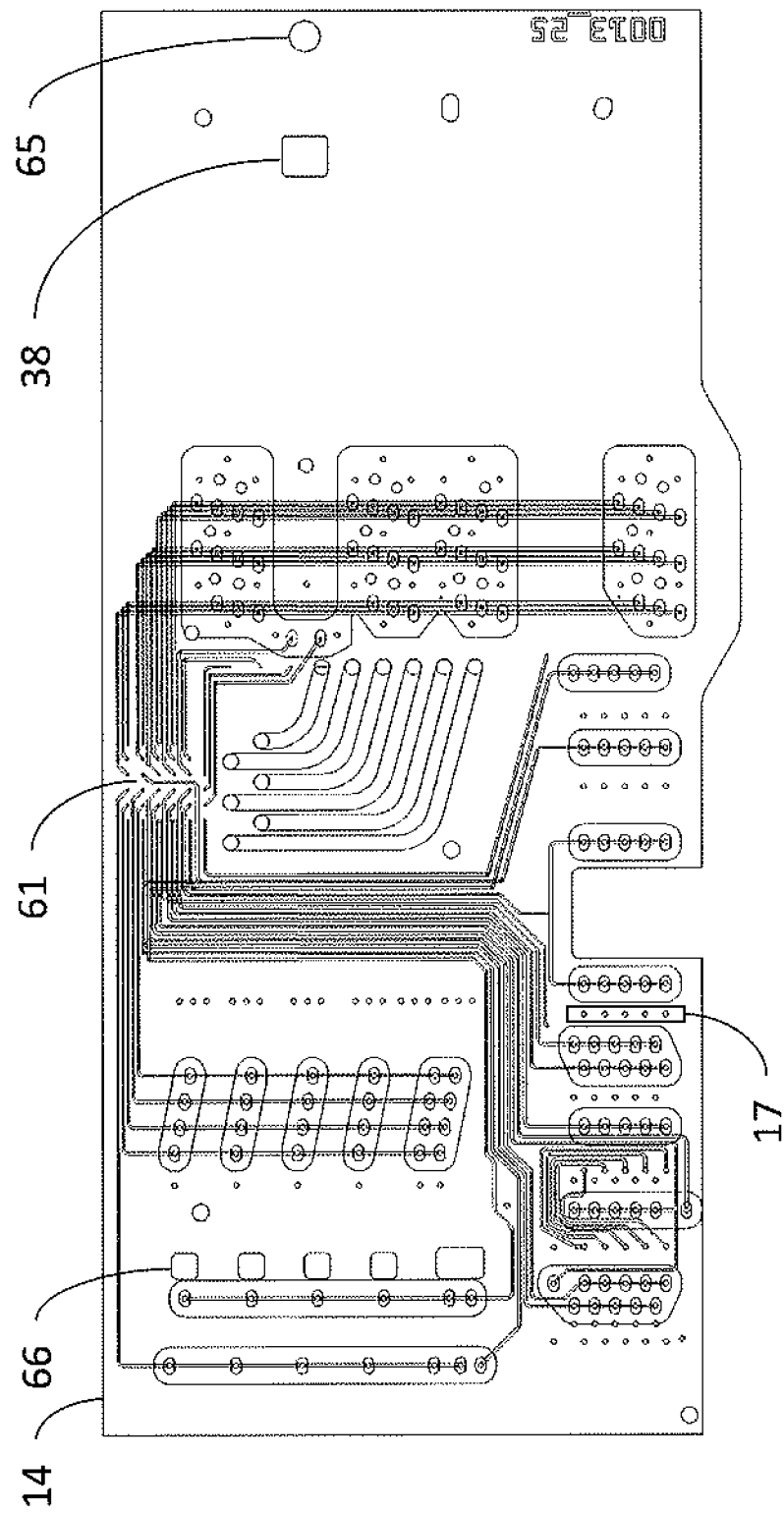
FIG. 44 is a transparent view of the pneumatic plate of FIG. 42 showing the features of both top and bottom sides of the pneumatic plate.

Pneumatic subassembly. This subassembly couples the pneumatic drive of the instrument to the fluidic subassembly to pneumatically drive fluids within the fluidic subassembly and to pneumatically activate valves within the biochip. The pneumatic channels 210 couple the pneumatic drive to the valve chamber. This subassembly is fabricated by CNC machining a channel and chambers onto each of the two sides of a thermoplastic sheet (FIG. 44). The features in the thin plastic films include through holes are aligned to the corresponding features on the CNC machined layer to provide access to the pneumatic sandwich layer. Bonding is accomplished thermally but can also be performed ultrasonically, with solvents, and using adhesives. Similarly, the same features within the fluidic and pneumatic layers can also be fabricated by injection molding.

Valve subassembly—This subassembly is positioned between the pneumatic subassembly and the fluidic subassembly. In this construct, the valve assembly consists of an elastomeric membrane 202 that is 0.005" thick. When pneumatically activated, this layer will deflect to control flow of fluids (including air) within the fluidic layer. A top pressure sensitive adhesive layer 206 is used to attach the membrane to the top pneumatic layer. A bottom pressure sensitive adhesive layer is used to attach the membrane layer 206 to the fluidic layer. The pressure sensitive layers are patterned by laser cutting. The pressure sensitive adhesive layer can also be patterned by methods including die cutting or punching. The elastomeric membrane is from 0.005"-0.015" thick and the material can be rubbers such as silicone.

The valve was constructed by assembling the three subassemblies together. The fluidic assembly and pneumatic assembly are fastened together by thermal bonding. Similarly, the pneumatic and fluidic plates can be fastened together by the use of a number of mechanical fasteners including screws, rivets, thermal heat staking and ultrasonic welding.

These valves are normally open. Fluids will flow through the channel within the fluidic layer, up the through hole, into the valve body, out the $2^{nd}$ through hole and back into the channel within the fluidic layer. When a pressure is applied to the pneumatic channel, the pressure deflects the valve membrane and pushes this membrane against the valve seats and floor of the valve fluidic chamber. This seals off the path between the through holes and stops flow through the valve. The valve structure incorporates membrane and PSA elements that have high degrees of compliance such that, on assembly, their compression accommodates for any local variations in flatness of two parts being bonded. This accommodation enhances the ability to form effective seals around the valves.

An experiment was conducted to assess the valve sealing pressure. The pneumatic channels of the valve were connected to a pneumatic drive, VD. A volume of dyed liquid (water) was loaded into a portion of the fluidic channel that coupled to the valve. The input to the fluidic channel was connected to another pneumatic drive FD. The pressure of VD was set and held constant through the experiment. The pressure of FD was gradually increased until the fluid flow within the channel was observed. The pressure at which the fluid began to flow is the burst pressure of the valve for a given valve sealing pressure. The burst pressure for the valve for valve sealing pressures of 5, 15, and 22 psig were 3, 13.5 and 20 psig respectively. This data shows that a pneumatic sealing pressure of larger than 2 psig that of the fluidic drive pressure is acceptable for sealing. In the biochips of Examples 5 and 6, the valve sealing pressure is set to a common pressure (22 psig) for most of the process steps. This is effective in controlling multiple valves simultaneously and for controlling flow channels of up to 18 psig of pressure. Although a fixed valve drive pressure is adequate for most functions, a variable system allows the valve pressure to be increased (for cases in which the fluidic drive pressure requirements are high) and to be reduced (prior to opening the valves) to minimize any agitation of the fluids when the valve membrane is activated.

When the valve is used during vacuum process steps and a fluid is draw fluid through the valve, a vacuum also needs to be applied to both the fluidic and pneumatic line to maintain the valve in an open position. To close this valve, pressure is applied as above.

Figure 10:
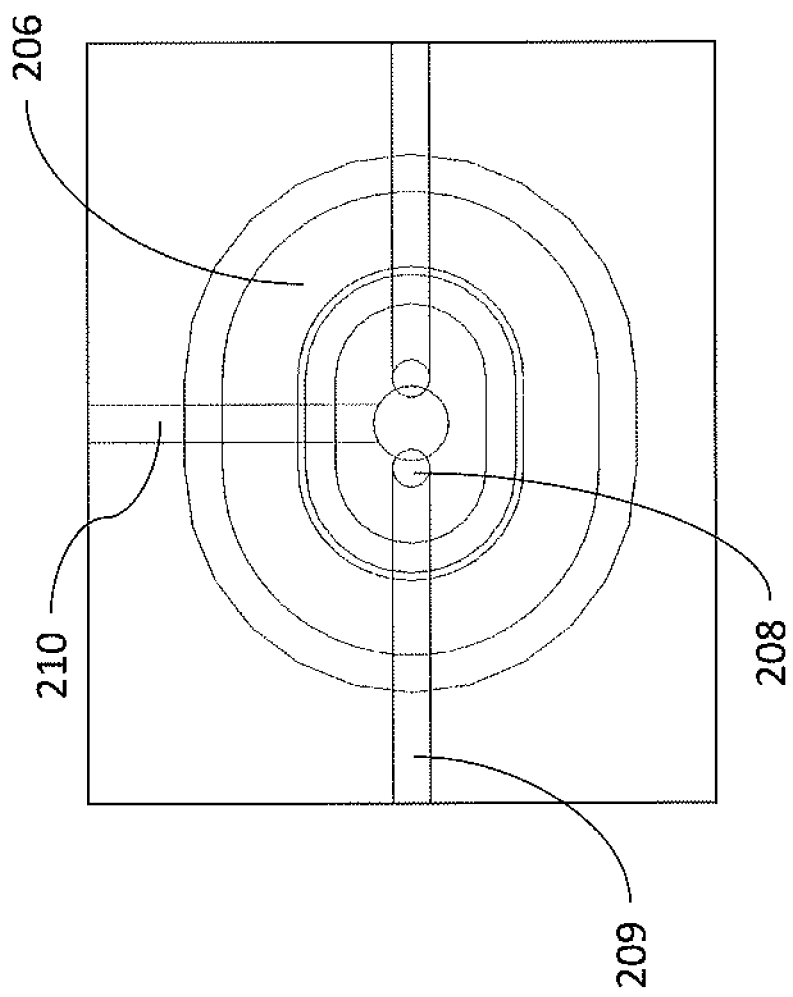
FIG. 10 is a top view schematic of an embodiment of an elastomeric membrane valve with PSA tape.
Figure 11:
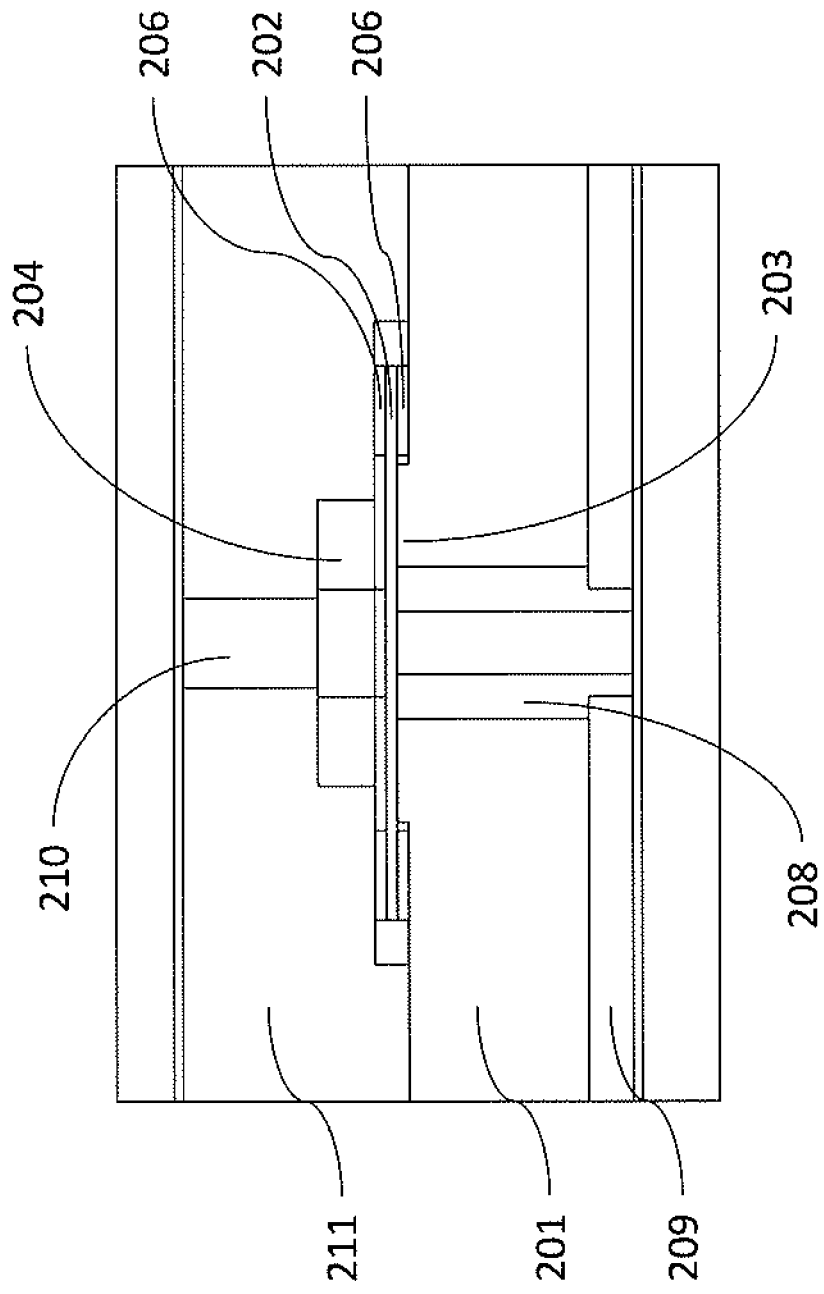
FIG. 11 is a cross-sectional view schematic of the valve of claim 10.

Although all of the valves in the biochips of Examples 4, 5, and 6 are in the normally open configuration, those valves and the several types of valves in this example can be designed in a normally closed configuration. For example, FIG. 10 is a top view of the PSA tape and elastomeric membrane valve for normally closed operation. FIG. 11 is the cross-sectional view of the PSA tape and elastomeric membrane valve for a normally closed configuration. The construction of this valve is different than that of FIGS. 8 and 9 in that the valve seats are raised such that they are in intimate contact with the valve membrane layer in the unactivated state. The valve membrane with the valve seats on fabrication are placed under tension during fabrication and assembly. To open the valve, a vacuum is applied to pull the valve membrane away from the valve seats. Note that all valves in this Example (except for the structure of FIGS. 10 and 11) are normally open. For some applications, it may be advantageous to incorporate one time use valves, namely valves that are not designed to be repeatedly opened and closed during the assay process, but rather which, for example, begin the process in an open state and close once during the assay process.

Figure 12:
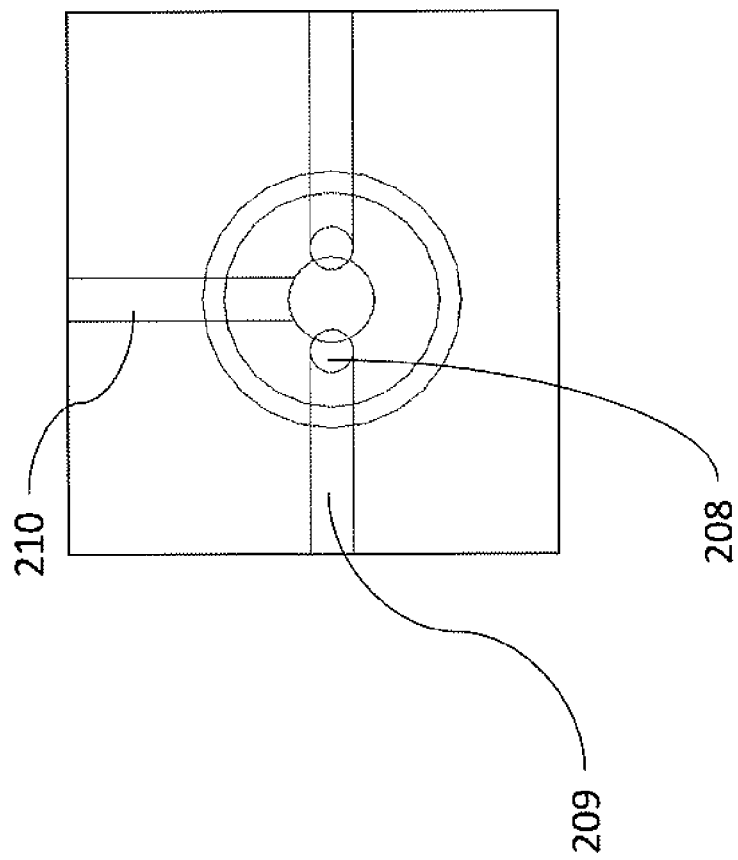
FIG. 12 is a top view schematic of an embodiment of a pneumatically actuated valve with a rigid valve membrane.
Figure 13:
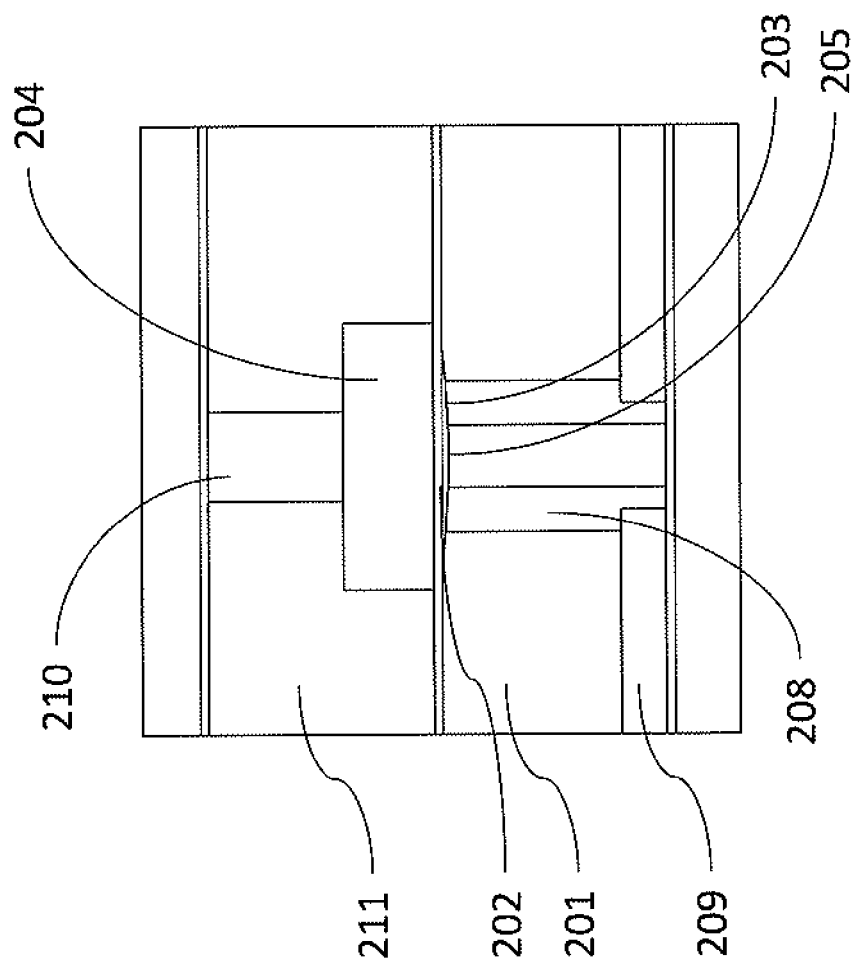
FIG. 13 is a cross-sectional view of the pneumatically actuated valve with rigid valve membrane of FIG. 12.

The top view of a pneumatically actuated valve with a rigid valve membrane with normally open configuration is shown in FIG. 12. A cross-sectional view of the pneumatically actuated valve with a rigid valve membrane for control of fluids and air is shown in FIG. 13. Components of the valve structure include a valve membrane 202, valve seats 203, pneumatic chamber 204, fluidic chamber 205, fluidic through holes 208, fluidic channel 209, and pneumatic channel 210. This valve is fabricated by assembling 3 components:

Fluidic subassembly. This subassembly contains a channel for fluid (liquid or air) flow. The channel is interrupted by a set of through holes 208 that pass through to the surface. These through holes form the valve seats 203 for the valve assembly. Alternatively, the channel can be routed along the top side of the fluidic plate and be interrupted as it passes though the valve. The channel ends form the valve seats for this assembly. This assembly is fabricated by injection molding the channels and through holes in a thermoplastic. In this case, the valve membrane 202 is a thin film thermoplastic film that is bonded. The fluidic chamber 205 of this structure is fashioned to the shape of the rigid membrane under full deflection to effect sealing.

Figure 72:
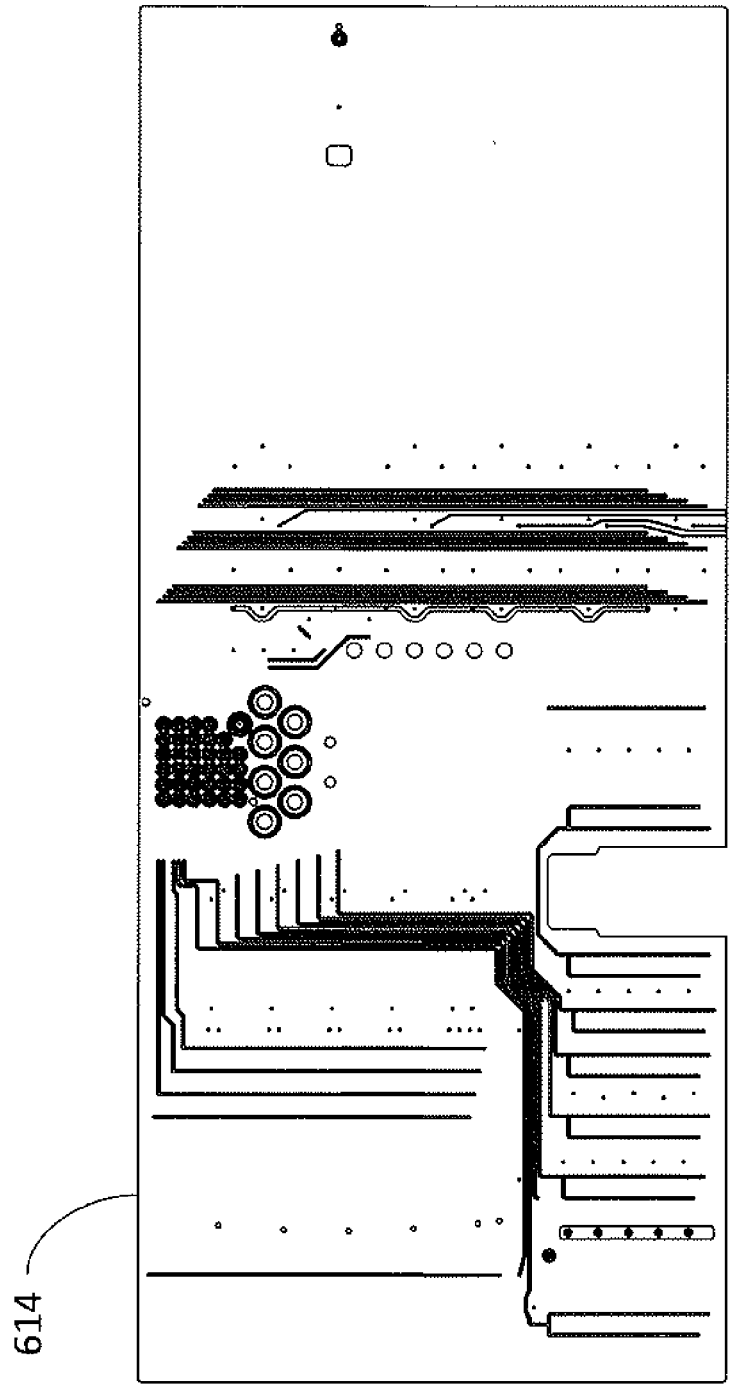
FIG. 72 is a top view schematic of an embodiment of a pneumatic plate of a pneumatic assembly in accordance with the present technology.
Figure 73:
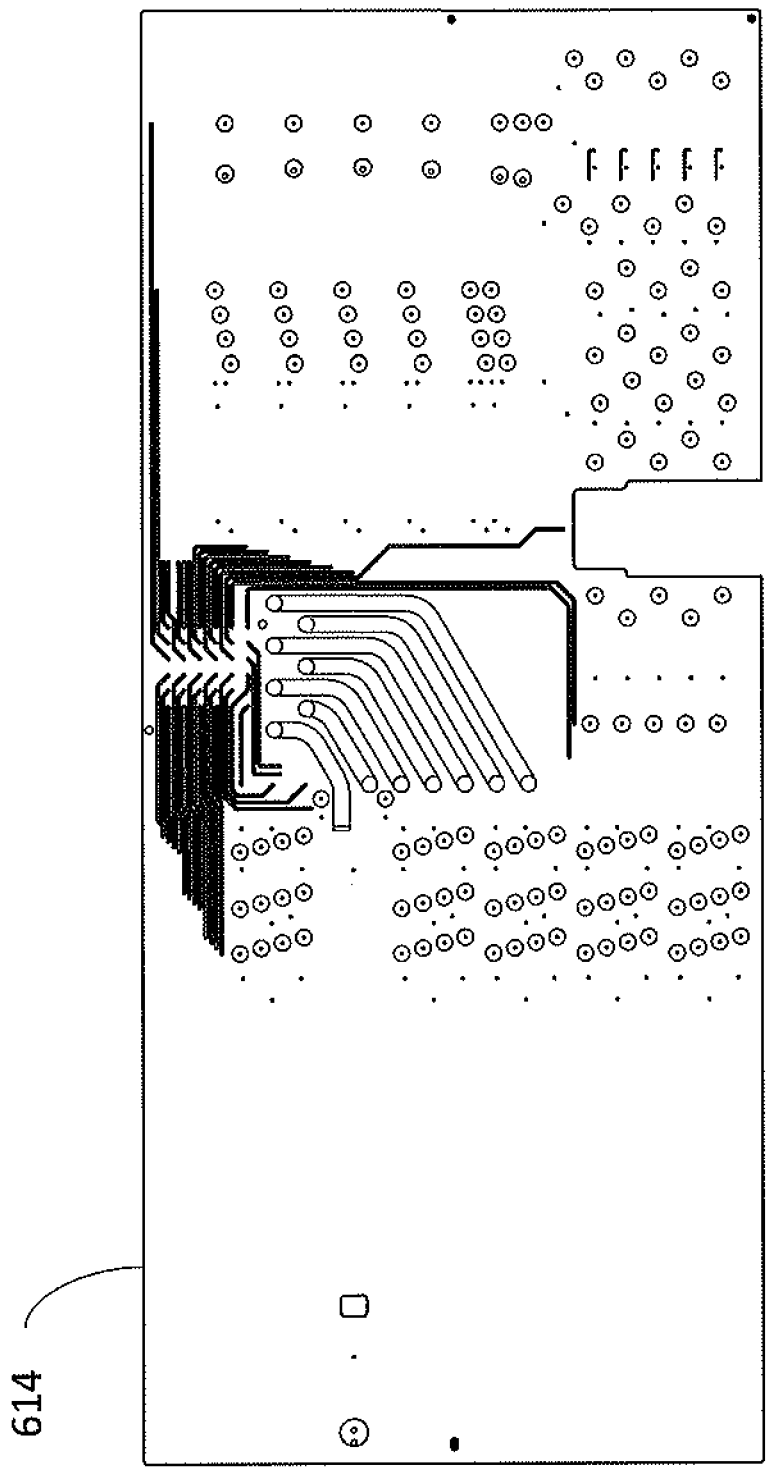
FIG. 73 is a bottom view schematic of the pneumatic plate of FIG. 72.

Pneumatic subassembly. This subassembly couples the pneumatic drive of the instrument to the fluidic subassembly to pneumatically drive fluids within the fluidic subassembly and to pneumatically activate valves within the biochip. The pneumatic channel couple the pneumatic drive to the valve chamber. This subassembly is fabricated by injection molding channel and chamber features in thermoplastic (FIGS. 72 and 73). The features in the thin plastic films include through holes are aligned to the corresponding features on the injection molded layer to provide access to the pneumatic subassembly. Bonding is accomplished thermally but can also be performed ultrasonically, with solvents, and using adhesives.

Valve subassembly. This subassembly located between the pneumatic subassembly and the fluidic subassembly. In this construct, the valve assembly consists of a thin thermoplastic film. The film can be between 10 to 250 microns thick. In Example 6, films of thermoplastic of 40 microns, 50 microns and 100 microns were used. When pneumatically activated, this layer deflects to control flow of fluids (including air) within the fluidic layer. The valve was constructed by assembling the three subassemblies together. The fluidic assembly and pneumatic assembly were bonded together thermally or by solvents. Alternatively, a double-sided adhesive can also be used to adhere the top and bottom assemblies together. The thin thermoplastic, rigid valve membrane is integral to the fluidic layer, a significant advantage during biochip assembly.

These valves are normally open. Fluids flow through the channel within the fluidic layer, up the through hole, into the valve body, out the $2^{nd}$ through hole and back into the channel within the fluidic layer. When pressure is applied to the pneumatic channel, the pressure deflects the rigid valve membrane and pushes this membrane against the valve seats and floor of the valve fluidic chamber to seal off the path between the through holes and stops flow through the valve.

An experiment was conducted to assess the valve sealing pressure by fabricating a valve using the methods above with a 100 micron membrane. The pneumatic channels of the valve were connected to a pneumatic drive VD. A volume of dyed liquid (water) was loaded into a portion of the fluidic channel coupled to the valve. The input to the fluidic channel was connected to another pneumatic drive FD. The pressure of FD was set and held constant through the experiment. The pressure of VD was gradually decreased from a high level 80 psig until the fluid within the channel is observed to flow. The valve sealing pressure required to hold an FD of 1, 2, 3, 4, and 5 psig was 14.6, 28, 54, 65.5, and 81.5 psig respectively. The rigid membrane used in this valve construction requires the application of a higher pressure to seal the fluid flows. Reducing the valve membrane thickness from 100 microns to 50 microns and 40 microns substantially reduced the requirements for pressure to seal against fluid flows. For vacuum operation in which fluids are drawn through the channels, a vacuum is applied to the valve to maintain it in an open position.

Figure 14:
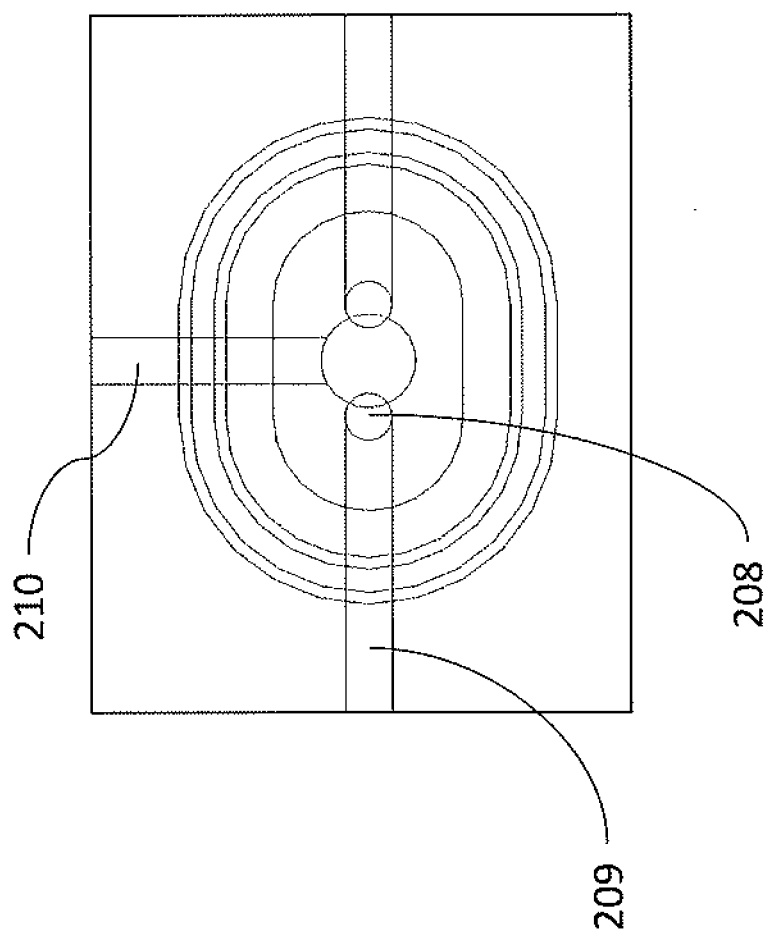
FIG. 14 is a top view schematic of an embodiment of a clamped elastomeric membrane valve.
Figure 15:
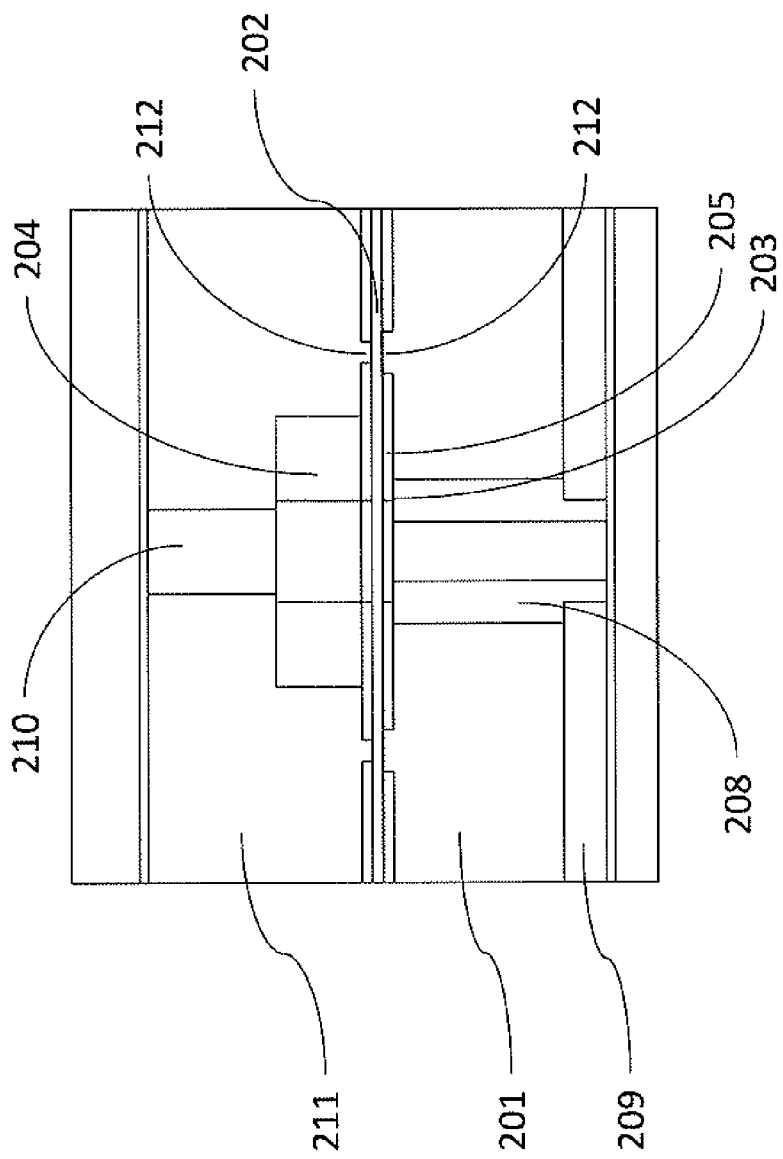
FIG. 15 is a cross-sectional view of the clamped elastomeric membrane valve of FIG. 12.

FIG. 14 shows a top view of a clamped, normally open elastomeric membrane valve. The cross-sectional view of this pneumatically actuated valve for control of fluids and air is shown in FIG. 15. Components of the valve structure include a valve membrane 202, valve seats 203, pneumatic chamber 204, fluidic chamber 205, fluidic through holes 208, fluidic channel 209, pneumatic channel 210, and compression rings 212. This valve is fabricated by assembling 3 subassemblies. An advantage of this structure is that it is quite simple and does not require PSA tape.

Figure 36:
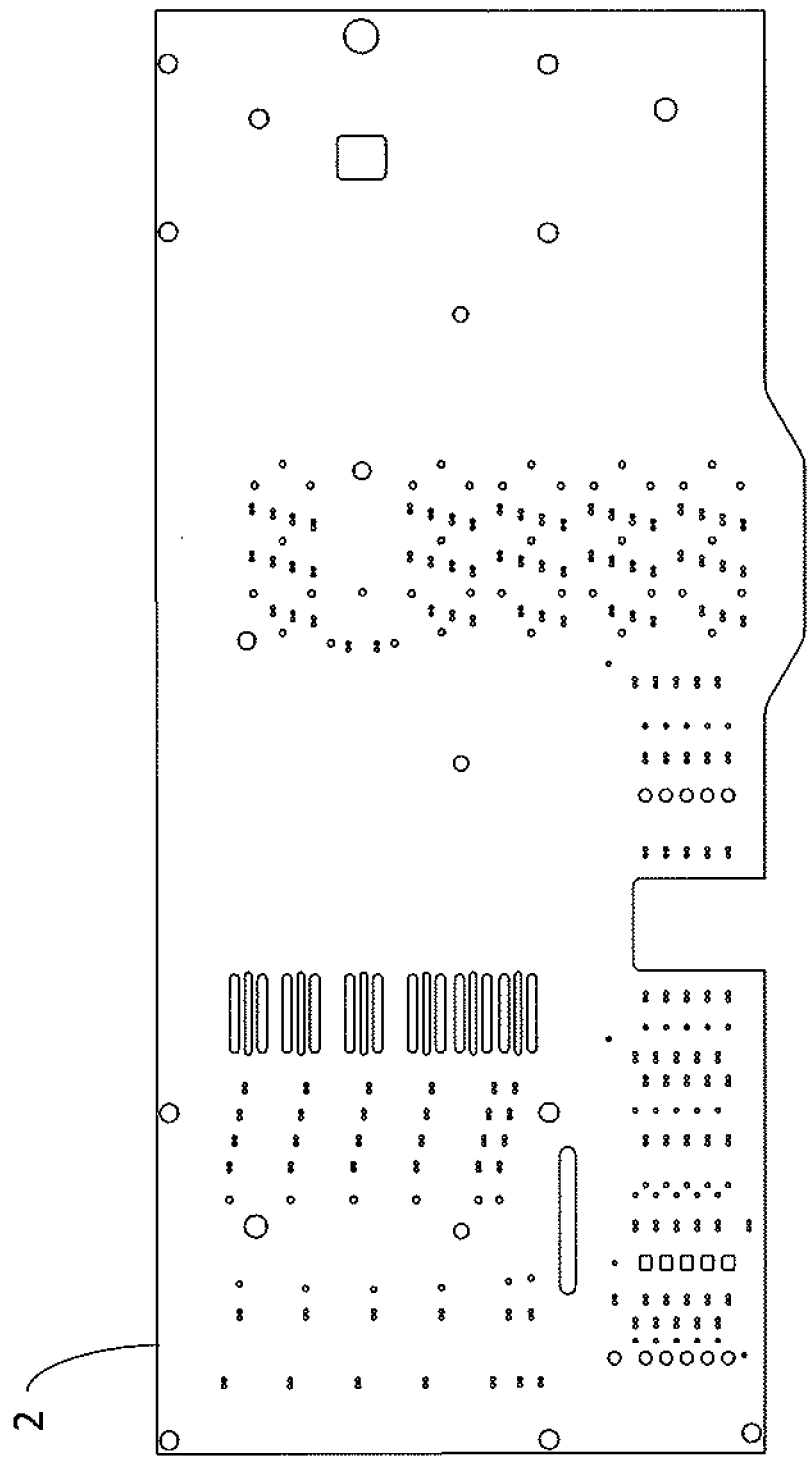
FIG. 36 is a top view schematic of an embodiment of a patterned thin film for attachment to the top of the fluidic plate.
Figure 37:
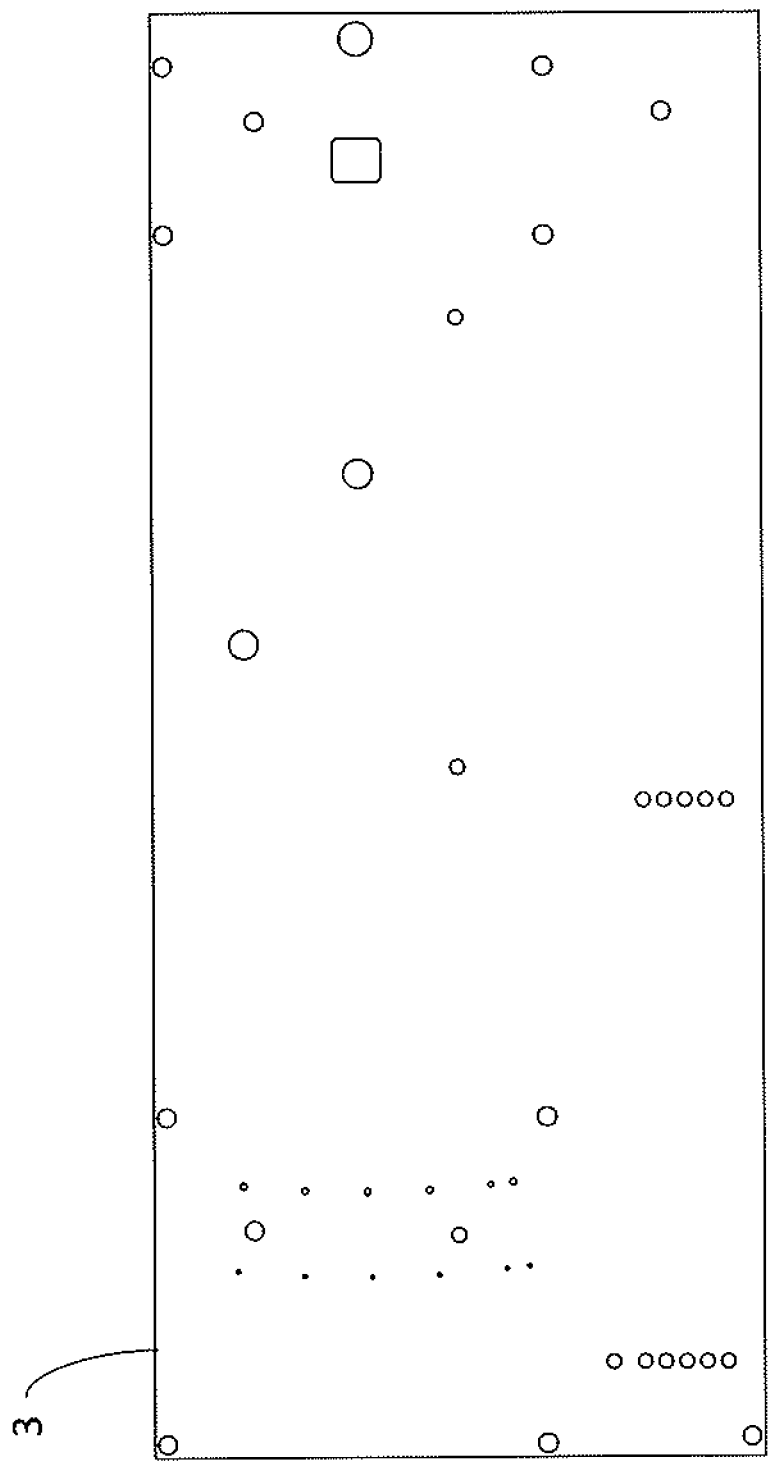
FIG. 37 is a bottom view schematic of an embodiment of a patterned thin film for attachment to the bottom of the fluidic plate.

Fluidic subassembly—This subassembly contains a channel for fluid 209 (liquid or air) flow. The channel is interrupted by a set of through holes 208 that pass through to the surface. At the surface these through holes form the valve seats 203 for the valve assembly. It is fabricated by CNC machining the channels and through holes in a thermoplastic sheet (FIG. 33) and covering both sides with thin plastic films (FIG. 36 and FIG. 37). In this case the thin film plastic is a thermoplastic film is bonded. The films have themselves been patterned by CNC machining, and have features including through holes that are aligned to the corresponding features on the CNC machined layer to provide access to the fluidic sandwich layer. Similarly, the same features within the fluidic and pneumatic layers can also be fabricated by injection molding. A set of valve membrane compression rings are formed around the fluidic chamber 212.

Pneumatic subassembly—This subassembly couples the pneumatic drive of the instrument to the fluidic subassembly to pneumatically drive fluids within the fluidic subassembly and to pneumatically activate valves within the biochip. The pneumatic channels 210 couple the pneumatic drive to the valve chamber. This subassembly is fabricated by CNC machining a channel and chambers onto each of the two sides of a thermoplastic sheet (FIG. 12). The features in the thin plastic films include through holes are aligned to the corresponding features on the CNC machined layer to provide access to the pneumatic sandwich layer. Bonding is accomplished thermally but can also be performed ultrasonically, with solvents, and using adhesives. Similarly, the same features within the fluidic and pneumatic layers can also be fabricated by injection molding. A set of valve membrane compression rings are formed around the pneumatic chamber 211. The compression rings of the fluidic and pneumatic chambers are coincident with each other and will align with each other.

Valve subassembly—This subassembly located between the pneumatic subassembly and the fluidic subassembly. In this construct, the valve assembly consists of a silicone membrane 202 that is 0.005" thick. When pneumatically activated, this layer will deflect to control flow of fluids (including air) within the fluidic layer.

The valve is constructed by assembling the three subassemblies together. The fluidic assembly and pneumatic assembly are fastened together by thermal bonding. Similarly, the pneumatic and fluidic plates can be fastened together by the use of a number of mechanical fasteners including screws, rivets, thermal heat staking, and ultrasonic welding. The pneumatic and fluidic layers are bonded such that the membrane layer between the compression rings (212) is compressed. The degree of compression will range from 5% to 60% and is a function of the durometer and thickness of the valve membrane. The degree of compression is sufficient when the pneumatic drive is sealed within the pneumatic chamber and the fluids do not leak from the fluidic chambers.

Venting Structures

The microfluidic component of the apparatus uses venting membranes to vent air and to serve as a barrier to fluid flows. The venting membranes that were used in the biochips of Example 5 and 6 were selected based on the surface tension of the liquid being transported and the surface free energy. When a significant differential exists between the two, the contact angle between the solid surface and the liquid is high and liquid droplets will be repelled from the membrane surface and not foul the membrane. Another consideration is the air-flow rates through the membrane. It must be sufficiently high to allow unrestricted venting of air. Typically, for a given material, the differential between surface free energy and surface tension increases with decreasing pore size however, the air flow rate is inversely proportional to the port size. For example, the surface tension of water is 73 dynes/cm, isopropyl Alcohol 22 dynes/cm, and for oil 30 dynes/cm.

Venting membranes used in the biochip include those made of: Polytetrafluoroethylene (PTFE), a widely used material in medical venting and gas filtration. It is an inert material that offers excellent flow properties and high chemical resistance. Dimensional instability of cut shapes of this membrane type can cause difficulties in robotic handling in over-molding operations. PTFE is incompatible with gamma or E-beam sterilization because chain scission causes loss of integrity when the material is exposed to ionizing radiation; Polyvinylidene fluoride (PVDF) is a durable material that offers good flow properties and broad chemical resistance. It is available in both natural and super-hydrophobic forms; Ultra-high molecular weight polyethylene (UPE) is a more recent entry into the medical venting and gas filtration market. It is a naturally hydrophobic material that offers excellent flow properties and broad chemical resistance; Modified acrylic membrane treated to be hydrophobic is an economical choice for venting applications. It is oleophobic, hydrophobic, and chemically compatible.

Figure 16:
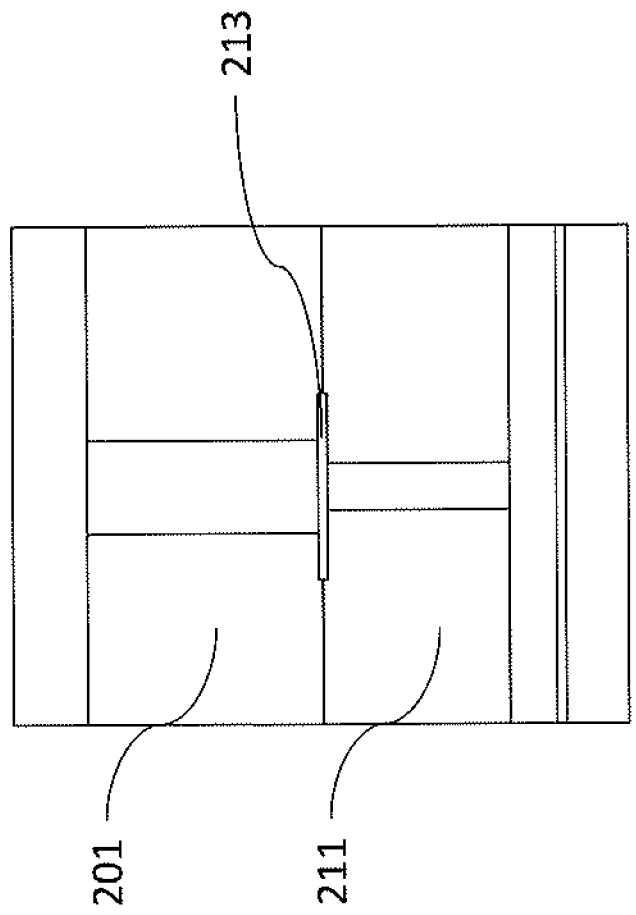
FIG. 16 is a cross-sectional view schematic of a vent membrane configuration used in an embodiment of a biochip in accordance with the present technology.
Figure 17:
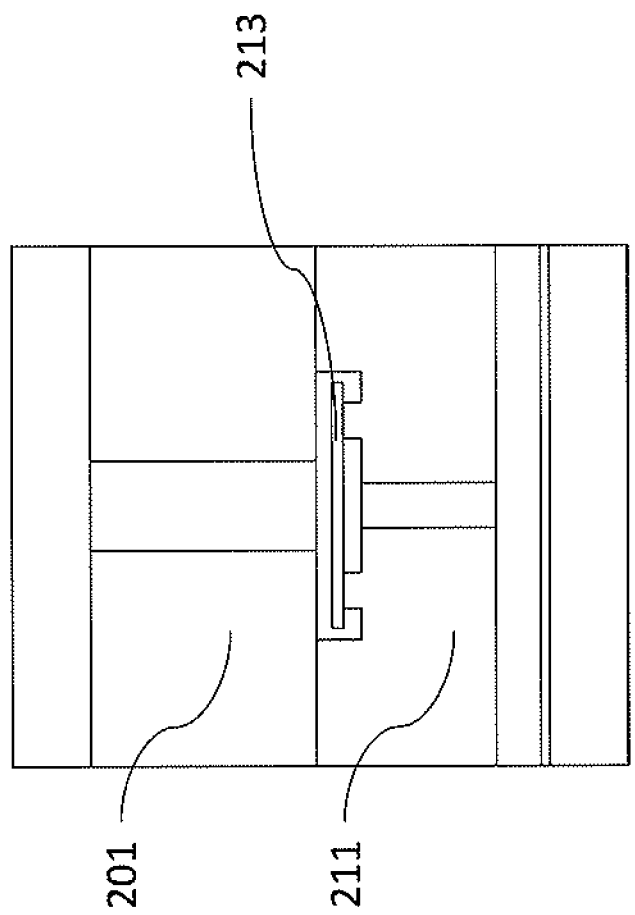
FIG. 17 is a cross-sectional view schematic of a vent membrane configuration used in another embodiment of a biochip in accordance with the present technology.

FIG. 16 shows a cross sectional view of a vent membrane configuration used in the biochips of Example 5. The vent membrane (FIG. 16, 213) is incorporated into the structure placing the membrane between the pneumatic and fluidic layers and by thermal bonding. FIG. 17 shows a cross sectional view of a vent membrane configuration (FIG. 17, 213) that was used in the biochips of Example 6. In this vent membrane configuration, the vent membrane is welded to the fluidic layer with a weld ridge.

Example 3

Biochip Interface

Figure 58:
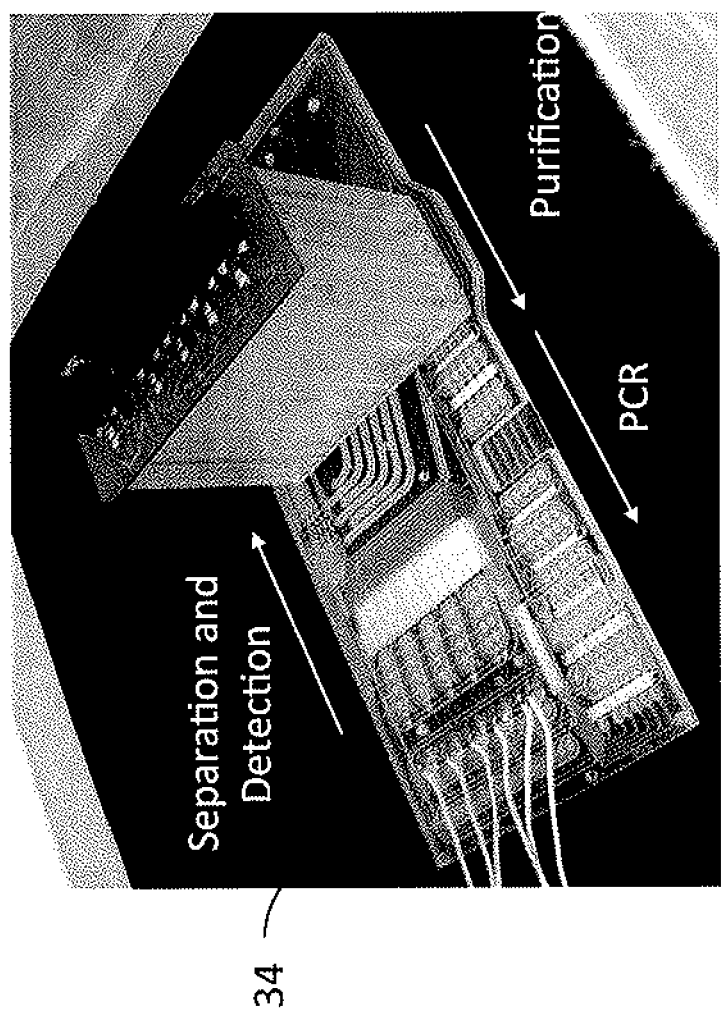
FIG. 58 is a photograph of an embodiment of a biochip assembly in accordance with the present technology and including arrows to indicate the direction of process flows.

The biochips of the invention interface with an instrument. The instrument provides all the subsystems required for the completion of sample analyses including high and low voltage power subsystems, thermal cycling subsystems, pneumatic subsystems, magnetic subsystems, mechanical subsystems, optical subsystems, ruggedization subsystems, process control subsystems, and computer subsystems as shown in FIG. 58. The instrument to biochip interface will involve one or more of these subsystems, depending on the microfluidic drive and the series of processes to be performed within the biochip. In the case of the examples herein, the interface of the biochips and the instrument are pneumatic, electrical, optical, and mechanical as follows:

Pneumatic Subsystem Interface.

Figure 18:
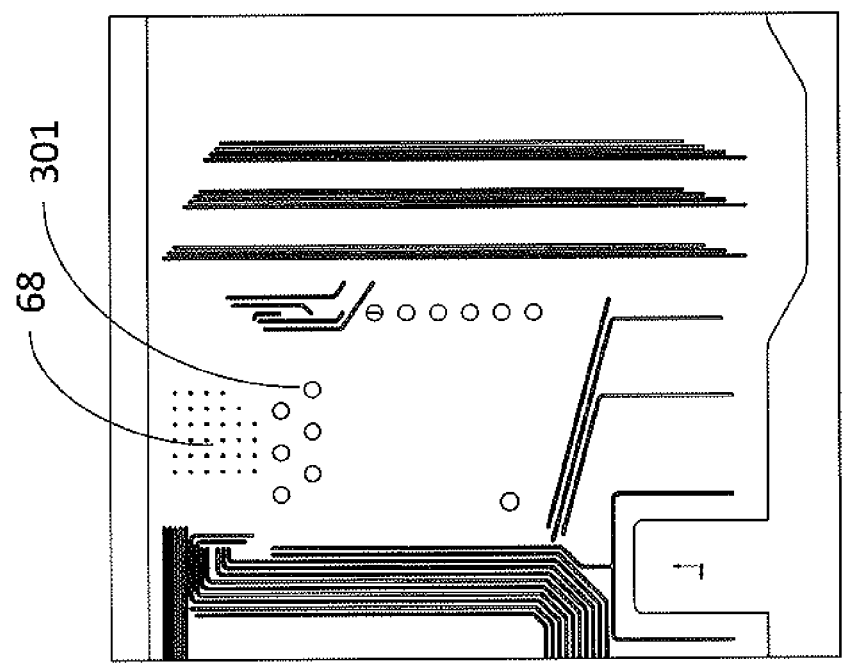
FIG. 18 is a top view schematic of a pneumatic plate with the manifold and surrounding areas expanded of an embodiment of a biochip in accordance with the present technology.

The pneumatic subsystem is coupled to the biochip through a pneumatic manifold. FIG. 18 shows the pneumatic manifold area for the biochip of Example 5 and consists of a series of pneumatic ports that are located on the top side of the pneumatic plate. Five types of ports are incorporated with the pneumatic interface:

Low flow drives. Low flow ports are used to supply pneumatic for activation of valves and drive of fluidics through the biochip.

High flow drives. High flow ports are used to supply air required for processes such as agitation by bubbling and drying of the purification membrane, requiring flows of up to 19 SLPM. The port sizes are enlarged to minimize pressure drops.

High pressure drive. This port is used to supply up to 400 psig required for sieving matrix filling. Condensate ports. Condensate generated by mechanical pumps within the instrument can optionally be driven into a chamber of the biochip through the pneumatic interface.

Instrument test ports. Test ports can be incorporated into the pneumatic manifold for testing of the instrument pneumatic system and confirming alignment of the pneumatic manifold of the instrument to that of the biochip.

The pneumatic ports are positioned in an array, with 34 low flow ports and 7 high flow ports. The location of this pneumatic manifold was selected based in part on the following considerations:

Minimizing the surface area of the interface site. The more compact the pneumatic interface region, the less that local shrinkage and warping during injection molding will interfere with the interface, allowing improved alignment.

Collecting all pneumatic ports at a single interface site. This approach was taken to simplify the instrument, an advantage in a system that is ruggedized and will be utilized outside the laboratory. Typically, the single interface will be centrally located within the biochip footprint, but it may also be located at an end of the biochip. Alternatively, multiple interfaces could be distributed across the biochip. In the biochips of Examples 5 and 6, the pneumatic ports are centralized in one location to allow for a compact coupling point between the instrument and biochip. This organization and positioning of the manifold simplifies routing of the pneumatic lines within the biochip as compared to either having decentralized ports or having all ports located at an extreme end of the biochip. This also increases the tolerance of the alignment between the manifold and the pneumatic ports and simplifies routing of the pneumatic tubing within the instrument.

Location of ports on the biochip based on feature density—There are areas on the fluidic and pneumatic plates where the feature density is low. It is optimal to locate the pneumatic manifold in these areas when possible. In general, optimal use of space on the biochip (i.e., the rational packing of all microfluidic and macrofluidic features) is important to maximize the feature density and process complexity of a biochip of given dimensions. In the biochips of Examples 5 and 6, the pneumatic ports are located on the top side of the pneumatic layer. Similarly, the pneumatic ports can also be located on the bottom side of the fluidic layer and be coupled to the instrument through the chip holder. The absolute location of the ports is determined by feature density, functional utility, and ease of design. In the biochips of Examples 5 and 6, the thermal cycling regions are located on the bottom side of the fluidic subassembly, requiring clamping pressure from above to establish efficient thermal contact with the thermal cycler. Accordingly, the centralized pneumatic ports were positioned on the top side of the pneumatic subassembly such that a single clamping mechanism could function to simultaneously interface with the biochip thermally and pneumatically.

Closed system—As noted above, the biochips of the invention are closed systems such that all liquids are located within the biochip during and after processing. Vent membranes (as described in Example 2) are used to block fluid from inadvertently flowing from the biochip into the pneumatic manifold of the instrument.

Figure 19:
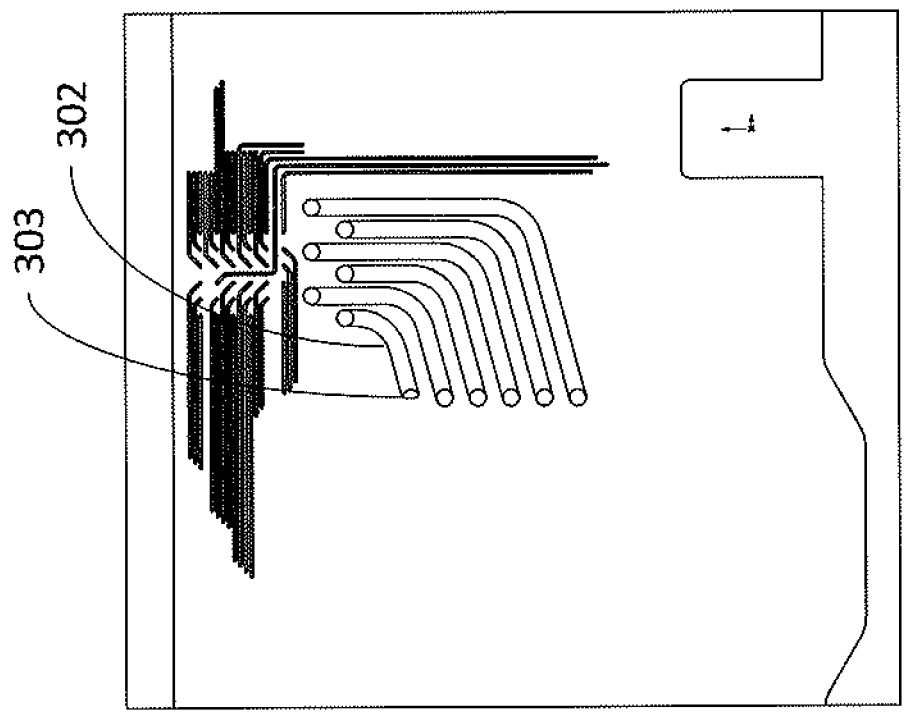
FIG. 19 is a bottom view schematic of a pneumatic plate with the manifold and surrounding areas expanded of an embodiment of a biochip in accordance with the present technology.
Figure 20:
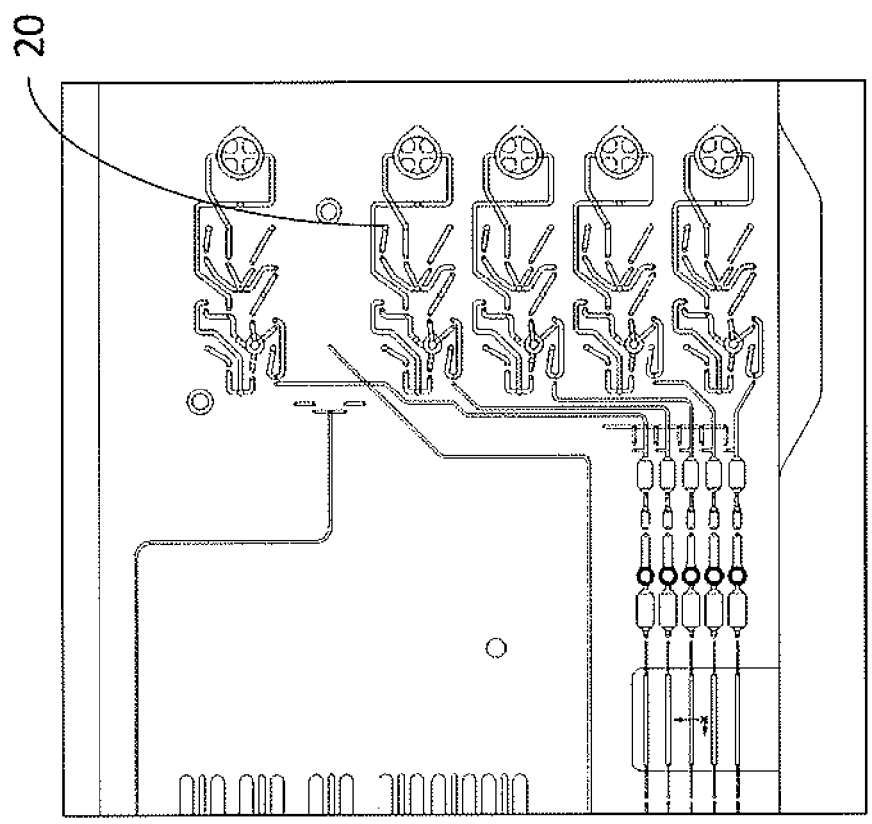
FIG. 20 is a transparent view schematic of a fluidic plate with the purification region and surrounding areas expanded of an embodiment of a biochip in accordance with the present technology.
Figure 39:
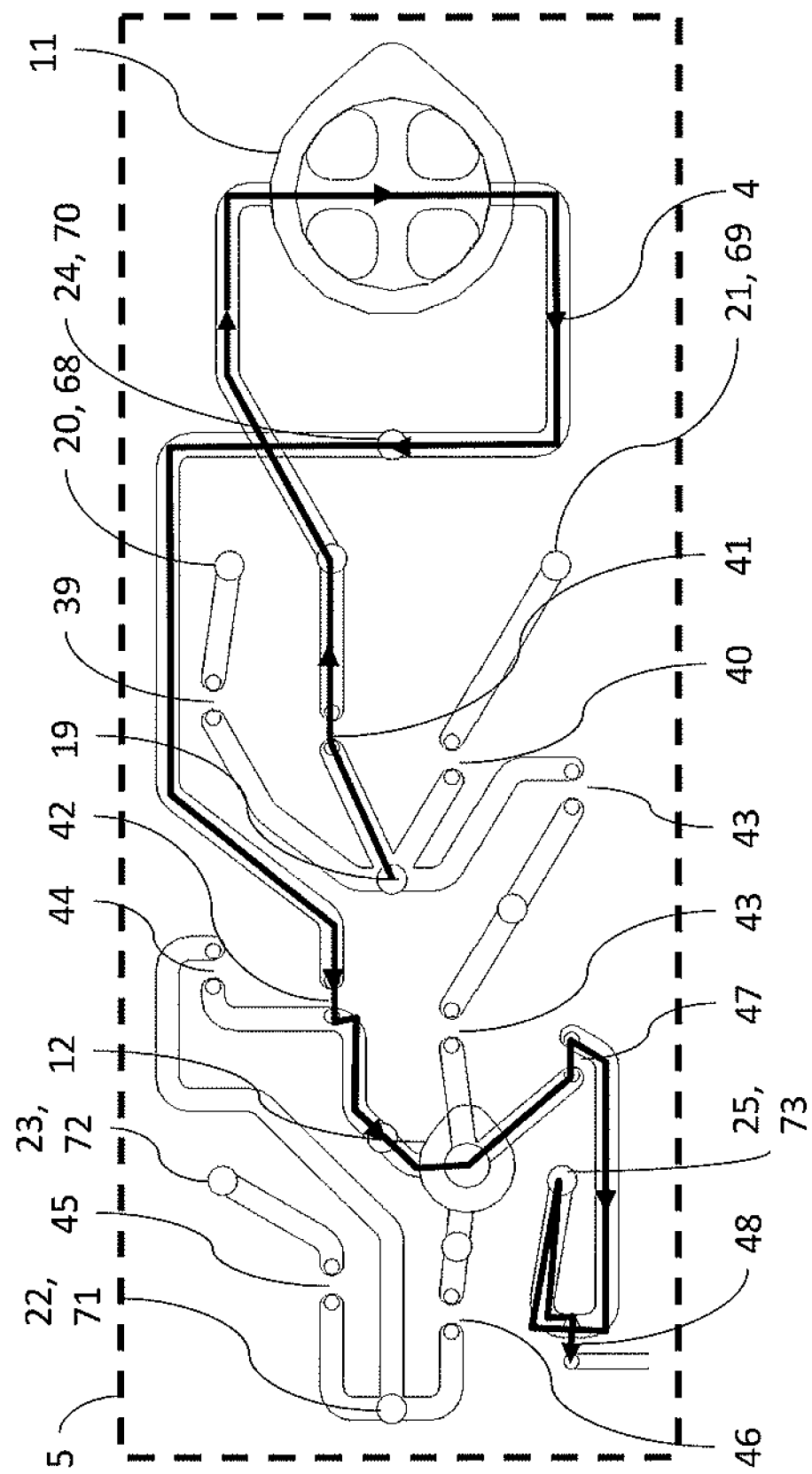
FIG. 39 is a top expanded view schematic of the fluidic plate of FIG. 38 showing a portion of the path through a purification region.
Figure 47:
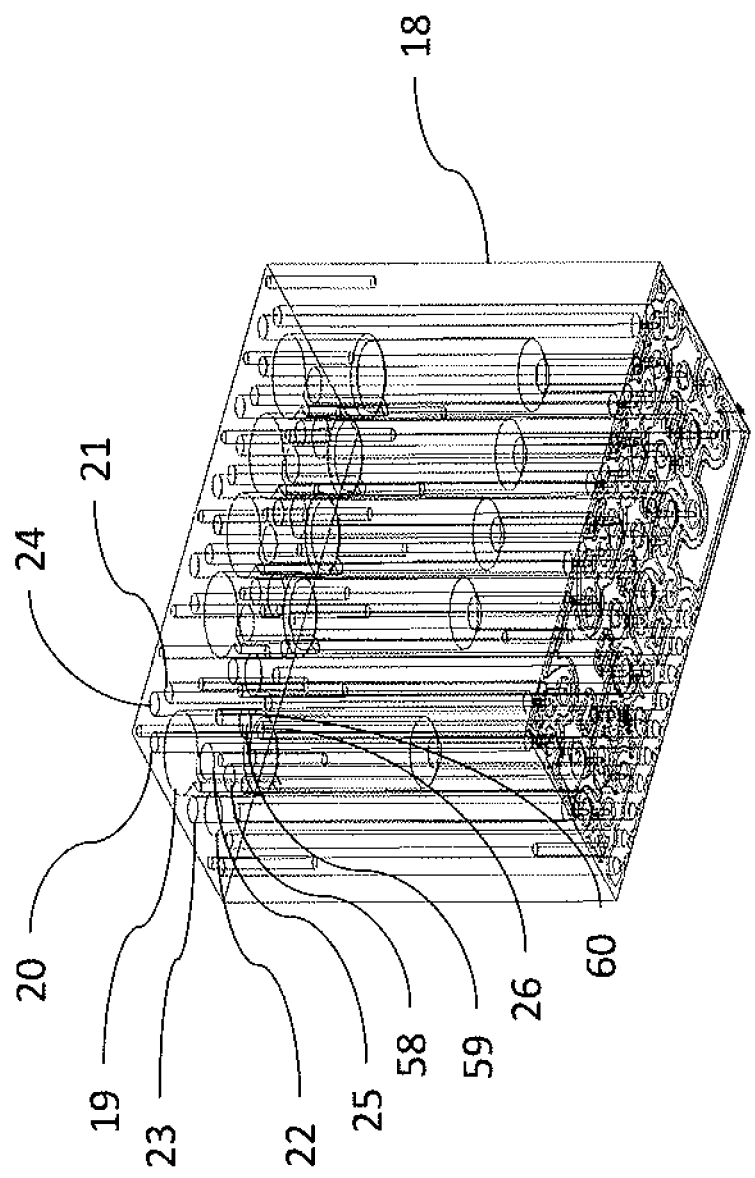
FIG. 47 is a transparent view schematic of an embodiment of macrofluidic block included in an embodiment of a macrofluidic processing subassembly.
Figure 48:
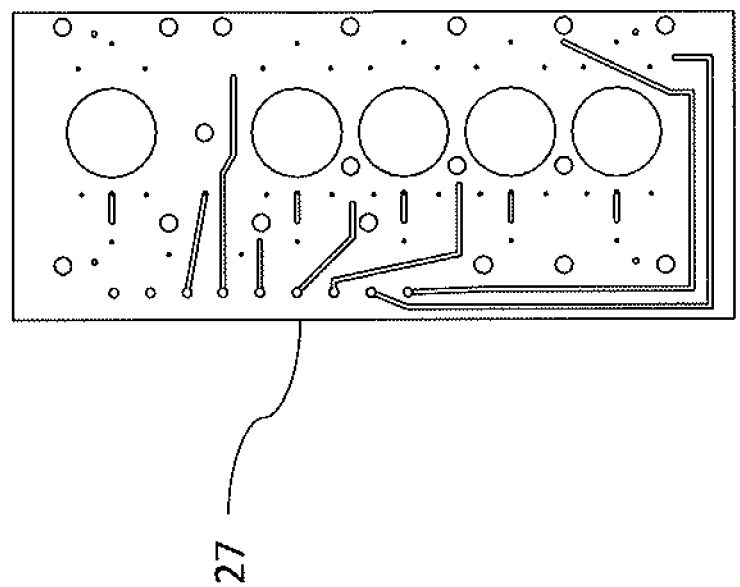
FIG. 48 is a top view schematic of an embodiment of a top layer of a cover to the macrofluidic block.

As an illustration of pneumatic flow and the pneumatic manifold, the approach to driving fluids within the macrofluidic processing subsystem for the "lysis step" of Example 5 will be presented. To effect this step, the lysis drive line DL1 (FIG. 39, 68) was activated to drive the lysis solution from the lysis reagent chamber (FIG. 39, 20) into the swab chamber (FIG. 39, 19). The process controller activated the solenoid relay on the instrument which applied the desired pressure on the drive line DL1 port on the pneumatic interface (FIG. 39, 20). Air is driven through the pneumatic interface at the DL1 port (FIG. 18, 301) of the pneumatic manifold, along pneumatic channel of the pneumatic plate (FIG. 18, 302) to the microfluidic interface port within the pneumatic plate (FIG. 19, 303). This interface port routed the pneumatic drive pressure through the pneumatic channels within the macrofluidic processing block (FIG. 47, 26) and into the cover of the macrofluidic processing subassembly (FIG. 48, 27). The cover in turn routed the pneumatic drive along a channel (FIGS. 48 and 53, 304) into the lysis reagent chamber (FIG. 47, 20). Taken together, the resultant step is the transfer of the lysis reagent from the lysis reagent chamber through the fluidic subassembly, and ultimately, to the swab chamber (FIG. 20, 20).

Similarly, if the reagents within the chamber are sealed by foils as in Example 1, then the pneumatic drive is applied in a two step action, where the first step is to generate a pulse to burst the foil, and the second step is similar to the non-RSR illustration above.

High Voltage Subsystem Interface

The high voltage subsystem is coupled to the biochip through a set of electrode pins and a wiring harness. Alternatively, a set of etched thin metal electrodes can also be fabricated. In this setting, electrode pins are inserted into the anode and cathodes by press fitting into the biochip. The electrode pins make contact to electrode strips located on the top of the pneumatic subassembly and also inserted by press fitting. This electrode strip is coupled to the instrument by a set of spring loaded electrodes on the instrument. The electrode strips are fabricated of Beryllium Copper (BeCu), a high performance metal which can be fabricated into a wide variety of components. Its mechanical and electrical properties make it the ideal material for EMI/RFI shielding products. The electrode strip can also be fabricated from other metals.

Optical Subsystem Interface

As described in patent application Ser. No. 12/396,110, published as 2009/00229983 entitled "Ruggedized Apparatus for Analysis of Nucleic Acid and Proteins," and Ser. No. 12/080,745, published as 2009/0020427 entitled Plastic Microfluidic Separation and Detection Platforms," both of which are incorporated herein by reference, the laser is coupled to the separation and detection window of the pneumatic-valve-fluidic stack (Examples 5 and 6) through an opening in the chip holder. A set of photodiodes is used to enable lane finding of the lanes within the separation and detection biochip.

Thermal Subsystem Interface

The thermal cycler and biochip are positioned such that the thermal cycling chambers are centered within the TEC elements, as described in application Ser. No. 12/080,746, published as 2009/0023603 entitled "Methods for Rapid Multiplexed Amplification of Target Nucleic Acids," which is incorporated herein by reference. A clamping force of 90 lbs is required to achieve good contact between the thermal cycling chambers and the TEC to accurately generate the temperature cycling profiles. The clamping pressure is generated by the clamp arm and compression of a silicone pad. The clamping arm exerts the pressure required to push down on the silicone pad.

Figure 21:
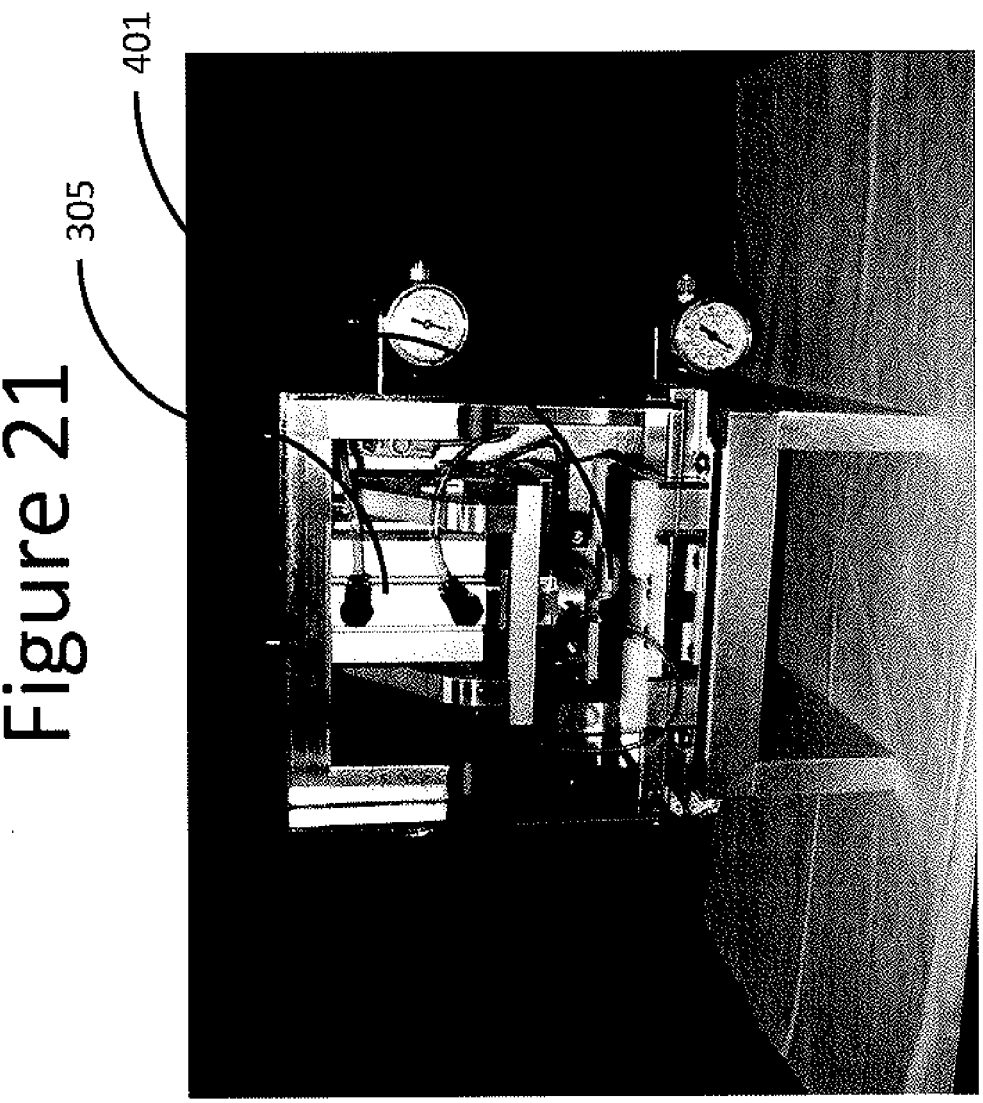
FIG. 21 is a photograph of a pneumatically activated cylinder used to exert a controlled force onto a biochip.
Figure 22:
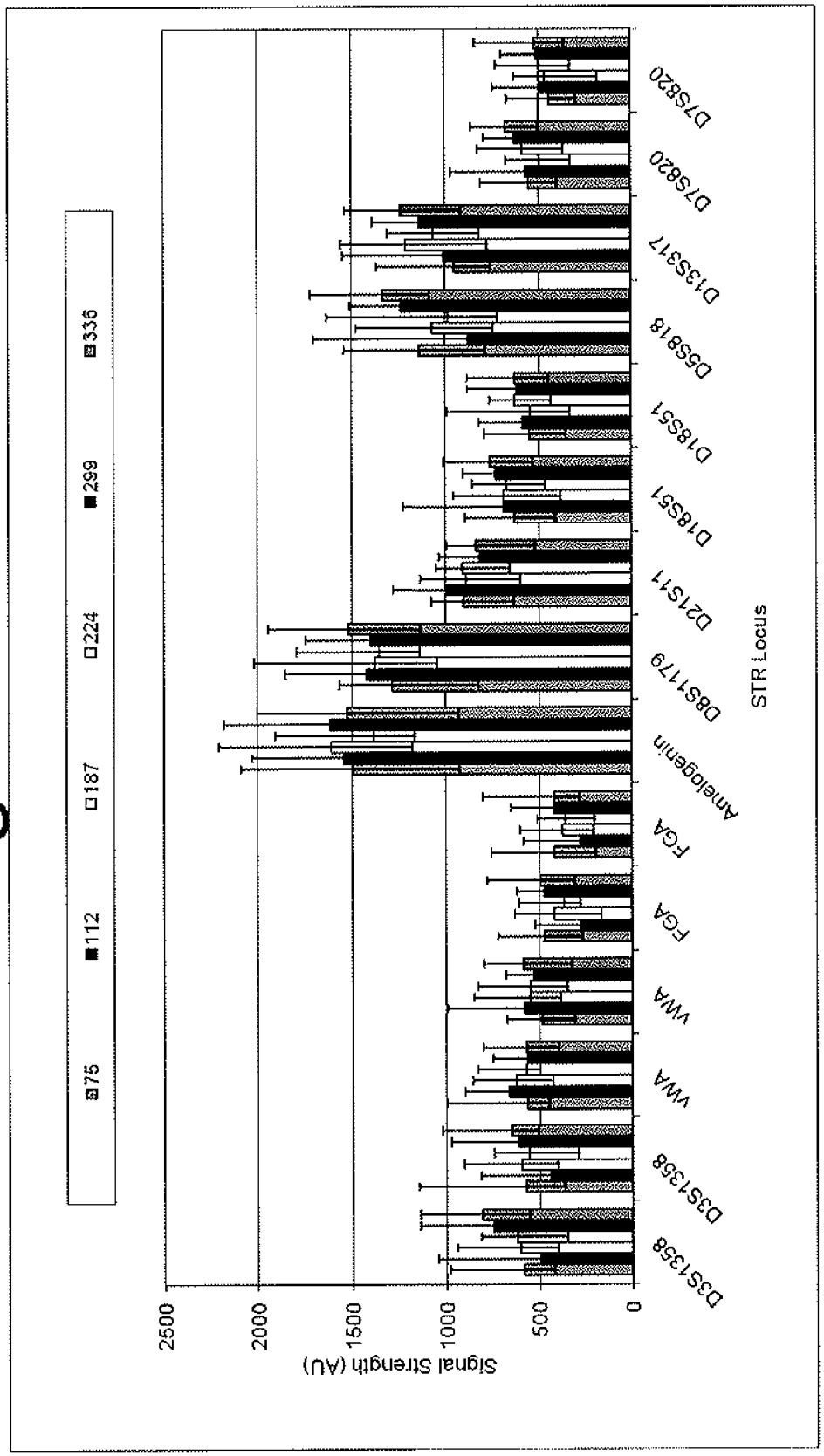
FIG. 22 is a bar graph comparing signal strength at each STR locus for various pressures applied to the biochip by the pneumatically activated cylinder of FIG. 21. In the graph, pressures of 75, 112, 187, 224, 299, and 336 psig were applied, and, for each locus, signal strengths are recorded for each pressure (increasing pressures from left to right).

An experiment to assess the clamping force required for efficient thermal transfer was performed. A pneumatically activated cylinder (FIG. 21, 305) was used to exert a controlled force onto a PCR biochip (FIG. 21, 401). At each level of force, the PCR was performed following standard protocols (See, Giese, H., et al. (2009). "Fast multiplexed polymerase chain reaction for conventional and microfluidic short tandem repeat analysis." *J Forensic Sci* 54(6): 1287-96, which is incorporated herein by reference), and STR profiles were analyzed. The data showed that at a force of below 75 lbs, inconsistent STR profiles were generated. When forces above 75 lbs were applied, consistent and effective amplification was observed (FIG. 22).

The separation and detection subsystem is coupled to the heaters on the chip holder to maintain a temperature of 50° C. Temperature uniformity is important and the clamping of the biochip onto the heater plates contributes to the establishment and maintenance of temperature uniformity.

Mechanical Alignment

To align all biochip to instrument interfaces, the biochip is placed onto the chip holder of the instrument containing a set of mechanical alignment guides. These guides provide alignment of the interface features of the biochip to the instrument to within ±0.020". The guides register the chip at three locations along the edge of the pneumatic plate, near to the corners to locate the origin and orientation. In this configuration the guides have a cutout to locate only against the pneumatic layer (this minimizes any effect of slight misalignments between the fluidic and pneumatic plate layers).

Example 4

Figure 23:
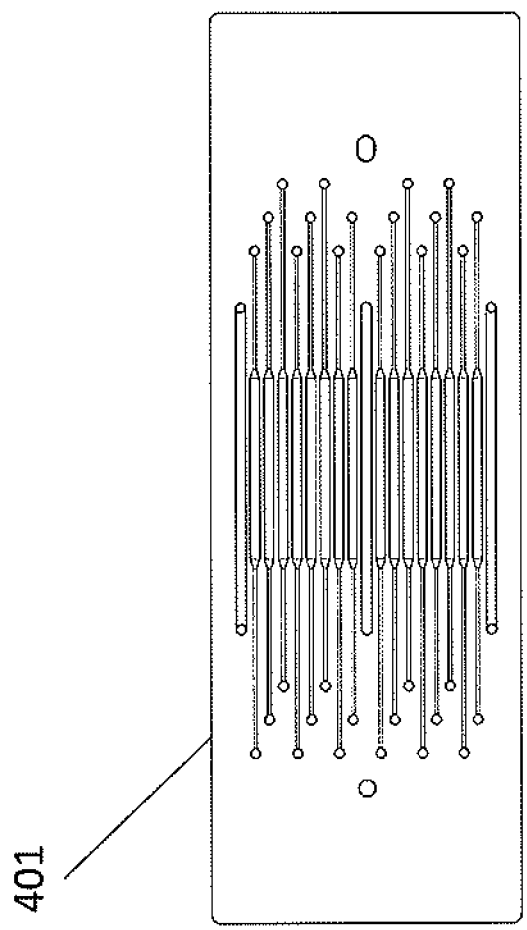
FIG. 23 is a top view schematic of an embodiment of an injection molded biochip in accordance with the present technology.

CNC-Machined Biochip that Accepts and Mixes DNA and PCR Reagents and Performs 16-Plex Amplification Reaction in 17 Minutes for Sixteen Samples Simultaneously The PCR biochip 401 of FIG. 23 was injection molded in a slide format and successfully tested for rapid multiplexed PCR. This biochip is 25 mm×75 mm×1.1 mm thick. The system allows multiplexed amplification on STR fragments from a single genome equivalent of human DNA (6 pg of DNA, essentially a single-copy limit of detection) as described in Giese, H., et al. (2009). "Fast multiplexed polymerase chain reaction for conventional and microfluidic short tandem repeat analysis." *J Forensic Sci* 54(6): 1287-96.

Figure 24:
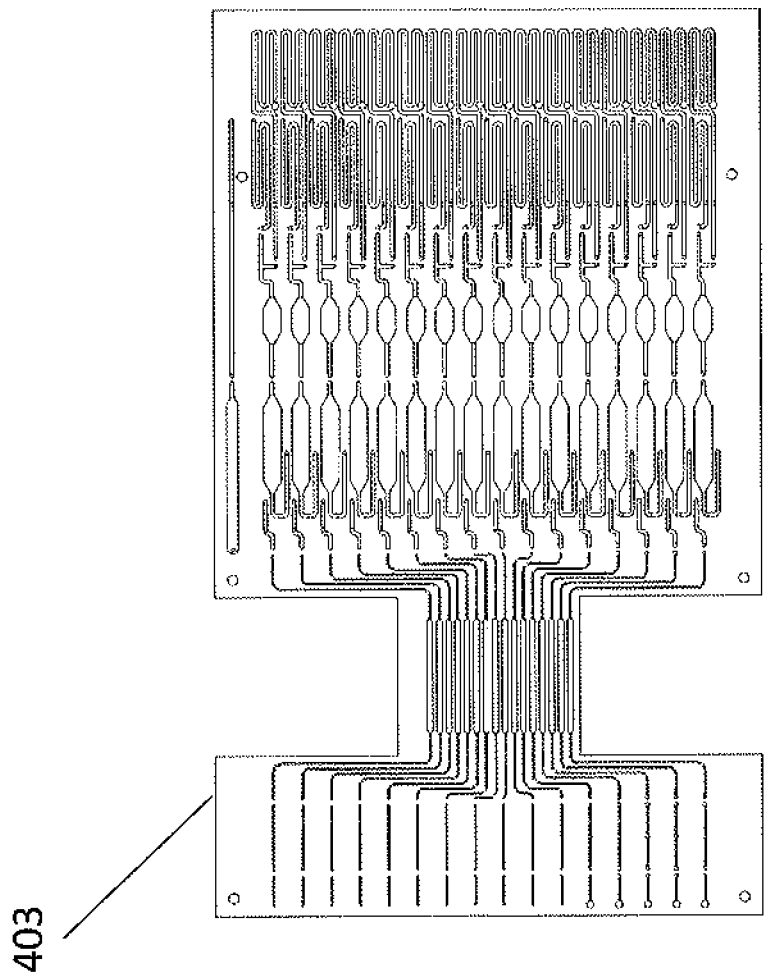
FIG. 24 is a top view schematic of an embodiment of fluidic layer 1 of a biochip in accordance with the present technology.
Figure 25:
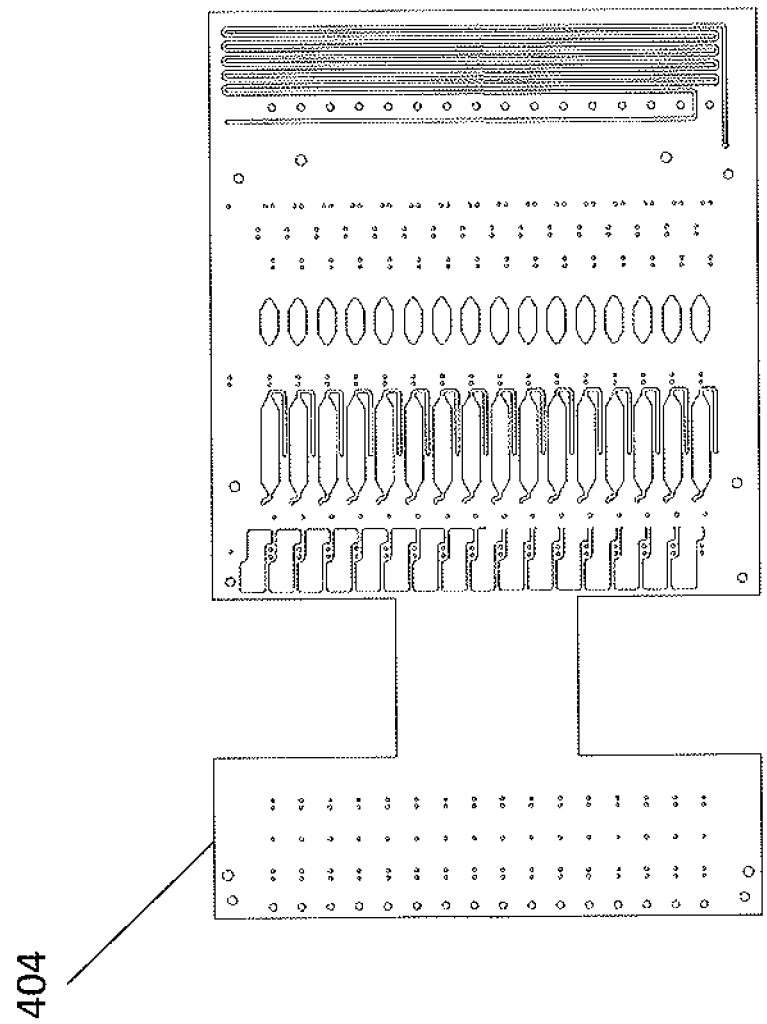
FIG. 25 is a top view schematic of an embodiment of a fluidic layer 2 of a biochip in accordance with the present technology.
Figure 26:
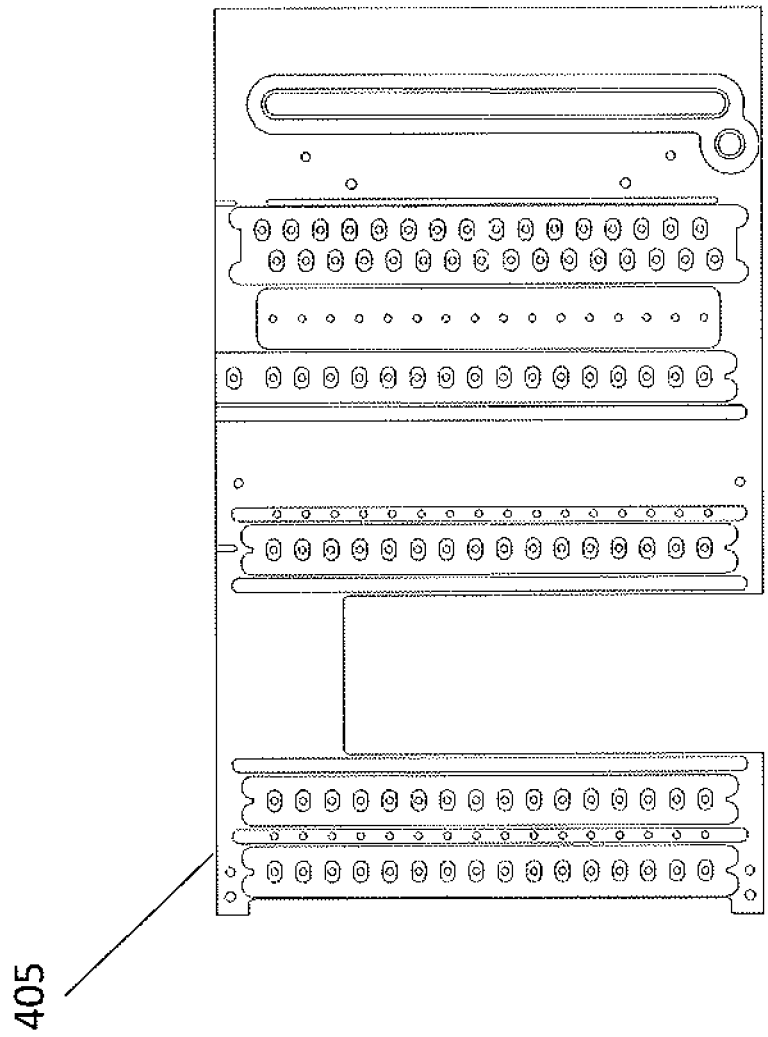
FIG. 26 is a top view schematic of an embodiment of a pneumatics layer 1 of a biochip in accordance with the present technology.
Figure 27:
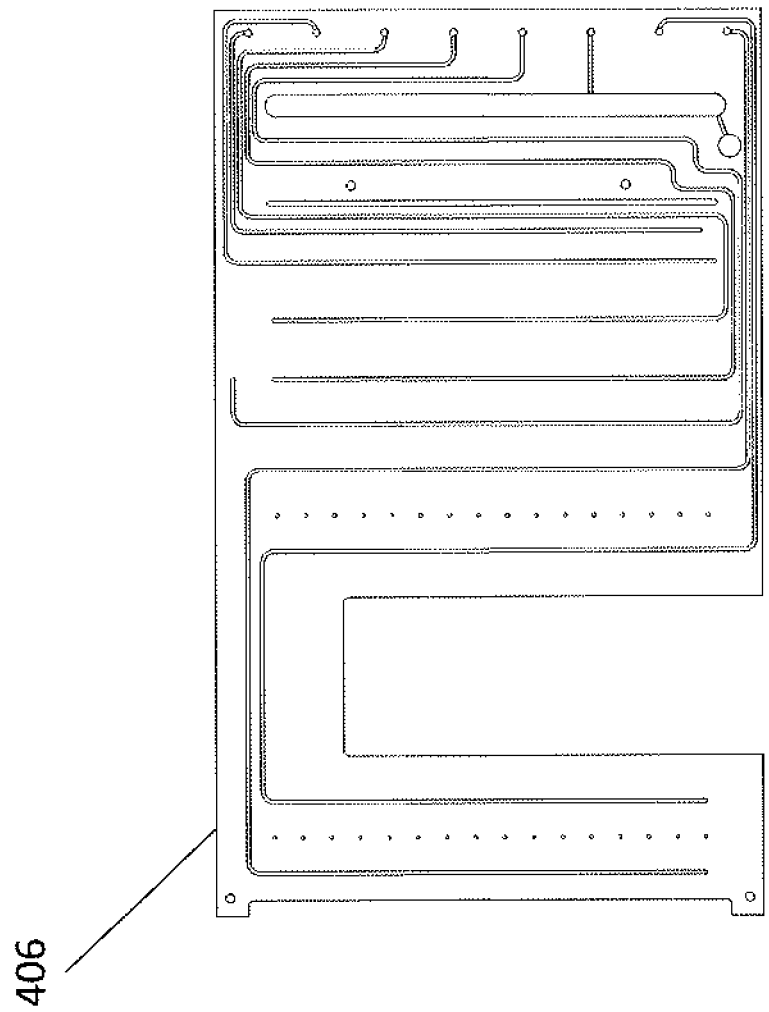
FIG. 27 is a top view schematic of an embodiment of a pneumatic layer 2 of a biochip in accordance with the present technology.

Based on that result, a biochip (footprint of 76.2 mm×127 mm) was designed and fabricated by CNC-machining Fluidic layer 1 (FIG. 24, 403) and fluidic layer 2 (FIG. 25, 404), pneumatic layer 1 (FIG. 26, 405) and pneumatic layer 2 (FIG. 27, 406) are fabricated by CNC machining from a thermoplastic sheet. The fluidic subassembly (FIG. 28, 407) was fabricated by assembling fluidic layer 1 (FIG. 24, 403), fluidic layer 2 (FIG. 25, 404) and an unpatterned thin thermoplastic film and thermally bonding. The pneumatics subassembly (FIG. 29, 408) was fabricated by thermal bonding pneumatic layer 1 (FIG. 26, 405), pneumatics layer 2 (FIG. 27, 406). The biochip assembly (FIG. 30, 409) was fabricated by bonding the fluidics subassembly (FIG. 28, 407) to the pneumatic subassembly (FIG. 30, 409) and incorporating an elastomeric, normally open valve subassembly as described in Example 2.

Figure 28:
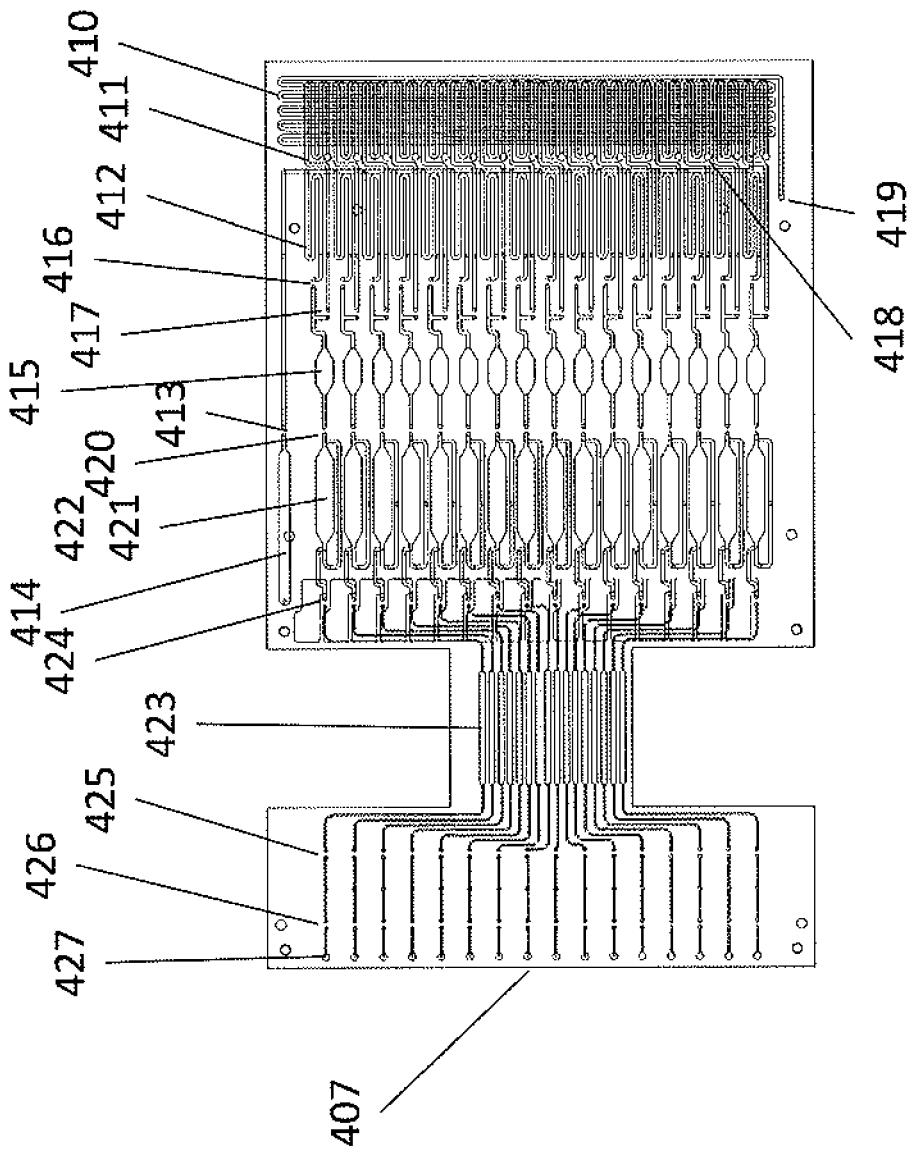
FIG. 28 is a transparent top view schematic of an embodiment of a fluidics subassembly including the first fluidic plate of FIG. 24 bonded to the second fluidic plate of FIG. 25.
Figure 31:
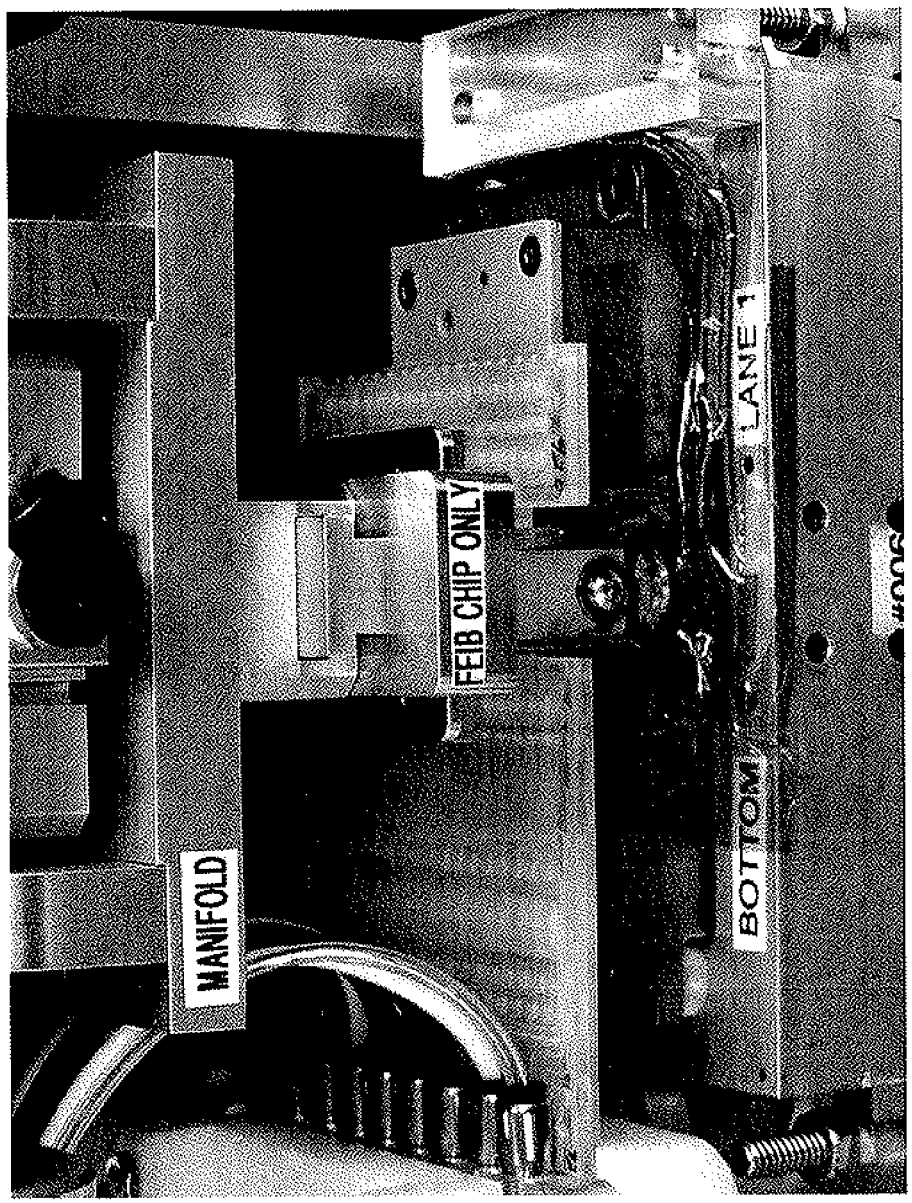
FIG. 31 is a photograph of an embodiment of a pneumatic and thermal cycling instrument for use in connection with biochips.

To test the biochip, 160 microliters of PCR reagent master mix, sufficient for 16 samples of amplification, was prepared and inserted into the master mix reagent reservoir (FIG. 28, 410) of the CNC-machined biochip. 9.3 microliters of DNA (total template of 1 ng) was inserted into each of the sample wells (FIG. 28, 411). The biochip was connected to the pneumatic/thermal cycling instrument (FIG. 31). An automated script with the following steps was executed:

Initialization. All valves were closed.

Queue sample and reagent. PCR reagent was pneumatically driven into the PCR metering chambers of the biochip (FIG. 28, 412) by applying 1 psig to drive line DR (FIG. 28, 419). A volume of 9 microliters of master mix was metered. The sample for each lane was queued at a vent membrane by applying 1 psig to drive line DS (FIG. 28, 418).

Remove excess PCR reagent. Excess PCR master mix was removed from the distribution channels by flowing into the reagent waste chamber (FIG. 28, 414) by opening valve WV (FIG. 28, 413) and applying 1 psig to drive line DR (FIG. 28, 419). The reagent waste chamber (FIG. 28, 414) was sealed by closing valve WV (FIG. 28, 413) and drive line DR (FIG. 28, 419) was deactivated.

Move reagent into joining chamber (JC). The PCR master mix was pneumatically driven into the joining chamber (FIG. 28, 415) by opening valves RV (FIG. 28, 416) and applying a pneumatic drive pressure of 1 psig to DR (FIG. 28, 418) for 30 seconds. Reagent valves RV (FIG. 28, 416) was closed and DR (FIG. 28, 418) was deactivated.

Move sample into joining chamber (JC). Sample was pneumatically driven into the joining chamber (FIG. 28, 415) by opening valves SV (FIG. 28, 415) and applying a pneumatic drive pressure of 1 psig for 30 seconds to DS (FIG. 28, 419). The sample and PCR master mix were joined together in the joining chamber to form the PCR solution. Valve SV (FIG. 4.6, 415) is closed and drive line DS (FIG. 4.6, 419) was deactivated. 4.6, 419).

Move PCR solution into mixing chamber (MC). The PCR solution was into the mixing chamber (FIG. 28, 421) by opening Valve JCV (FIG. 28, 420) and RV (FIG. 28, 416) and applying a pressure of 1 psig for 30 seconds to DR (FIG. 28, 418).

Mix the sample and reagent. Reciprocal mixing was performed by driving the PCR solution into an air chamber AC (FIG. 28, 422) by opening valves RV (FIG. 28, 416; valve JCV is already open) and applying a drive pressure to DR (FIG. 28 418) that linearly increases from 0-15 psig and then from 15-0 psig (over 30 seconds). This was repeated 2 times. Valves JCV (FIG. 28, 420) and RV (FIG. 28, 416) were closed and DR (FIG. 28, 418) was deactivated.

Move PCR solution into PCR chambers (PC). The PCR solution was moved into the PCR chamber (FIG. 28, 423) by opening valves PV1 (FIG. 28, 424), PV2 (FIG. 28, 425), JCV (FIG. 28, 420) and RV (FIG. 28, 416) and applying a pressure of 0.5 psig for 30 seconds to drive line DR (FIG. 28, 418). Valves PV1 (FIG. 28, 424), PV2 (FIG. 28, 425), JCV (FIG. 28, 420) and RV (FIG. 28, 416) were closed.

Thermal cycle. Valves PV1 (FIG. 28, 424) and PV2 (FIG. 28, 425) were closed, and thermal cycling was performed with a 28 cycle protocol that required 17 minutes.

Figure 29:
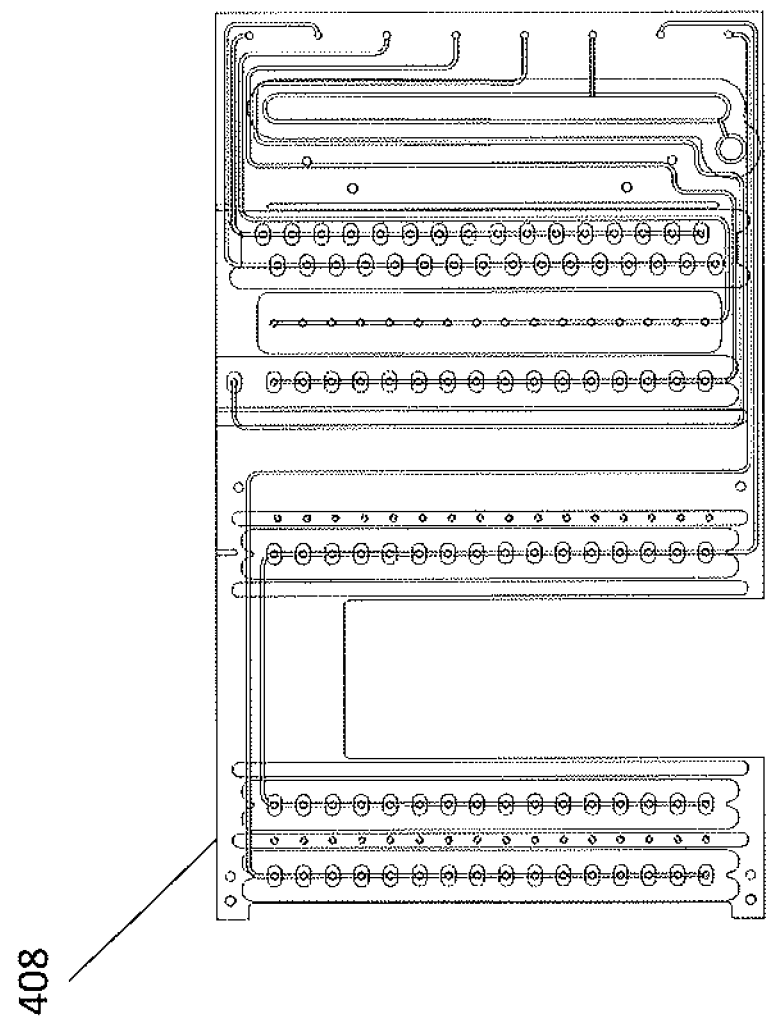
FIG. 29 is a transparent top view schematic of an embodiment of a pneumatic subassembly including the first pneumatic plate of FIG. 26 bonded to the second pneumatic plate of FIG. 27.
Figure 30:
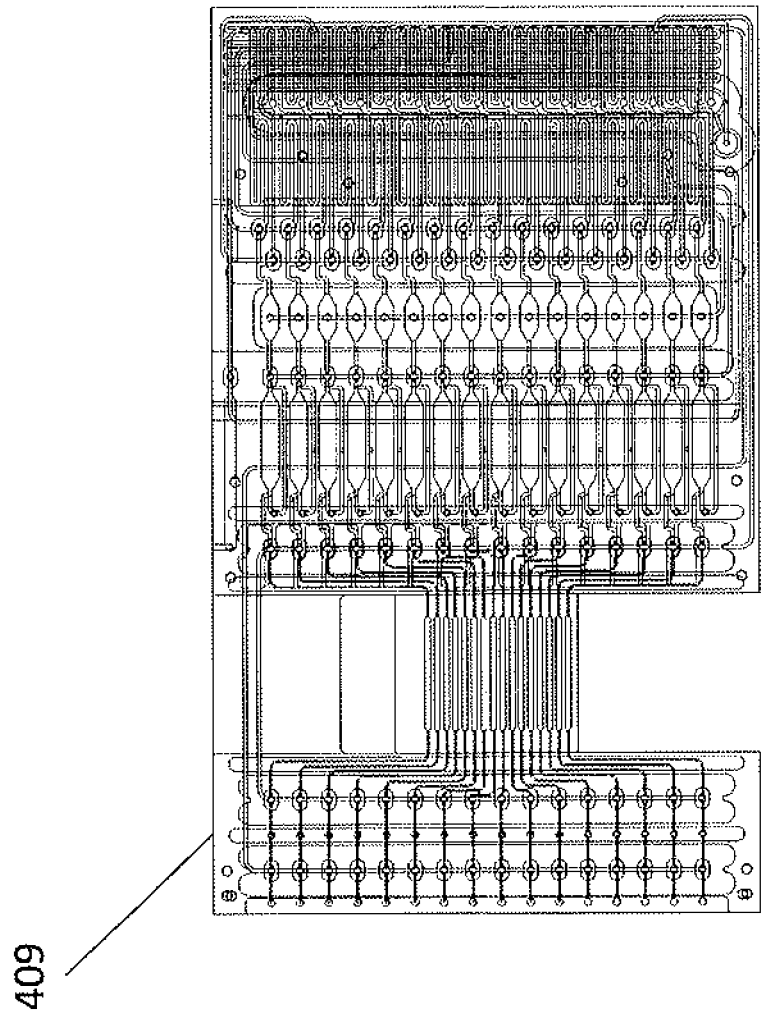
FIG. 30 is a transparent top view schematic of a biochip formed by the attachment of the pneumatics subassembly of FIG. 29 to the fluidics subassembly of FIG. 28.

Retrieve PCR product. Valves OV1 (FIG. 4.6, 426), PV1 (FIG. 28, 424), PV2 (FIG. 28, 425), JCV (FIG. 28, 420) and RV (FIG. 28, 416) were opened. A pipette tip was used to manually retrieve PCR product from port OP (FIG. 29, 427). PCR products were retrieved from the 16 biochip samples.

Figure 32:
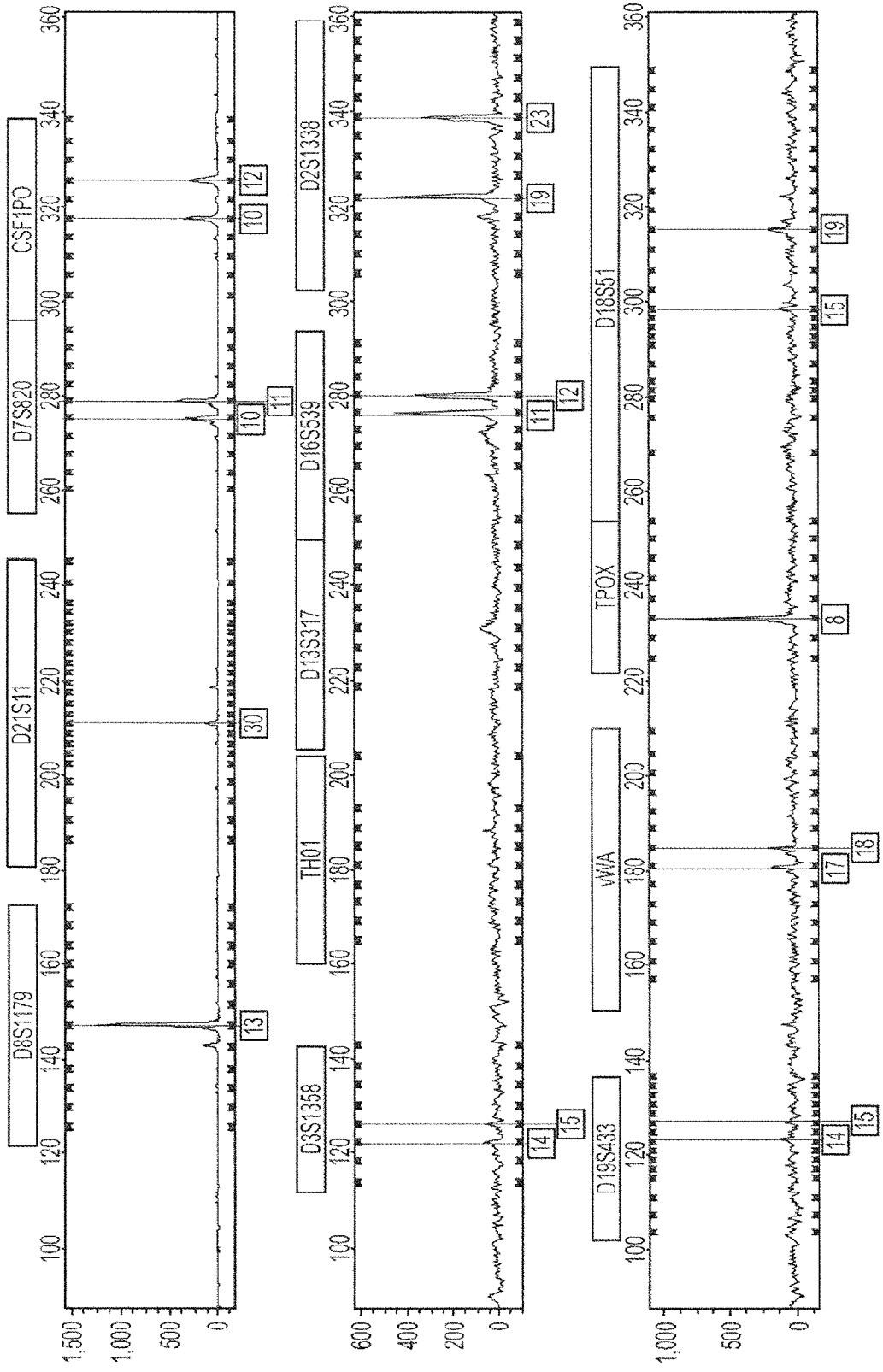
FIG. 32 is a STR profile for a PCR analysis of a sample within a biochip in accordance with the present technology.
Figure 32:
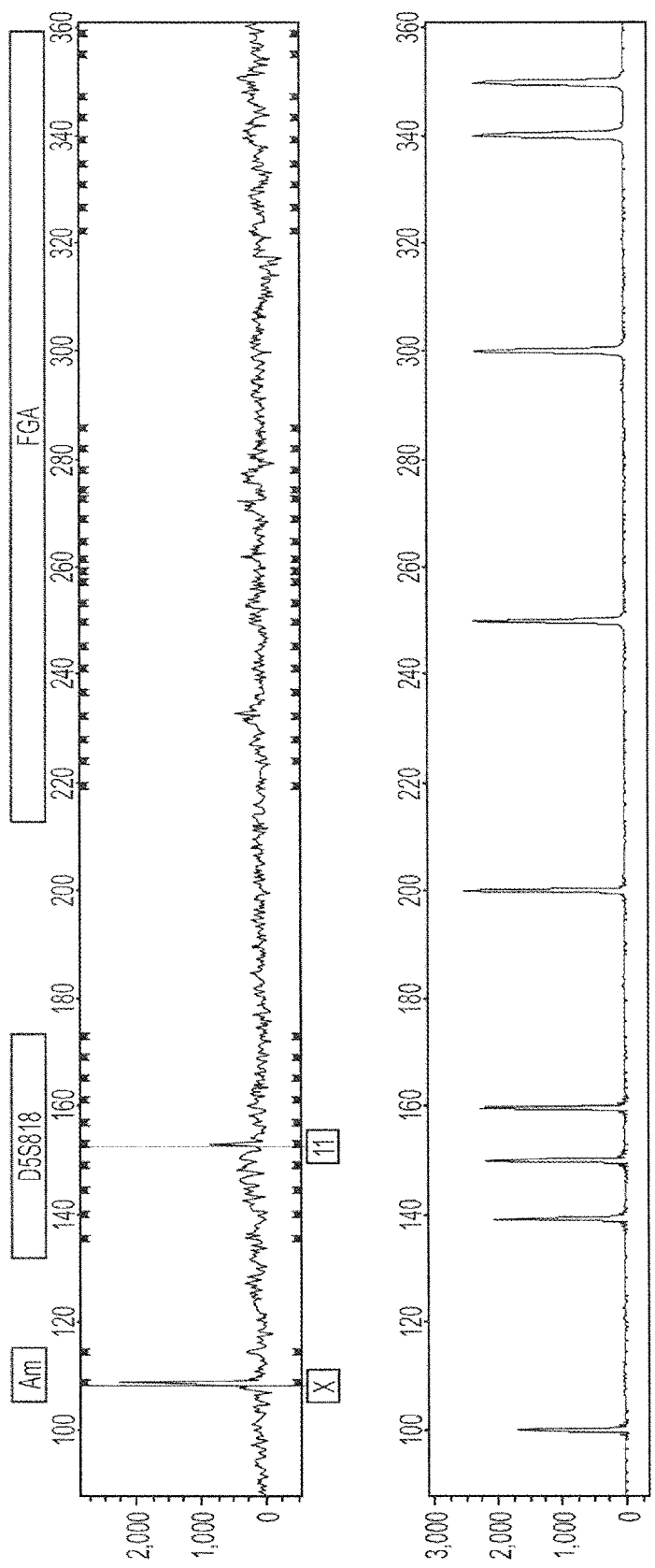

Results. Following the execution of the script, the PCR reaction was removed from each channel and separated and detected on Genebench. A representative STR profile for the reaction is shown in FIG. 32.

Example 5

Figure 33:
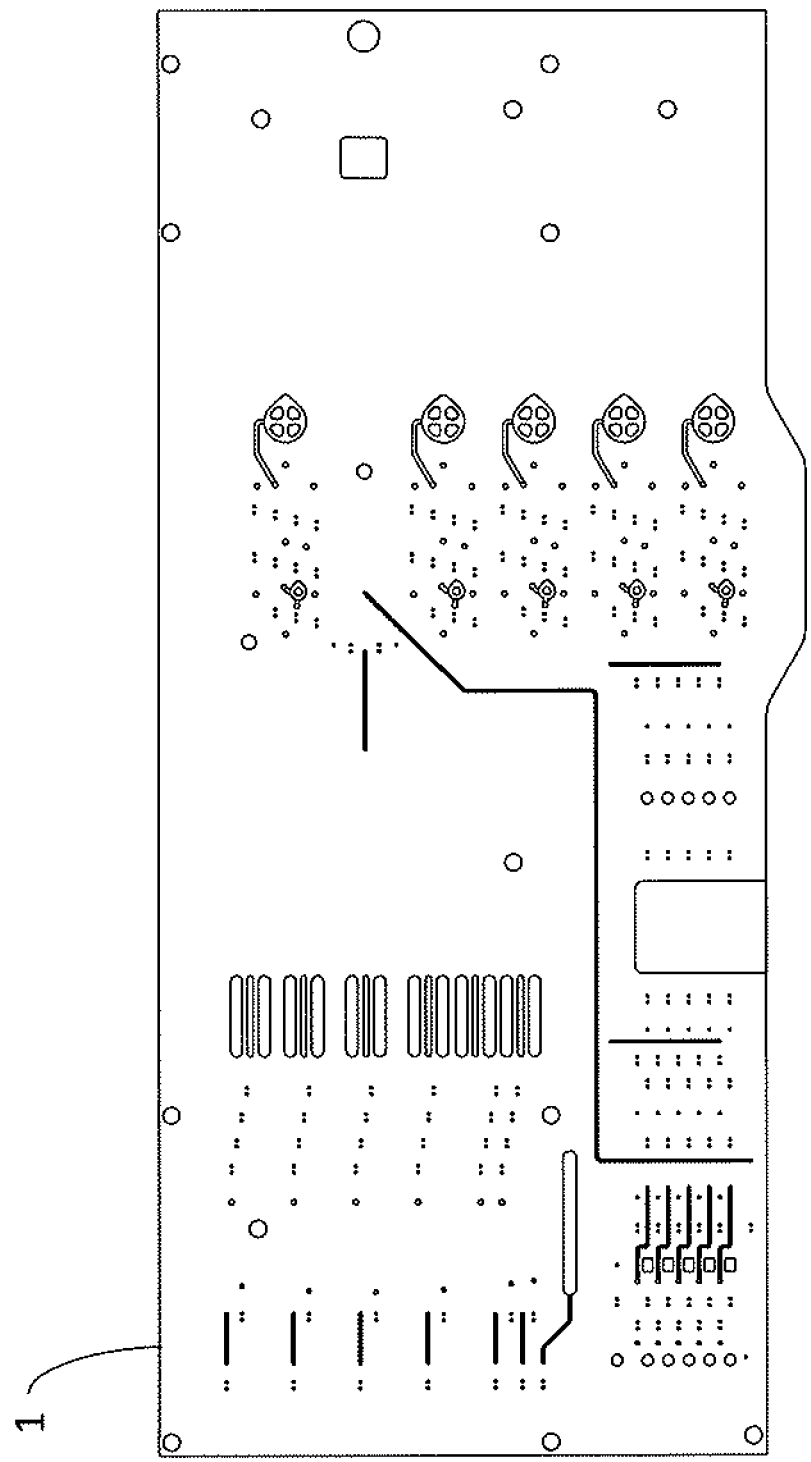
FIG. 33 is a top view schematic of an embodiment of a fluidic plate included in an embodiment of a fluidic assembly in accordance with the present technology.
Figure 34:
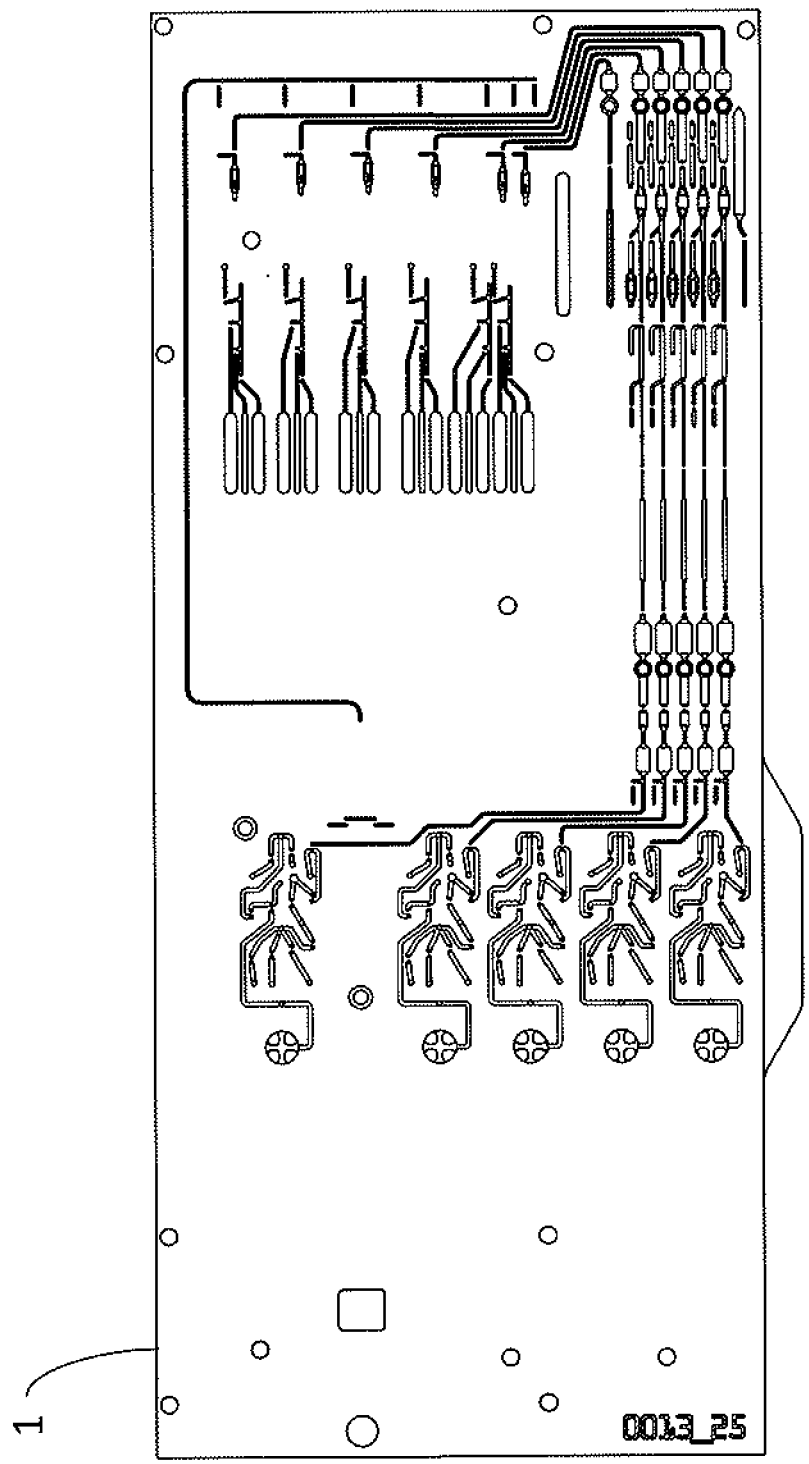
FIG. 34 is a bottom view schematic of the fluidic plate of FIG. 33.
Figure 35:
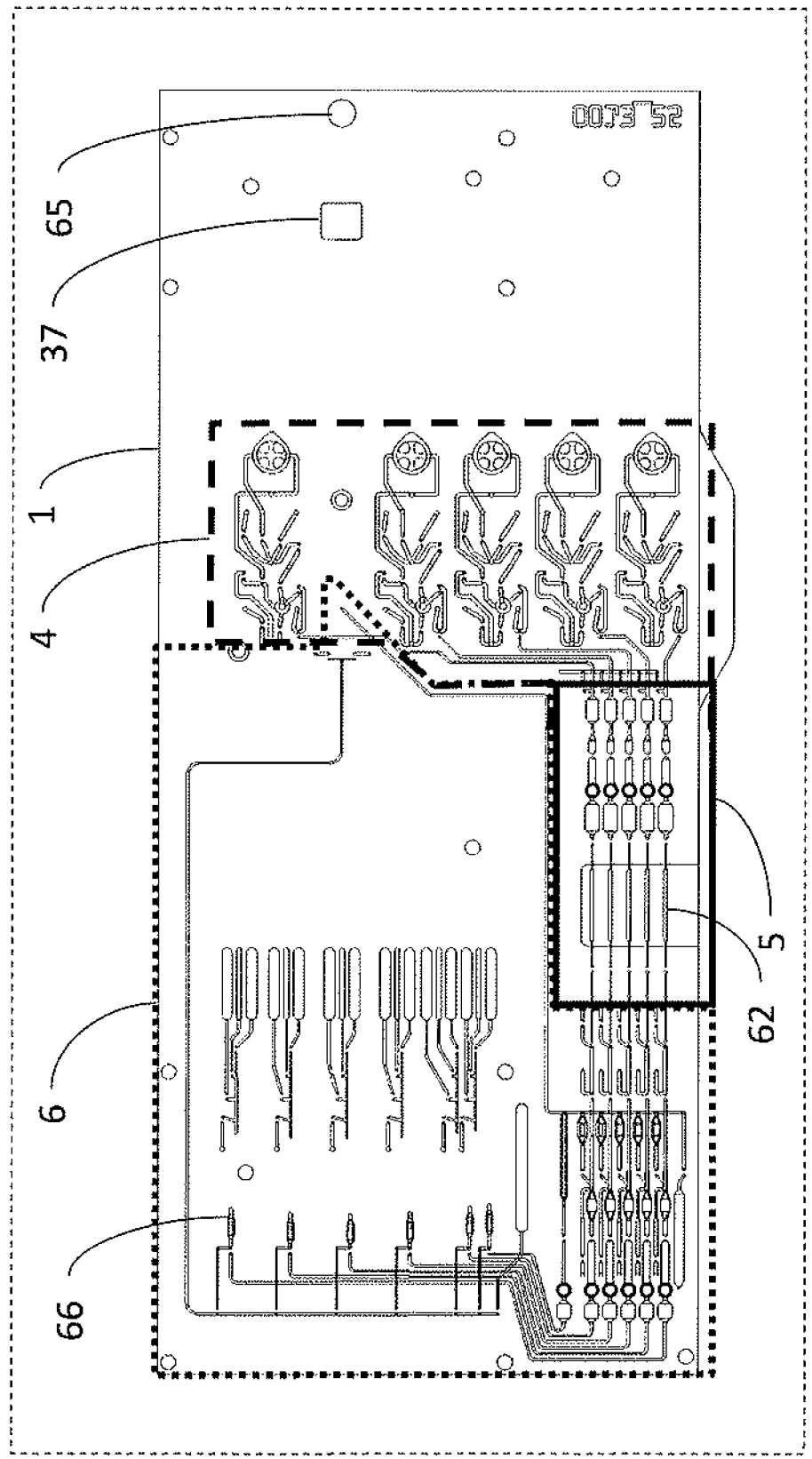
FIG. 35 is a transparent view schematic of the fluidic plate showing the features of both the top and bottom sides of the plate.

CNC Machining of a Fully Integrated Biochip that Purifies Nucleic Acids, Amplifies the Purified DNA, Electrophoretically Separates the Amplified DNA and Generates an STR Profile Using an Automated Script A stationary, unitary plastic biochip that accepts 5 buccal swabs and generates STR profiles consists of the following parts:

Fluidic subassembly—This subassembly transfers and processes fluids within the biochip, interacting with the pneumatic subassembly, macrofluidic processing subassembly, valve subassembly, and separation and detection subassembly. The fluidic plate of the fluidic subassembly was fabricated by CNC machining an interconnected set of channels and chambers onto both the top and bottom sides of a COP sheet. The fluidic plate has dimensions of 276 mm×117 mm×2.5 mm. FIG. 33 shows the top side of the fluidic plate 1, FIG. 34 shows the bottom side of the fluidic plate 1, and FIG. 35 shows a transparent view of the fluidic plate 1, showing features from both sides. The CNC-machined fluidic plate was fabricated by machining an injection-molded blank with a thickness of 2.5 mm. Both the top and bottom sides of the plate are covered with patterned thin plastic films. FIG. 36 shows the top patterned thin film 2 and FIG. 37 shows the bottom patterned thin film 3; the thin films have a thickness of 100 microns. An advantage of having features present on both the top and bottom of the fluidic plate is that only one fluidic plate is required for the assembly (two plates would be required otherwise). In general, minimizing the number of plates in an assembly is a major advantage in that it makes alignment of parts more straightforward and reliable, minimizes the effects of differential warpage and shrinkage, and thereby allows more effective assembly at reduced cost.

Figure 38:
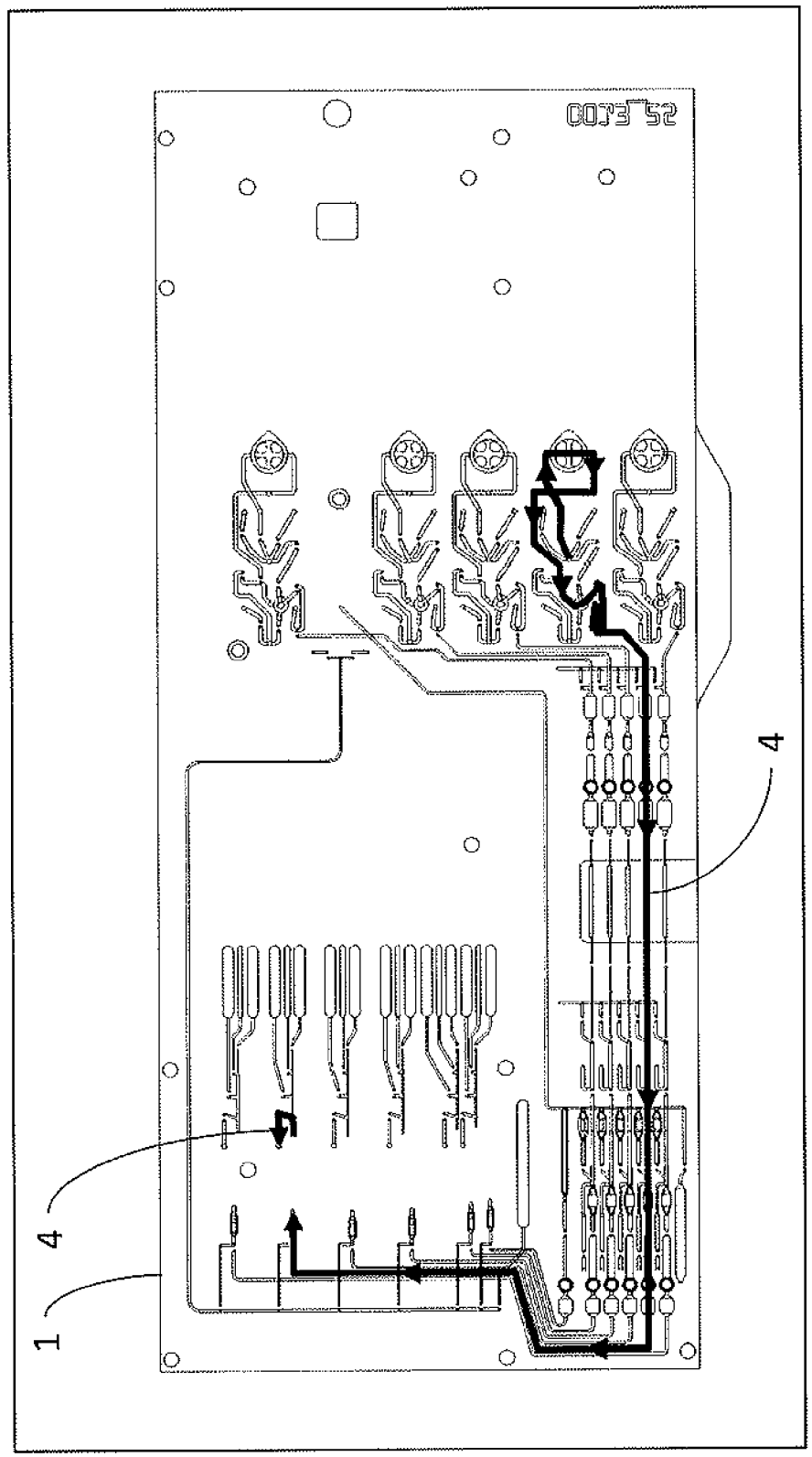
FIG. 38 is a top view schematic of an embodiment of a fluidic plate with a line illustrating a path a single sample takes through the fluidic plate.

The channels in this biochip can be characterized as follows: 1) Sample processing channels. Each buccal swab to be analyzed corresponds to a unique set of channels that perform DNA purification, PCR amplification, separation and detection, and all the process steps required to conduct these nucleic acid manipulations. The unique set of channels for each sample do not communicate with the sets of channels for other samples. That is to say, channels do not communicate from sample to sample and do not share chambers (other than an anode chamber), filter regions, or membrane regions related to other samples, thereby preserving the purity of each sample and avoiding inadvertent sample mixing or cross contamination. Certain pneumatic drive lines split to drive multiples samples in parallel, but the driving is accomplished pneumatically, preserving the integrity of each sample. Moreover, the unique set of channels for each sample is a closed pathway; only air form the pneumatic drivelines enter the biochip, and only air through vent membranes leave the biochip—liquid reagents are provided by the biochip and liquids do not leave the biochip. FIG. 38 shows the path 4 a single sample takes through the fluidic plate. FIG. 39 shows an expanded view of this path 4 through the purification region 5, FIG. 40 shows an expanded view of this path 4 through the amplification region 6, and FIG. 41 shows an expanded view of this path 4 taken through the separation and detection region 7. It is important to note that the direction of electrophoresis is opposite to that of purification and amplification. This direction change is facilitated by through holes in the fluidic layer that pass sample to the separation and detection layer just below. 2) Gel processing channels. These channels are utilized to fill the separation and detection subassembly with sieving matrix and buffer in preparation for separation and detection. That is to say, the channels are filled from common reagent reservoirs. After purification, amplification, and pre-electrophoresis are complete, each separation channel receives a unique sample via sample-specific cathodes. Each sample has a unique cathode chamber and separation channel, and all samples share a single anode chamber through which electrophoresis reagents are loaded.

The fluidic plate contains a particulate filter region, a purification membrane region, and several types of chambers, including metering chambers, reconstitution chambers, mixing chambers, joining chambers, waste chambers, and cathode and anode chambers. These chambers and regions are in line with the channels and have shapes and dimensions determined by the required functionality. For example, a reagent metering chamber (FIG. 40, 8) is characterized by different dimensions and volumes than a cathode chamber (FIG. 41, 9) or a reconstitution chamber (FIG. 40, 10).

The channels, chambers, and filter and membrane regions are covered, in this case by bonding thin thermoplastic films (CNC-machined or injection molded plates can also form the covers). The sandwich of thin film—fluidic layer—thin film is termed the "fluidic subassembly." The films have themselves been patterned by CNC machining, and the thin films of the invention can also be patterned by a number of processes including die cutting or punching and laser cutting. These thin films have features including through holes that are aligned to the corresponding features on the CNC machined fluidic layer to provide access to the features of the fluidic layer. For example, sample passes from the fluidic layer through the through holes in the bottom patterned thin film to the separation and detection subassembly. Prior to bonding the top and bottom thin films to the plate, additional components are also incorporated for functions including particulate filtration (FIG. 39, 11), DNA purification (FIG. 39, 12), and venting (FIG. 41, 13). Bonding of the patterned thin films to the fluidic plate was accomplished thermally but can also be performed ultrasonically, with solvents, and using adhesives. Features on the plate and films can be added to facilitate the bonding method; for example, energy director ridges can be placed at the sites of ultrasonic welding.

Figure 42:
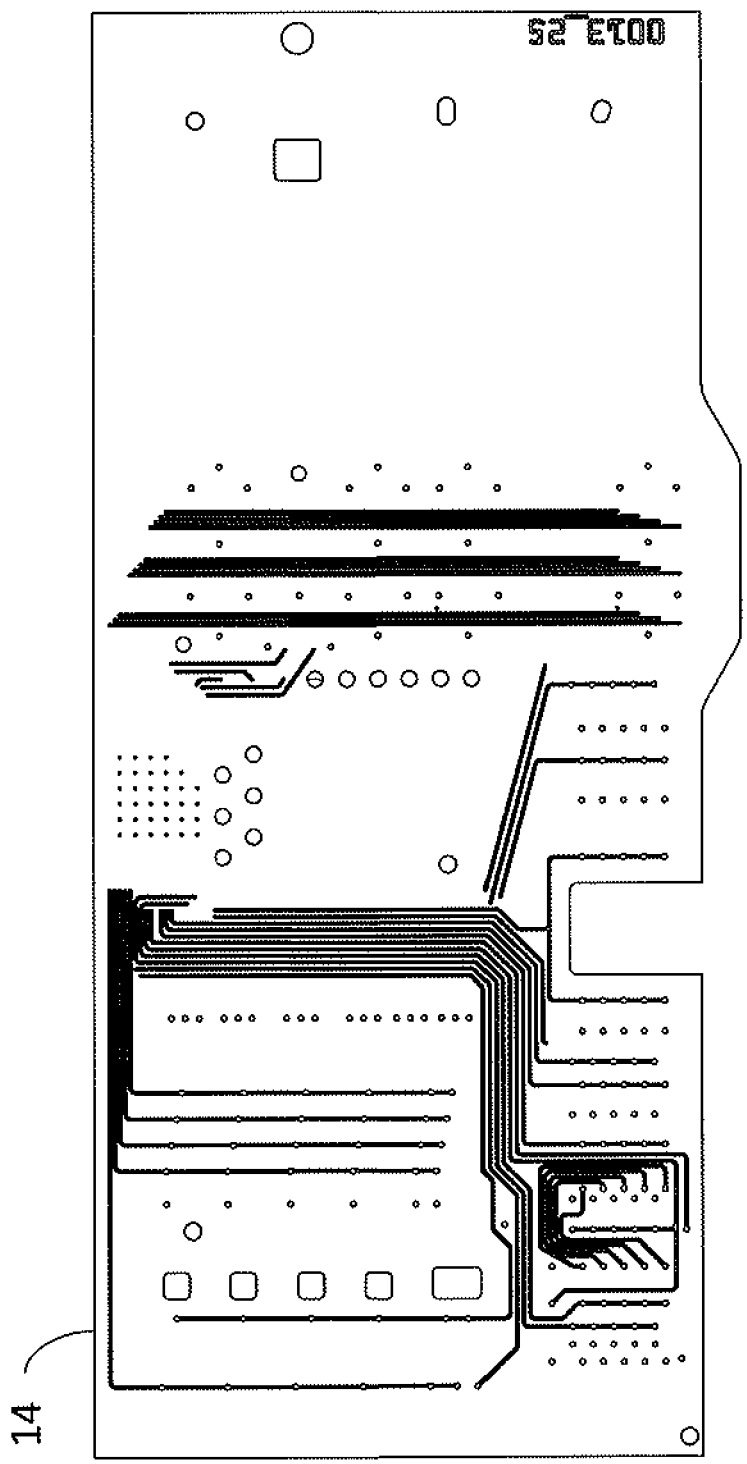
FIG. 42 is a top view schematic of an embodiment of a pneumatic plate included in an embodiment of a pneumatic assembly in accordance with the present technology.
Figure 43:
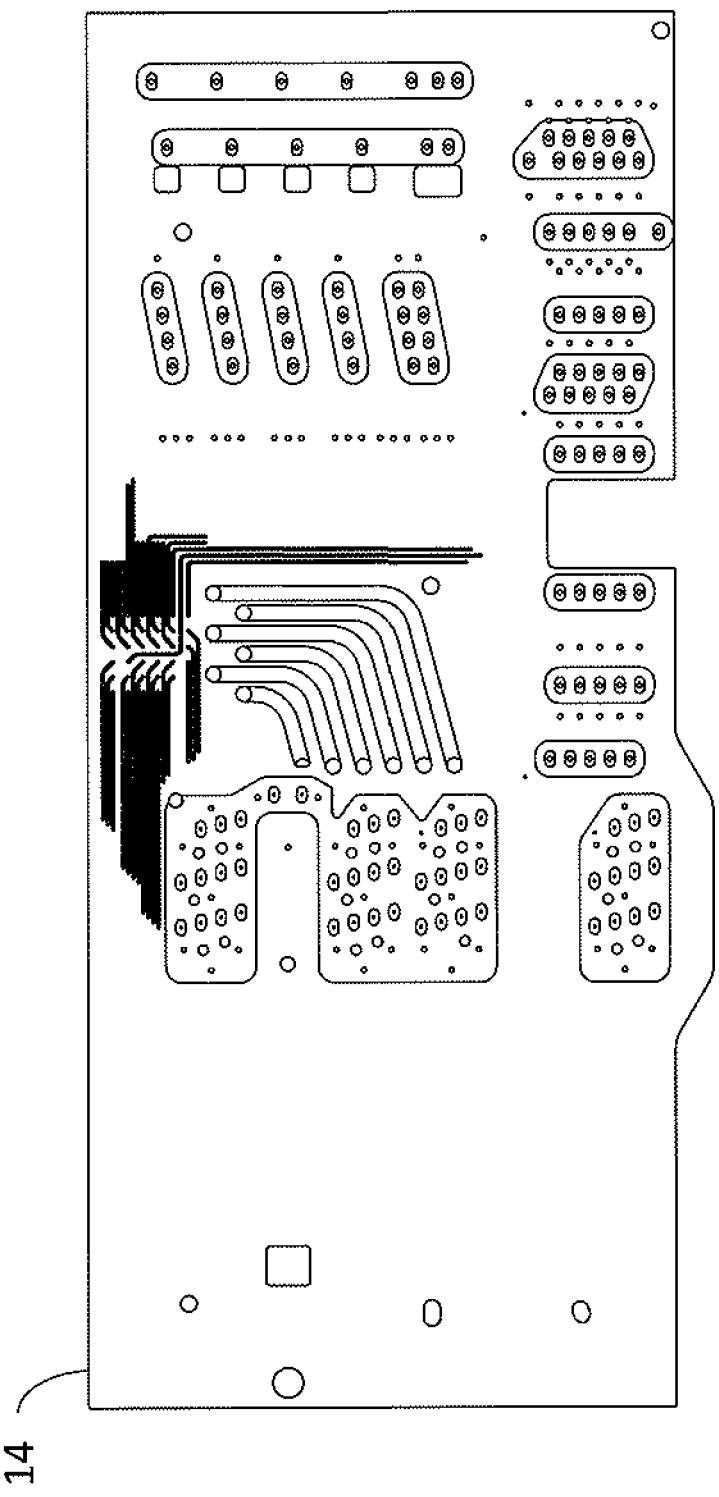
FIG. 43 is a bottom view schematic of the pneumatic plate of FIG. 42.
Figure 45:
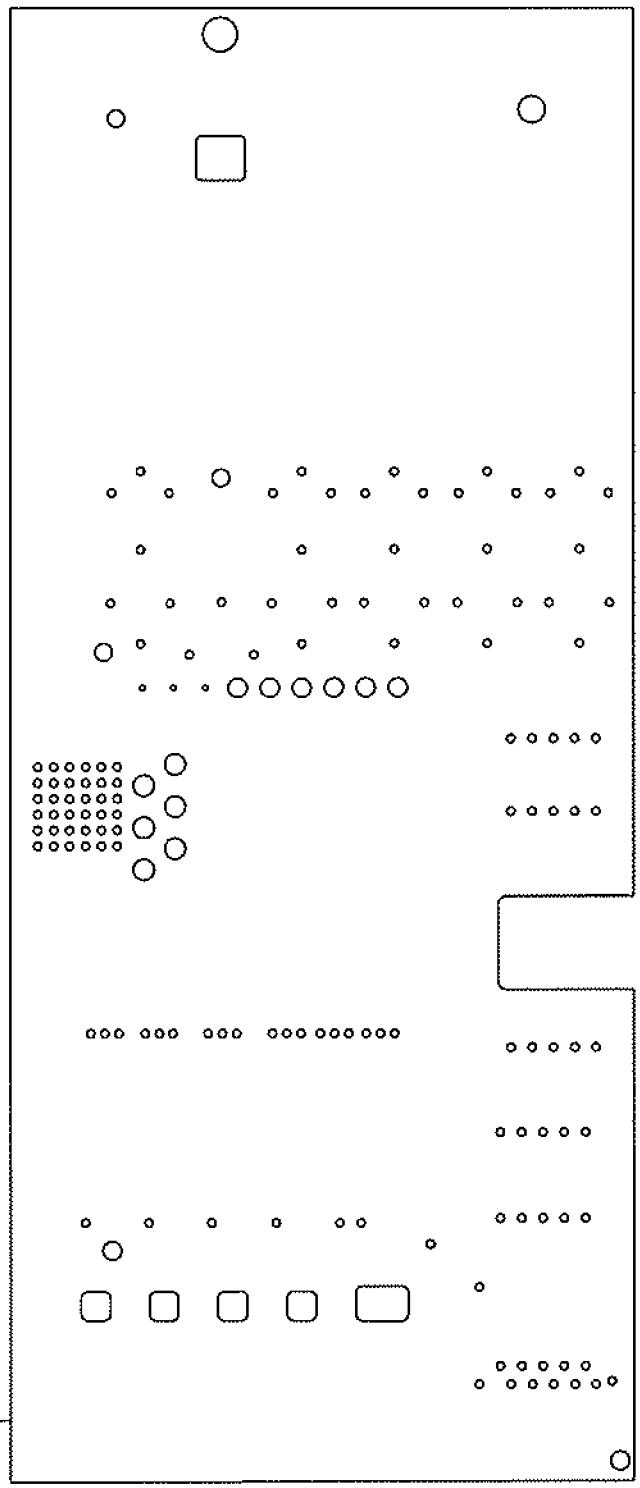
FIG. 45 is a top view schematic of an embodiment of a patterned thin film for attachment to the top side of the pneumatic plate.
Figure 46:
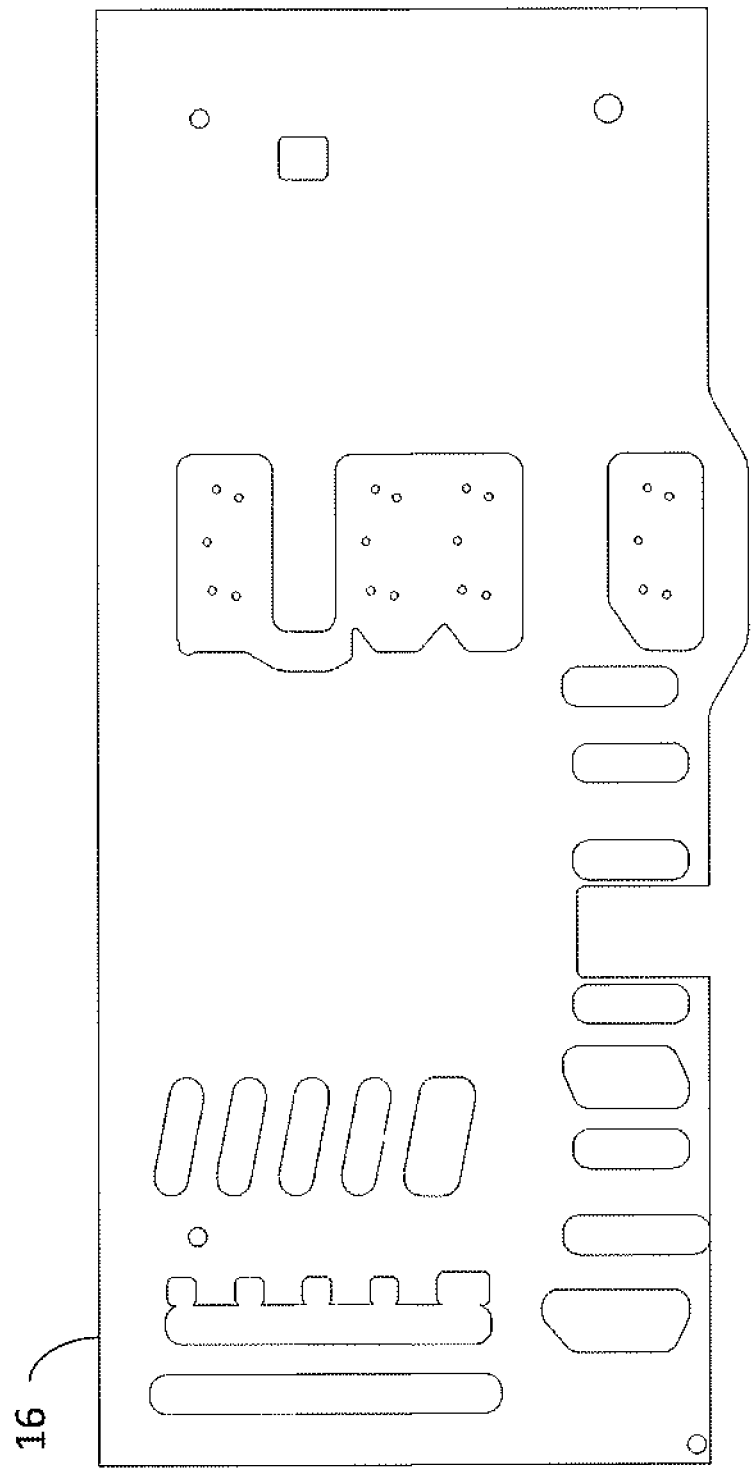
FIG. 46 is a bottom view schematic of an embodiment of a patterned thin film for attachment to the bottom side of the pneumatic plate.

Pneumatic subassembly—This subassembly couples the pneumatic drive of the instrument (as described in Example 3), to the fluidic subassembly, macrofluidic processing subassembly, valve subassembly, and separation and detection subassembly to pneumatically drive fluids and activate valves within the biochip. This subassembly is fabricated by CNC machining an interconnected series of pneumatic drive lines onto each of the two sides of a COP sheet. Some of the drivelines are sample-specific and others are related to non-sample specific functions such as gel filling. FIG. 42 shows the top side of the pneumatic plate 14, FIG. 43 shows the bottom side of the pneumatic plate 14, and FIG. 44 shows a transparent view of the pneumatic plate 14, showing features from both sides. The pneumatic plate has dimensions of 276.7 mm×117.3 mm×2.50 mm. The CNC-machined pneumatic plate was fabricated by machining an injection-molded blank with a thickness of 2.5 mm. The top side of the pneumatic plate is covered with a patterned thin plastic film 15 (FIG. 45). The bottom side of the pneumatic plate is covered with an intact thin film 16, and certain regions of this film are cut out following bonding (FIG. 46) to allow access to the plate from the valve subassembly. Both the patterned and unpatterned thin films have a thickness of 100 microns. Patterns can be cut prior to bonding (as in the case of the top pneumatic film) or following bonding (as is the case with the bottom pneumatic film). The reason a post-bonding patterning step was selected was because the large cut-out regions were readily removed post-bonding. Bonding of the thin films to the pneumatic plate was accomplished thermally but can also be performed ultrasonically, with solvents, and using adhesives. Features on the plate and films can be added to facilitate the bonding method; for example, energy director ridges can be placed at the sites of ultrasonic welding. Finally, the pneumatic plate can also have fluidic features and vice versa. This can be useful if, for example, the fluidic plate is saturated with features and the pneumatic plate has available space. The pneumatic plate in this case would still be referred to as a pneumatic plate because of its position in the overall biochip and the fact that the majority of its features were pneumatic. Regardless of their location, pneumatic lines and channels contain only air. In contrast, fluidic features contain liquids and air.

The features in the thin plastic films include through holes that are aligned to the corresponding features on the CNC machined pneumatic layer to provide direct access to the pneumatic layer or indirect access to the fluidic layer via the pneumatic layer. For example, reagents in chambers of the macrofluidic processing subassembly pass through the through holes of the pneumatic subassembly (thin films and pneumatic plate) on their way to the fluidic subassembly. Bonding of the patterned thin films to the pneumatic plate was accomplished thermally but can also be performed ultrasonically, with solvents, by clamping, and using adhesives.

Valve subassembly—This subassembly is located between the pneumatic subassembly and the fluidic subassembly. It consists of an elastomeric material, which, when pneumatically activated, will deform, thereby stopping flow of fluids (including air) within the fluidic layer. This subassembly consists of an elastomeric film that can be deflected, but any of the valve assemblies described in Example 2 can be incorporated.

Pneumatic-valve-fluidic stack—This subassembly is fabricated by assembling the pneumatic subassembly, valve subassembly, and fluidic subassembly, and thermally bonding the stack together. Vent membranes (FIG. 44, 17) are incorporated into this subassembly by placing them over the venting features of the fluidic subassembly (FIG. 35, 13) and corresponding features in the pneumatic subassembly. The vent membrane is in the form of a single strip that is used to cover the venting features of multiple samples simultaneously. One vent membrane strip is applied to cover many venting areas. In general, reduction in part counts allows for ease of assembly, whether manual or automated. Bonding of the two subassemblies can also be performed thermally, ultrasonically, with solvents, by clamping, and using adhesives. Features on the plate and films can be added to facilitate the bonding method; for example, energy director ridges can be placed at the sites of ultrasonic welding or an additional bonding layer can be used to facilitate thermal bonding.

Macrofluidic processing subassembly—This subassembly consists of two major elements: a macrofluidic block and a cover. This subassembly accepts samples, provides reagents to the biochip, and serves as the interface between microfluidic and macrofluidic volumes and processes, as further described in application Ser. No. 12/699,564 entitled "Nucleic Acid Purification," which is incorporated herein by reference. FIG. 47 shows the macrofluidic block 18 with swab 19, lysis solution 20, ethanol 21, wash solution 22, and elution solution 23 reagent chambers, and fluidic processing chambers for lysate holding 24, eluate homogenization 25, air 58, TTE 59, and formamide 60 chambers. The dimensions of the block are 102.8 mm×50.5 mm×74.7 mm. The macrofluidic block utilizes volumes from 0.15-3.0 ml and interfaces with the pneumatic subassembly and the cover. The side of the block contains pneumatic drive lines 26; these originate at the pneumatic interface of the pneumatic subassembly and pass through it to the block. From the block, the drive lines pass to the cover. While some embodiments, including the embodiment described in this Example 5, include the macroprocessing subassembly, not all biochips in accordance to the technology described herein include the macroprocessing subassembly. For example, a sample of DNA or purified cells could be injected into a biochip including the pneumatic subassembly and the fluidics subassembly connected by the valve assembly.

Figure 49:
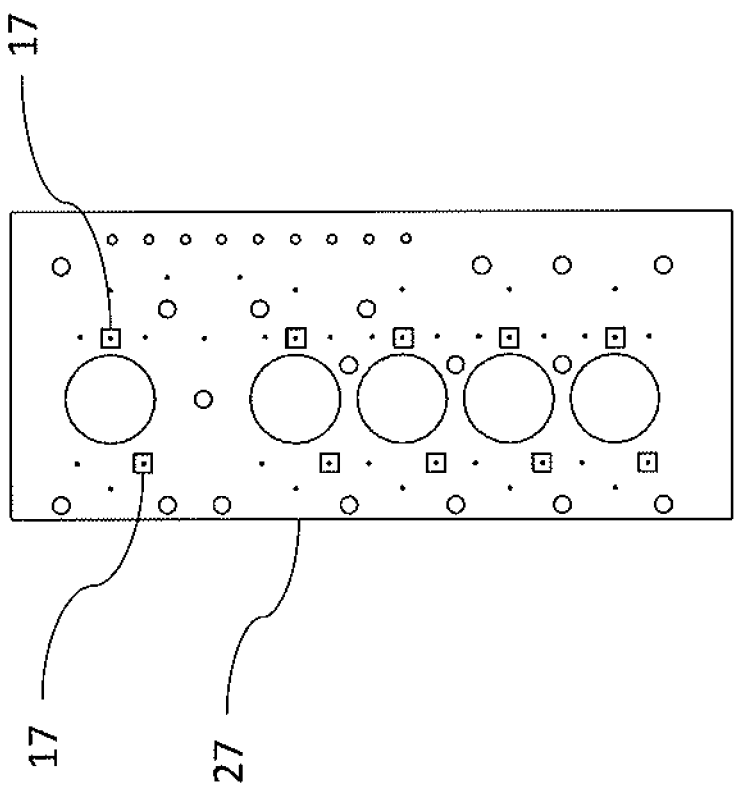
FIG. 49 is a bottom view schematic of an embodiment of a top layer of the cover.
Figure 50:
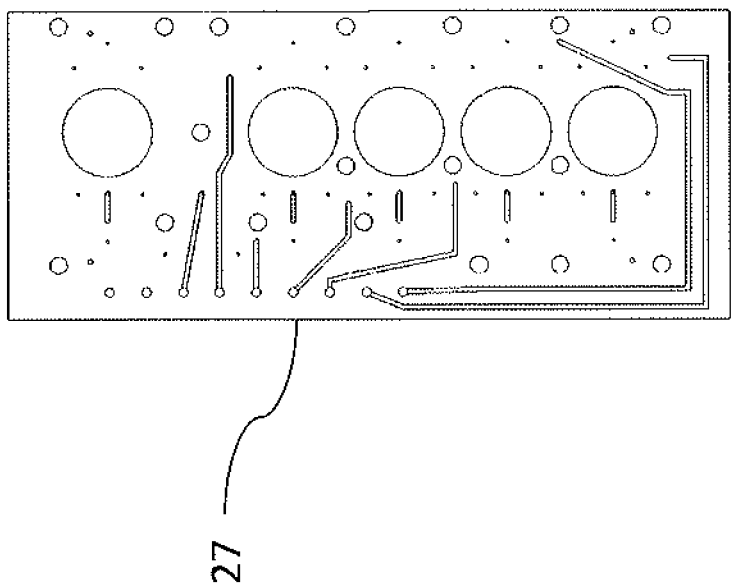
FIG. 50 is a top transparent view schematic of the top layer of the cover.
Figure 51:
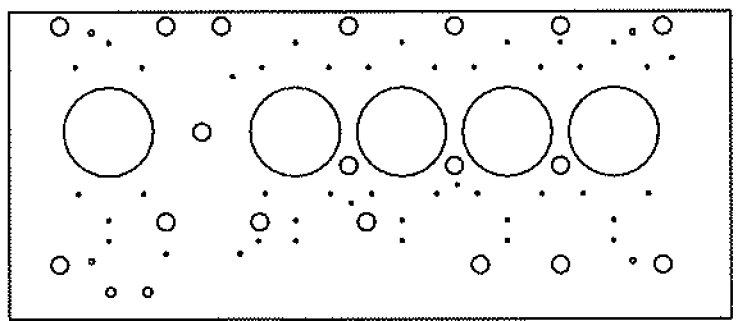
FIG. 51 is a top view schematic of another embodiment of a second layer of a cover to the macrofluidic block.

FIGS. 48-54 show the cover. The cover consists of three layers. FIG. 48 shows the top of cover layer 1 27, FIG. 49 shows the bottom of cover layer 1 27, and FIG. 50 shows a transparent view of cover layer 1 27. FIG. 51 shows cover layer 2 28. FIG. 52 shows the top of cover layer 3 29, FIG. 53 shows the bottom of cover layer 3 29, and FIG. 54 shows a transparent view of cover layer 3 29. The dimensions of the assembled cover are 50.8 mm×118.4×4.5 mm. The cover functions to bring pneumatic drive lines from the side of the block to the top of the macrofluidic chambers to facilitate reagent transfer, bubbling, and fluidic processing. The cover also has venting features associated with the swab chambers 30 and Eluate holding chambers 31. The vent membranes isolate the chambers in that they do not allow fluid to escape while allowing air to escape to normalize pressure. The cover also serves to hold the swab in place. Optionally, the swab cap or cover can incorporate a locking mechanism to hold the sample in place.

The macrofluidic block and cover components were fabricated by CNC machining a thermoplastic. Alternatively, these parts can be fabricated by injection molding and compression injection molding and extrusion. To mold the macrofluidic processing block aspect ratios are greater than 2 and draft angles of less than 1° C. are incorporated into the design. The macrofluidic block was attached to the cover by clamping using a gasket and screws. The block is attached to the pneumatic subassembly using double-sided PSA. Alternatively, the block attachments can be made by solvent and thermal bonding.

Additional approaches to macrofluidic processing are described in pending application Ser. No. 12/699,564 entitled "Nucleic Acid Purification," incorporated by reference herein. The macrofluidic processing assembly offers substantially flexibility to the applications of the biochip. The liquid reagents and their volumes can be readily modified based on the types of sample manipulations being performed. The swab chamber can be modified to accept a wide variety of samples including different types of swabs, blood samples, and environmental samples. In certain circumstances, these changes can be made with minimal changes to the pneumatic-valve-fluidic stack; for example, simply changing the lyophilized cakes in the stack would allow an entirely different amplification assay to be performed on a different sample type.

Figure 55:
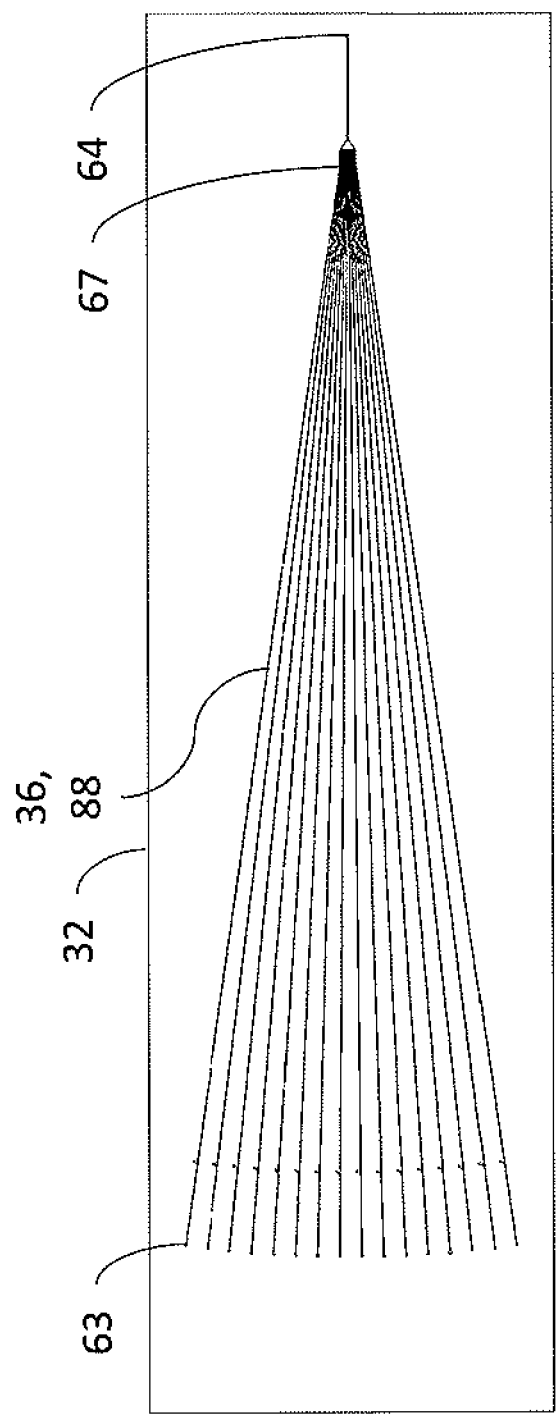
FIG. 55 is a top view schematic of an embodiment of a separation and detection biochip for pressure injection.

Separation and detection subassembly—This subassembly is used for the separation and detection of nucleic acids and consisted of 16 microchannels, each with an injection and separation portion. Detailed description of separation and detection in plastic biochips is found in application Ser. No. 12/080,745, published as 2009/0020427 entitled "Plastic Microfluidic Separation and Detection Platforms,", incorporated herein by reference. Two approaches to sample injection have been utilized, pressure loading and cross injection. FIG. 55 shows the separation and detection biochip for pressure injection 32. It functions by pneumatically driving the sample for separation and detection to the start of the separation column for electrokinetic injection. The cross-sectional dimension of the separation channel (90 microns wide and 40 microns deep) and length of the channel between the anode and the cathode (24 cm) was equal for all channels. This subassembly was fabricated by embossing onto a thin thermoplastic sheet. Alternately the subassembly can be made by extrusion or injection molding. Through holes were fabricated within the embossed sheet to provide access to the channels from the microfluidic subassembly. The channels were covered by bonding a thin thermoplastic sheet over them.

Figure 56:
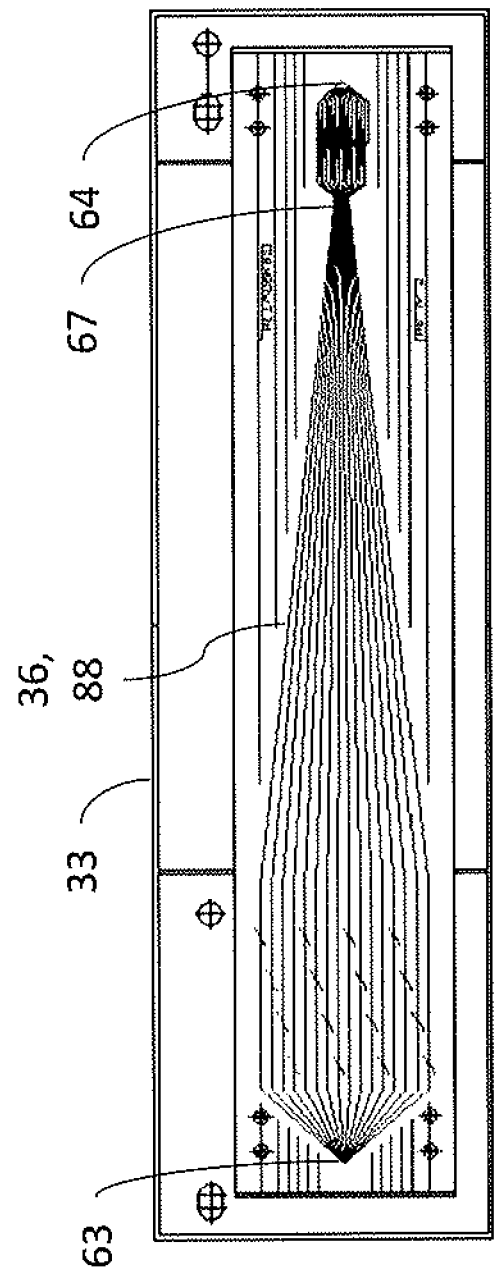
FIG. 56 is a top view schematic of an embodiment of a separation and detection biochip for cross injection for electrokinetic transport of a sample.

FIG. 56 shows the separation and detection biochip for cross injection for electrokinetic transport of the sample for separation and detection to the start of the separation column for electrokinetic injection 33. The dimensions of the biochip are 77.7 mm×276 mm×376 microns. The cross-sectional dimension of the separation channel (90 microns wide and 40 microns deep) and length of the channel between the anode and the cross-injector (25 cm) was equal for all channels. Six of the 16 channels were active in this subassembly. The separation lengths (distance between the intersection and the excitation/detection window) for each of the channels range from 16 to 20 cm long. The cross-sectional area of the channels between the cathode well and the injector was adjusted such that all the electrical resistances, and hence electric fields between the cathode and the intersection are essentially equal under bias. This ensured that the electric fields experienced by the samples were identical regardless of the separation channel into which a sample was loaded. The intersection voltages for all channels were essentially identical. The sample inlet and sample waste arms for sample injection were both 2.5 mm long. The offset between both channels was 500 microns. This subassembly was fabricated by embossing onto a thin thermoplastic sheet. Alternatively, the subassembly may be fabricated by extrusion or injection molding. Through holes were fabricated within the embossed sheet to provide access to the channels from the microfluidic subassembly. The channels were covered by solvent bonding another thin thermoplastic sheet. Alternatively, the sheet can be attached by thermal bonding or thermal-assisted solvent bonding.

Figure 57:
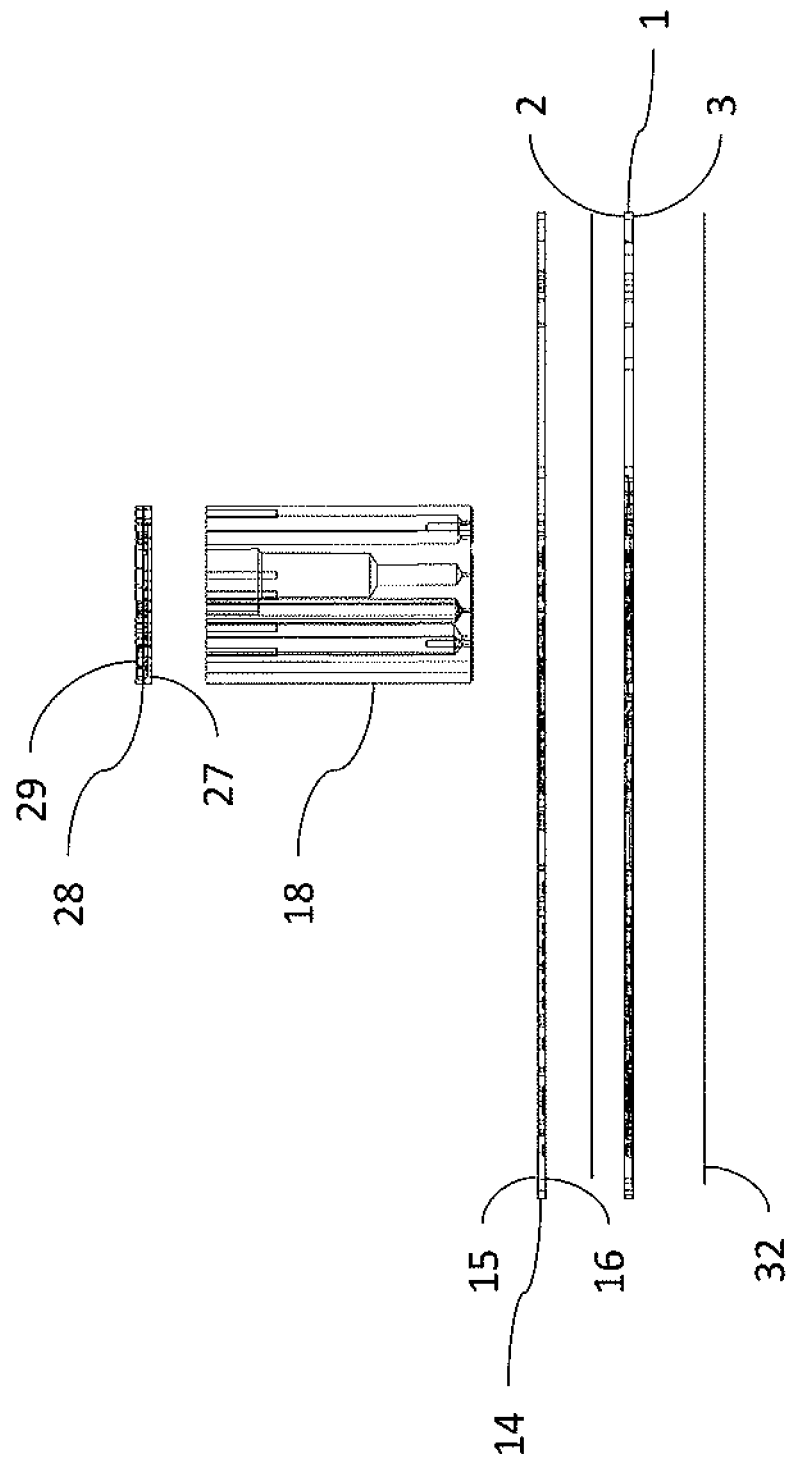
FIG. 57 is a side view schematic stack up of an embodiment of a biochip in accordance with the present technology.

The separation and detection subassembly (whether pressure loading or cross injection format) was attached to the fluidic subassembly using adhesive tape, and the subassemblies were oriented such that nucleic acid flow in within the separation and detection biochip was conducted in the opposite direction as NA purification and amplification. That is to say that the nucleic acids traveled through the separation and detection subassembly in the reverse direction from the general flow of fluids during purification and PCR amplification. This reverse of direction by using opposite sides of the subassembly allows the complex biochip to have a substantially reduced length. FIG. 57 illustrates how all the layers—the macrofluidic cover 27, 28, and 29; the macrofluidic block 18, pneumatic layer with top and bottom films 13, 15 and 16; valve subassembly layer; fluidic layer with top and bottom film 1, 2, and 3; and separation and detection biochip 32 or 33 are stacked together to form the biochip. FIG. 58 is a photo of the biochip assembly 34 with arrows indicating the direction of process flows.

With reference to FIGS. 39 and 41, to run the biochip the following reagents were loaded into the macrofluidic processing subassembly prior to the test:

Lysis solution (FIG. 39, 20), 550 microliters—Chaotropic salt based reagent for lysing cells and releasing DNA from samples.

Ethanol (FIG. 39, 21), 550 microliters—Together with the lysis solution, lyses cells and facilitates DNA binding to the silica based purification filter.

Wash solution (FIG. 39, 22), 3 ml—Ethanol based reagent for washing the purification filter to remove proteins and other biological materials to generate pure DNA.

Elution solution (FIG. 39, 23), 300 microliters, —Tris-EDTA based reagent that releases the purified DNA from the purification filter and stabilizes the DNA.

TTE buffer (FIG. 41, 58), 1.6 ml—Tris-Taps-EDTA based reagent for electrophoresis.

Formamide (FIG. 41, 59) 150 microliters—Denaturation solution for diluting PCR product to prepare the sample for separation and detection. By mixing sample and formamide at a ratio of approximately 1:4 (range from 1:50 to 1 to 1.5), it is not necessary to perform heating or snap cooling to effect denaturation. The obviation of the conventional heat/cooling steps simplifies the instrument.

With reference to FIGS. 40 and 41, the following lyophilized reagents were loaded into the fluidic subassembly of the biochip prior to the test:

PCR cake FIG. 40, 10, —Lyophilized PCR reaction mix.

Internal lane (sizing) standard (ILS) cake FIG. 41, 35—Lyophilized DNA fragments that are fluorescently labeled to allow the electrophoretic mobility of the amplified fragments to be correlated to molecular weights.

An advantage of this approach is that all lyophilized reagents are located within one subassembly. This allows for improved supply chain management as the conditions for filling lyophilized cakes (low humidity and static) are quite different from and much more demanding than those for filling liquids. Accordingly, liquid and lyophilized reagents can be filled separated and in parallel. Optionally, a lyophilized cake containing allelic ladder and ILS fragments can be inserted into the top cake chamber 35 for STR analytic runs.

The following reagent was loaded into the separation and detection section of the biochip prior to the test:

Sieving matrix (FIG. 55, 36 and FIG. 56, 36)—High molecular weight linear polyacrylamide solution for electrophoretic sieving of DNA.

Figure 59:
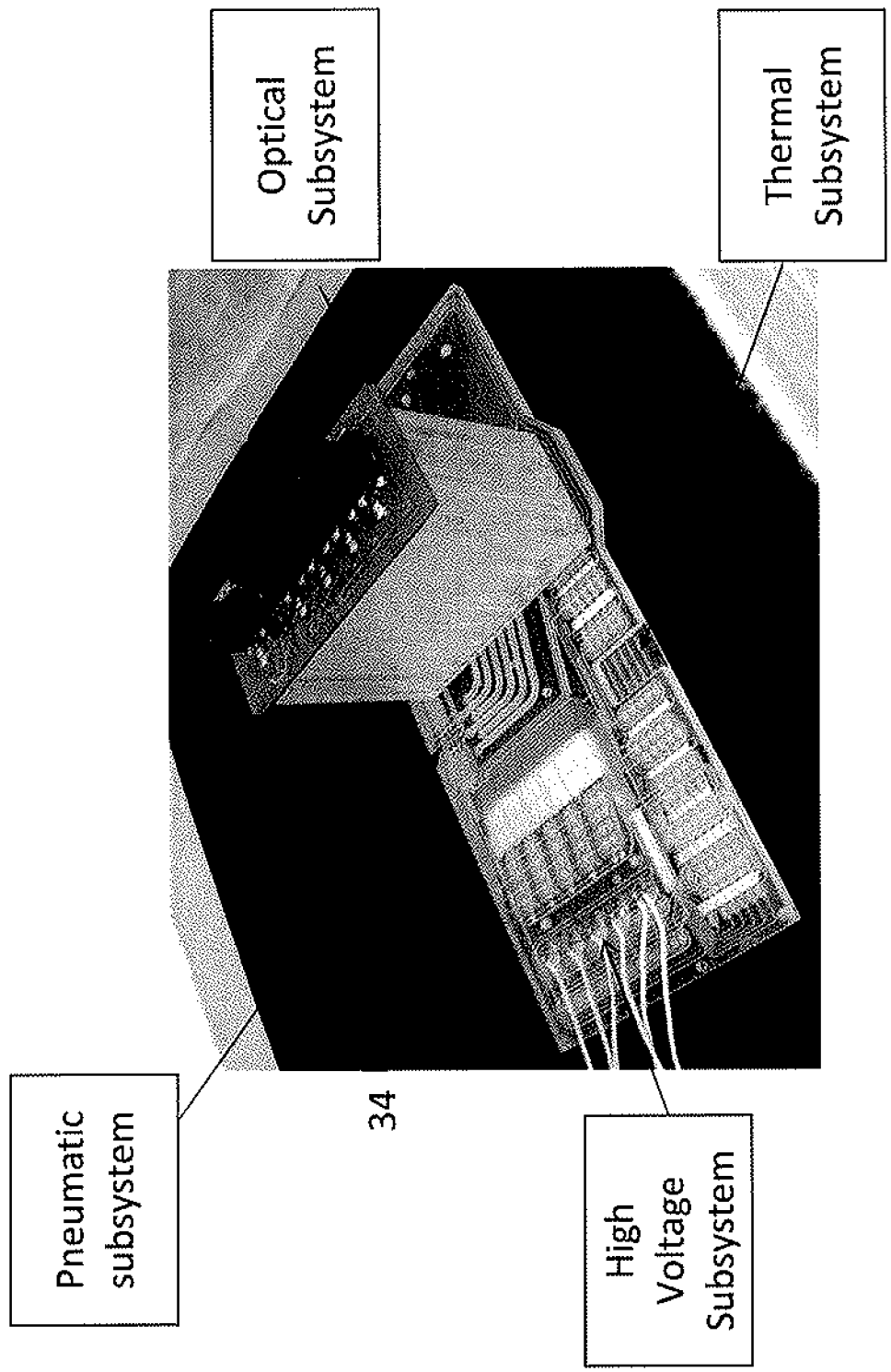
FIG. 59 is a photograph of the biochip assembly of FIG. 58. The biochip assembly interfaces with an optical subsystem, a thermal subsystem, a high voltage subsystem and pneumatic subsystem, and process control subsystem.

The biochip was inserted to a single, fully integrated instrument that contains the following subsystems (FIG. 59) as described in U.S. patent application Ser. No. 12/396,110, entitled Ruggedized Apparatus for Analysis of Nucleic Acid and Proteins, Published as 2009/0229983 (See, e.g., para. 65-76); U.S. patent application Ser. No. 12/080,746 entitled Methods for Rapid Multiplexed Amplification of Target Nucleic Acids, Published as 2009/0023602 (See, e.g, para. 54 and 56-67): U.S. patent application Ser. No. 12/080,751 entitled Integrated Nucleic Acid Analysis, Published as 2009/0059222 (See, e.g., para. 139-144); U.S. patent application Ser. No. 12/080,745, entitled Plastic Microfluidic Separation and Detection Platforms, Published as 2009/0020427 (See, e.g., para 95), all of which are incorporated herein in their entireties, by reference. The subsytems include:

Pneumatic subsystem—A pneumatic and vacuum pump is connected to a pneumatic manifold (FIG. 44, 61 as described in Example 4) through a set of tanks and solenoid valves. This manifold is in turn connected to the pneumatic ports of the biochip through the pneumatic interface. The solenoid valves are controlled by the process controller.

Thermal subsystem—A peltier based thermal cycling system is coupled to the thermal cycling chambers (FIG. 35, 62) of the biochip to rapidly cycle the reactions within these channels. As noted in Example 4, a clamp applies pressure to the amplification region to allow efficient thermal transfer with the thermal cycler. The reaction temperatures and dwell times are controlled by the process controller.

High voltage subsystem—A high voltage power supply is coupled to the anode (FIG. 55, 63) and cathode (FIG. 55, 64) portions of the separation biochip. Note that the anode electrodes pass through the pneumatic and fluidic pates at anode portion (FIG. 44, 65 and FIG. 35, 65) and the cathode electrode is incorporated into the cathode portion within the fluidic plate and pneumatic plates (FIG. 44, 66 and FIG. 35, 66) to gain access to the separation and detection biochip. Application of a high voltage generates an electric field along the channels to effect pre-electrophoresis, sample injection, and separation and detection. The high voltage subsystem is controlled by the process controller.

Figure 67:
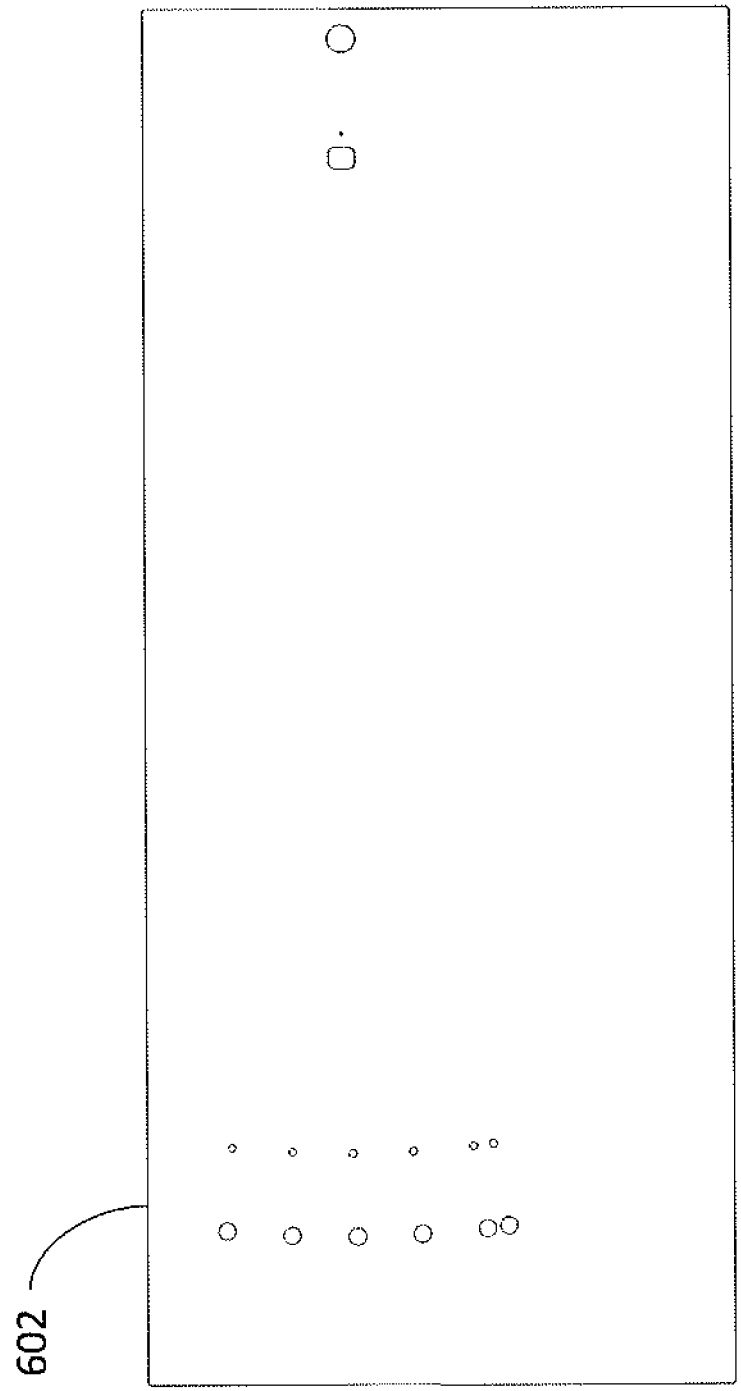
FIG. 67 is a bottom view schematic of an embodiment of a bottom patterned thin film for attachment to the bottom side of the fluidic plate of FIG. 65.

Optical subsystem—An optical system is coupled to the excitation and detection window of separation and detection biochip that is within the biochip (FIGS. 55, 67 and 56, 67). Note that the light passes through an open window on the pneumatic and fluidic plates (refer to FIG. 44, 38 and FIG. 35, 37). The optical system consists of a laser that is used to induce fluorescence from labeled DNA fragments within the separation channel. A set of dichroic mirrors is used to separate wavelength components of the fluorescence. A set of photomultiplier tubes are used to detect the fluorescence signals. A set of optical components is used to transfer light (laser excitation and emitted fluorescence) between the laser and the separation and detection biochip, and the separation and detection biochip and the detectors. The optical subsystem is controlled by the process controller.

Process controller—A computer based controller that can accept a pre-defined process script and implement the script automatically by reading the script and controlling the subsystems accordingly. Note that the computer also performs data processing and data analysis as required.

The sample-in to results out process was performed as follows. Five swabs were collected from donors. The swabs were collected by pressing the head of a Bode Secur-swab swab to the inside of the cheek as instructed by the manufacturer. Each of the 5 swabs was inserted into one of the swab chambers of the biochip, the biochip was placed into the instrument, and the automated process script was initiated to carry out the swab-in to results-out analysis. An automated script with the following steps was executed:

Initialization. All valves on the biochip were closed by applying pressure on valve lines. The valves in Example 5 were actuated with 20 psig of pressure to close and vented to atmosphere to open. The exception is valve V3 (FIG. 39, 41) which was maintained in the open position by the application of a vacuum of −11 psig. For simplicity, valve numbers are referred to based on their position relative to the pneumatic plate (even though the valves are actually located within the valve assembly).

Lysis. 550 microliters of lysis solution was pneumatically loaded from the lysis reagent chamber (FIG. 39, 20) into the swab chamber (FIG. 39, 19) by opening valve V1 (FIG. 39, 39) and applying a pressure of 3 psig to drive line DL1 (FIG. 39, 68) for 30 seconds and then 5.5 psig for 60 sec. Valve V1 (FIG. 39, 39) was closed and drive line 1 (FIG. 39, 68) was deactivated. 550 microliters of ethanol from the ethanol reagent chamber (FIG. 39, 21) was pneumatically loaded into the swab chamber (FIG. 39, 19) by opening valve V2 (FIG. 39, 40) and applying a drive pressure of 5.5 psig to drive line 2 (FIG. 39, 69) for 30 seconds.

Chaotic bubbling. Air was pneumatically driven into the swab chamber (FIG. 39, 19) by opening valve V2 (FIG. 39, 40) and applying a pneumatic pressure of 5.5 psig to drive line 2 (FIG. 39, 69) for 30 seconds. Valve 2 (FIG. 39, 40) was closed and drive line 2 (FIG. 39, 69) was deactivated. The air that was driven into the swab chamber bubbled through the lysis solution chaotically agitating both the lysis reagent and the swab head. This lysed the cells and released DNA.

Queuing. The lysate was pulled from the swab chamber (FIG. 39, 19) through a particulate filter (FIG. 39, 11) into a holding chamber (FIG. 39, 24) by maintaining valve V3 (FIG. 39, 41) in the open position while applying a vacuum of −7 psig to drive line 3 (FIG. 39, 70) for 30 seconds to transfer the lysate. Valve 3 (FIG. 39, 41) was closed and drive line 3 (FIG. 39, 70) was deactivated.

DNA binding. Lysate from the holding chamber (FIG. 39, 24) was pneumatically driven through the purification filter (FIG. 39, 12) and into the swab chamber (FIG. 39, 19) by opening valve V4 (FIG. 39, 42) and a set of valves V5 (FIG. 39, 43) and applying a pressure of 5 psig for 60 sec to drive line DL3 (FIG. 39, 70). Valves V4 (FIGS. 39, 42) and V5 (FIG. 39, 43) were closed and DL3 (FIG. 39, 70) was deactivated. DNA within the lysate bound to the purification filter (FIG. 39, 12). Note that the swab chamber also served as a waste chamber following generation and processing of the lysate; this dual use eliminated the need for another large volume chamber on the macrofluidic block. Separate waste chambers from each sample can optionally be included if retention of lysate is desired.

Wash. Wash solution was pneumatically driven from the wash reagent chamber (FIG. 39, 22) through the purification filter (FIG. 39, 12) into the swab chamber (FIG. 39, 19) by opening valves V5 (FIGS. 39, 43) and V6 (FIG. 39, 46), and applying a pneumatic pressure of 13 psig to drive line DL4 (FIG. 39, 71) for 90 seconds. Valves V5 (FIGS. 39, 43) and V6 (FIG. 39, 46) were closed and DL4 (FIG. 39, 71) deactivated. 3 ml of wash was passed through the purification filter to remove contaminants and particulate debris from the bound DNA. Two additional washes allowed cleaning of adjacent channels.

Dry. Air was pneumatically driven through the purification filter (FIG. 39, 12) and into the swab chamber (FIG. 39, 19) by opening valve V5 (FIG. 39, 43) and V6 (FIG. 39, 46), and applying a pressure of 13 psig to drive line DL4 (FIG. 39, 46) for 185 seconds. Valves V5 and V6 were closed and DL4 (FIG. 39, 71) was deactivated. The air partially to fully dries the purification filter.

Elution. Elution buffer is pneumatically driven from the elution reagent chamber (FIG. 39, 23) through the purification filter (FIG. 39, 12) and into an eluate holding chamber (FIG. 39, 25) by opening valves V6 (FIG. 39, 46), V7 (FIGS. 39, 45) and V8 (FIG. 39, 47) and applying a pressure of 5 psig to drive line DL5 (FIG. 39, 72) for 120 seconds. Valves V6 (FIG. 39, 46), V7 (FIGS. 39, 45) and V8 (FIG. 39, 47) were closed and DL5 (FIG. 39, 72) was deactivated. 300 microliters of elution buffer was passed through the purification filter (FIG. 39, 12) to release purified DNA that was bound to the purification filter.

Homogenization. Air was pneumatically driven into the eluate holding chamber by opening valve V6 (FIGS. 39, 46), and V8 (FIG. 39, 47) and applying a pressure of 5 psig to drive line DL4 (FIG. 39, 71) for 60 seconds. Valves V6 (FIGS. 39, 46), and V8 (FIG. 39, 47) were and DL4 (FIG. 39, 71) was deactivated. The air that was driven into the eluate holding chamber bubbles through the eluate to agitation and homogenize the DNA within the eluate. Optionally, a portion of the eluate can be routed to a storage chamber or onto a storage filter if a retention sample of the purified DNA is desired.

Eluate metering. Eluate was pneumatically driven from the Eluate holding chamber (FIG. 39, 25) into the eluate metering chambers (FIG. 40, 8) by opening Valve V10 (FIG. 39, 48) and applying pressure to DL6 (FIG. 39, 73) 1 psig for 40 seconds. Valves V10 (FIG. 39, 48) was closed and DL6 (FIG. 39, 73) was deactivated. Each eluate filled the metering chamber and stopped at a vent membrane. Excess eluate was pneumatically driven back into the Eluate holding chamber by opening valves V10 (FIGS. 39, 48) and V11 (FIG. 40, 50) and applying a pressure of 2 psig to Drive line DL7 (FIG. 40, 49) for 25 seconds. Valves V10 (FIGS. 39, 48) and V11 (FIG. 40, 50) were closed and DL7 (FIG. 40, 49) was deactivated.

Reconstitute PCR cake. The eluate was pneumatically driven from the eluate metering chamber (FIG. 40, 8) into the PCR cake chamber (FIG. 40, 10) by opening valves V11 (FIGS. 40, 50) and V12 (FIG. 40, 51) and applying a drive sequence of 0.2 psig for 30 seconds, then 0.4 psig for 30 sec, then 0.6 psig for 60 sec to drive line DL7 (FIG. 41, 49). Valves V11 (FIGS. 40, 50) and V12 (FIG. 40, 51) were closed and (FIG. 41, 49) was deactivated. 20.5 microliters of metered eluate was transferred to reconstitute the cake containing the lyophilized PCR reaction mix to generate the PCR mix for amplification.

Transfer into thermal cycling chamber. PCR reaction mix was pneumatically driven from the cake chamber (FIG. 40, 10) into the thermal cycling chambers (FIG. 40, 62) by opening valves V11 (FIG. 40, 50), V12 (FIG. 40, 51), V13 (FIGS. 40, 52), and V14 (FIG. 40, 53), and applying a sequentially increasing drive pressure sequence of 0.2 psig for 30 seconds, then 0.4 psig for 30 sec, then 0.6 psig for 30 sec to drive line DL7 (FIG. 40, 49). Valves V11 (FIG. 40, 50), V12 (FIG. 40, 51), V13 (FIGS. 40, 52), and V14 (FIG. 40, 53) were closed, and DL7 (FIG. 40, 49) was deactivated. The PCR reaction mix was transferred into the thermal cycling chambers and stops at the queuing vent membrane.

Thermal cycle. A thirty-one cycle protocol was applied to cycle the reaction within the thermal cycling chambers (FIG. 40, 62) to generate labeled amplicons. (See, Giese, H., et al. (2009). "Fast multiplexed polymerase chain reaction for conventional and microfluidic short tandem repeat analysis." *J Forensic Sci* 54(6): 1287-96, and application Ser. No. 12/080,746, published as 2009/0023603, entitled "Methods for Rapid Multiplexed Amplification of Target Nucleic Acids," both of which are incorporated herein by reference), The cycling conditions were as follows: Hotstart 93° C.×20 seconds followed by 31 cycles of (93° C.×4 seconds, 56° C.×15 seconds, and 70° C.×7 seconds) followed by a final extension of 70° C.×90 seconds.

Meter PCR product. PCR product was pneumatically driven from the thermal cycling chambers (FIG. 40, 62) into the PCR metering chamber (FIG. 41, 74) by opening valves V11 (FIG. 40, 50), V12 (FIG. 40, 51), V13 (FIG. 40, 52), V14 (FIGS. 40, 53), and V30 (FIG. 41, 111) and applying a sequentially increasing drive pressure sequence of 0.2 psig for 30 seconds, then 0.4 psig for 30 sec, then 0.6 psig for 45 sec drive line DL7 (FIG. 40, 49). Valves V11 (FIG. 40, 50), V12 (FIG. 40, 51), V13 (FIG. 40, 52), V14 (FIGS. 40, 53) and V30 (FIG. 41, 111) were closed and DL7 (FIG. 40, 49) was deactivated. The PCR product flows into the metering chamber and stops at a vent membrane.

Meter formamide. Formamide was pneumatically driven from the formamide reagent chamber (FIG. 41, 60) into the formamide metering chamber (FIG. 41, 76) by applying a pressure of 1 psig for 50 seconds to drive line DL8 (FIG. 41, 75). Drive line DL8 (FIG. 41, 75) was deactivated. In this step, a $6^{th}$ volume of formamide was metered (FIG. 41, 77) for reconstituting a cake to generate a control sample. The formamide flows into the metering chamber and stops at a vent membrane. Excess formamide is pneumatically driven from the formamide chamber into a waste chamber by opening valve V15 (FIG. 41, 54) and applying a pressure of 3 psig for 180 seconds to drive line DL8 (FIG. 41, 75). Valve V15 (FIG. 41, 54) was closed and DL8 (FIG. 41, 75) was deactivated. All of the excess formamide reagent chamber and drive line was transferred into the waste chamber.

Join PCR product and formamide. Metered PCR product was pneumatically driven from the PCR metering chamber (FIG. 41, 74) into the joining chamber (FIG. 41, 78) by opening valve V18 (FIG. 41, 57), V17 (FIGS. 41, 80) and V20 (FIG. 41, 81) and applying a 4 step drive profile of 0.0.2, 0.3, 0.4, and 0.5 psig for 30, 30, 30, and 30 sec respectively to drive line DL9 (FIG. 41, 79). Valve V18 (FIG. 41, 57), V17 (FIGS. 41, 80) and V20 (FIG. 41, 81) were closed and DL9 (FIG. 41, 79) was deactivated. Metered formamide was pneumatically driven from the formamide metering chamber (FIG. 41, 76) into the joining chamber (FIG. 41, 78) by opening valve V16 (FIGS. 41, 55) and V20 (FIG. 41, 81) and applying an increasing pressure of 0.2, 0.4 and 0.6 psig for 30, 30, and 60 seconds to drive line DL8 (FIG. 41, 75). Valve V16 (FIGS. 41, 55) and V20 (FIG. 41, 81) were closed and DL8 (FIG. 41, 75) was deactivated. The joining chamber allows the metered PCR and the metered formamide which originate from two independent flow to be combined to form the sample for separation and detection.

Reconstitute ILS cake. The sample for separation and detection was pneumatically driven into the ILS cake chambers (FIG. 41, 35) by opening valves V16 (FIGS. 41, 55) and V19 (FIG. 41, 56), and applying an increasing pressure of 0.2, 0.4 and 0.6 psig for 30, 30, and 60 seconds to drive line DL8 (FIG. 41, 75). V16 (FIGS. 41, 55) and V19 (FIG. 41, 56) were closed and DL8 (FIG. 41, 75) was deactivated. The sample for separation and detection which is composed of 4.1 microliters of PCR product and 16.4 microliters of formamide reconstituted the ILS cake within the chamber to generate the separation and detection sample.

Reconstitute Control+ILS cake. The $6^{th}$ metered formamide volume is pneumatically driven into the control+ILS cake chamber (FIG. 41, 83) by opening valves V16 and V20, and applying an increasing pressure of 0.2, 0.4 and 0.6 psig for 30, 30, and 60 seconds to drive line DL9. V16 and V20 are closed and DL9 is deactivated. The 20.5 microliters of formamide reconstituted the cake within the chamber to generate the separation and detection sample.

Inject samples into separation channel. The 6 separation and detection samples were pneumatically driven from the cake chambers (FIGS. 41, 35 and 82) through a debubbling chamber (FIG. 41, 83) to fill the cathode chamber (FIG. 41, 84) and a sample waste chamber (FIG. 41, 85) by opening valve V21 (FIGS. 41, 86) and V22 (FIG. 41, 87) and applying a pressure to drive line DL8 (FIG. 41, 74) with a sequentially stepped profile of 0.4, 0.6, 1.0, 1.5 and 2.0 psig for 30, 30, 30, 30, and 30 seconds respectively. (FIGS. 41, 86) and V22 (FIG. 41, 87) were closed and DL8 (FIG. 41, 74) was deactivated. The DNA within the sample was injected from the cathode chamber (FIG. 41, 84) into the separation portion of the biochip (FIG. 56 and FIG. 55, 88), by applying a voltage of 4400 V was applied to bias the cathode (FIGS. 55 and 56, 63) and anode (FIGS. 55 and 56, 64) for 35 seconds.

Separate and detect DNA. TTE was pneumatically driven from the from the TTE reagent reservoir (FIG. 41, 59) to fill the cathode (FIG. 41, 84) and to fill TTE waste chambers (FIGS. 41, 92, 93, and 13) by opening valves V25 (FIG. 41, 91), V24 (FIG. 41, 90), V26 (FIG. 41, 95), V27 (FIGS. 41, 96), and V28 (FIG. 41, 97) and applying a pressure to drive line DL10 (FIG. 41, 98) for 2 psig for 240 seconds. valves V25 (FIG. 41, 91), V24 (FIG. 41, 90), V26 (FIG. 41, 95), V27 (FIGS. 41, 96), and V28 (FIG. 41, 97) were closed and DL10 (FIG. 41,98) was deactivated. The flow of TTE through the cathodes displaced the sample within the cathodes. DNA that was injected into the separation portion of the S&D biochip (FIG. 55) traveled down the separation portion of the biochip (FIG. 56, 88), when a 6400 V was applied to bias the cathode (FIG. 55, 63) and anode (FIG. 55, 64) for 30 min. The optical system was also activated to effect laser induced fluorescence excitation and detection at the excitation and detection window. The laser was set to 200 mW and the data collection rate of 5 Hz is implemented. The fluorescent signal travels through the detection path to the photomultiplier tubes. There, the fluorescence is converted into a signal that is recorded by the system software.

Figure 60:
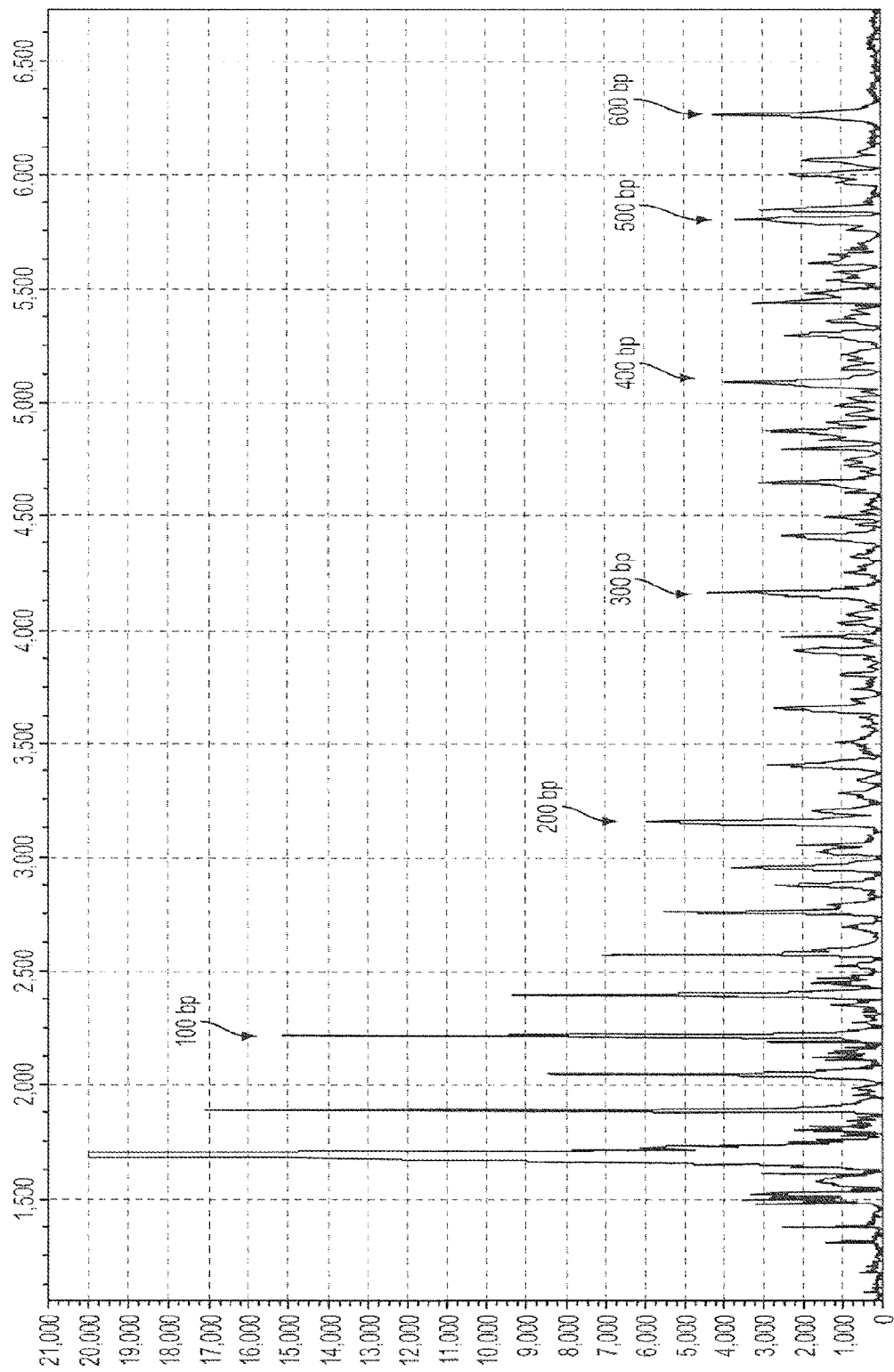
FIG. 60 is a control electropherogram generated for the control ILS sample (fragments fluorescently labeled with ROX) within an embodiment of a biochip in accordance with the present technology.
Figure 61:
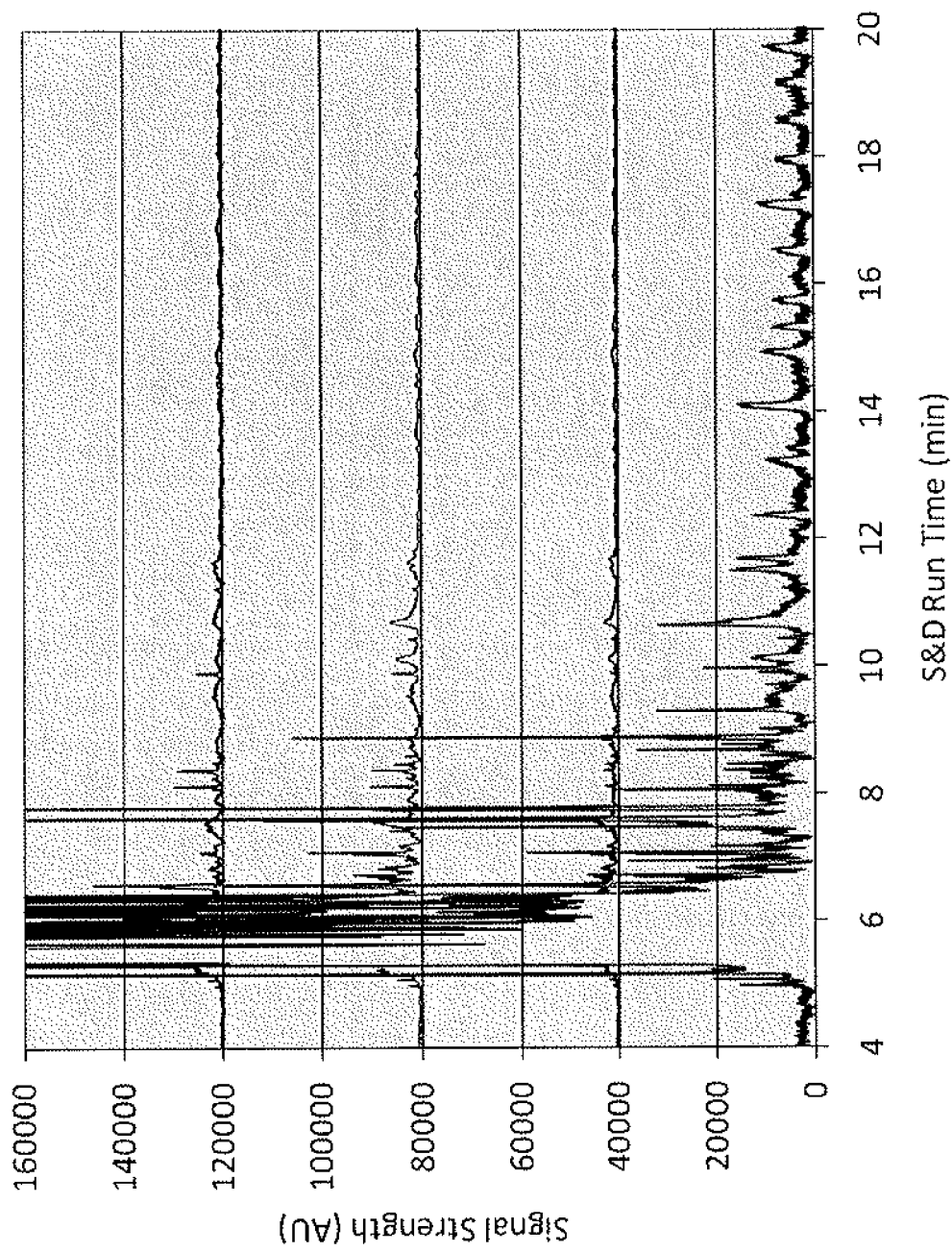
FIG. 61 is an electropherogram showing the sizes of the STR fragments generated for one buccal swab sample following an automated script. Each of fluorescent dyes used to label the STR primers in the PCR reaction mix and the ILS are shown in individual panels. Fluorescein-labeled fragments are shown in the top panel, JOE-labeled fragments are shown in the second panel from the top, TAMRA-labeled fragments are shown in the third panel from the top, and ROX-labeled ILS fragments are shown in the bottom panel.

Electropherograms (FIGS. 60 and 61) were generated following the scripted process steps as outlined above. The control electropherogram (FIG. 60) was generated for the control ILS sample (fragments fluorescently labeled with ROX). The x-axis represents data collection counts, with each count indicating the time at which the labeled fragment arrive at the detection zone. Several of the size standards are indicated by arrows, and lower molecular weight fragments migrate more rapidly than higher molecular weight fragments and are detected earlier (i.e. to the left of the graph). The Y-axis shows the relative fluorescent units (rfu) for each peak. FIG. 61 shows the sizes of the STR fragments generated for one buccal swab sample. Each of fluorescent dyes used to label the STR primers in the PCR reaction mix and the ILS are shown in individual panels. Fluorescein-labeled fragments are shown in the top panel, JOE-labeled fragments are shown in the second panel from the top, TAMRA-labeled fragments are shown in the third panel from the top, and ROX-labeled ILS fragments are shown in the bottom panel. The x- and y-axes are the same as described for FIG. 60. The entire process from insertion of samples to generation of the electropherogram required approximately 90 minutes and approximately 215 scripted process steps. Many process steps can be shortened, and the process can be performed in less than 45 minutes if desired.

Example 6

Figure 62:
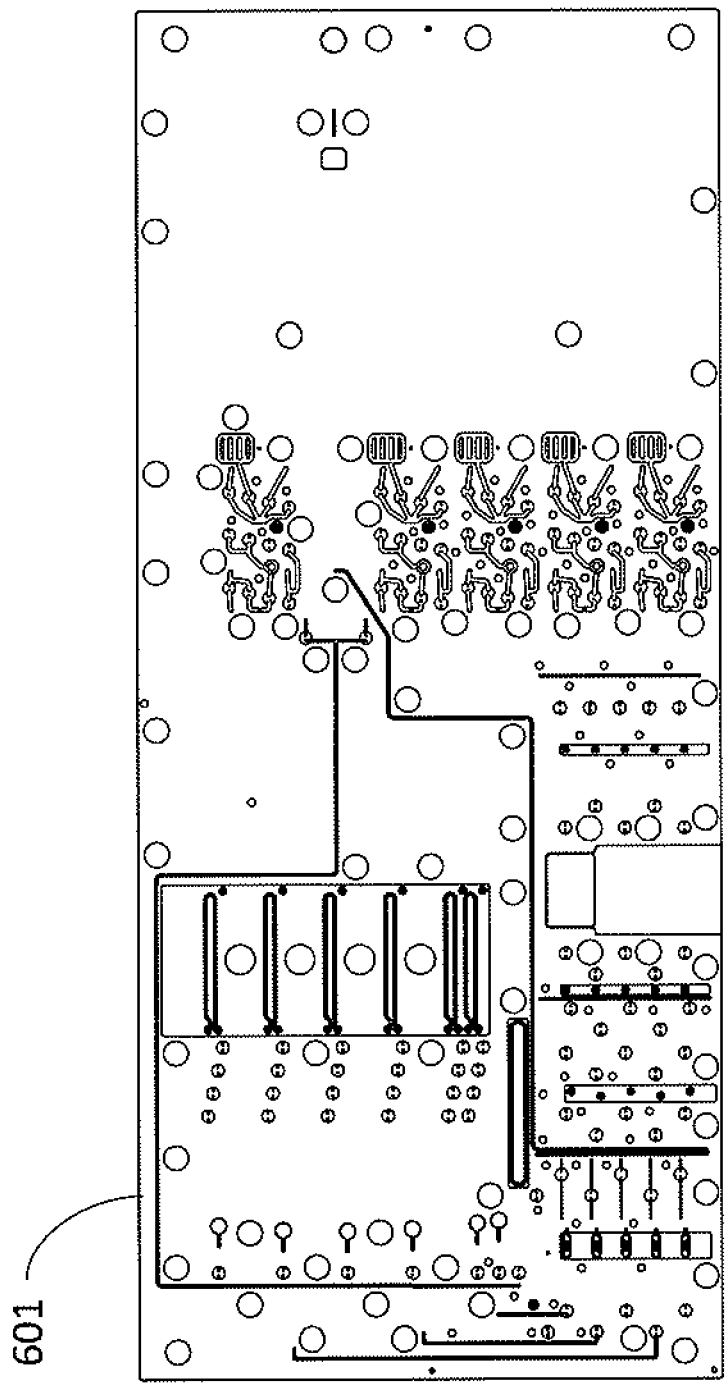
FIG. 62 is a top view schematic of an embodiment of a fluidic plate of a fluidic subassembly in accordance with the present technology.
Figure 63:
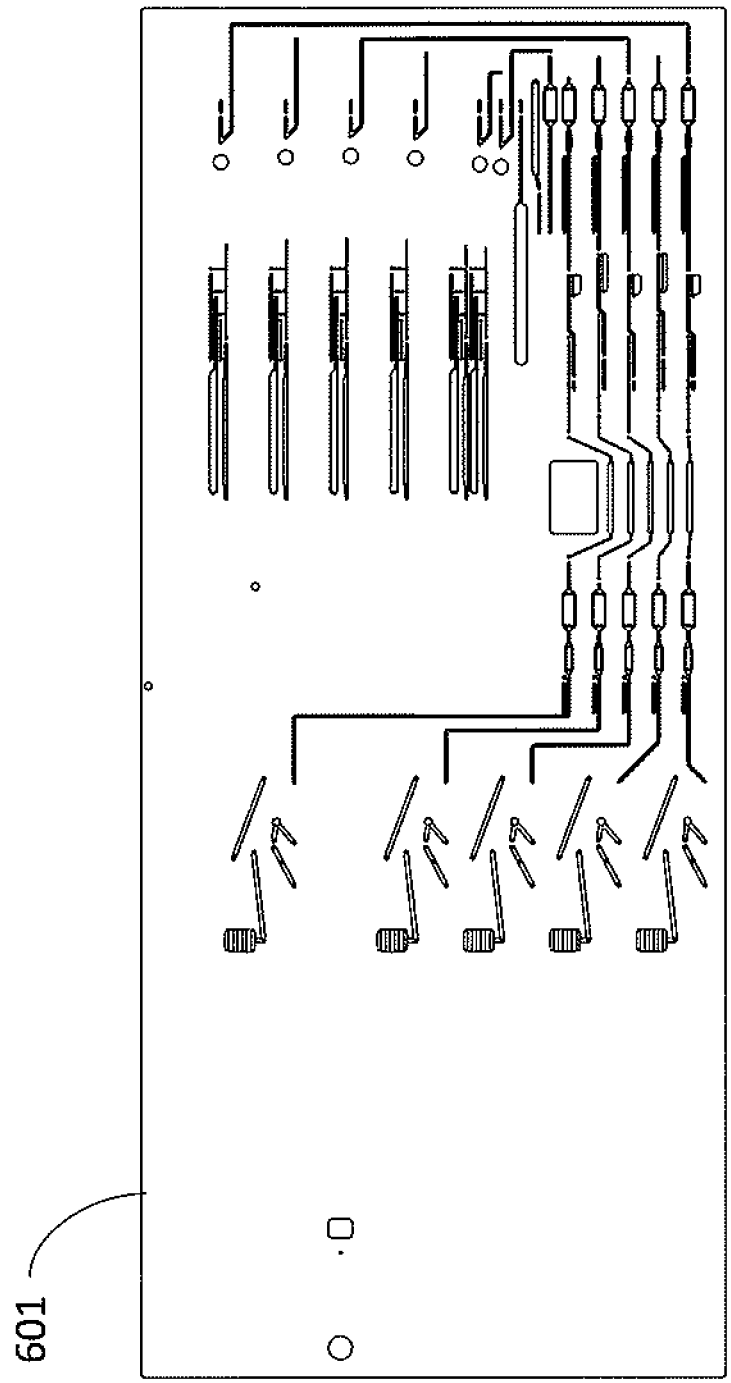
FIG. 63 is a bottom view schematic of the fluidic plate of FIG. 62.
Figure 64:
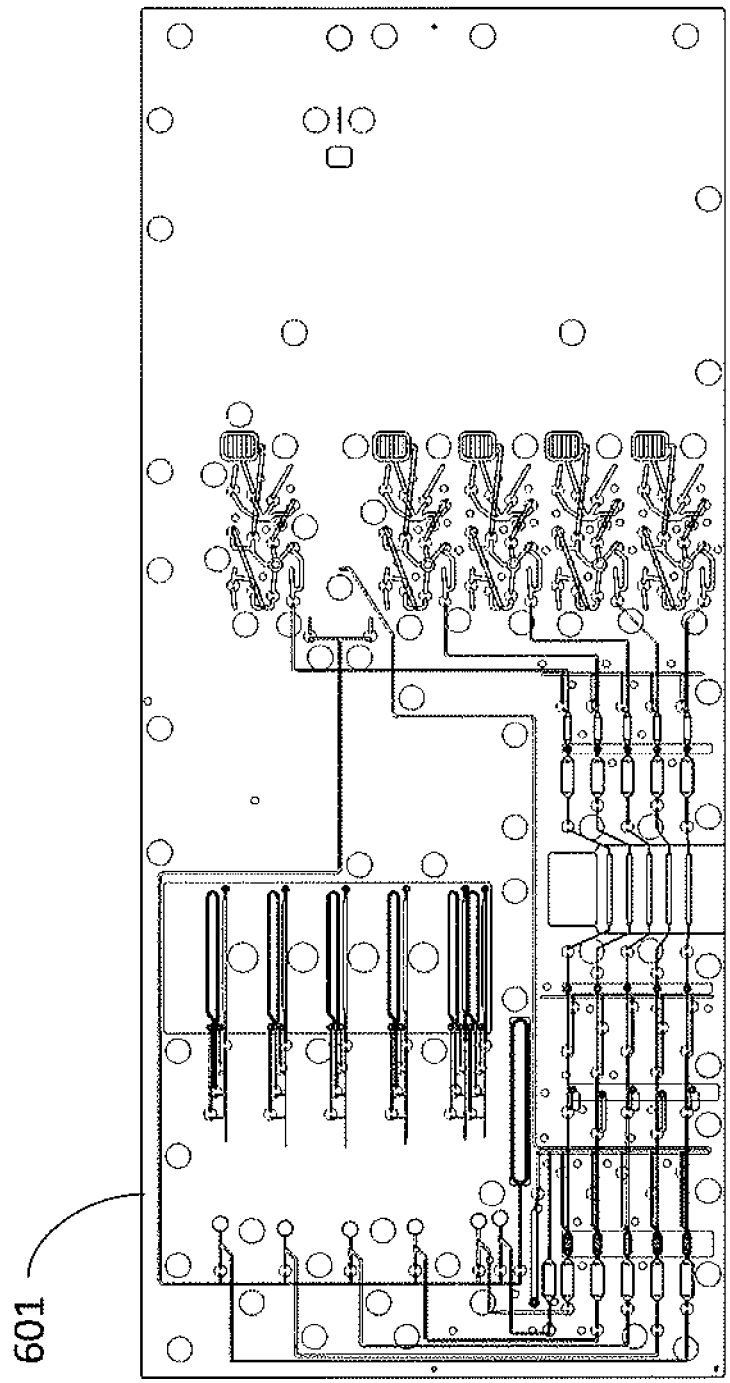
FIG. 64 is a transparent view schematic of the fluidic plate showing both top side features of FIG. 62 and bottom side features of FIG. 63.
Figure 65:
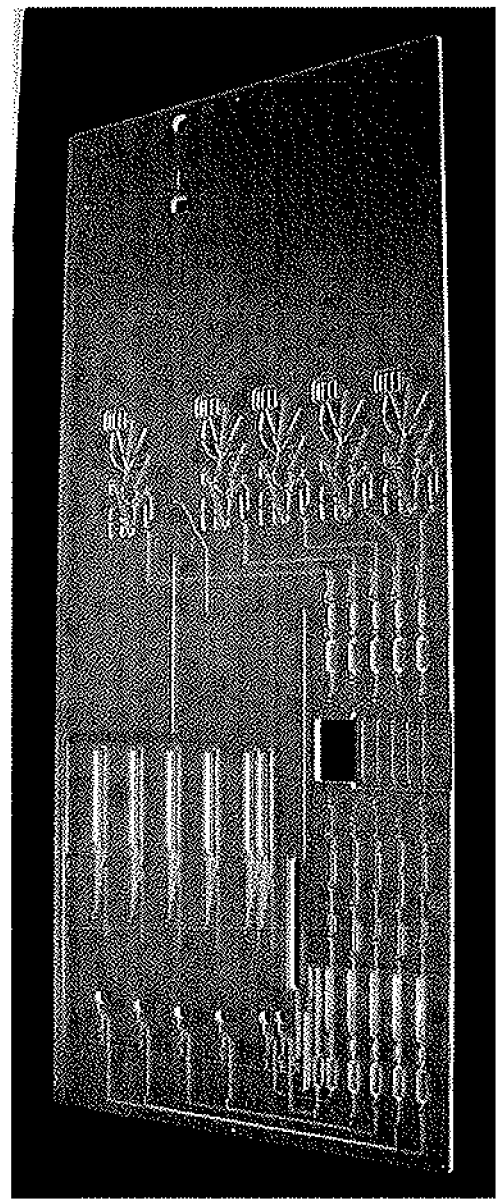
FIG. 65 is a photograph of an embodiment of an injection molded fluidic plate.
Figure 66:
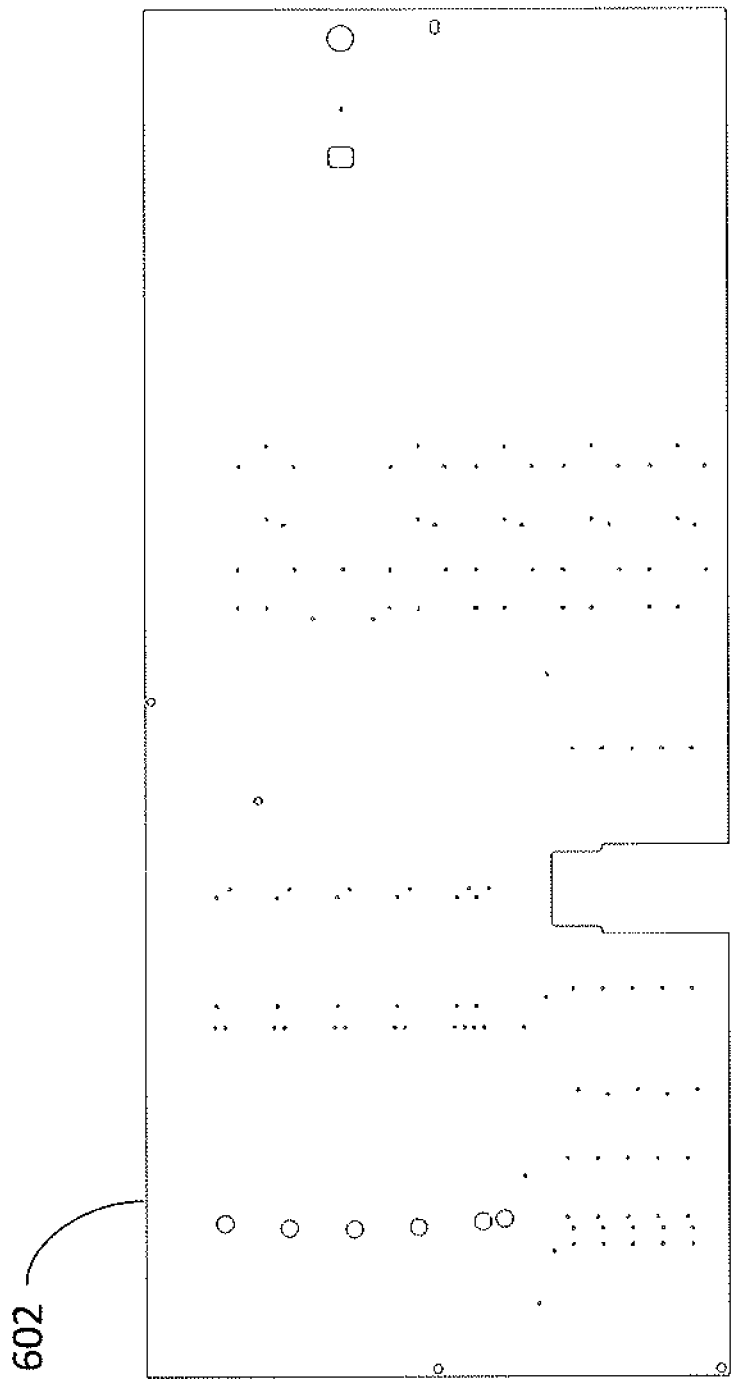
FIG. 66 is a top view schematic of an embodiment of a top patterned thin film for attachment to the top side of the fluidic plate of FIG. 65.

Injection Molding of a Fully Integrated Biochip that Purifies Nucleic Acids, Amplifies the Purified DNA, Electrophoretically Separates the Amplified DNA and Generates an STR Profile Using an Automated Script This biochip resembles that of Example 5, with the fluidic and pneumatic plates fabricated by injection molding. The stationary, unitary plastic biochip that accepts 5 buccal swabs and generates STR profiles consists of the following parts:

Fluidic subassembly—This subassembly transfers and processes fluids within the biochip, interacting with the pneumatic subassembly, macrofluidic processing subassembly, valve subassembly, and separation and detection subassembly. It was fabricated by injection molding of COP with an interconnected set of channels, chambers, and membrane and filter features on both the top and bottom sides of the thermoplastic sheet. FIG. 62 shows the top side of the fluidic plate 601, FIG. 63 shows the bottom side of the fluidic plate 601, and FIG. 64 shows a transparent view of the fluidic plate 601, showing features from both sides. FIG. 65 shows a photo of the injection molded fluidic plate 601. The injection molded fluidic plate has dimensions of 276 mm×117 mm×2.5 mm. Both the top and bottom sides of the plate are covered with patterned thin plastic films. FIG. 66 shows the top patterned thin film 602 and FIG. 67 shows the bottom patterned thin film 603.

Figure 68:
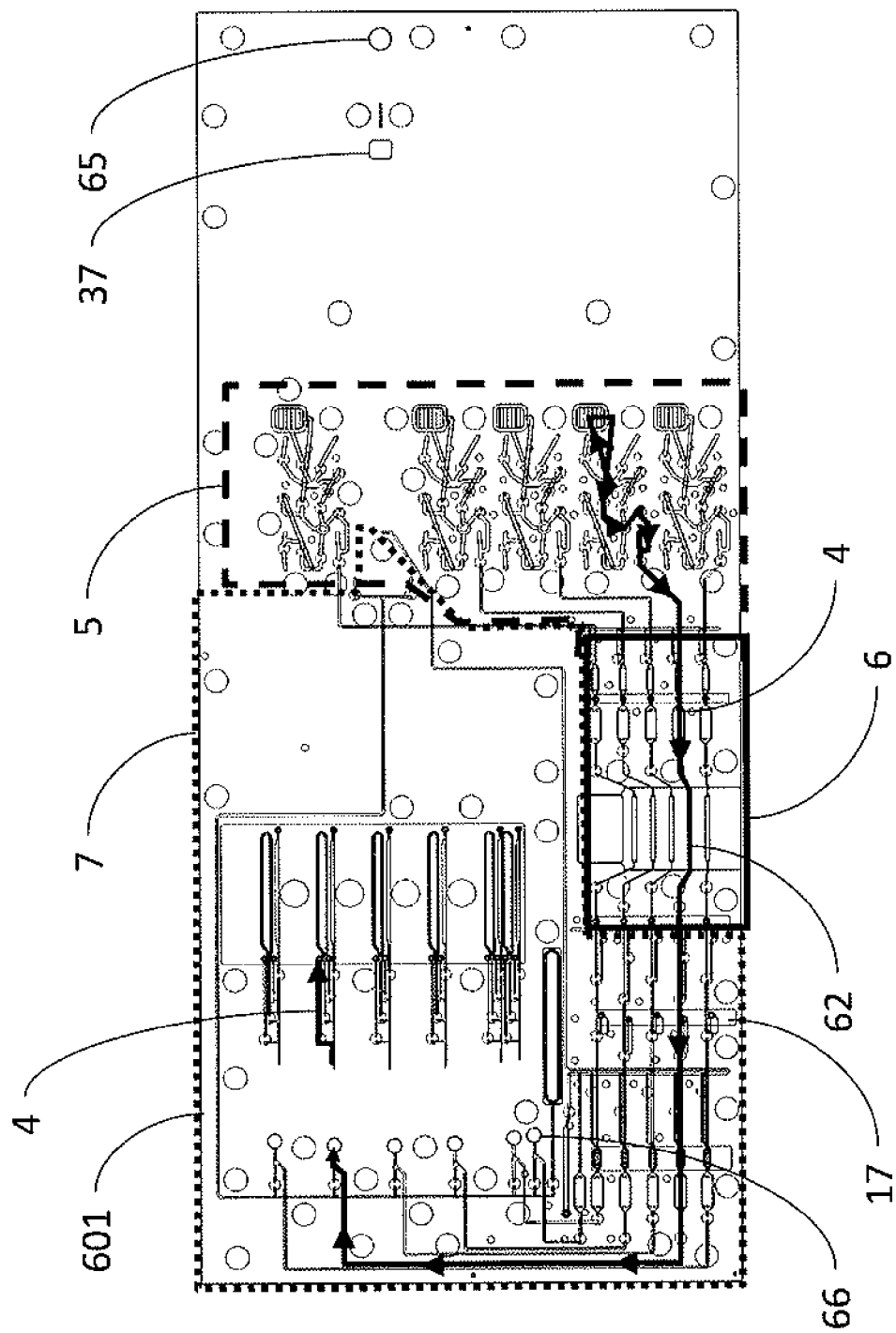
FIG. 68 is a top view schematic of an embodiment of a fluidic plate with a line illustrating a path of a single sample takes through the fluidic plate.
Figure 69:
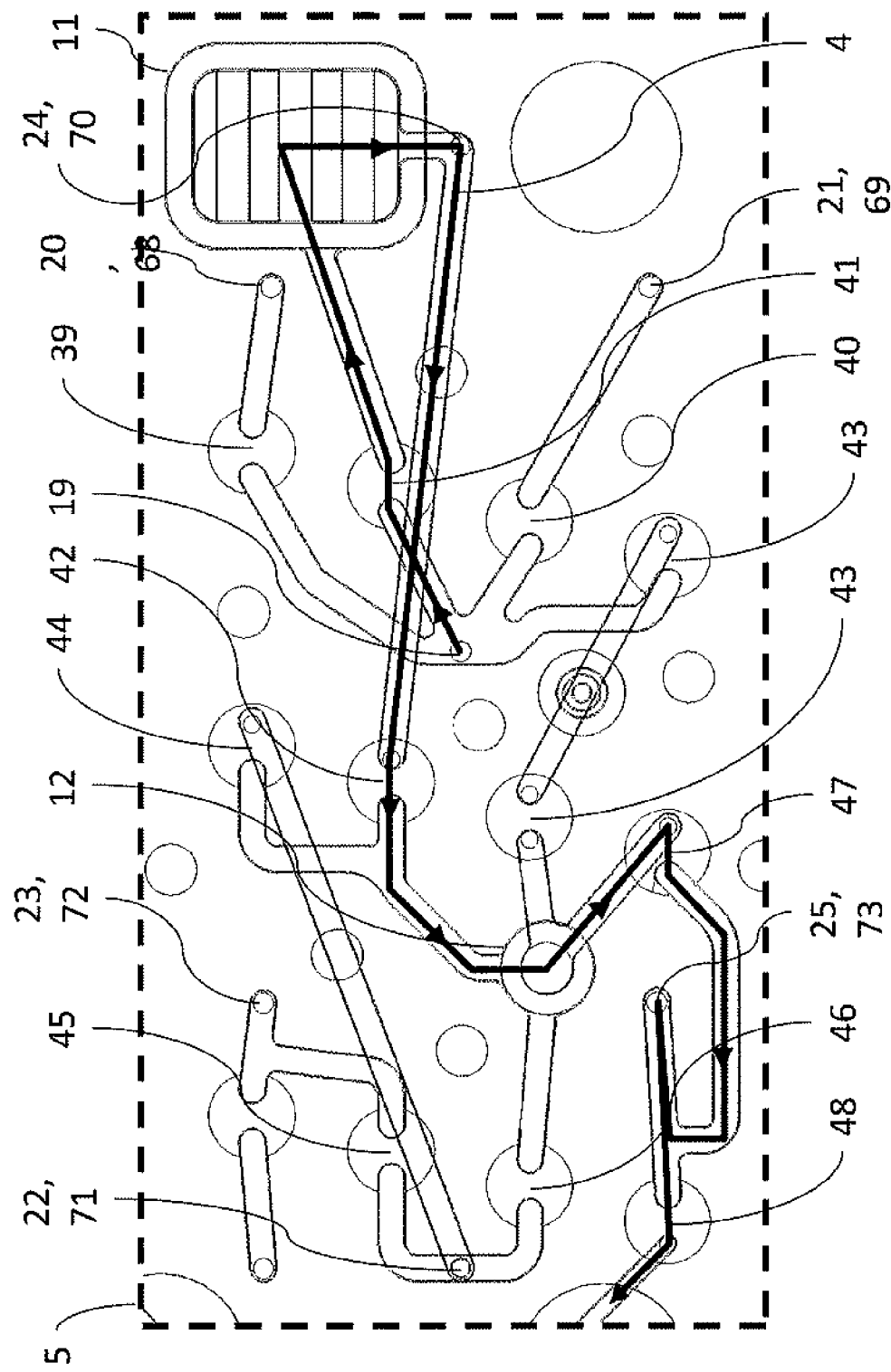
FIG. 69 is a top expanded view schematic of the fluidic plate of FIG. 68 showing a portion of the path through a purification region.

The flow path for a single sample within the injection molded fluidic plate is shown in FIG. 68. The sample flows path 4 passes through a purification section (FIG. 68, 5), PCR section (FIG. 68, 6) and separation and detection section (FIG. 68, 7). Expanded views of the purification section, PCR section and separation and detection sections are shown in FIGS. 69, 70, and 71 respectively. The injection molded fluidic plate has a particulate filter region (FIG. 69, 11), a purification membrane region (FIG. 69, 12), and several types of chambers, including metering chambers (FIG. 69, 8), reconstitution chambers (FIG. 69, 10), joining chambers (FIG. 70, 78), waste chambers (FIGS. 70, 92, 93, and 94), and cathodes (FIG. 71, 84) and an anode (FIG. 64, 65).

The top and bottom sides of the fluidic plate were covered with patterned thin plastic films and attached by solvent bonding. Bonding of the patterned thin films to the fluidic plate can also be performed ultrasonically, thermally, and using adhesives. Features on the plate and films can be added to facilitate the bonding method; for example, energy director ridges can be placed at the sites of ultrasonic welding. The thin films have a thickness of 100 microns and were fabricated by CNC machining; optionally, they can be fabricated by die cutting, or laser cutting. The features in the thin plastic films include through holes and were aligned to the corresponding features on the injection molded layer to provide access to the fluidic sandwich layer. Purification membranes (FIG. 69, 12), particulate filters (FIG. 69, 11) and vent membranes were attached to this subassembly by thermal welding prior to bonding of the thin films. Similarly, these membranes and filters can be attached by ultrasonic welding and heat staking.

Figure 74:
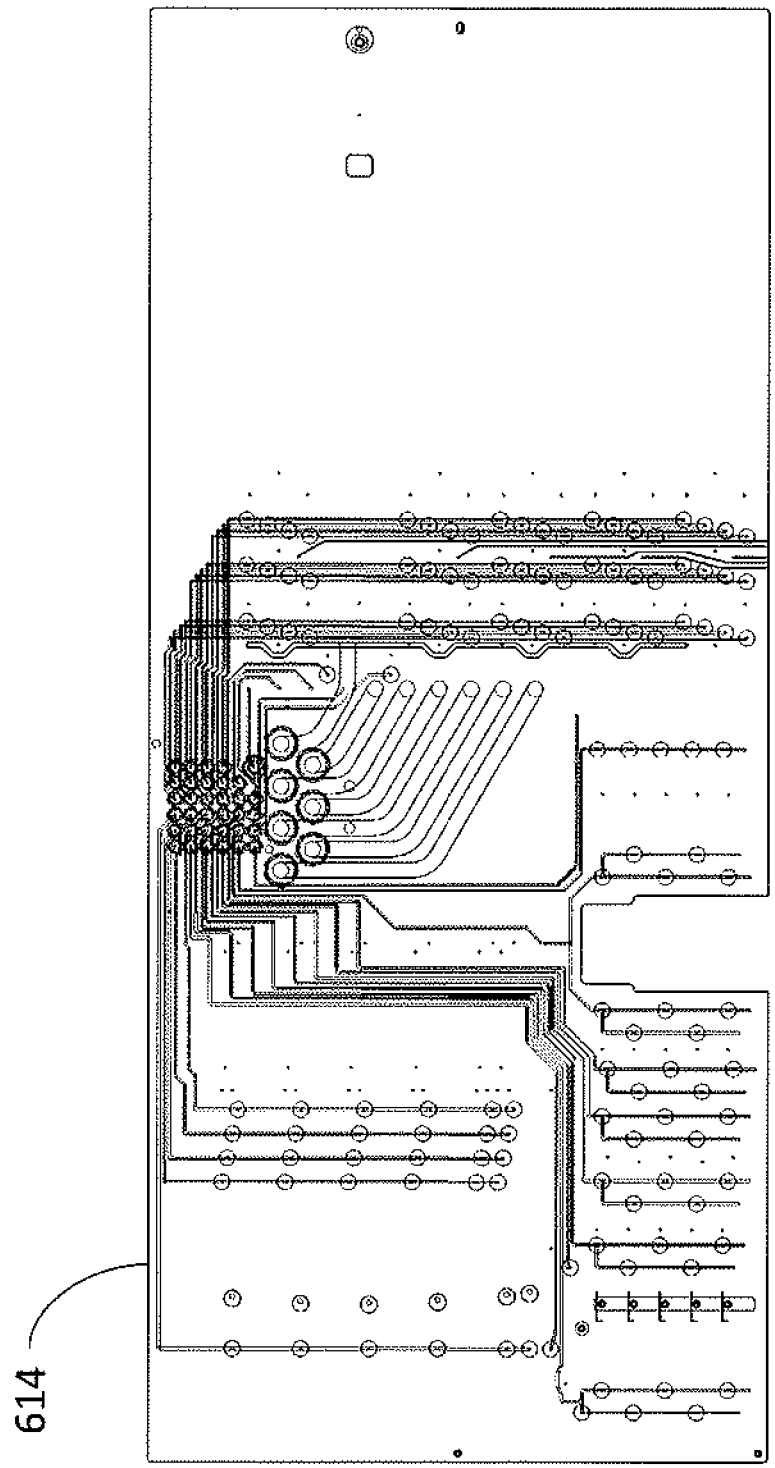
FIG. 74 is a transparent top view of the pneumatic plate showing both top and bottom sides of the pneumatic plate of FIGS. 72 and 73.
Figure 75:
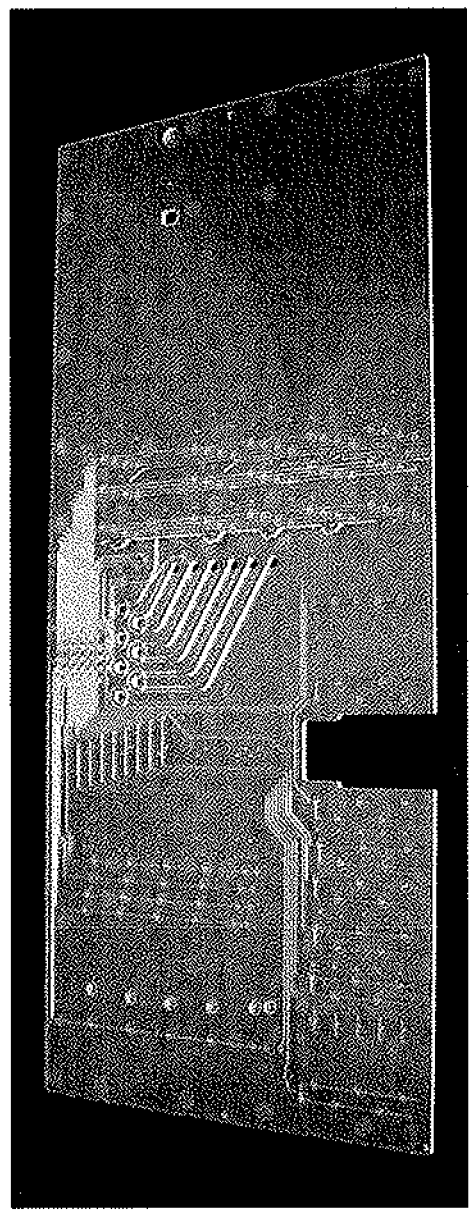
FIG. 75 is a photograph of an embodiment of an injection molded pneumatic plate.
Figure 76:
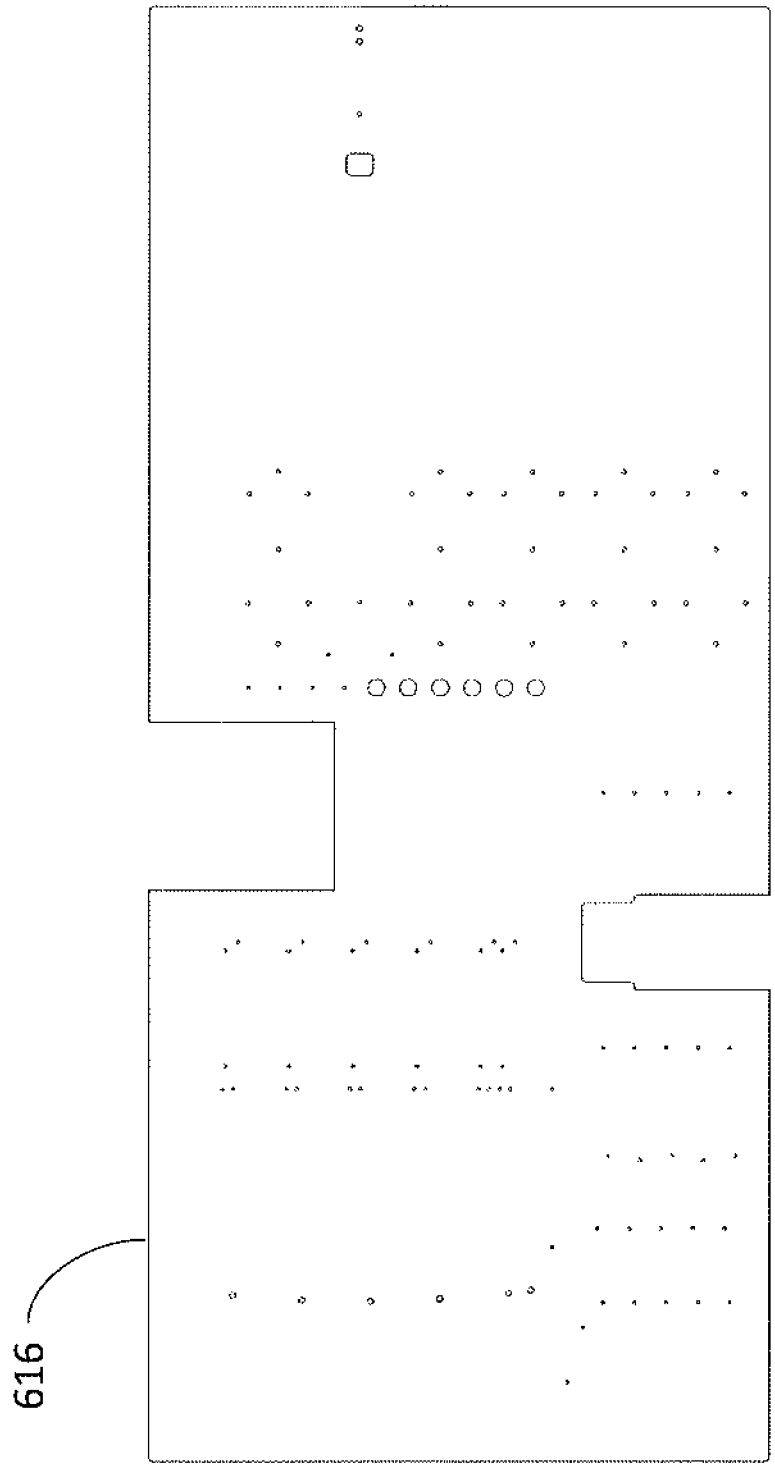
FIG. 76 is a top view schematic of an embodiment of a patterned thin film for attachment to a top side of the injection molded pneumatic plate of FIG. 75.

Pneumatic subassembly—This subassembly couples the pneumatic drive of the instrument to fluidic subassembly (as described in Example 4) to pneumatically drive fluids within the fluidic subassembly and to pneumatically activating valves within the biochip. This subassembly was fabricated by injection molding of COP with an interconnected set of channels, chambers, and membrane and filter features on both the top and bottom sides of the thermoplastic sheet. FIG. 72 shows the top side of the pneumatic plate, FIG. 73 shows the bottom side of the pneumatic plate, and FIG. 74 shows a transparent view of the pneumatic plate, showing features from both sides. FIG. 75 shows a photograph of the injection molded pneumatic plate. The injection molded pneumatic plate has dimensions of 277.6 mm×117.7 mm×2.50 mm. Following bonding, all pneumatic subassembly features align with the fluidic subassembly features. The top side of the plate is covered with patterned thin plastic film with through holes to allow access to the plate. FIG. 76 shows the top patterned thin film. The bottom side of the plate is covered when the patterned thin film representing the valve subassembly is attached by solvent bonding; the thin film is patterned by CNC machining. The thin films have a thickness of 100 microns. Patterns can be cut prior to bonding or following bonding. Prior to bonding the top and bottom thin films to the pneumatic plate, vent membranes are incorporated (FIG. 68, 17). Attachment of the thin films to the pneumatic plate was accomplished with solvents but can also be performed ultrasonically, thermally, and using adhesives.

The macrofluidic processing subassembly and separation and detection subassembly are the same as described in Example 5. In this biochip, the valve assembly is a thin thermoplastic film that is 40 microns, 50 microns, or 100 microns thick. The pneumatically actuated rigid valve layer (described in Example 2) separates the pneumatic and the fluidic assemblies. When pneumatically activated, this layer deflects to control flow of fluids (including air) within the fluidic layer.

The pneumatic-valve-fluidic stack subassembly was fabricated by solvent bonding the pneumatic assembly to the fluidic assembly. The chambers and channels on the bottom side of the pneumatic plate are sealed when solvent bonded to the fluidic layer. The macrofluidic block was attached to the cover by clamping using a gasket and screws. The block was attached to the pneumatic subassembly using double-sided PSA tape. Alternatively, the block attachments can be made by solvent and thermal bonding. Finally, the separation and detection subassembly was attached to the fluidic subassembly using PSA tape, and the subassemblies were oriented such that nucleic acid flow in within the separation and detection biochip was conducted in the opposite direction as NA purification and amplification.

To test the biochip, liquid and lyophilized reagents are loaded as described in Example 5 and the biochip is inserted into the fully integrated instrument of Example 5. Five buccal swabs are collected from donors, and each of the 5 swabs was inserted one of the swab chambers of the biochip. An automated script with the following steps is executed:

Initialization. All valves on the biochip are closed by applying pressure of 75 psig on all valve lines. The exception is valve V3 which was maintained in the open position by the application of a vacuum of −11 psig. For simplicity, valve numbers are referred to based on their position relative to the pneumatic plate (even though the valves are actually located within the valve assembly).

Lysis. 550 microliters of lysis solution is pneumatically loaded from the lysis reagent chamber (FIG. 69, 20) into the swab chamber (FIG. 69, 19) by opening valve V1 (FIG. 69, 39) and applying a pressure of 3 psig to drive line DL1 (FIG. 69, 68) for 30 seconds and then 5.5 psig for 60 sec. Valve V1 (FIG. 69, 39) is closed and drive line 1 (FIG. 69, 68) is deactivated. 550 microliters of ethanol from the ethanol reagent chamber (FIG. 69, 21) is pneumatically loaded into the swab chamber (FIG. 69, 19) by opening valve V2 (FIG. 69, 40) and applying a drive pressure of 5.5 psig to drive line 2 (FIG. 69, 69) for 30 seconds.

Chaotic bubbling. Air is pneumatically driven into the swab chamber (FIG. 69, 19) by opening valve V2 (FIG. 69, 40) and applying a pneumatic pressure of 5.5 psig to drive line 2 (FIG. 69, 69) for 30 seconds. Valve 2 (FIG. 69, 40) is closed and drive line 2 (FIG. 69, 69) is deactivated. The air that is driven into the swab chamber bubbles through the lysis solution chaotically agitating both the lysis reagent and the swab head. This lysed the cells and released DNA.

Queuing. The lysate is pulled from the swab chamber (FIG. 69, 19) through a particulate filter (FIG. 69, 11) into a holding chamber (FIG. 69, 24) by maintaining valve V3 (FIG. 69, 41) in the open position while applying a vacuum of −7 psig to drive line 3 (FIG. 69, 70) for 30 seconds. Valve 3 (FIG. 69, 41) is closed and drive line 3 (FIG. 69, 70) is deactivated.

DNA binding. Lysate from the holding chamber (FIG. 69, 24) is pneumatically driven through the purification filter (FIG. 69, 12) and into the swab chamber (FIG. 69, 19) by opening valve V4 (FIG. 69, 42) and a set of valves V5 (FIG. 69, 43) and applying a pressure of 5 psig for 60 sec to drive line DL3 (FIG. 69, 70). Valves V4 (FIGS. 69, 42) and V5 (FIG. 69, 43) were closed and DL3 (FIG. 69, 70) is deactivated. DNA within the lysate binds to the purification filter (FIG. 69, 12). Note that the swab chamber also serves as a waste chamber following generation and processing of the lysate; this dual use eliminates the need for another large volume chamber on the macrofluidic block. Separate waste chambers from each sample can optionally be included if retention of lysate is desired.

Wash. Wash solution is pneumatically driven from the wash solution chamber (FIG. 69, 22) through the purification filter (FIG. 69, 12) into the swab chamber (FIG. 69, 19) by opening valves V5 (FIGS. 69, 43) and V6 (FIG. 69, 46), and applying a pneumatic pressure of 13 psig to drive line DL4 (FIG. 69, 71) for 90 seconds. Valves V5 (FIGS. 69, 43) and V6 (FIG. 69, 46) were closed and DL4 (FIG. 69, 71) deactivated. 3 ml of wash is passed through the purification filter to remove contaminants and particulate debris from the bound DNA. Two additional washes allow cleaning of adjacent channels.

Dry. Air is pneumatically driven through the purification filter (FIG. 69, 12) and into the swab chamber (FIG. 69, 19) by opening valve V5 (FIG. 69, 43) and V6 (FIG. 69, 46), and applying a pressure of 13 psig to drive line DL4 (FIG. 69, 46) for 185 seconds. Valves V5 and V6 are closed and DL4 (FIG. 69, 71) is deactivated. The air partially to fully dries the purification filter.

Elution. Elution buffer is pneumatically driven from the elution reagent chamber (FIG. 69, 23) through the purification filter (FIG. 69, 12) and into an eluate holding chamber (FIG. 69, 25) by opening valves V6 (FIG. 69, 46), V7 (FIGS. 69, 45) and V8 (FIG. 69, 47) and applying a pressure of 5 psig to drive line DL5 (FIG. 69, 72) for 120 seconds. Valves V6 (FIG. 69, 46), V7 (FIGS. 69, 45) and V8 (FIG. 69, 47) are closed and DL5 (FIG. 69, 72) was deactivated. 300 microliters of elution buffer is passed through the purification filter (FIG. 69, 12) to releases purified DNA that was bound to the purification filter. Optionally, a portion of the eluate can be routed to a filter for storage as a retention sample. In this case, the filter would be incorporated into a mechanism that would allow it to be removed from the biochip.

Homogenization. Air is pneumatically driven into the eluate holding chamber by opening valve V6 (FIGS. 69, 46), and V8 (FIG. 69, 47) and applying a pressure of 5 psig to drive line DL4 (FIG. 69, 71) for 60 seconds. Valves V6 (FIGS. 69, 46), and V8 (FIG. 69, 47) were and DL4 (FIG. 69, 71) is deactivated. The air that is driven into the eluate holding chamber bubbles through the eluate to agitation and homogenize the DNA within the eluate.

Eluate metering. Eluate is pneumatically driven from the Eluate holding chamber (FIG. 69, 25) into the eluate metering chambers (FIG. 70, 8) by opening Valve V10 (FIG. 69, 48) and applying pressure to DL6 (FIG. 69, 73) 1 psig for 40 seconds. Valves V10 (FIG. 69, 48) is closed and DL6 (FIG. 69, 73) is deactivated. Each eluate fills the metering chamber and stopped at a vent membrane. Excess eluate is pneumatically driven back into the Eluate holding chamber by opening valves V10 (FIGS. 69, 48) and V11 (FIG. 70, 50) and applying a pressure of 2 psig to Drive line DL7 (FIG. 70, 49) for 25 seconds. Valves V10 (FIGS. 69, 48) and V11 (FIG. 70, 50) were closed and DL7 (FIG. 70, 49) is deactivated.

Reconstitute PCR cake. The eluate is pneumatically driven from the eluate metering chamber (FIG. 70, 8) into the PCR cake reconstitution and reciprocation chamber (FIG. 70, 610) by opening valve V11 (FIG. 70, V11) and linearly increasing the drive pressure of DL7 (FIG. 71, 49) from 0 to 15 psig over 15 seconds. The chamber of (FIG. 70, 610) is designed to hold the lyophilized PCR cake, allow reconstitution of the PCR cake, and reciprocal mixing of the PCR reaction. The volume of the chamber is approximately 2.2 times that of the eluate which is defined by the eluate metering chamber (FIG. 70, 8). The PCR cake is placed and located at the input side of the chamber. The output of the chamber is sealed by a valve. The air between the eluate and the valve V13 (FIG. 71, 52) is compressed allowing the eluate to move within the chamber and come in contact with the lyophilized PCR cake. The cake is allowed to reconstitute by maintaining the pressure of DL7 at 15 psig for 60 seconds. 11.5 microliters of metered eluate is transferred to reconstitute the cake containing the lyophilized PCR reaction mix to generate the PCR mix for amplification.

Reciprocally Mix the PCR solution—The PCR solution (i.e. PCR cake that is reconstituted with eluate) is then moved from the PCR reconstitution and reciprocation chamber (FIG. 70, 10) back to the eluate metering chamber (FIG. 70, 8) by linearly decreasing the pressure of drive line DL7 from 15 psig to 0 psig over 15 seconds. The air between the eluate and valve V13 (FIG. 71, 52) is compressed and acts as an air spring to push against the PCR mix moving it towards the metering chamber (FIG. 71, 8). The PCR mix is reciprocally mixed by linearly increasing the drive pressure of DL7 from 0 psig to 15 psig over 15 seconds, and then from 15 psig to 0 psig over 15 seconds. Valve V12 (FIG. 70, 49) is closed and drive line DL7 (FIG. 70, 49) is deactivated Transfer into thermal cycling chamber. PCR reaction mix is pneumatically driven from the eluate metering chamber (FIG. 70, 8) into the thermal cycling chambers (FIG. 70, 62) by opening valves V11 (FIG. 70, 50), V13 (FIGS. 70, 52), and V14 (FIG. 70, 53), and applying a sequentially increasing drive pressure sequence of 0.2 psig for 30 seconds, then 0.4 psig for 30 sec, then 0.6 psig for 30 sec to drive line DL7 (FIG. 70, 49). Valves V12 (FIGS. 70, 51) and V14 (FIG. 70, 53) were closed, and DL7 (FIG. 70, 49) is deactivated. The PCR reaction mix is transferred into the thermal cycling chambers and stops at the queuing vent membrane.

Thermal cycle. A thirty-one cycle protocol is applied to cycle the reaction within the thermal cycling chambers (FIG. 70, 62) to generate labeled amplicons. The cycling conditions are as follows: Hotstart 93° C.×20 seconds followed by 31 cycles of (93° C.×4 seconds, 56° C.×15 seconds, and 70° C.×7 seconds) followed by a final extension of 70° C.×90 seconds.

Meter PCR product. PCR product is pneumatically driven from the thermal cycling chambers (FIG. 70, 62) into the PCR metering chamber (FIG. 71, 74) by opening valves V11 (FIG. 70, 50), V13 (FIGS. 70, 52) and V14 (FIGS. 70, 53) and V30 (FIG. 71, 111), and applying a sequentially increasing drive pressure sequence of 0.2 psig for 30 seconds, then 0.4 psig for 30 sec, then 0.6 psig for 45 sec drive line DL7 (FIG. 70, 49). Valves V11 (FIG. 70, 50), V13 (FIG. 70, 52), V14 (FIGS. 70, 53), and V30 (FIG. 71, 111) were closed and DL7 (FIG. 70, 49) is deactivated. The PCR product flows into the metering chamber and stops at a vent membrane.

Meter formamide. Formamide is pneumatically driven from the formamide reagent chamber (FIG. 71, 60) into the formamide metering chamber (FIG. 71, 76) by applying a pressure of 1 psig for 50 seconds to drive line DL8 (FIG. 71, 75). Drive line DL8 (FIG. 71, 75) is deactivated. In this step, a $6^{th}$ volume of formamide is metered (FIG. 71, 77) for reconstituting a cake to generate a control sample. The formamide flows into the metering chamber and stops at a vent membrane. Excess formamide is pneumatically driven from the formamide chamber into a waste chamber by opening valve V15 (FIG. 71, 54) and applying a pressure of 3 psig for 180 seconds to drive line DL8 (FIG. 71, 75). Valve V15 (FIG. 71, 54) is closed and DL8 (FIG. 71, 75) is deactivated. All of the excess formamide reagent chamber and drive line is transferred into the waste chamber.

Join PCR product and formamide. Metered PCR product is pneumatically driven from the PCR metering chamber (FIG. 71, 74) into the joining chamber (FIG. 71, 78) by opening valve V18 (FIG. 71, 57), V17 (FIGS. 71, 80) and V20 (FIG. 71, 81) and applying a 4 step drive profile of 0.0.2, 0.3, 0.4, and 0.5 psig for 30, 30, 30, and 30 sec respectively to drive line DL9 (FIG. 71, 79). Valve V18 (FIG. 71, 57), V17 (FIGS. 71, 80) and V20 (FIG. 71,81) were closed and DL9 (FIG. 71, 79) is deactivated. Metered formamide is pneumatically driven from the formamide metering chamber (FIG. 71, 76) into the joining chamber (FIG. 71, 78) by V20 (FIG. 71, 81) by applying an increasing pressure of 0.2, 0.4 and 0.6 psig for 30, 30, and 60 seconds to drive line DL8 (FIG. 71, 75). Valve V20 (FIG. 71, 81) is closed and DL8 (FIG. 71, 75) is deactivated. The joining chamber allows the metered PCR and the metered formamide which originate from two independent flow to be combined to form the sample for separation and detection.

Reconstitute ILS cake. The sample for separation and detection is pneumatically driven from the joining chamber (FIG. 71, 78) into the ILS cake chambers (FIG. 71, 635) and ILS+Control cake chamber (FIG. 71, 682) by opening valves V20 (FIG. 71, 81) and linearly increasing the drive pressure of DL8 (FIG. 71, 75) from 0 to 15 psig over 15 seconds. The air between the sample and the valve V21 (FIG. 71, 86) is compressed allowing the sample to move within the chamber and come in contact with the lyophilized ILS cake. The cake is allowed to reconstitute by maintaining the pressure of DL8 (FIG. 71, 75) at 15 psig for 60 seconds. 11.5 microliters of metered sample is transferred to reconstitute the cake containing the lyophilized internal lane standard to generate the separation and detection sample.

Reciprocally Mix the separation and detection solution— The PCR solution (i.e. ILS cake that is reconstituted with metered formamide and metered PCR product) is then moved from the ILS reconstitution and reciprocation chamber (FIG. 71, 635) back to the joining chamber (FIG. 71, 78) by linearly decreasing the pressure of drive line DL8 (FIG. 71, 75) from 15 psig to 0 psig over 15 seconds. The air between the eluate and valve V13 (FIG. 71, 52) is compressed and will acts as an air spring to push against the separation and detection sample to mix moving it towards the formamide metering chamber (FIG. 71, 76). The separation and detection sample is reciprocally mixed by linearly increasing the drive pressure of DL8 (FIG. 71, 75) from 0 psig to 15 psig over 15 seconds, and then from 15 psig to 0 psig over 15 seconds. Drive line DL8 (FIG. 71, 75) was deactivated.

Inject samples into separation channel. The 5 separation and detection samples are pneumatically driven from the joining chamber (FIG. 71, 78) and control sample from the formamide metering chamber (FIG. 71, 76) through the ILS cake chamber (FIGS. 71, 635, and 682), which now acts as a debubbling chamber to fill the cathode chamber (FIG. 71, 84) and a sample waste chamber (FIG. 71, 85) by opening valve V21 (FIGS. 71, 86) and V22 (FIG. 71, 87) and applying a pressure to drive line DL9 (FIG. 71, 79) with a sequentially stepped profile of 0.4, 0.6, 1.0, 1.5 and 2.0 psig for 30, 30, 30, 30, and 30 seconds respectively. Valves V21 (FIGS. 71, 86) and V22 (FIG. 71, 87) are closed and DL8 (FIG. 71, 74) is deactivated. The DNA within the sample is injected from the cathode chamber (FIG. 71, 84) into the separation portion of the biochip (FIG. 55 and FIG. 56, 88), by applying a voltage of 4400 V is applied to bias the cathode (FIGS. 55 and 56, 63) and anode (FIGS. 55 and 56, 64) for 35 seconds.

Separate and detect DNA. TTE is pneumatically driven from the from the TTE reagent reservoir (FIG. 71, 59) to fill the cathode (FIG. 71, 84) and to fill TTE waste chambers (FIGS. 71, 92, 93, and 13) by opening valves V25 (FIG. 71, 91), V24 (FIG. 71, 90), V26 (FIG. 71, 95), V27 (FIGS. 71, 96), and V28 (FIG. 71, 97) and applying a pressure to drive line DL10 (FIG. 71,98) for 2 psig for 240 seconds. valves V25 (FIG. 71, 91), V24 (FIG. 71, 90), V26 (FIG. 71, 95), V27 (FIGS. 71, 96), and V28 (FIG. 71, 97) were closed and DL10 (FIG. 71,98) is deactivated. The flow of TTE through the cathodes displaces the sample within the cathodes. DNA that is injected into the separation portion of the S&D biochip (FIG. 55 or 5.24) travels injected down the separation portion of the biochip, when a 6400 V is applied to bias the cathode (FIGS. 55 and 56, 63) and anode (FIGS. 55 and 56, 64) for 30 min. The optical system is also activated to effect laser induced fluorescence excitation and detection at the excitation and detection window. The laser is set to 200 mW and the data collection rate of 5 Hz is implemented. The fluorescent signal travels through the detection path to the photomultiplier tubes. There, the fluorescence is converted into a signal that is recorded by the system software.

Electropherograms are generated for the samples and control following the scripted process steps as outlined above. The entire process from insertion of samples to generation of the electropherogram requires approximately 90 minutes. Many process steps can be shortened, and the process can be performed in less than 45 minutes if desired.

FIG. 77 illustrates the relationship of scripted processing steps and resultant processing steps for one portion of the process. Eluate is pneumatically driven from the Eluate holding chamber (FIG. 39, 25) to result in a metered volume into the eluate metering chambers (FIG. 39, 8) with the 10 step script of FIG. 77. The script steps consisting of 5 valve and drive line state changes to move eluates from the holding chambers to the metering chambers. The next 5 script steps remove the excess eluate and push this volume into the holding chamber. Accordingly, the 10 scripted processing steps (increasing and decreasing pressures on valves and drive lines) correspond to two resultant processing steps (the movement of sample from the eluate holding chamber to the eluate metering chamber and the movement of excess sample back to the eluate holding chamber).

Example 7

Sample Splitting to Eliminate the Need for Nucleic Acid Quantitation

The amount of nucleic acids in a given sample, whether a forensic, clinical, or biothreat sample, is highly variable. In certain nucleic acid manipulations, reaction conditions require a particular range of input nucleic acid to be effective. In the laboratory, this problem is often solved by performing a nucleic acid quantitation step prior to a given manipulation. Nucleic acid quantitation has been developed for microfluidic applications as described in patent application Ser. No. 12/816,370 entitled "Improved Methods for Forensic DNA Quantitation," incorporated herein by reference.

The instant invention provides another solution to the problem of requiring a certain range of nucleic acids in a microfluidic biochip. This approach does not involve quantitation but instead is based on diluting a given sample one or more times to provide 2 or more nucleic acid concentrations for analysis, preferably in parallel. The invention is exemplified using touch samples. Touch samples are forensic samples that consist of cells (primarily epithelial) that are left on surfaces after exposure to the human body. They include fingerprints, skin cells found on clothing (e.g. a shirt collar), and oral epithelial cells found on the opening of a soda can or the rim of a drinking glass. The quantity of DNA that is recovered from touch DNA samples is highly variable. Touch samples generally contain up to 100 ng of DNA, and most touch samples contain from 0.5-10 ng DNA. Accordingly, the Touch Sample System will process swabs containing 0.5-100 ng DNA.

Although it is likely that most touch samples will contain less than 10 ng of DNA, an unknown touch sample must be processed with the expectation that the full 200-fold range of DNA must be processed correctly. In a manual amplification system, amplifying 0.5 ng would be reasonable but amplifying 100 ng would not. Accordingly, in manual systems, DNA purified from touch samples is generally quantified prior to amplification. The microfluidic biochips of the invention allow touch sample DNA to be processed without quantitation by splitting purified DNA into two aliquots within the fluidic subassembly. One aliquot of the eluted DNA is amplified neat (assuming less than 10 ng DNA is present in the amplification mix) and the other is diluted 20-fold (assuming 5-100 ng DNA is present in the reaction mix). Both the neat and diluted aliquots are amplified and separated and detected independently but in parallel. The neat sample allows effective amplification across a range of at least 0.05-10 ng of purified DNA, and the diluted sample allows effective amplification across a range of at least 1-200 ng of purified DNA; the entire range of DNA content that cab be assayed effectively extends over a range of at least 40,000-fold.

Sample splitting microfluidics are incorporated into the biochips of Examples 5 and 6 as follows. DNA is eluted in a volume of 20 microliters using the same DNA purification protocol. At this volume, the eluate holding chamber is removed from the macrofluidic processing subsystem, and a 20 microliter eluate holding chamber is placed on the fluidic plate of the fluidic subassembly. On that plate, the 20 microliters of purified DNA is routed to parallel paths:

- In the neat path, 12 microliters of DNA is metered in a metering chamber, transferred to the PCR cake reconstitution chamber, and transferred to the PCR chambers for amplification. The chambers will be expanded slightly to accommodate approximately 10 microliters of reconstituted reaction mix.
- In the dilution path, approximately 2 microliters of DNA is metered and joined with 38 µl of metered Elution Solution. The diluted solution is then transferred to the cake reconstitution chamber, and transferred to the PCR chambers for amplification.
- Following amplification, the two solutions are processed in parallel through separation and detection.

Figure 78:
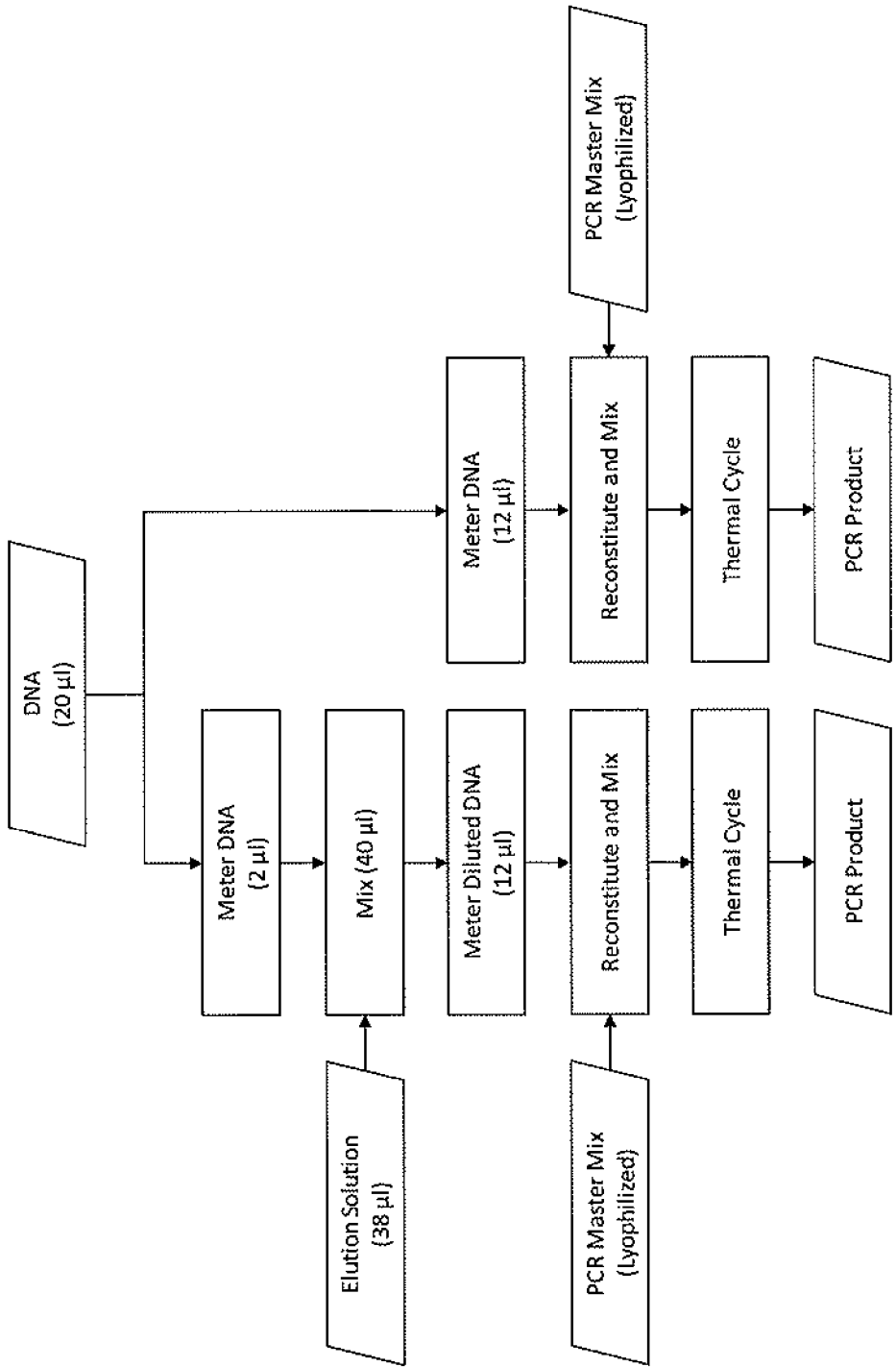
FIG. 78 is a flowchart of an embodiment of a sample splitting and dilution microfluidic circuit.

A flowchart of the sample splitting and dilution microfluidic circuit is shown in FIG. 78. Optionally, the purified DNA sample can be split into more than two aliquots for subsequent processing, and the diluted sample can be further diluted to generate additional aliquots for processing. For touch samples, such dilution is not necessary, but certain forensic, clinical diagnostic, and biothreat samples may contain much more DNA and their analysis facilitated by the processing of three or more aliquots.

Example 8

Plastic Background Fluorescence

The separation and detection biochips are fabricated in thermoplastic. Thermoplastics polymers when exposed to laser excitation autofluoresce to generate a background noise that is detected and processed by the detection system. This autofluorescence degrades the signal-to-noise ratio of real signal peaks which raises the limit of detection of the system. Conventional S&D biochips for separation and detection are fabricated in glass or quartz substrates which exhibit less autofluorescence per unit thickness compared to plastic substrates. Several considerations must be made when performing laser induced fluorescence detection with plastic substrates:

(1) Selecting a plastic material that exhibits low autofluorescence—Cyclin olefin copolymer (COC) and Cyclic olefin polymer (COP) thermoplastic material is used to fabricate the separation and detection biochips that are used in Examples 5 and 6. These thermoplastics exhibit inherently lower autofluorescence in the visible wavelength range as compared to other polymers.

Figure 79:
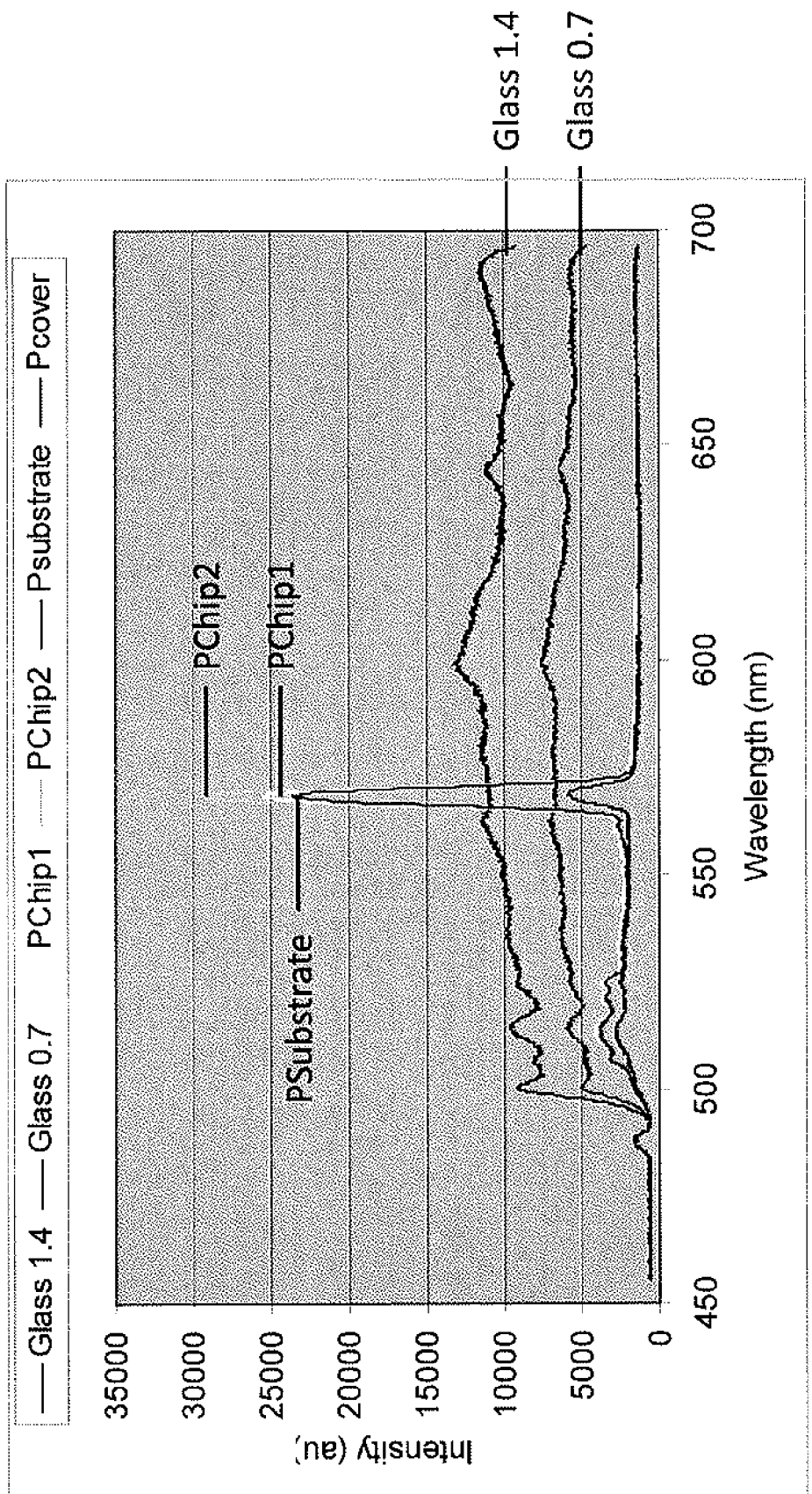
FIG. 79 is a graph showing background fluorescence of several materials at different thicknesses.

(2) Reducing the thickness of plastic substrate that is excited by the laser—The thickness of the material used is limited by the ability of the structure to withstand the gel filling pressures which may exceed 350 psig. The biochips used in Examples 5 and 6 are fabricated by embossing channel features into a 188 micron thick thermoplastic sheet and then bonding another 188 micron thick thermoplastic sheet to cover the channels. An experiment to measure the background fluorescence on glass and plastic substrates was conducted by placing several substrates (plastic 188 nm, plastic 376 nm, borosilicate glass 0.7 nm, and borosilicate glass 1.4 nm) onto the separation and detection window of the Genebench optical detection instrument. (See generally, App. Ser. No. 12/080,745, published as 2009/0020427 entitled "Plastic Microfluidic Separation and Detection Platforms,") 200 mW of laser excitation was applied to the substrate and signal was collected. FIG. 79 shows the background fluorescence of low fluorescence plastic (188 microns and 376 microns thick) and borosilicate glass (0.7 mm and 1.4 mm thick). The data shows that the background fluorescence for thin films of plastic is 4 to 7 times lower than that of 0.7 mm and 1.4 mm thick borosilicate glass.

(3) Incorporating a filter to reduce background emission—Although the background fluorescence is low in general, plastic does exhibit a high autofluorescence at approximately 569 nm. This emission peak is a result of Raman fluorescence that is generated when plastic is excited by a 488 nm laser. The spectra of the peak shows that it is centered about 569 nm and has a full width of 5 nm. The Raman fluorescence can be eliminated by using a notch filter with a center wavelength of approximately 570 nm and a rejection band between approximately 5 to 10 nm. An experiment to assess the improvement in signal to noise by using a notch filter to eliminate the Raman plastic fluorescence was conducted. A set of 3 separation and detection runs was performed without a notch filter, and another set was performed with a notch filter installed at the input to the PMT box. FIG. 80 summarizes the results of the data. The data shows that the filter reduces the peak-to-peak noise for the yellow channel from 67 to 39 relative fluorescence units (rfu). The filter also reduces the absolute signal strengths from 1520 to 1236 rfu, with an overall improvement in the signal to noise ratio from 23 to 32. A notch filter is useful in the optical systems of both integrated and unintegrated instruments in settings where the limit of detection is particularly important (e.g. the analysis of forensic touch samples and the diagnosis of infectious agents early in the course of a given disease when pathogen numbers are low).

Example 9

Design of a Fully Integrated Biochip that Purifies Nucleic Acids from Clinical Whole Blood Samples, Amplifies the Purified DNA, Sanger Sequences the Amplified DNA, Ultrafilters the Sequenced DNA, and Electrophoretically Separates the Ultrafiltered DNA and Generates Multiplexed DNA Sequence Using an Automated Script Pathogens such as staphylococci, streptococci, and *Yersinia enterocolitica* may be present in the extracellular components of the blood. A stationary, unitary plastic biochip that accepts 2 blood samples and generates DNA sequence from 8 loci of a given pathogen consists of a pneumatic—valve-fluidic stack, macrofluidic processing subassembly, and separation and detection subassembly. The biochip resembles the injection molded biochip of Example 6 with modifications as described below, and, based on an automated script, the process is conducted as follows:

The macrofluidic subassembly is composed of 12 chambers that hold preloaded reagents or serve as holding/reaction chambers during the DNA purification process. One chamber is used to accept the blood collection tube; six chambers are pre-filled with 3 mL of wash solution, 100 microliters of cell resuspension solution, 450 microliters of lysis solution, 550 microliters of absolute ethanol, 2 microliters of wash buffer, 2000 microliters of deionized water and 400 microliters of elution buffer.

The biochipset accepts a standard 3 cc vacutainer tube (for separation experiments, blood is collected in tubes containing appropriate anticoagulants). The blood collection tube is inserted into the biochip with the rubber stoppered end down. The purification process is initiated when the user presses a start button on the instrument. Within the instrument, the blood collection tube is pushed onto two hollow pins located at the base of blood collection tube cavity. The hollow pins pierce through the rubber stopper, and the blood collection tube is pressurized pneumatically to 5 psi to drive the blood from the blood collection tube through a through a filter with nominal pore size of 8 microns (such as Leukosorb B media, Pall Corporation, Port Washington, N.Y.) to remove leukocytes from the blood. The flowthrough is passed through a through a single layer of 0.2 micron polycarbonate track-etch membrane (SPI-Pore™ Track-Etch Membrane, Structure Probe, Inc., West Chester, Pa.) to concentrate the bacteria through capture on the membrane, and this flowthrough is routed to a waste chamber.

Resuspension solution (100 microliters) is applied to the surface of the track-etch membrane, resuspending the pathogens retained on the track etch membrane, and generating a concentrated pathogen suspension (which may also include residual leukocytes). This suspension is pneumatically driven into the lysis chamber. DNA purification is performed as described as in Examples 5 and 6, with all volumes proportionately lower. Chaotropic lysis reagent is driven into the lysis chamber, and air is pneumatically driven into the lysis/waste chamber to effect chaotic bubbling of the lysate. Ethanol from the ethanol reservoir is driven into the lysis/waste and mixed by chaotic bubbling. The lysate/ethanol mixture is pneumatically driven into the holding chamber and through the purification membrane and into the lysis/waste chamber. The membrane is subjected to a series of three washes, removing unbound material and residual lysis solution. The filter is then air-dried. 20.5 microliters of elution solution is pneumatically driven from the elution solution reservoir through the purification membrane to the eluate holding chamber. This smaller volume ensures that a large proportion of the isolated nucleic acids are amplified in the subsequent amplification reaction.

Eluate is pneumatically driven from the eluate holding chamber into the eluate metering chambers, and excess eluate is pneumatically driven back into the eluate holding chamber. The eluate is pneumatically driven from the eluate metering chamber into the PCR cake chamber. 20.5 microliters of metered eluate is transferred to reconstitute the cake containing the lyophilized PCR reaction mix to generate the PCR mix for amplification. The cake contains the same components as those of FIGS. 5 and 6, with the exception that the human STR primer pairs (one of each pair is fluorescently labeled) are replaced with a set of 80 primer pairs (neither member of each pair is labeled). The 80 primer pairs represent 8 specific loci for each of 10 pathogens, including staphylococci, streptococci, and *Yersinia enterocolitica* (much larger sets of loci are possible if desired). The reconstituted PCR reaction mix is pneumatically driven from the cake chambers into the thermal cycling chambers and stops at the queuing vent membrane. A thirty-one cycle amplification protocol is applied to cycle the reaction within the thermal cycling chamber. All scripted and process steps are performed essentially as described as in Examples 5 and 6.

PCR product is pneumatically driven from the thermal cycling chambers into the PCR metering chamber and stops at a vent membrane. Six microliters of the PCR product are mixed with 94 microliters of deionized water in a joining chamber. The joining chamber allows the metered PCR and the metered water (which originate from two independent flows) to be combined to form the sample for reconstitution of the lyophilized sequencing cake. The diluted PCR product is driven from the joining chamber and split into 8 metering chambers, each of which holds 11 microliters and are queued by a vent membrane. Each of the eight samples is driven to a sequencing cake reconstitution chamber. The eight cakes are slightly different versions of the Sanger reaction mix (based on the use of dye-labeled terminators, such that each extension product bears a single fluorescent label corresponding to the base at that position of the sequence), with each cake containing a unique set of ten sequencing primers—one for a locus for each of the ten pathogens of interest. For a given pathogen, one primer pair for a specific locus is in cake one, a second in cake two, etc.; this placement ensures a single DNA sequence is generate for a given pathogen from each cake. The reconstituted sequencing reaction mixes are pneumatically driven from the cake chambers into the cycle sequence cycling chambers (located just above the second thermal cycler) and stop at the queuing vent membrane; each cycling chamber holds 10 microliters. Cycle sequencing is performed as follows: 95° C. for 15 seconds followed by 30 cycles of [95° C. for 5 seconds, 50° C. for 10 seconds, and 60° C. for 25 seconds). For each of eight sequencing reactions (now a total of 16 for two blood samples), the 10 microliter sequencing reaction product is mixed with 100 microliters of deionized water in a joining chamber in preparation for ultrafiltration.

Electrophoretic separation performance can be greatly improved by purification of the sequencing product to remove ions necessary for sequencing (and the preceding PCR reaction) that interfere with the separation. A variety of methods can be employed, including ultrafiltration, in that small ions/primers/unincorporated dye labels are driven through a filter, leaving the desired product on the filter that then can be eluted and applied directly to separation and detection. Ultrafiltration media include polyethersulfone and regenerated cellulose "woven" filters, as well as track-etch membranes, in which pores of highly-uniform size are formed in an extremely thin (1-10 μm) membrane. The latter have the advantage of collecting product of size larger than the pore size on the surface of the filter, rather than capturing the product at some depth below the surface.

Accordingly, the diluted sequencing product was driven through ultrafiltration filter. The filter traps Sanger sequencing product but allows ions and the diluted sequencing buffers to pass through. The material on the filter was washed by pneumatically driving 200 μl of deionized water through the filter to further remove ions and buffer. Finally the cleaned Sanger sequencing product was eluted from the filter by pneumatically driving 10 μl of deionized water into the filter chamber to resuspend the Sanger sequencing product. The eluate is then pneumatically driven into the joining chamber. Formamide is pneumatically driven from the formamide reagent chamber into the formamide metering chamber. The formamide flows into the metering chamber and stops at a vent membrane. Excess formamide is pneumatically driven from the formamide chamber into a waste chamber. Ten microliters of metered ultrafiltered product is pneumatically driven from the metering chamber into the joining chamber. Metered formamide was pneumatically driven from the formamide metering chamber into the joining chamber. The joining chamber allows the metered ultrafiltered product and the metered formamide (which originate from two independent flows) to be combined to form the sample for separation and detection. Electrophoresis is conducted as described in Examples 5 and 6 with the exception that the biochip is heated to 60° C. The injection voltages and times, and separation voltages and times are identical to that of Examples 5 and 6. The two blood samples are processed such that they generate 16 channels of product for separation and detection. In general, the number of separation channels per sample is equivalent to the largest number of loci and primer pairs being interrogated for one of the pathogens under evaluation.

The optical system is activated to effect laser induced fluorescence excitation and detection. The laser is set to 200 mW and the data collection rate of 5 Hz is implemented. Following color correction, an automated basecaller generates sequence from lanes that contain one of the ten pathogens for which amplification and sequencing primers were incorporated in the amplification and sequencing cakes, respectively. Approximately 500 bp of sequenced are generated per lane.

The biochip can be modified in many ways, based on the clinical sample type and the pathogens to be identified. For example, certain bacteria such as *Francisella tularenis* and *Chlamydia trachomastis* spend a significant portion of their life cycles within mammalian cells. Some are obligate intracellular organisms and others are optionally intracellular. The DNA purification process for such intracellular bacteria in blood is similar to that described above with a major exception. Following application of whole blood on and through the cell separation filter, the leukocytes trapped by the filter contain the DNA of interest. The filter is washed, resuspended in 100 microliters, and subjected to guanidinium-based purification as described in Example I with corresponding reduction is reagent volume.

If desired, the apparatus can be design to initially lyse the leukocytes (osmotically, for example), taking advantage of the relative ease of lysis of mammalian cells as compared to bacteria. In this setting, the intact intracellular bacteria are released, and the cell extract is based through a bacterial capture filter and washed. Bacterial DNA is then purified as described in above. Similarly, whole blood can be lysed in the absence of cell separation, allowing extracellular or intracellular bacterial or viral DNA to be purified.

Example 10

Fully Integrated CNC-Machined and Injection Molded Biochips that Store and Release Reagents, Purify Nucleic Acids, Amplify the Purified DNA, Electrophoretically Separate the Amplified DNA and Generate an STR Profile Using an Automated Script Biochips of the invention can be designed to incorporate a variety of features based on the specific application requirements. For example, another biochip can be constructed by incorporating the single tube Reagent Storage and Release structures of Example 1 into the biochip design of Example 5.

A biochip with these features was fabricated by CNC-machining essentially as described in Example 5. The macrofluidic processing subassembly is based on same design as that of Example 5. FIG. 47 shows the macrofluidic block 18 with swab 19, lysis solution 20, ethanol 21, wash solution 22, and elution solution 23 reagent chambers, and fluidic processing chambers for lysate holding 24, eluate homogenization 25, air 58, TTE 59, and formamide 60 chambers.

The lysis solution 20, ethanol 21, wash solution 22, and elution solution 23 reagent chambers have the RSR structures of FIG. 1: foil seals (101) were thermally bonded to the top and bottom of each reagent storage chamber (102). The bottom foil was bonded first, liquid reagents were filled (indicated by shading of 102), and the top foil was then bonded, sealing the reagent storage chamber. The top cover (103) contained pneumatic drive lines that provide pressure required to burst the foils.

Figure 81:
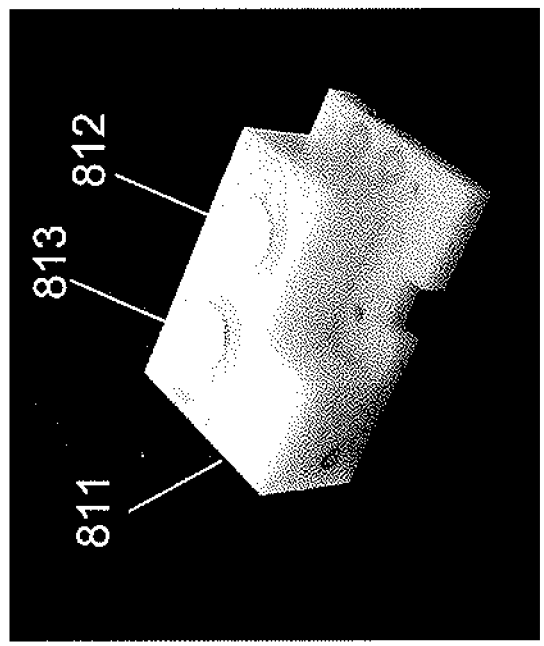
FIG. 81 is a photograph of a second macrofluidic processing assembly termed the Matrix loading assembly.

A second macrofluidic processing assembly (811) (termed the "Matrix loading assembly"; FIG. 81) is included in the biochip. This subassembly contains sieving matrix (812) and electrophoresis buffer (813), both with the RSR structures of FIG. 1. During the initial stages of sample processing, electrophoresis buffer was loaded from the Matrix loading assembly via the anode of the Separation and Detection subassembly (FIG. 55). The foil seals were burst and reagents were released by applying pneumatic drive pressure of 45 psig to the chambers. The electrophoresis buffer reagent was then pneumatically driven into the anode chamber at 1 psig. Next, sieving matrix was loaded into the electrophoresis channels via a hole in the Separation and Detection subassembly (FIG. 55) by applying a pneumatic drive pressure of 300 psig. Performing sieving matrix loading in parallel with sample processing (e.g. the nucleic acid purification) reduces the total time required from sample introduction to STR profile generation. Following matrix loading, pre-electrophoresis is optionally performed.

Figure 82:
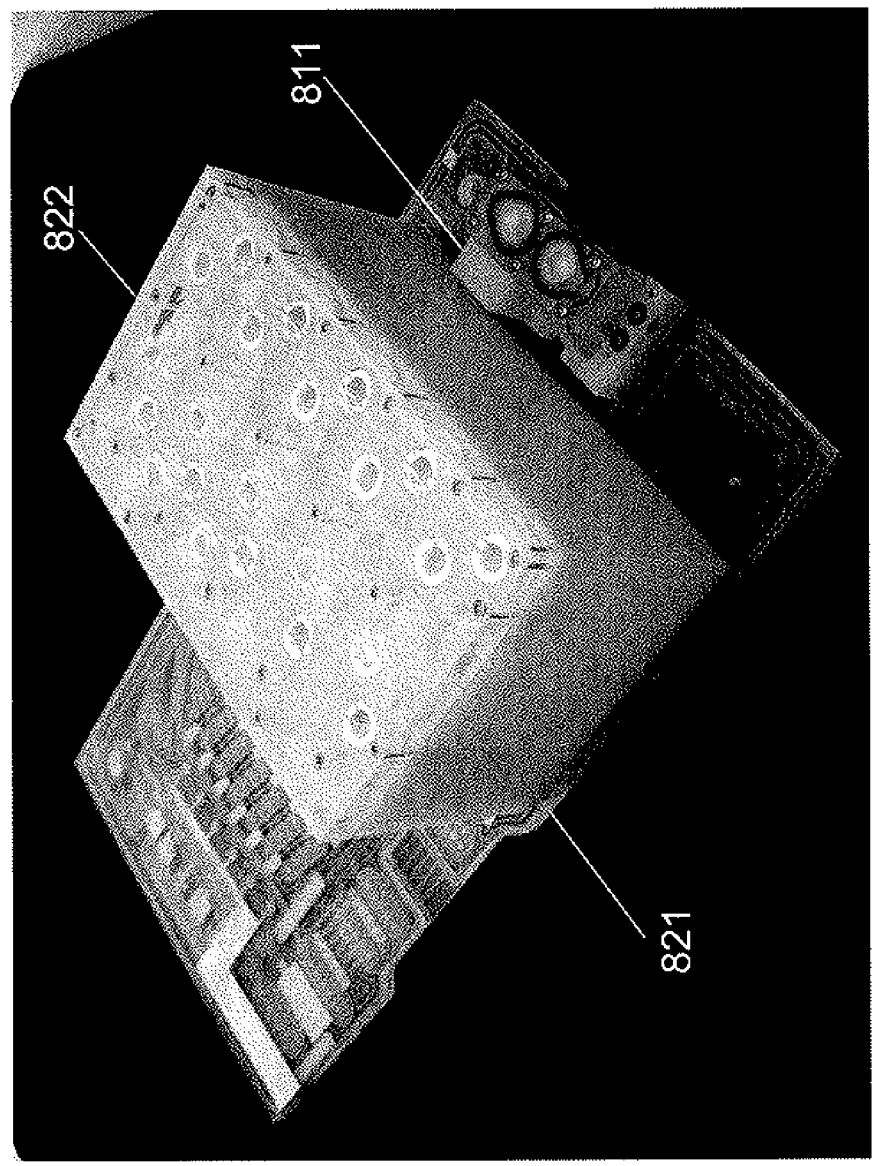
FIG. 82 is a photograph of a biochipset fabricated by CNC-machining.

A photograph of this biochipset, fabricated by CNC-machining (821), is shown in FIG. 82. Lysis solution, ethanol, wash solution, elution solution, TTE buffer, and formamide were pre-loaded in the macrofluidic subassembly (822) and sieving matrix and TTE buffer were pre-loaded in the matrix loading assembly (811)—all liquid reagents were in chambers with RSR structures for storage and automated release. Lyophilized reagents located within the fluidic subassembly included the PCR reaction cake and ILS cake of Example 5 and an allelic ladder cake. The sample-in to results out process was performed as follows. Five swabs were collected from donors. The swabs were collected by pressing the head of a Bode SecurSwab swab to the inside of the cheek as instructed by the manufacturer. Each of the 5 swabs was inserted into one of the swab chambers of the biochip. The biochip was inserted to a single, fully integrated instrument as described in Example 5, and the automated process script was initiated to carry out the swab-in to results-out analysis. The automated script was performed as described in Example 5, with the addition of a step to burst the top and bottom foils of each liquid reagent chamber and the parallel filling of sieving matrix in the channels of the Separation and Detection subassembly.

Figure 83:
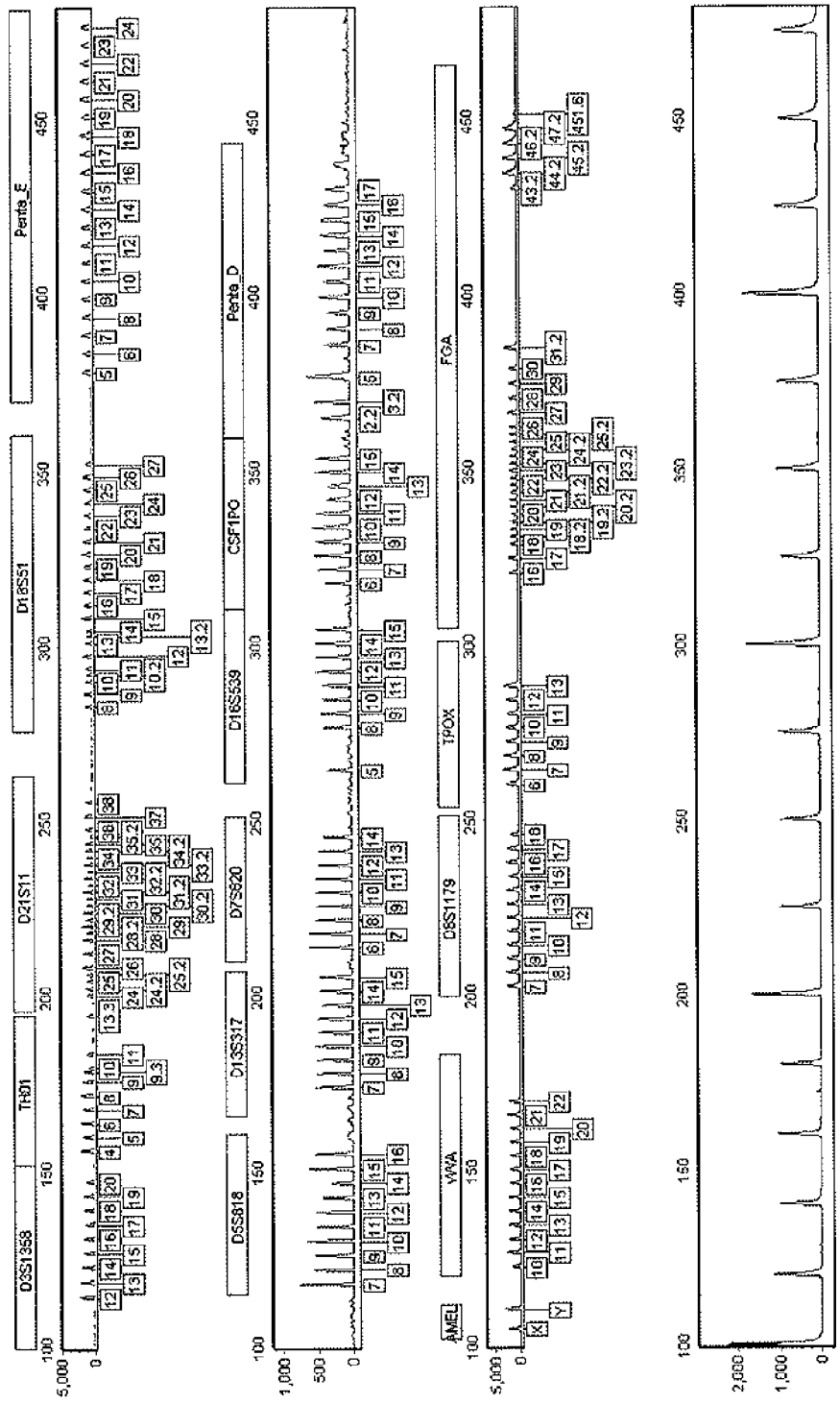
FIG. 83 is an electropherogram generated for the allelic ladder sample (fragments fluorescently labeled with fluorescein, JOE, TAMRA, and ROX) of Example 10.
Figure 84:
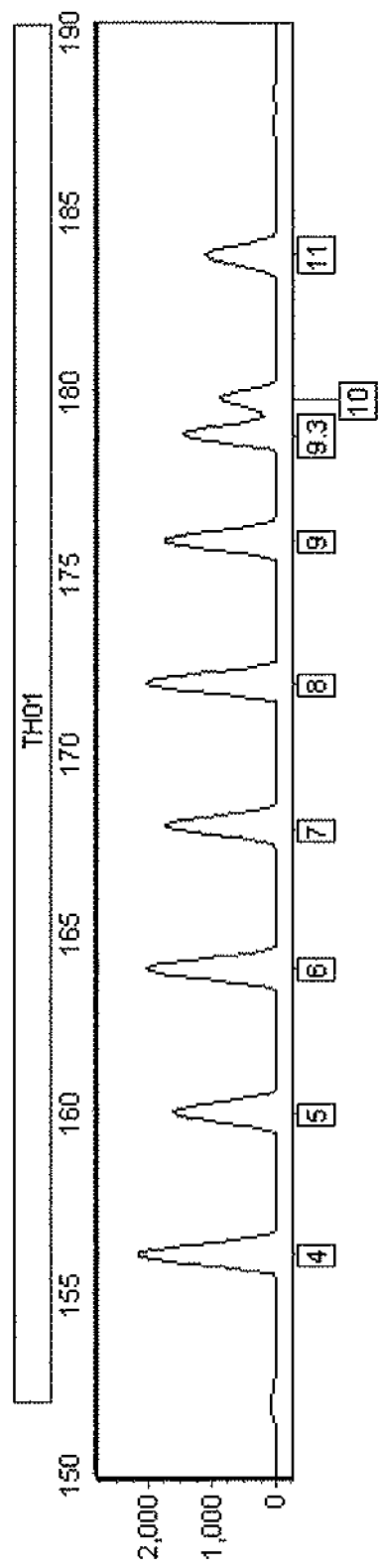
FIG. 84 is an electropherogram depicting single base pair resolution, as indicated by the clear separation of the Th01 9.3 and 10 alleles shown within a portion of the allelic ladder from one of the buccal swab samples of FIG. 85.
Figure 85:
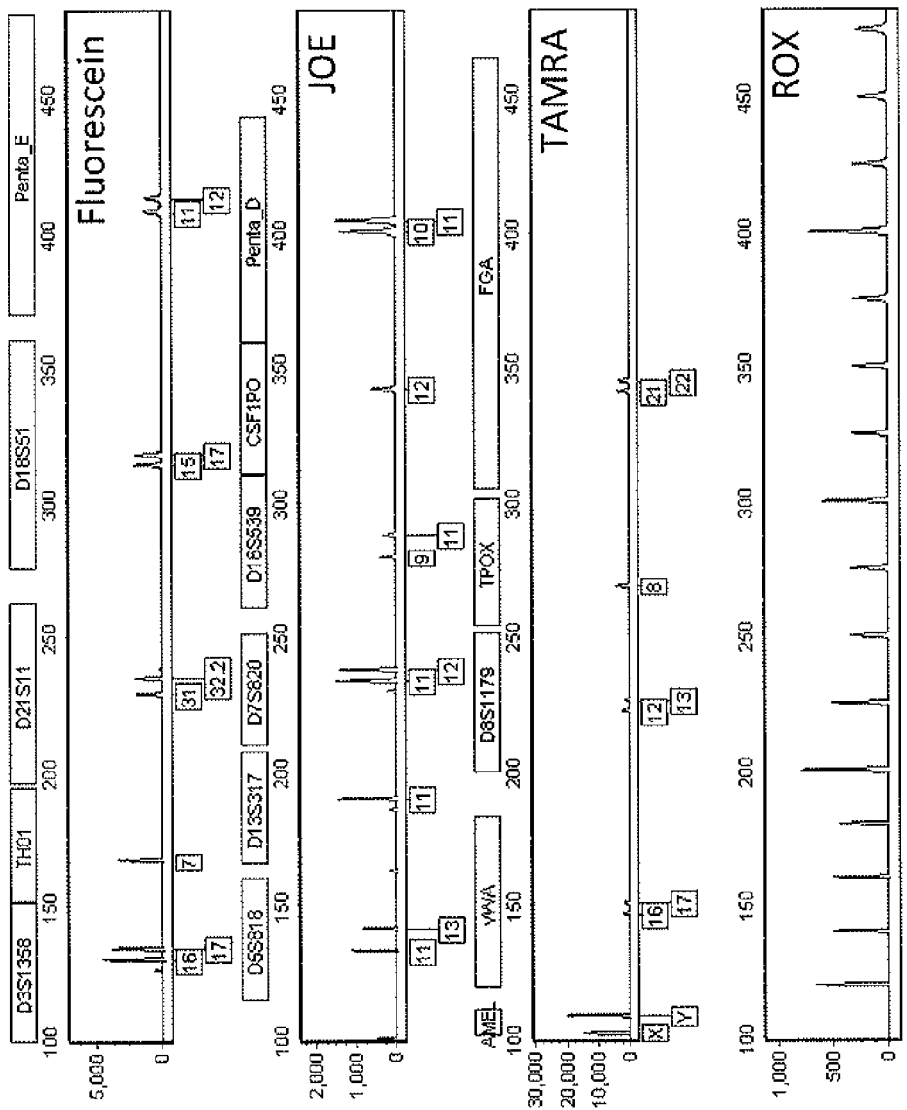
FIG. 85 is electrophertic data generated using the biochip of Example 10.

An electropherogram (FIG. 83) was generated for the allelic ladder sample (fragments fluorescently labeled with fluorescein, JOE, TAMRA, and ROX). Resolution is single base pair (FIG. 84) as indicated by the clear separation of the Th01 9.3 and 10 alleles shown within a portion of the allelic ladder. The electrophoretic data from one of the buccal swab samples is shown in FIG. 85. Each of fluorescent dyes used to label the STR primers (fluorescein, JOE, and TAMRA) in the PCR reaction mix and the ILS (ROX) are shown in individual panels. Fluorescein-labeled STR fragments are shown in the top panel, JOE-labeled STR fragments are shown in the second panel from the top, TAMRA-labeled STR fragments are shown in the third panel from the top, and ROX-labeled ILS fragments are shown in the bottom panel. The x-axis shows fragment size in base pairs and the Y-axis shows relative fluorescence units. Beneath each fragment, the allele calls are presented in boxes (two calls for heterozygous alleles and one for homozygous alleles). The electrophoretic raw data was first subjected to color baseline subtraction and smoothing followed by color correction to separate the signals from each of the fluorescent dyes. Following this data processing, the software then performed allele calling based on using the known fragment sizes of the ILS to assign sizes to the STR peaks in the electropherogram and to assign an allele call to each sized peak. The results is a full profile, with called alleles generated from all 16 loci in the multiplexed PCR reaction of the fully integrated system. The entire process from insertion of samples to generation of the electropherogram required approximately 94 minutes, and data processing and allele calling required less than two minutes.

Liquid traps were inserted within the biochipset to prevent the back flow of reagents from the reservoirs into the pneumatic drive lines. Two forms of liquid traps were used within the biochipset: Dessicat (Molecular sieves) inserted within the macrofluidic processing assembly are used to absorb liquid that may be present within the pneumatic drive lines while allowing relatively unrestricted air flow. Filter membranes (synthetic fels) were inserted within the SC cover and are used to absorb liquid from the swab chambers during chaotic bubbling steps while allowing relatively unrestricted air flow. Vent membranes were also used to allow air flow through the membranes but halt liquids. Within the instrument drive lines that can be exposed to liquids (e.g. from an unintentional operator spill of a liquid onto the biochip or instrument) can be protected with a liquid trap between the biochipset and the pneumatic subsystem.

Figure 86:
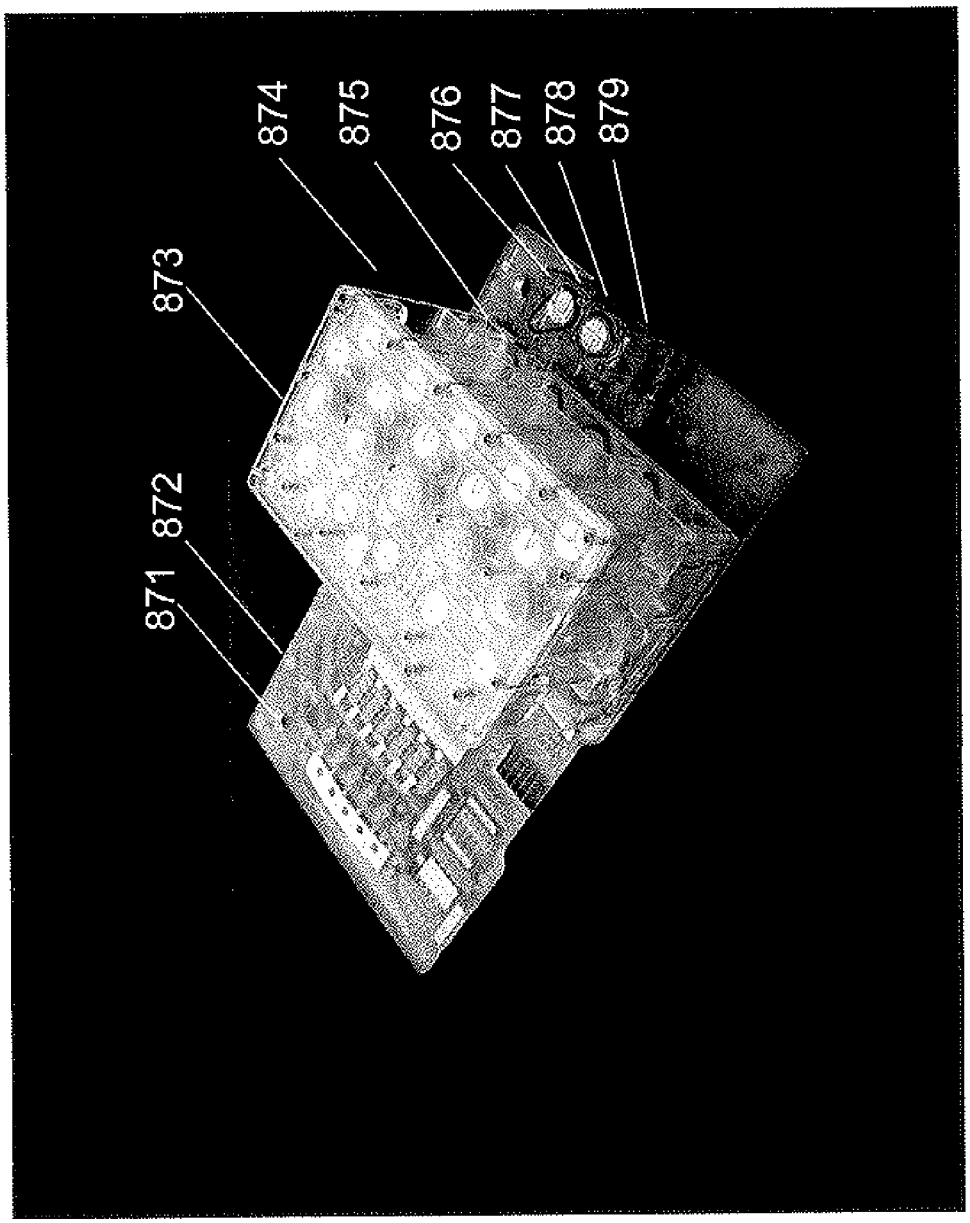
FIG. 86 is a photograph of an embodiment of an injection molded biochip.
Figure 87:
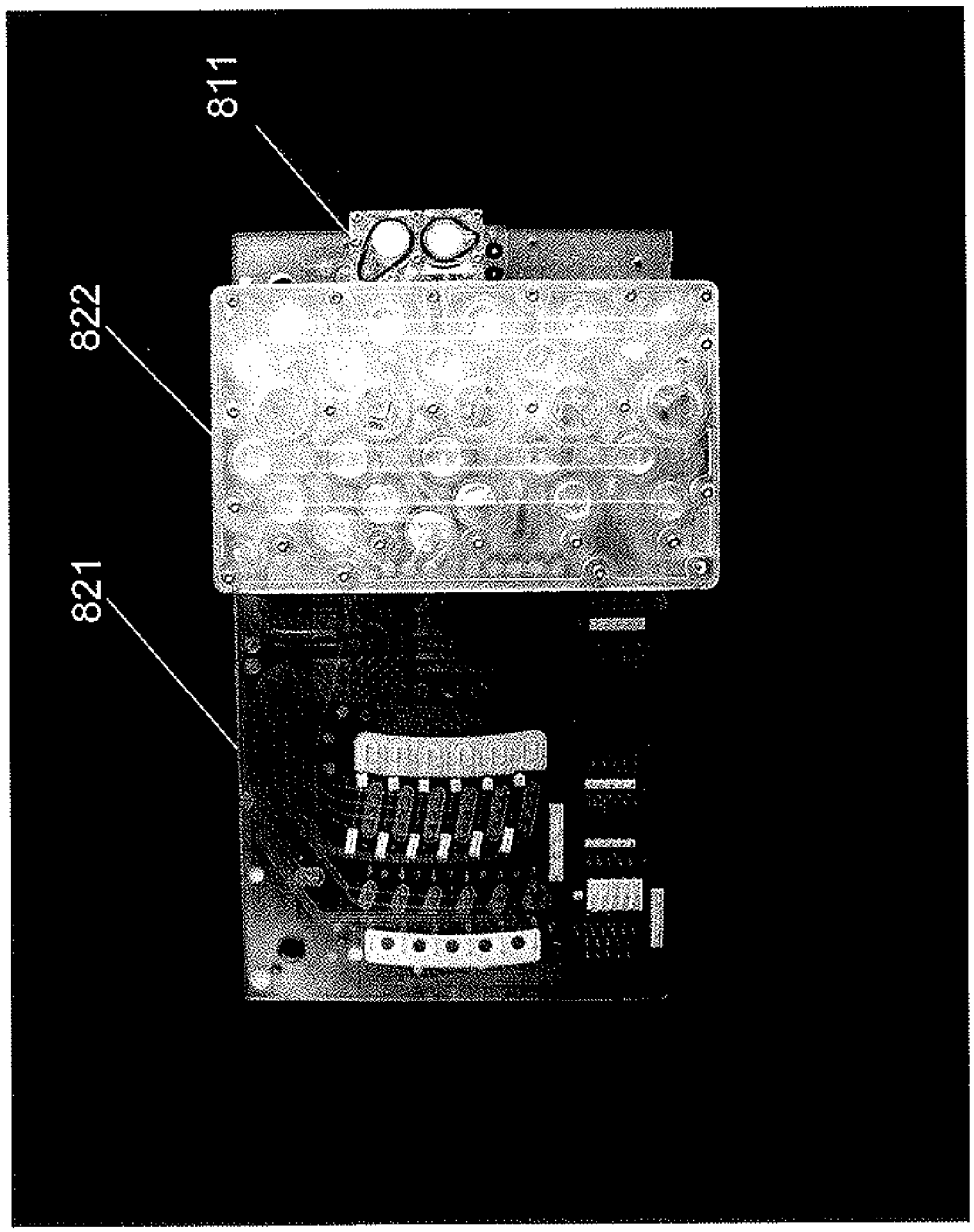
FIG. 87 is a photograph showing the top view of the injection molded biochip of FIG. 86.
Figure 88:
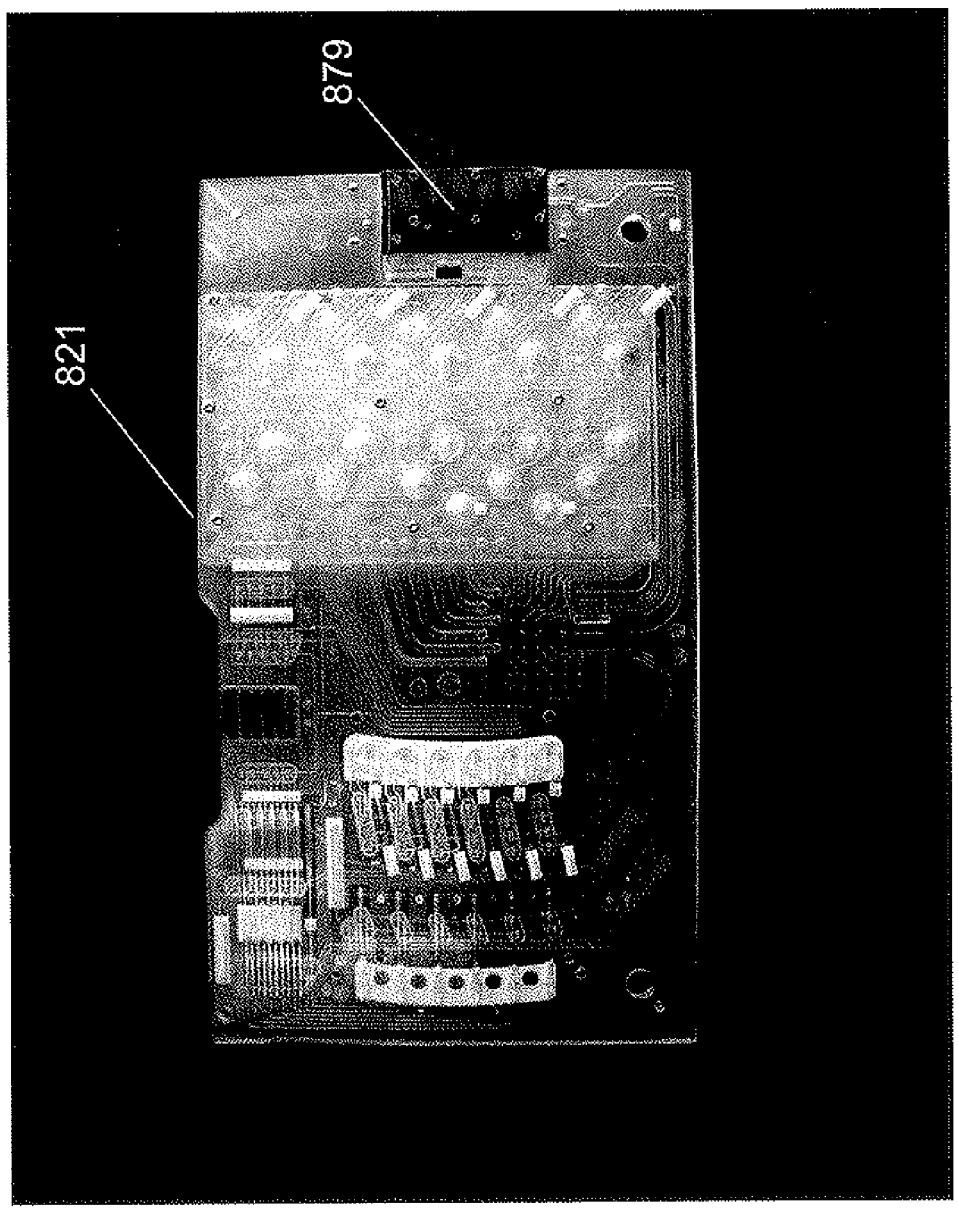
FIG. 88 is a photograph showing the bottom view of the injection molded biochip of FIG. 86.
Figure 89:
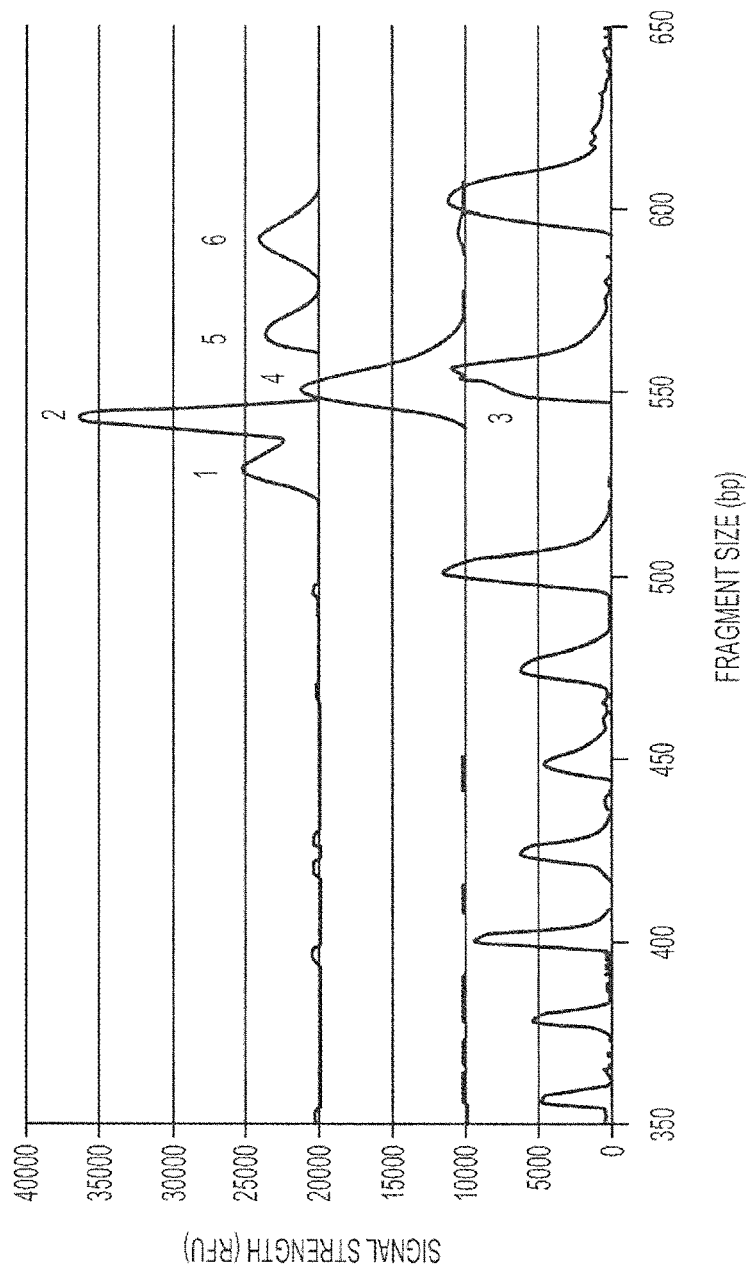
FIG. 89 is a raw data plot of signal strength (RFU) versus S&D run time for the biochip of Example 11.

Using the same design as the CNC-machined biochip (including RSR features), an injection molded biochip was fabricated (FIGS. 86-88). FIG. 86 is a photograph of the injection molded biochip, FIG. 87 shows the top view of the injection molded biochip, and FIG. 88 shows the bottom view of the injection molded biochip. Parts fabricated from COP by injection molding include the pneumatic plate (871), fluidic plate (872), cover to the macrofluidic processing assembly (873), block of the macrofluidic processing assembly (874), spacer plate for the macrofluidic processing assembly (875), cover to the matrix loading assembly (876), block of the matrix loading assembly (877), and spacer plate for the matrix loading assembly (878). These injection molded parts were assembled (including thin films, filters, membranes, and RSR components) to form the biochip as described in Examples 1 and 5.

Example 11

A Fully Integrated Biochip that Purifies Bacterial Nucleic Acids, Performs Multiplex Amplification on the Purified DNA, and Electrophoretically Separates the Resulting Amplicons to Generate Fragment Sizes and Colors Diagnostic of the Pathogen Using an Automated Script The fully integrated biochips of the invention are capable of analyzing a wide variety of sample types and performing a wide variety of assays, based on the specific design features of the biochip and the composition of the reagents utilized. Depending on the sample type, features and process steps including sample concentration and sample separation into multiple components (as described in Example 9) may be implemented.

The fully-integrated biochip of Example 5 can accept a variety of sample types in addition to buccal swabs. Forensic swabs from crime scene samples containing blood or epithelial cells (e.g. fingerprints, palmprints, or touch samples in general), clinical swabs (e.g. vaginal, cervical, wound), veterinary swabs, food safety swabs, and environmental swabs, among others, can be utilized. Tissue samples and liquid samples (including blood, exudate, transudate, urine and other clinical fluids) can be placed in the swab chamber (FIG. 39, 19) for subsequent processing.

A fresh overnight culture of *B. cereus* (ATCC 4342) in 8 ml tryptic soy broth (TSB) media was prepared from a single colony on TSB-agar plate. A 1000-fold dilution of the stock homogenized bacteria mixture was used to obtain cell counts under a light microscope using a Petroff-Hausser cell counter. 100 μl solution containing $10^5$ *B. cereus* cells was transferred onto a dried human buccal swab. The presence of human cells and DNA on the swabs models a clinical swab sample in which the vast majority of DNA is derived from the human patient whereas only a small fraction of total nucleic acid is derived from the pathogen or pathogens.

The spiked swab was then placed into the in the swab chamber (FIG. 39, 19) of the biochipset of Example 5. Nucleic acid purification, amplification, and separation and detection were performed essentially as described in Example 5. The major difference is that the lyophilized PCR cake located within the PCR cake chamber (FIG. 40, 10) containing primer pairs that target the 7 house-keeping genes used in *B. cereus* MLST (see Read, T., et al. (2010). "Rapid multi-locus sequence typing using microfluidic biochips." *PLoS One* 5(5): e10595). The primer pairs used for PCR were designed to amplify fragments of seven *B. cereus* sensu latu housekeeping genes with sizes ranging from 348-504 base pairs. FIG. 89 is the raw data plot of signal strength (RFU) versus S&D run time. Six of the expected loci are present, diagnostic of the presence of *B. cereus* in the sample. Peaks 1, 2, 3, 4, 5, and 6 are the pur (532 bp), pycA (547 bp), glpF (550 bp), tpi (551 bp), pta (569 bp), and gmk (598 bp) amplicons; respectively. The ilvD amplicon is frequently missing in *B. cereus* strains due to point mutations at a primer site, and its absence in the *B. cereus* strain present in the sample was confirmed by conventional amplification.

The successful identification of a bacterial pathogen in a complex sample can be extended in a variety of ways. In particular, the lysate and eluate volumes can be reduced to generate a more concentrated eluate of purified nucleic acids. These and many related changes (e.g. overall volume and chamber size reductions, optimization of the thermal cycling script) can be utilized to generate single copy level of detection.

Example 12

Fully Integrated Biochips that Store and Release Reagents, Lyse Cells, Directly Amplify DNA Present in the Lysate, Electrophoretically Separate the Amplified DNA and Generate an STR Profile Using an Automated Script Certain process steps and analogous features can be combined or eliminated to speed sample processing, reduce the size of the biochip, or both. For example, forensic laboratories processing buccal and blood samples can eliminate the DNA purification step by lysing cells and directly amplifying the lysate. Termed "direct PCR," this technique is sometimes based on the lysis of cells on FTA paper and the inclusion of additives in the PCR reaction to minimize inhibition. The AmpFISTR® Identifiler® Direct PCR Amplification Kit (Applied Biosystems, Foster City, Calif.), Ampdirect Plus (Whatman, Florham Park, N.J.), and the PowerPlex® 18D System (Promega Corporation, Madison, Wis.) are three of several such products.

The biochipsets of Examples 5, 6, and 10 are modified such that macrofluidic processing subassembly eliminates the purification reagent chambers but maintains the lysis solution chamber. Lysis solution is placed in a dedicated chamber for each sample or is present as a single chamber and distributed to the five samples. Alternatively, an FTA paper sample can be resuspended and placed into the sample chamber, eliminating the need for a lysis reagent. The lysed sample is then driven to reconstitute the lyophilized PCR cake for direct amplification followed by separation and detection as described in Examples 5, 6, and 10. The biochip is fabricated based on the teachings of the present invention, and the volume of the macrofluidic processing block is approximately 80% smaller than those of Examples 5, 6, and 10.

Sample manipulations that can be performed in the biochips of Examples 5, 6, and 10 include combinations of nucleic acid extraction; cell lysis; cell separation; differential cell lysis; differential filtration; total nucleic acid purification; DNA purification; RNA purification; mRNA purification; protein purification; pre-nucleic acid amplification cleanup; nucleic acid amplification (e.g. both singleplex and multiplex end-point PCR, Real-time PCR, reverse transcription PCR, asymmetric PCR, nested PCR, LATE PCR, touchdown PCR, digital PCR, rolling circle amplification, strand displacement amplification, and multiple displacement amplification); Y-STR amplification; mini-STR amplification; single nucleotide polymorphism analysis; VNTR analysis; RFLP analysis; post-nucleic acid amplification cleanup; pre-nucleic acid sequencing cleanup; nucleic acid sequencing (e.g. Sanger sequencing, pyrosequencing, and single molecule sequencing); post-nucleic acid sequencing cleanup; reverse transcription; pre-reverse transcription cleanup; post-reverse transcription cleanup; nucleic acid ligation; SNP analysis; nucleic acid hybridization; electrophoretic separation and detection; immunoassays; binding assays; protein assays; enzymatic assays; mass spectroscopy; and nucleic acid and protein quantification. The biochips may combine 2 or more of these sample manipulations, 3 or more, 4 or more, 5 or more, 6 or more, 7 or more, 8 or more, 10 or more, 12 or more, 15 or more, 20 or more, or 25 or more. The sample splitting described in Example 7 can also be utilized to split a sample into 2 or more aliquots, with each aliquot being subjected to a unique set of sample manipulations. The biochips of the invention allow a substantial amount of information to be gained from the interrogation of a given sample.

Although several embodiments of the invention have been described, it will be apparent to a person skilled in the art that various modifications to the details thereof shown and described may be made without departing from the scope of the invention.

What is claimed is:

1. A biochip made from the method comprising:

injection molding a macrofluidic block, said block comprising: (i) a means for receiving at least one unprocessed sample, (ii) a fluid transfer means positioned and configured so that in the fully manufactured biochip said fluid transfer means is in fluid communication with a fluidic plate, and (iii) at least one molded feature therein, said feature having a top end and a bottom end;
bonding a first foil seal to either said top end or said bottom end to form at least one reagent storage chamber having an open end;
filling said at least one reagent storage chamber with a liquid reagent;
bonding a second foil seal to said open top end to form at least one filled reagent storage chamber in said macrofluidic block;
injection molding said fluidic plate having a top surface and a bottom surface, each of said top and bottom surfaces comprising a plurality of microfluidic features, and at least one through hole extending from said top surface to said bottom surface to connect the fluidic top surface to the bottom surface;
injection molding a pneumatic plate having a top surface and a bottom surface, each of said top and bottom surfaces comprising a plurality of microfluidic features and at least one through hole extending from said top surface to said bottom surface to connect the pneumatic top surface to the bottom surface;
aligning said macrofluidic block and said fluidic plate so that in the fully manufactured biochip sample processed in said macrofluidic block is transferred to said fluidic plate by the fluid transfer means;
aligning the pneumatic and fluidic plates using said at least one through hole;
wherein said reagent storage chamber may be filled prior or subsequent to the first or second aligning steps and said macrofluidic block, fluidic and pneumatic plates may be injected molded in any order or sequence.

2. A biochip made from the method comprising:
injection molding a macrofluidic block, said block comprising: (i) a means for receiving at least one unprocessed sample, (ii) a fluid transfer means positioned and configured so that in the fully manufactured biochip said fluid transfer means is in fluid communication with a fluidic plate, and (iii) at least one molded feature therein, said feature having a top end and a bottom end;
bonding a first foil seal to either said top end or said bottom end to form at least one reagent storage chamber having an open end;
filling said at least one reagent storage chamber with a liquid reagent;
bonding a second foil seal to said open top end to form at least one filled reagent storage chamber in said macrofluidic block;
injection molding said fluidic plate having a top surface and a bottom surface, each of said top and bottom surfaces comprising a plurality of microfluidic features at least two of which have a draft angle of less than 2 degrees, and at least one through hole extending from said top surface to said bottom surface to connect the fluidic top surface to the bottom surface;
injection molding a pneumatic plate having a top surface and a bottom surface, each of said top and bottom surfaces comprising a plurality of microfluidic features, and at least one through hole extending from said top surface to said bottom surface to connect the pneumatic top surface to the bottom surface;
aligning said macrofluidic block and said fluidic plate so that in the fully manufactured biochip sample processed in said macrofluidic block is transferred to said fluidic plate by the fluid transfer means;
aligning the pneumatic and fluidic plates using said at least one through hole;
wherein said reagent storage chamber may be filled prior or subsequent to the first or second aligning steps and said macrofluidic block, fluidic and pneumatic plates may be injected molded in any order or sequence.

3. A biochip made from the method comprising:
fabricating a macrofluidic block, said block comprising: (i) a means for receiving at least one unprocessed sample, (ii) a fluid transfer means positioned and configured so that in the fully manufactured biochip said fluid transfer means is in fluid communication with a fluidic plate, and (iii) at least one molded feature therein, said feature having a top end and a bottom end;
bonding a first foil seal to either said top end or said bottom end to form at least one reagent storage chamber having an open end;
filling said at least one reagent storage chamber with a liquid reagent;
bonding a second foil seal to said open top end to form at least one filled reagent storage chamber in said macrofluidic block;
fabricating said fluidic plate having a top surface and a bottom surface, each of top and bottom surfaces comprising at least one microfluidic feature, and at least one through hole extending from said top surface to said bottom surface to connect the top surface to the bottom surface;
fabricating a pneumatic plate to include a pneumatic top surface, a pneumatic bottom surface and at least one through hole extending from the pneumatic top surface to the pneumatic bottom surface to connect the pneumatic top surface to the bottom surface, each of the pneumatic top and bottom surfaces comprise a plurality of microfluidic features;
aligning said macrofluidic block and said fluidic plate so that in the fully manufactured biochip sample processed in said macrofluidic block is transferred to said fluidic plate by the fluid transfer means;
aligning the pneumatic and fluidic plates using said at least one through hole;
wherein at least one of the macrofluidic block, fluidic plate or pneumatic plate is fabricated by injection molding.

4. A biochip made from the method comprising:
injection molding a macrofluidic block, said block comprising: (i) a means for receiving at least one unprocessed sample, (ii) a fluid transfer means positioned and configured so that in the fully manufactured biochip said fluid transfer means is in fluid communication with a fluidic plate, and (iii) at least one molded feature therein, said feature having a top end and a bottom end;
bonding a first foil seal to either said top end or said bottom end to form at least one reagent storage chamber having an open end;
filling said at least one reagent storage chamber with a liquid reagent;
bonding a second foil seal to said open top end to form at least one filled reagent storage chamber in said macrofluidic block;
injection molding said fluidic plate having a top surface and a bottom surface, each of said top and bottom surfaces comprising a plurality of microfluidic features, and at least one through hole extending from said top surface to said bottom surface to connect the fluidic top surface to the bottom surface;
injection molding a pneumatic plate having a top surface and a bottom surface, each of said top and bottom surfaces comprising a plurality of microfluidic features, at least two of which have a draft angle of less than 2 degrees, and at least one through hole extending from said top surface to said bottom surface to connect the pneumatic top surface to the bottom surface;

aligning said macrofluidic block and said fluidic plate so that in the fully manufactured biochip sample processed in said macrofluidic block is transferred to said fluidic plate by the fluid transfer means;

aligning the pneumatic and fluidic plates using said at least one through hole;

wherein said reagent storage chamber may be filled prior or subsequent to the first or second aligning steps and said macrofluidic block, fluidic and pneumatic plates may be injected molded in any order or sequence.

5. A biochip made from the method comprising:

injection molding a macrofluidic block, said block comprising: (i) a means for receiving at least one unprocessed sample, (ii) a fluid transfer means positioned and configured so that in the fully manufactured biochip said fluid transfer means is in fluid communication with a fluidic plate, and (iii) at least one molded feature therein, said feature having a top end and a bottom end;

bonding a first foil seal to either said top end or said bottom end to form at least one reagent storage chamber having an open end;

filling said at least one reagent storage chamber with a liquid reagent;

bonding a second foil seal to said open top end to form at least one filled reagent storage chamber in said macrofluidic block;

injection molding said fluidic plate having a top surface and a bottom surface, each of said top and bottom surfaces comprising a plurality of microfluidic features, and at least one of said surfaces comprises a region of at least one square centimeter in which at least two of the plurality of microfluidic features are at a pitch of at least 1.00 mm, and at least one through hole extending from said top surface to said bottom surface to connect the fluidic top surface to the bottom surface;

injection molding a pneumatic plate having a top surface and a bottom surface, each of said top and bottom surfaces comprising a plurality of microfluidic features, and at least one through hole extending from said top surface to said bottom surface to connect the pneumatic top surface to the bottom surface;

aligning said macrofluidic block and said fluidic plate so that in the fully manufactured biochip sample processed in said macrofluidic block is transferred to said fluidic plate by the fluid transfer means;

aligning the pneumatic and fluidic plates using said at least one through hole;

wherein said reagent storage chamber may be filled prior or subsequent to the first or second aligning steps and said macrofluidic block, fluidic and pneumatic plates may be injected molded in any order or sequence.

6. A biochip made from the method comprising:

injection molding a macrofluidic block, said block comprising: (i) a means for receiving at least one unprocessed sample, (ii) a fluid transfer means positioned and configured so that in the fully manufactured biochip said fluid transfer means is in fluid communication with a fluidic plate, and (iii) at least one molded feature therein, said feature having a top end and a bottom end;

bonding a first foil seal to either said top end or said bottom end to form at least one reagent storage chamber having an open end;

filling said at least one reagent storage chamber with a liquid reagent;

bonding a second foil seal to said open top end to form at least one filled reagent storage chamber in said macrofluidic block;

injection molding said fluidic plate having a top surface and a bottom surface, each of said top and bottom surfaces comprising a plurality of microfluidic features, and at least one through hole extending from said top surface to said bottom surface to connect the fluidic top surface to the bottom surface;

injection molding a pneumatic plate having a top surface and a bottom surface, each of said top and bottom surfaces comprising a plurality of microfluidic features, and at least one of said surfaces comprises a region of at least one square centimeter in which at least two of the plurality of microfluidic features are at a pitch of at least 1.00 mm, and at least one through hole extending from said top surface to said bottom surface to connect the pneumatic top surface to the bottom surface;

aligning said macrofluidic block and said fluidic plate so that in the fully manufactured biochip sample processed in said macrofluidic block is transferred to said fluidic plate by the fluid transfer means;

aligning the pneumatic and fluidic plates using said at least one through hole;

wherein said reagent storage chamber may be filled prior or subsequent to the first or second aligning steps and said macrofluidic block, fluidic and pneumatic plates may be injected molded in any order or sequence.

7. A biochip made from the method comprising:

injection molding a macrofluidic block, said block comprising: (i) a means for receiving at least one unprocessed sample, (ii) a fluid transfer means positioned and configured so that in the fully manufactured biochip said fluid transfer means is in fluid communication with a fluidic plate, (iii) at least one molded feature therein, said feature having a top end and a bottom end, and (iv) a plurality of microfluidic features in a region of at least one square centimeter in which at least two of said plurality are at a pitch of at least 1.00 mm;

bonding a first foil seal to either said top end or said bottom end to form at least one reagent storage chamber having an open end;

filling said at least one reagent storage chamber with a liquid reagent;

bonding a second foil seal to said open top end to form at least one filled reagent storage chamber in said macrofluidic block;

injection molding said fluidic plate having a top surface and a bottom surface, each of said top and bottom surfaces comprising a plurality of microfluidic features, and at least one through hole extending from said top surface to said bottom surface to connect the fluidic top surface to the bottom surface;

injection molding a pneumatic plate having a top surface and a bottom surface, each of said top and bottom surfaces comprising a plurality of microfluidic features, and at least one through hole extending from said top surface to said bottom surface to connect the pneumatic top surface to the bottom surface;

aligning said macrofluidic block and said fluidic plate so that in the fully manufactured biochip sample processed in said macrofluidic block is transferred to said fluidic plate by the fluid transfer means;

aligning the pneumatic and fluidic plates using said at least one through hole;

wherein said reagent storage chamber may be filled prior or subsequent to the first or second aligning steps and said macrofluidic block, fluidic and pneumatic plates may be injected molded in any order or sequence.

8. A biochip made from the method comprising:
fabricating a macrofluidic block, said block comprising: (i) a means for receiving at least one unprocessed sample, (ii) a fluid transfer means positioned and configured so that in the fully manufactured biochip said fluid transfer means is in fluid communication with a fluidic plate; and (iii) at least one molded feature therein, said feature having a top end and a bottom end;
bonding a first foil seal to either said top end or said bottom end to form at least one reagent storage chamber having an open end;
filling said at least one reagent storage chamber with a liquid reagent;
bonding a second foil seal to said open top end to form at least one filled reagent storage chamber in said macrofluidic block;
fabricating said fluidic plate having a top surface and a bottom surface, each of top and bottom surfaces comprising at least one microfluidic feature, and to include a fluidic top surface, a fluidic bottom surface and at least one through hole extending from said top surface to said bottom surface to connect the top surface to the bottom surface;
fabricating a pneumatic plate to include a pneumatic top surface, a pneumatic bottom surface and at least one through hole extending from the pneumatic top surface to the pneumatic bottom surface to connect the pneumatic top surface to the bottom surface, each of the pneumatic top and bottom surfaces comprise a plurality of microfluidic features;
aligning said macrofluidic block and said fluidic plate so that in the fully manufactured biochip sample processed in said macrofluidic block is transferred to said fluidic plate by the fluid transfer means;
aligning the pneumatic and fluidic plates using said at least one through hole;
wherein at least one of the macrofluidic block, fluidic plate or pneumatic plate is fabricated by injection molding and wherein at least one of the injection molded parts has at least one square centimeter region which contains at least two microfluidic features at a pitch of at least 1.0 mm.

* * * * *